United States Patent
Joseph et al.

(10) Patent No.: US 11,672,802 B2
(45) Date of Patent: Jun. 13, 2023

(54) INDUCTION OF IMMUNE TOLERANCE BY USING METHOTREXATE

(71) Applicant: Genzyme Corporation, Cambridge, MA (US)

(72) Inventors: Alexandra Joseph, Lexington, MA (US); Susan Richards, Sudbury, MA (US); Melanie Ruzek, Acton, MA (US); Richard Garman, Natick, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 16/828,407

(22) Filed: Mar. 24, 2020

(65) Prior Publication Data

US 2020/0360385 A1 Nov. 19, 2020

Related U.S. Application Data

(63) Continuation of application No. 14/116,486, filed as application No. PCT/US2012/036405 on May 3, 2012, now abandoned.

(60) Provisional application No. 61/486,697, filed on May 16, 2011.

(51) Int. Cl.
*A61K 31/519* (2006.01)
*A61K 39/00* (2006.01)
*A61K 45/06* (2006.01)
*A61K 39/395* (2006.01)

(52) U.S. Cl.
CPC ........ *A61K 31/519* (2013.01); *A61K 39/0008* (2013.01); *A61K 39/39558* (2013.01); *A61K 45/06* (2013.01)

(58) Field of Classification Search
CPC combination set(s) only.
See application file for complete search history.

(56) References Cited

U.S. PATENT DOCUMENTS

| | | | |
|---|---|---|---|
| 4,080,325 | A | 3/1978 | Ellard |
| 4,558,690 | A | 12/1985 | Joyce |
| 5,028,697 | A | 7/1991 | Johnson et al. |
| 5,108,987 | A | 4/1992 | Faulk |
| 5,578,571 | A | 11/1996 | Zepperzauer et al. |
| 6,015,557 | A | 1/2000 | Tobinick et al. |

(Continued)

FOREIGN PATENT DOCUMENTS

| | | |
|---|---|---|
| AU | 2009/313053 A1 | 5/2010 |
| CN | 101910201 A | 12/2010 |

(Continued)

OTHER PUBLICATIONS

Munroe (Immune tolerance induction to enzyme-replacement therapy by co-administration of short-term, low-dose methotrexate in a murine Pompe disease model, Clinical and Experimental Immunology, Clinical and Experimental Immunology, 152: 138-146, 2008).*

(Continued)

*Primary Examiner* — Kathrien A Hartsfield
(74) *Attorney, Agent, or Firm* — Morrison & Foerster LLP

(57) ABSTRACT

The invention provides methods for reducing undesired immune responses, such as anti-drug antibody (ADA) responses and other T- and/or B-cell-mediated immune responses, in patients by using treatment with methotrexate.

6 Claims, 101 Drawing Sheets

(56) References Cited

U.S. PATENT DOCUMENTS

| | | | |
|---|---|---|---|
| 2006/0111316 | A1 | 5/2006 | Lawless |
| 2009/0155207 | A1 | 6/2009 | Hariri et al. |
| 2009/0196879 | A1 | 8/2009 | Melia et al. |
| 2010/0135992 | A1 | 6/2010 | Rother et al. |
| 2010/0135995 | A1 | 6/2010 | Madsen et al. |

FOREIGN PATENT DOCUMENTS

| | | |
|---|---|---|
| JP | 6174572 B2 | 8/2017 |
| TW | 2005/33363 A | 10/2005 |
| WO | WO-2010/041149 A2 | 4/2010 |
| WO | WO-2010/041149 A3 | 4/2010 |
| WO | WO-2012/158362 A1 | 11/2012 |

OTHER PUBLICATIONS

DiLillo (B10 cells and regulatory B cells balance immune responses during inflammation, autoimmunity, and cancer, Annal of the New York Academy of Sciences, 1183 (2010) 38-57).*

Amalfitano, A. et al. (2001). "Recombinant human acid α-glucosidase enzyme therapy for infantile glycogen storage disease type II: results of a phase I/II clinical trial," *Genet. Med.* 3(2):132-138.

Anderson, P.J., (Apr. 2005), "Tumor necrosis factor inhibitors: clinical implications of their different immunogenicity profiles," *Seminars in Arthritis Rheumatism*, 34(Suppl. 1):19-22.

Baert, F. et al. (2003). "Influence of immunogenicity on the long-term efficacy of infliximab in Crohn's disease," *N. Engl. J. Med.* 348(7):601-608.

Bartelds, G.M. et al. (2007). "Clinical response to adalimumab: relationship to anti-adalimumab antibodies and serum adalimumab concentrations in rheumatoid arthritis," *Ann. Rheum. Dis.* 66(7):921-926.

Bendtzen, K. et al. (2006). "Individualized monitoring of drug bioavailability and immunogenicity in rheumatoid arthritis patients treated with the tumor necrosis factor α inhibitor infliximab," *Arthritis Rheum.* 54(12):3782-3789.

Bennett, C.L. et al. (2005). "Long-term outcome of individuals with pure red cell aplasia and antierythropoietin antibodies in patients treated with recombinant epoetin: a follow-up report from the Research on Adverse Drug Events and Reports (RADAR) Project," *Blood* 106(10):3343-3347.

Boothpur, R. et al. (2009). "Serum sickness after treatment with rabbit antithymocyte globulin in kidney transplant recipients with previous rabbit exposure," *Am. J. Kidney Dis.* 55(1):141-143.

Buchler, M. et al. (2003). "Induction therapy by anti-thymocyte globulin (rabbit) in renal transplantation: a 1-yr follow-up of safety and efficacy," *Clin. Transplant* 17(6):539-545.

Busani, S. et al. (2006). "Thymoglobulin-induced severe cardiovascular reaction and acute renal failure in a patient scheduled for orthotopic liver transplantation," *Minerva Anestesiol.* 72(4):243-248.

Carter, N.A. et al. (2011). "Mice lacking endogenous IL-10-producing regulatory B cells develop exacerbated disease and present with an increased frequency of Th1/Th17 but a decrease in regulatory T cells," *J. Immunol.* 186:5569-5579.

Chung, D.T. et al., (2007), "Anti-thymocyte globulin (ATG) prevents autoimmune encephalomyelitis by expanding myelin antigen-specific Foxp3+ regulatory T cells", International Immunology, 19(8):1003-1010.

Cobbold, S.P. et al. (1990), "Reprogramming the immune system for tolerance with monoclonal antibodies," *Semin. Immunol.* 2(6):377-387.

Coles, A.J. et al. (2008), "Alemtuzumab vs. interferon beta-1a in early multiple sclerosis," *N. Engl. J. Med.* 359(17):1786-1801.

Coles, A.J. et al. (1999), "Monoclonal antibody treatment exposes three mechanisms underlying the clinical course of multiple sclerosis," *Ann. Neurol.* 46:296-304.

Currier (1993). "Low Dose Oral Methotrexate Treatment of Multiple Sclerosis: A Pilot Study," *J. Neurology, Neurosurgery, and Psychiatry* pp. 1217-1218.

Dickson, P. et al. (2008). "Immune tolerance improves the efficacy of enzyme replacement therapy in canine mucopolysaccharidosis I," *J. Clin. Invest.* 118(8):2868-2876.

Dobrzanski, M.J. et al., (Aug. 2008). "Ag-specific type 1 CD8 effector cells enhance methotrexate-mediated antitumor responses by modulating differentiated T cell localization, activation and chemokine production in established breast cancer," *Clin. Immunol.* 128(2):205-218.

Ewenstein, B.M. et al. (1997). "Nephrotic syndrome as a complication of immune tolerance in hemophilia B," *Blood* 89(3):1115-1116.

Garman, R.D. et al. (2004). "Methotrexate reduces antibody responses to recombinant human α-galactosidase A therapy in a mouse model of Fabry disease," *Clin. Exp. Immunol.* 137(3):496-502.

Gilliland, L.K. et al. (1999). "Elimination of the immunogenicity of therapeutic antibodies," *J. Immunol.* 162(6):3663-3671.

Goodeve, A. (2003). "The incidence of inhibitor development according to specific mutations-and treatment?," *Blood Coagul Fibrinolysis* 14(Suppl 1):S17-S21.

Hunley, T.E. et al. (2004). "Nephrotic syndrome complicating α-glucosidase replacement therapy for Pompe disease," *Pediatrics* 114(4):e532-e535.

International Search Report dated Oct. 2, 2012, for PCT Application No. PCT/US2012/36405, filed on May 3, 2012, four pages.—(131 PCT).

Iravani, M. et al. (Jun. 2005), "Cyclosporin A and mini short-term methotrexate vs cyclosporin A as graft-versus-host disease prophylaxis in patients with beta thalassemia major undergoing allogeneic blood and marrow transplantation," *Bone Marrow Transplant* 35(11):1095-1099.

Iwata, Y. et al. (2011). "Characterization of a rare IL-10-competent B-cell subset in humans that parallels mouse regulatory B10 cells," *Blood* 117:530-541.

Jones (2010). "Improvement in Disability After Alemtuzumab Treatment of Multiple Sclerosis is Associated with Neuroprotective Autoimmunity," *Brain Advance Access* pp. 1-16.

Joseph, A. et al. (2008). "Immune tolerance induction to enzyme-replacement therapy by co-administration of short-term, low-dose methotrexate in a murine Pompe disease model," *Clin. Exp. Immunol.* 152(1):138-146.

Jolivet, J. et al., (Jan. 1985), "Prevention of Methotrexate Cytotoxicity by Asparaginase Inhibition of Methotrexate Polyglutamate Formation", Cancer Research, 45:217-220.

Kano, Y. et al., (Jan. 15, 1988), "Effects of vincristine in combination with methotrexate and other antitumor agents in human acute lymphoblastic leukemia cells in culture", Cancer Res., 48(2)351-356.

Kieseler, B.C., et al., (2010), "Chemotherapeutics in the treatment of multiple sclerosis", Therapeutic Advances in Neurological Disorders, 277-291.

Kishnani, P.S. et al. (2010). "Cross-reactive immunologic material status affects treatment outcomes in Pompe disease infants," *Mol. Genet. Metab.* 99(1):26-33.

Khouri, I.F., et al., (2004), "Graft-versus-host disease Low-dose alemtuzumab (Campath ) in myeloablative allogenic stem cell transplantation for CD52-positive malignancies: decreased incidence of acute graft-versus-host-disease with unique pharmacokinetics" Bone Marrow Transplantation, 33:833-837.

Kremer, J.M. (2004). "Toward a better understanding of methotrexate," *Arthritis Rheum.* 50(5):1370-1382.

Lacana, E. et al. (2012). "The role of immune tolerance induction in restoration of the efficacy of ERT in Pompe disease," *Am. J. Med. Genet. Part C Semin. Med. Genet.* 160C:30-39.

Leader, B. et al. (2008). "Protein therapeutics: a summary and pharmacological classification," *Nat. Rev. Drug. Discov.* 7(1):21-39.

Locatelli, F. et al. (2007). "Pure red-cell aplasia "epidemic"—mystery completely revealed?" *Perit. Dial. Int. Suppl.* 2:S303-S307.

(56) References Cited

OTHER PUBLICATIONS

Lundquist, A.L. et al. (2007). "Serum sickness following rabbit antithymocyte-globulin induction in a liver transplant recipient: case report and literature review," *Liver Transpl.* 13(5):647-650.

Maini, R.N. et al. (1998). "Therapeutic efficacy of multiple intravenous infusions of anti-tumor necrosis factor alpha monoclonal antibody combined with low-dose weekly methotrexate in rheumatoid arthritis," *Arthritis Rheum.* 41(9):1552-1563.

Mashkovsky M.D., (2001), "Lekarstvennye Sredstva (Drugs)," Moscow, vol. 1, 14th edition, p. 11.

Matsushita, T. et al. (2008). "Regulatory B cells inhibit EAE initiation in mice while other B cells promote disease progression," *J. Clin. Investigation* 118:3420-3430.

Mendelsohn, N.J. et al. (2009). "Elimination of antibodies to recombinant enzyme in Pompe's disease," *N. Engl. J. Med.* 360(2):194-195.

Messinger, Y.H. et al. (2012). "Successful immune tolerance induction to enzyme replacement therapy in CRIM-negative infantile Pompe disease," *Genetics in Medicine* 14:135-142.

Passweg, J.R., et al., (2010), "Aplastic Anemia: First-line Treatment by Immunosuppresion and Sibling Marrow Transplantation", American Society of Hematology, pp. 36-42.

Peng, A. et al. (2010). "Phosphatidylinositol containing lipidic particles reduces immunogenicity and catabolism of factor VIII in hemophilia a mice," *AAPS J.* 12(3):473-481.

Phillips, J.T. et al. (2006). "Infusion-related hypersensitivity reactions during natalizumab treatment," *Neurology* 67(9):1717-1718.

Podgorny, P.J., (2010) "High Rabbit-Antihuman Thymocyte Globulin Levels Are Associated with Low Likelihood of Graft-vs-Host Disease and High Likelihood of Posttransplant Lymphoproliferative Disorder", American Society for Blood and Marrow Transplantation, 16:915-926.

Rosenberg, M. et al. (1999). "Immunosurveillance of alglucerase enzyme therapy for Gaucher patients: induction of humoral tolerance in seroconverted patients after repeat administration," *Blood* 93(6):2081-2088.

Ruzek, M.C. et al. (2009). "In vivo characterization of rabbit anti-mouse thymocyte globulin: a surrogate for rabbit anti-human thymocyte globulin," *Transplantation* 88(2):170-179.

Ruznek, M.C. et al. (2008). "Characterization of in vitro antimurine thymocyte globulin-induced regulatory T cells that inhibit graft-versus-host disease in vivo," *Blood* 111(3):1726-1734.

Sagoo, P. et al. (2010). "Development of a cross-platform biomarker signature to detect renal transplant tolerance in humans," *J. Clin. Investigation* 120(6):1848-1861.

Sakuma, Y. et al., (2002), "Short-Course Methotrexate and Long-Term Acceptance of Fully Allogeneic Rat Cardiac grafts: a Possible Mechanism of Tolerance", Transplant Immunology 10:49-54.

Schellekens, H. (2002). "Bioequivalence and the immunogenicity of biopharmaceuticals," *Nat. Rev. Drug. Discov.* 1(6):457-462.

Schellekens, H. (2002). "Immunogenicity of therapeutic proteins: clinical implications and future prospects," *Clin. Ther.* 24(11):1720-1740.

Schmidt, E. et al. (2009). "Immunogenicity of rituximab in patients with severe pemphigus," *Clin. Immunol.* 132(3):334-341.

Segundo, C. et al. (2001). "Thyroid-infiltrating B lymphocytes in Graves' disease are related to marginal zone and memory B cell compartments," *Thyroid* 11(6):525-530.

Seland (1974). "Evaluation of Antithymocyte Globulin in Acute Relapses of Multiple Sclerosis," *Neurology*, vol. 24, No. 134, Abstract Only.

Slavikova, V. et al. (1978). "Distribution and pharmacokinetics of methotrexate in localized chemotherapy of solid Gardner's lymphosarcoma," *Neoplasma* 25(2):211-216.

Somerfield, J. et al. (2010). "A novel strategy to reduce the immunogenicity of biological therapies," *J. Immunol.* 185(1):763-768.

Sun, B. et al. (2009). "Immunomodulatory gene therapy prevents antibody formation and lethal hypersensitivity reactions in murine pompe disease," *Mol. Ther.* 18(2):353-360.

Sun, B. et al. (2007). "Enhanced response to enzyme replacement therapy in Pompe disease after the induction of immune tolerance," *Am. J. Human Genet.* 81(5):1042-1049.

Tahir, H. et al. (2005). "Humanized anti-CD20 monoclonal antibody in the treatment of severe resistant systemic lupus erythematosus in a patient with antibodies against rituximab," *Rheumatology* 44(4):561-562.

Tanriover, B. et al. (2005). "Polyclonal antibody-induced serum sickness in renal transplant recipients: treatment with therapeutic plasma exchange," *Transplantation* 80(2):279-281.

Taylor, P.C. (Oct. 2001). "Anti-TNF therapy for rheumatoid arthritis and other inflammatory diseases," *Mol. Biotechnol.* 19(2):153-168.

Thorland, E.C. et al. (1999). "Anaphylactic response to factor IX replacement therapy in haemophilia B patients: complete gene deletions confer the highest risk," *Haemophilia* 5(2):101-105.

Vengerovsky A.I., (2003), "Farmakologicheskaya Nesovmestimost (Pharmacological Incompatibility)", Bulletin of Siberian Medicine, No. 3, pp. 49-56.

Walling, J. (2006). "From methotrexate to pemetrexed and beyond. A review of the pharmacodynamic and clinical properties of antifolates," *Invest. New Drugs* 24(1):37-77.

Weinblatt, M.E. et al. (1995). "CAMPATH-1H, a humanized monoclonal antibody, in refractory rheumatoid arthritis. An intravenous dose-escalation study," *Arthritis Rheum.* 38(11):1589-1594.

Winsor-Hines, D. et al. (2004). "Induction of immunological tolerance/hyporesponsiveness in baboons with a nondepleting CD4 antibody," *J. Immunol.* 173(7):4715-4723.

Written Opinion of the International Searching Authority dated Oct. 2, 2012, for PCT Application No. PCT/US2012/36405, filed on May 3, 2012, eight pages.—(131 PCT).

Xinqiang, S. et al. (2010). "Therapeutic efficacy of experimental rheumatoid arthritis with low-dose methotrexate by increasing partially CD4+CD25+ Treg cells and inducing Th1 to Th2 shift in both cells and cytokines," *Biomed. Pharmacother.* 64(7):463-471.

Yanaba, K. et al. (2009). "The development and function of regulatory B cells expressing IL-10 (B10 cells) requires antigen receptor diversity and TLR signals," *J. Immunol.* 182:7459-7472.

Ziegler, R.J. et al. (2008). "Ability of adeno-associated virus serotype 8-mediated hepatic expression of acid α-glucosidase to correct the biochemical and motor function deficits of presymptomatic and symptomatic Pompe mice," *Human Gene Ther.* 19(6):609-621.

Zinkernagel, R.M. (2000). "Localization dose and time of antigens determine immune reactivity," *Semin. Immunol.* 12(3):163-171.

\* cited by examiner

Anti-mATG Titers

Circulating mATG Levels

Spleen - T cells

Spleen - T cells

Figure 38A, cont'd
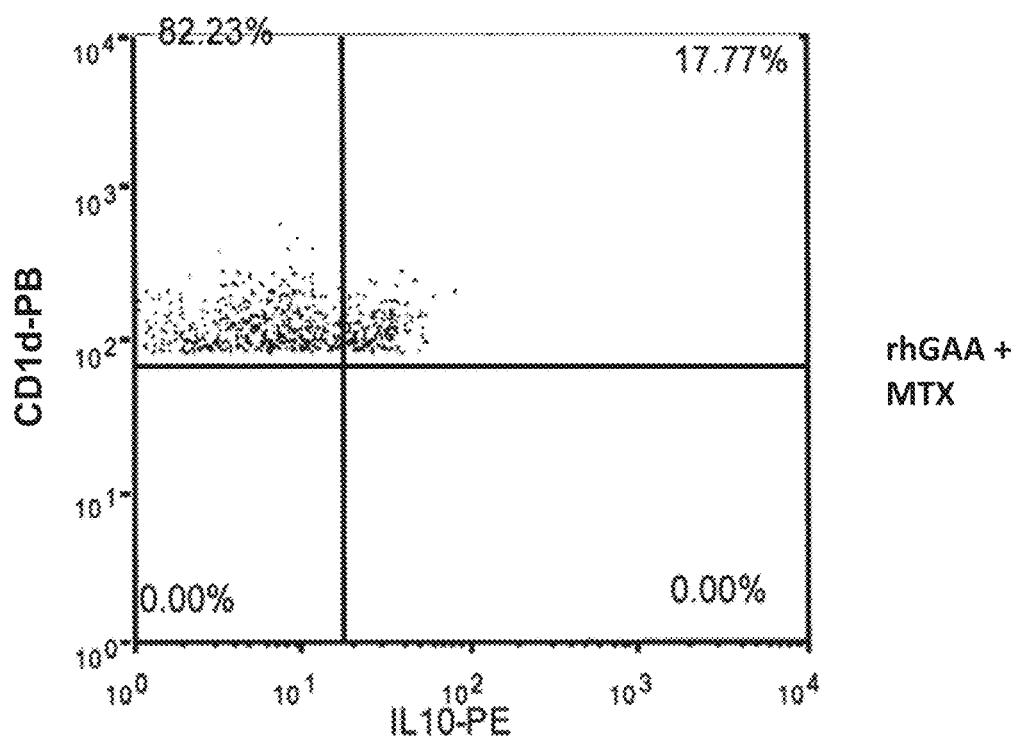
Figure 38B
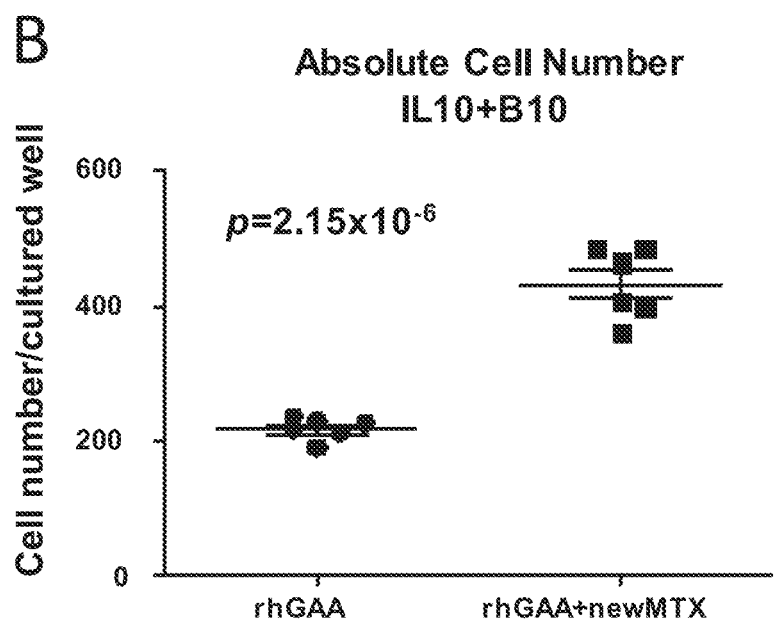

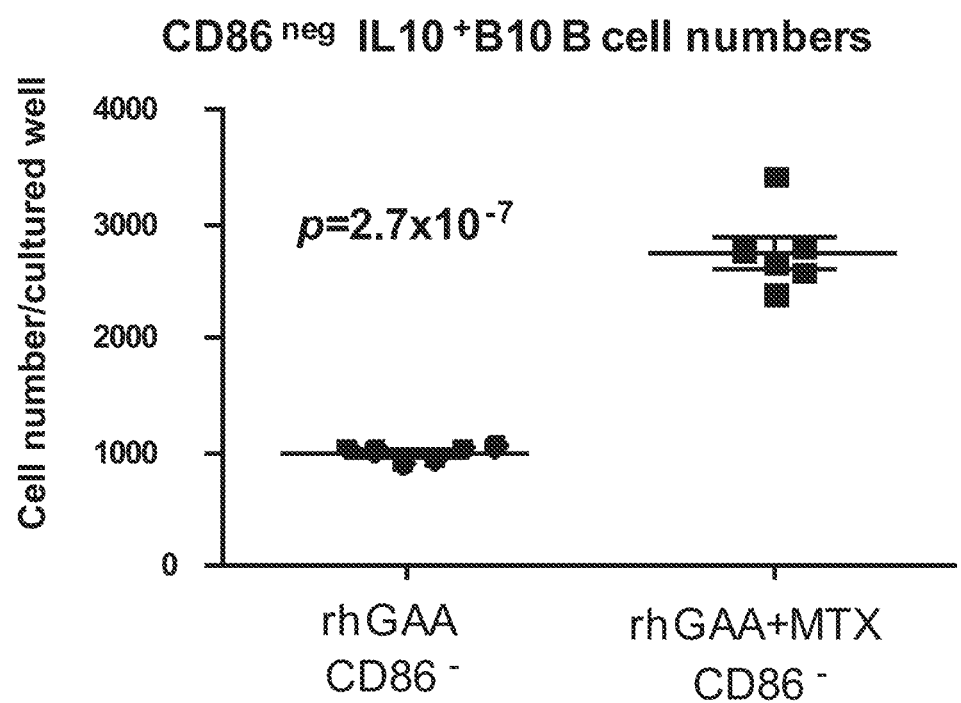
Figure 39B, cont'd

Figure 40A, cont'd
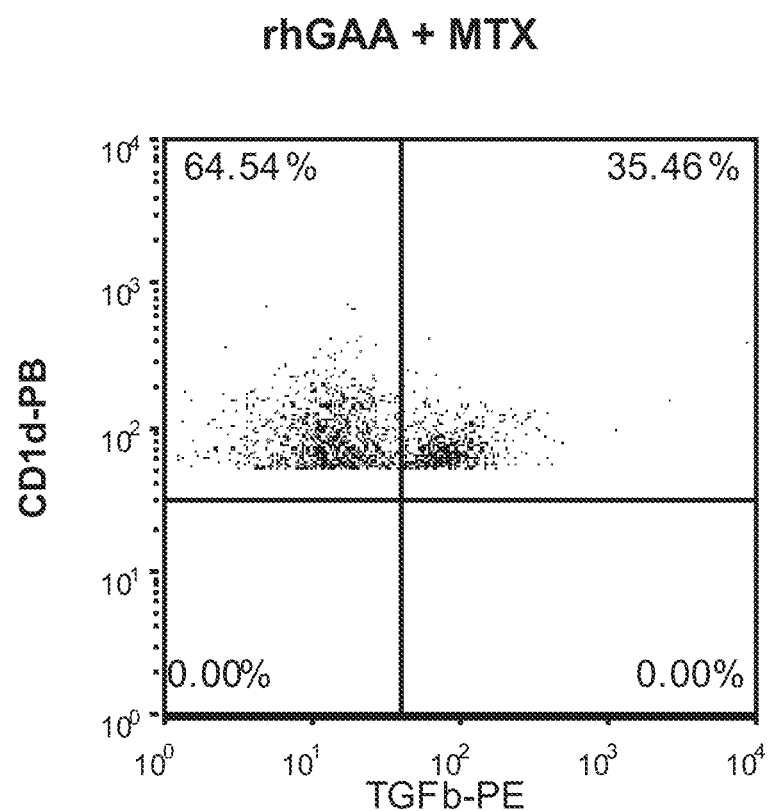

Figure 41A, cont'd
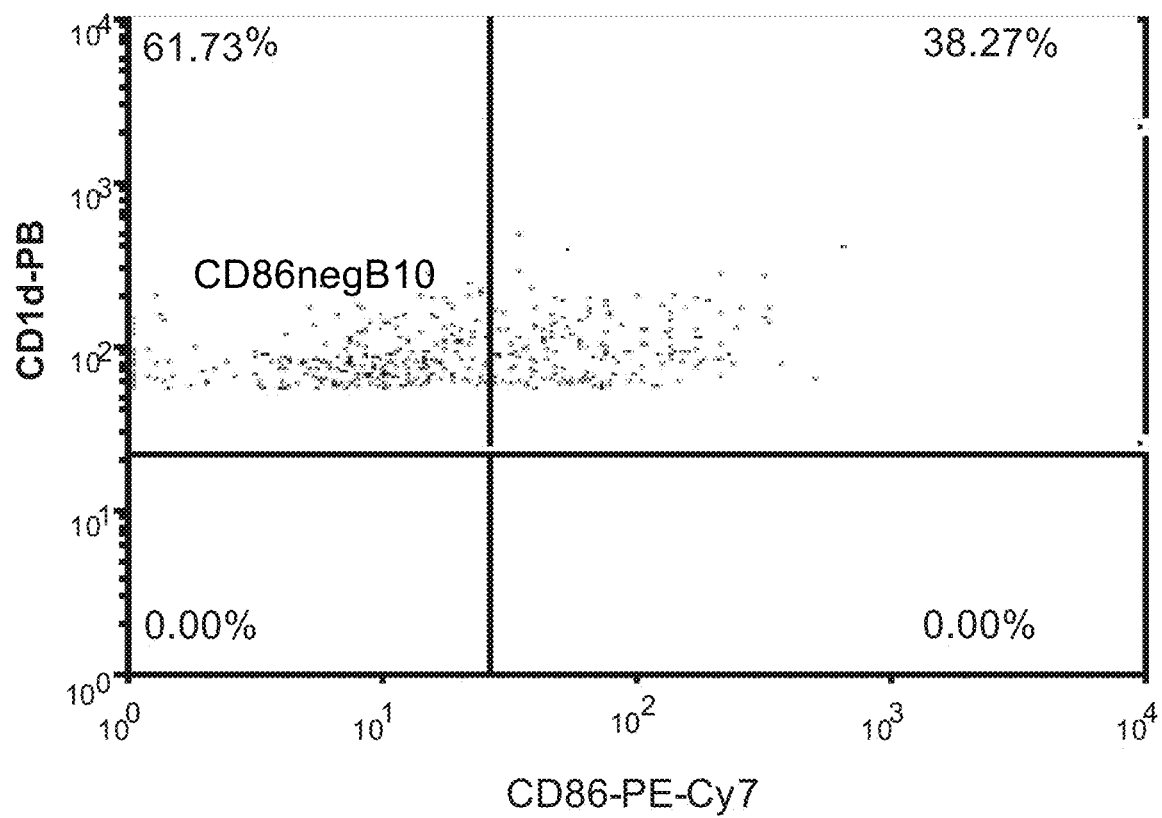

Figure 41B, cont'd
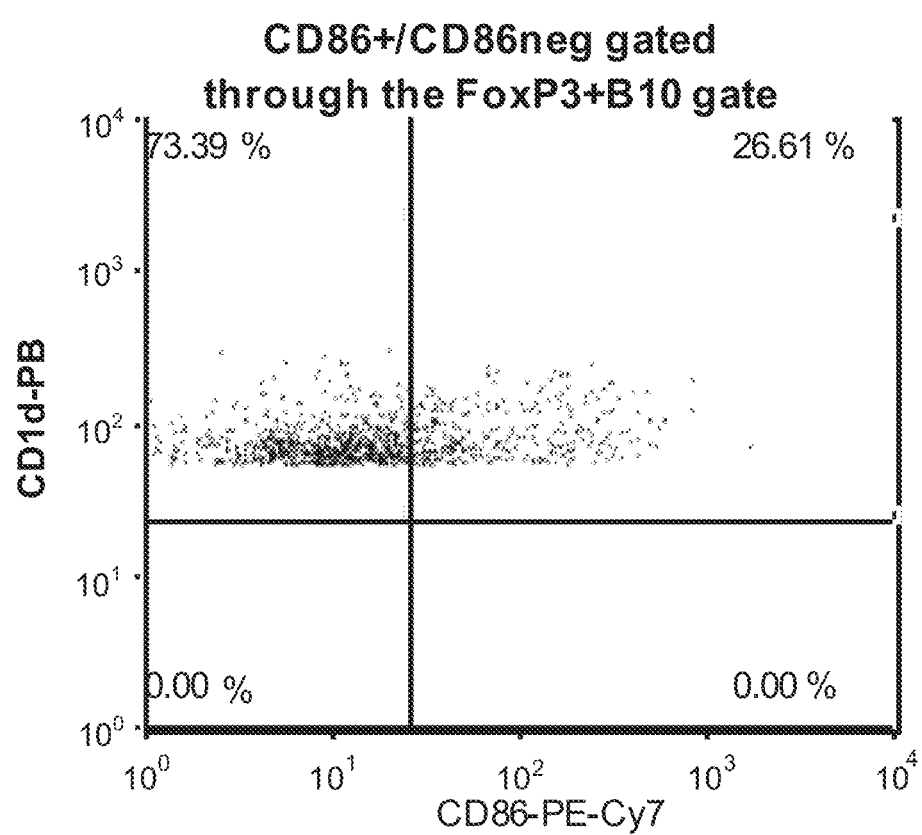

Figure 41C, cont'd
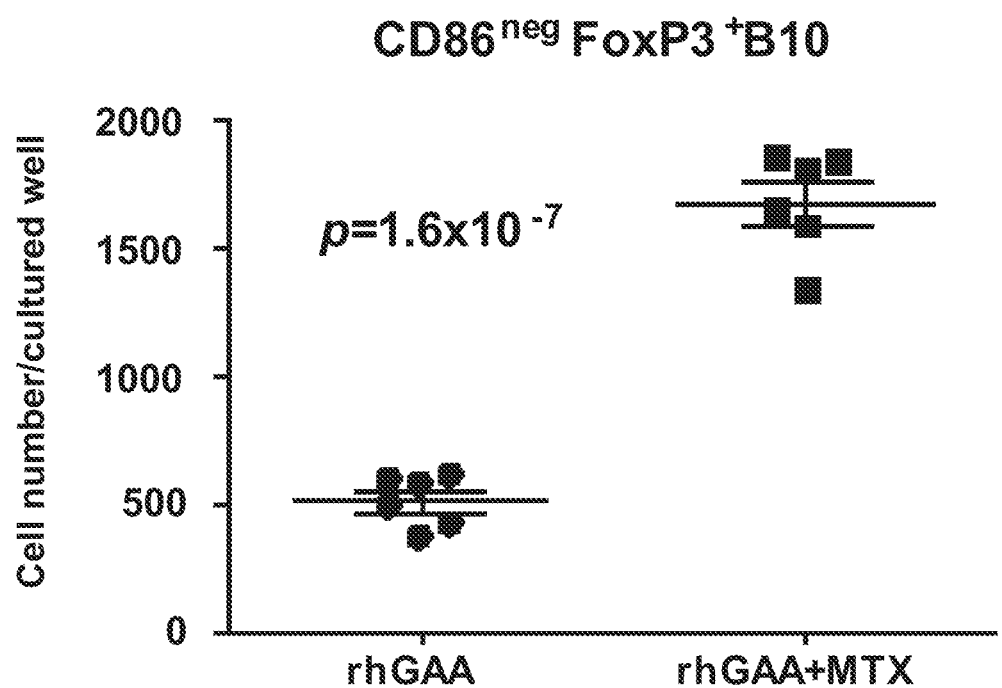

Figure 42A, cont'd
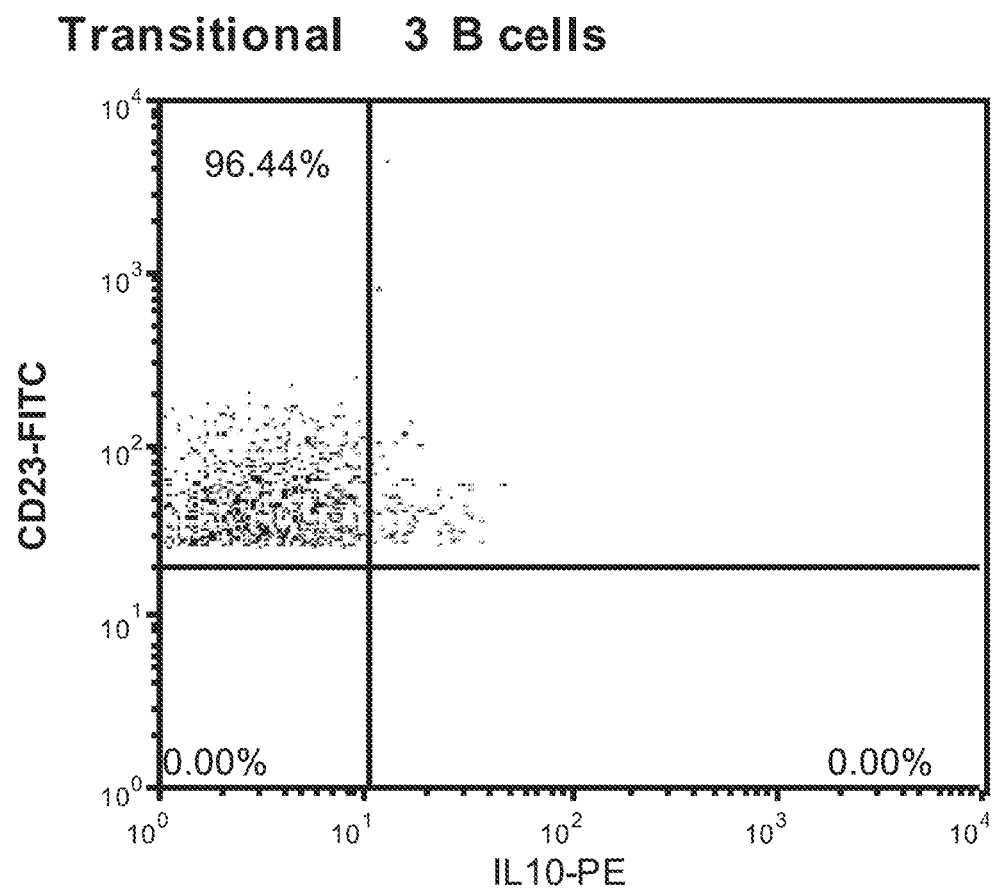

Figure 42B, cont'd
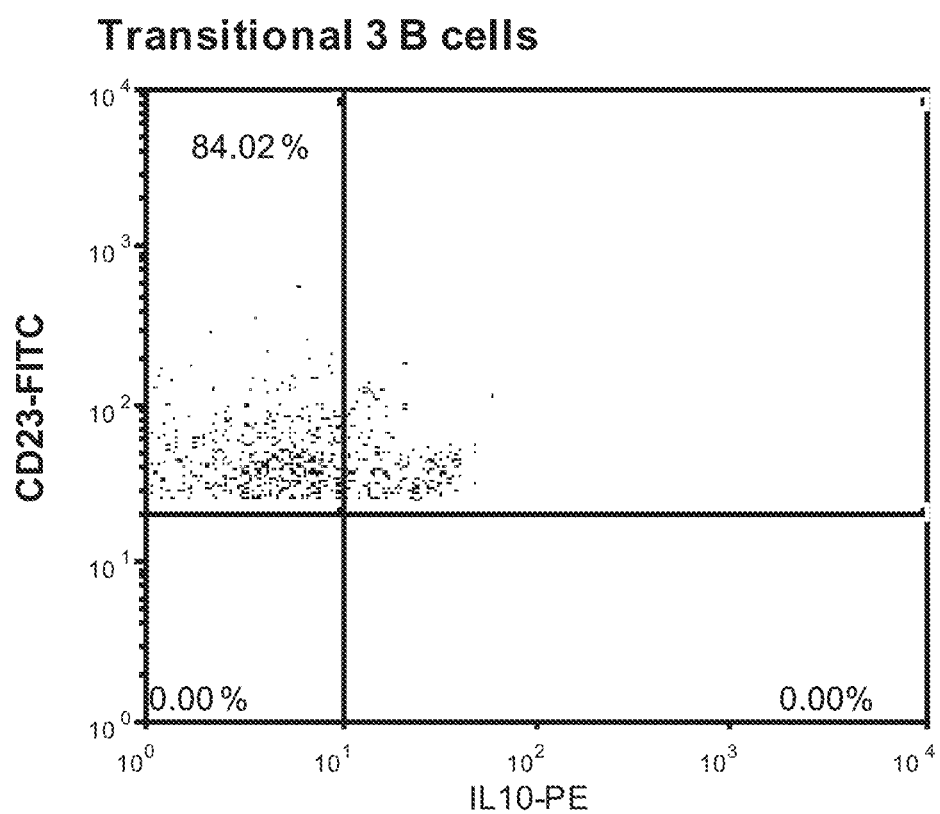

Figure 42C, cont'd
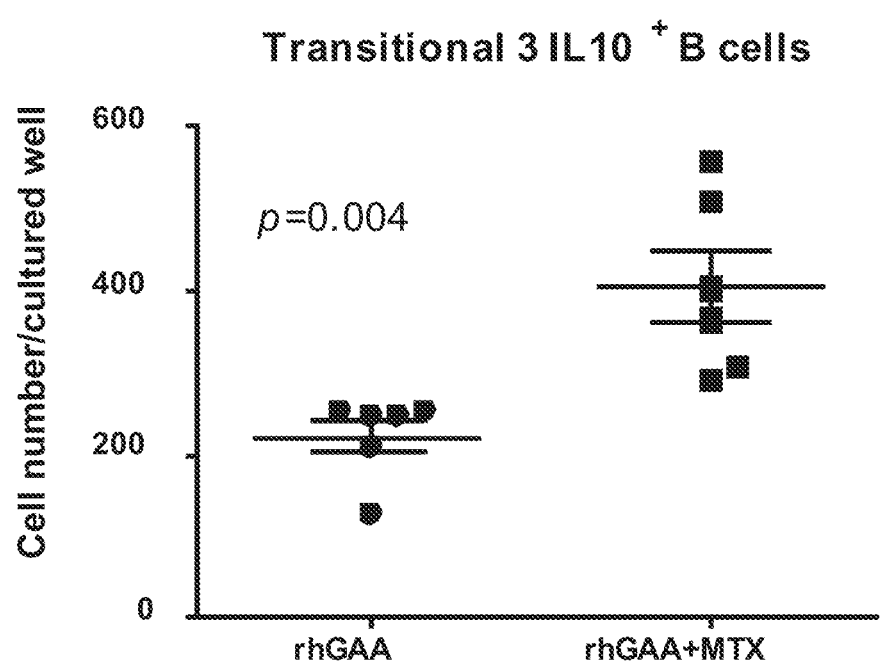

Figure 43A, cont'd
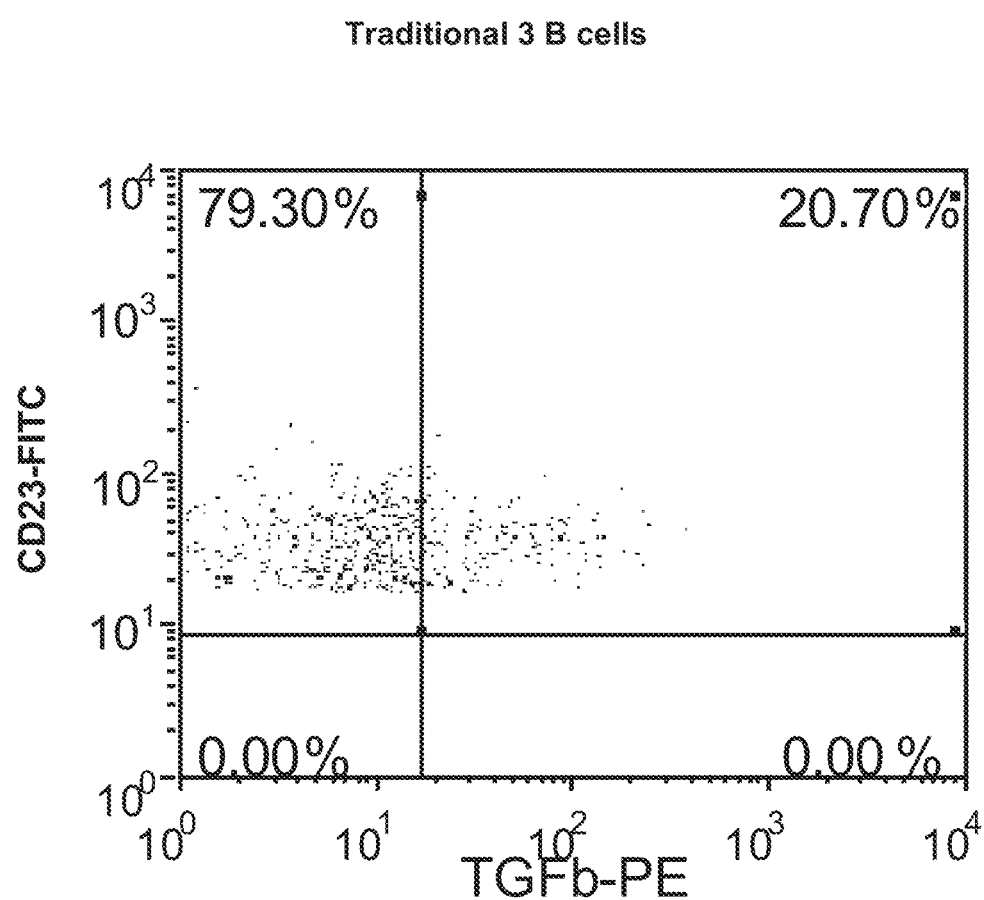

Figure 43B, cont'd
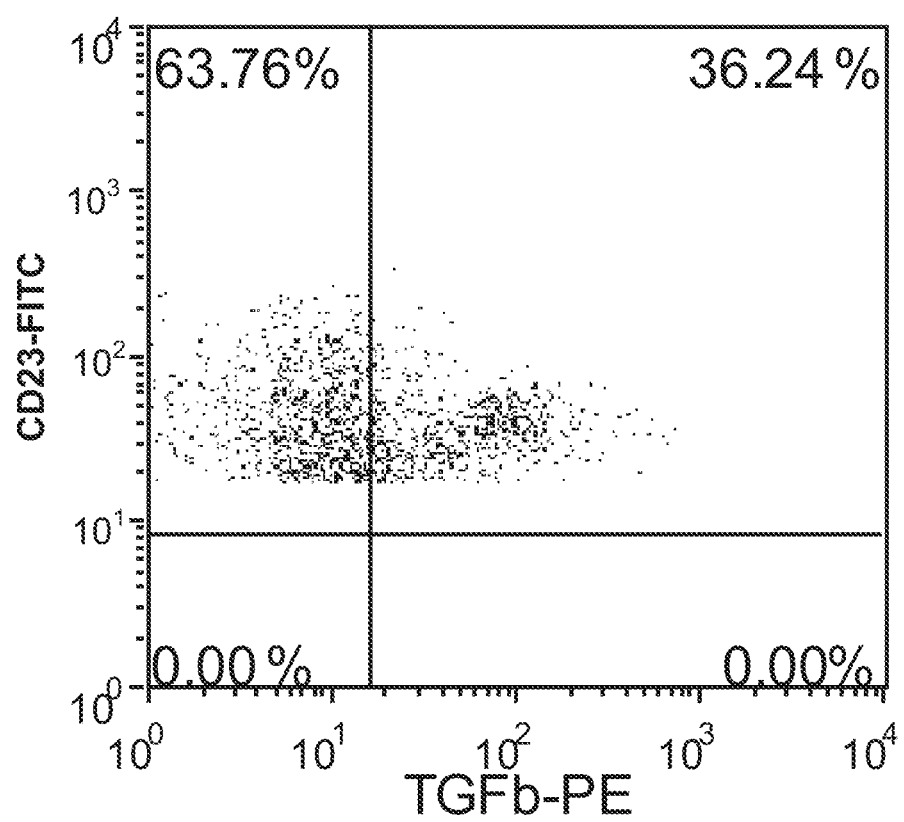

Figure 43C, cont'd
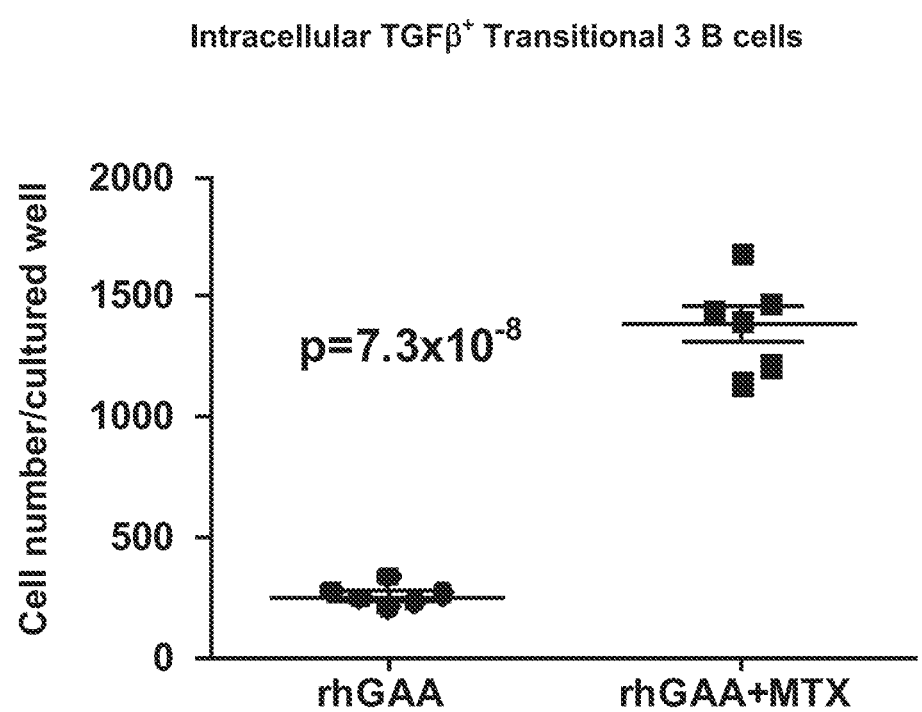

Follicular B cells

Transitional 2 B cells

Figure 44A, cont'd
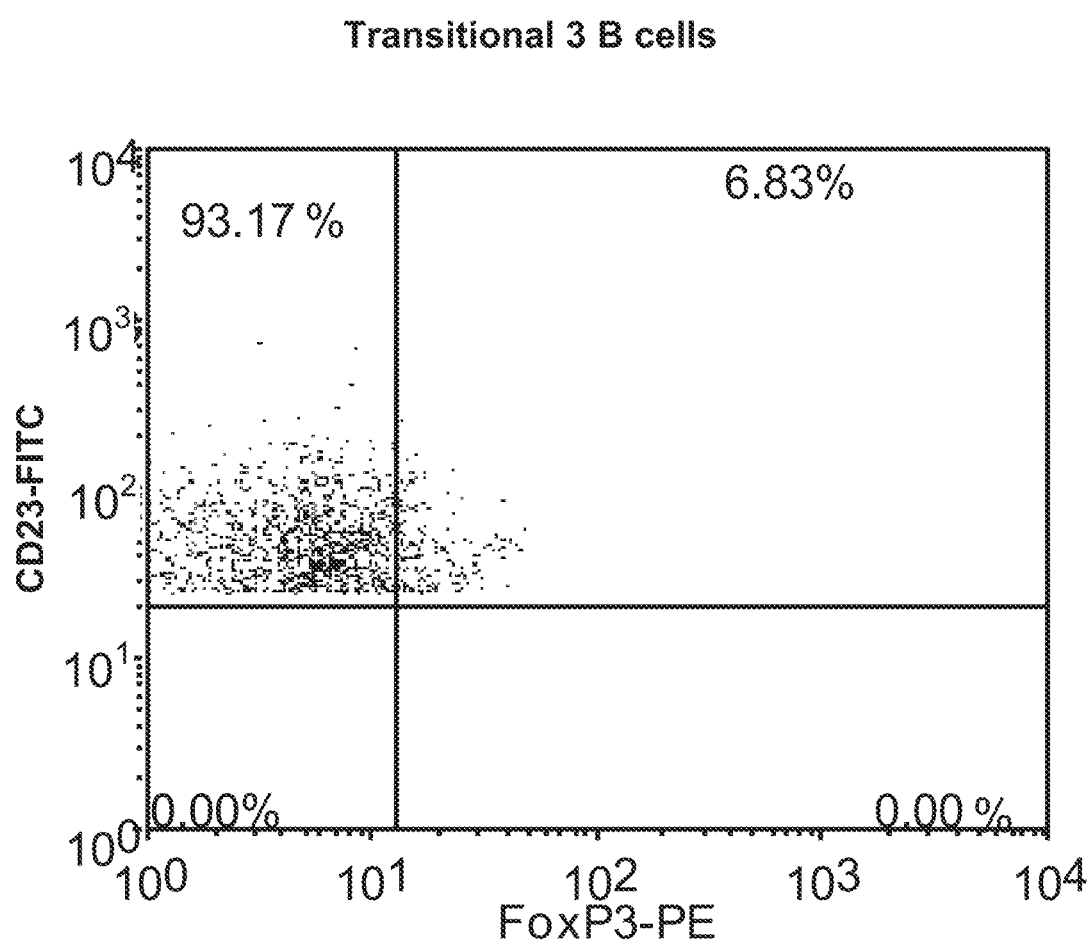

Figure 44B, cont'd
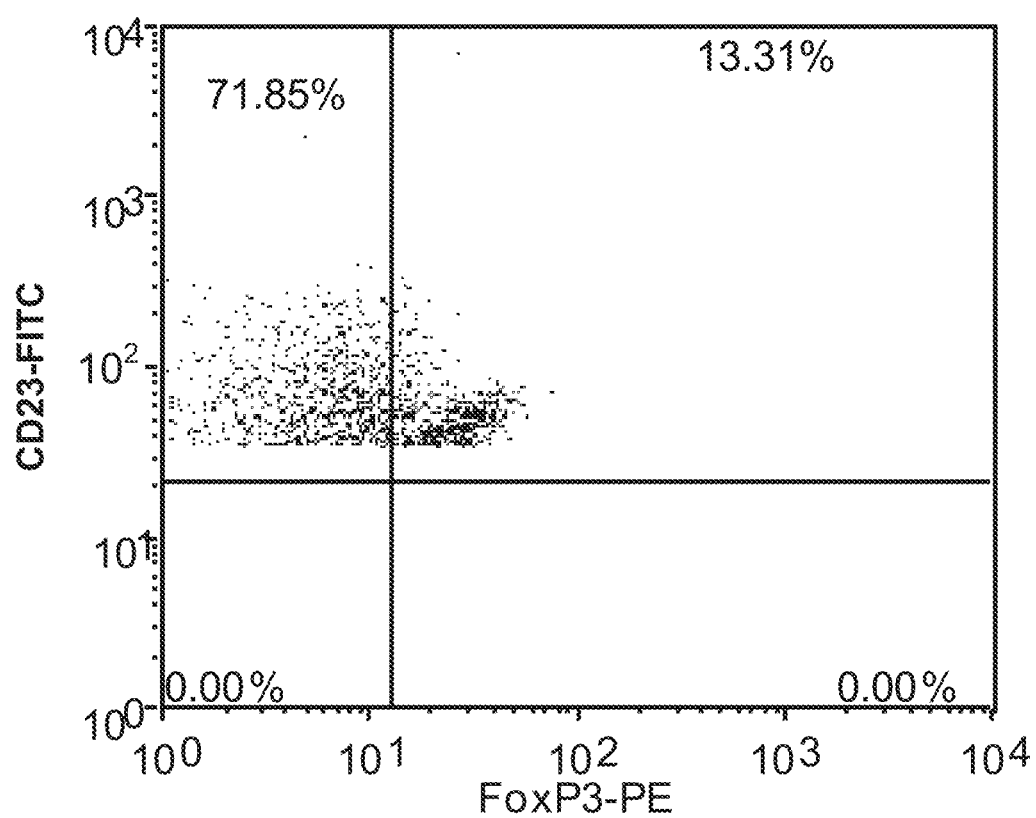

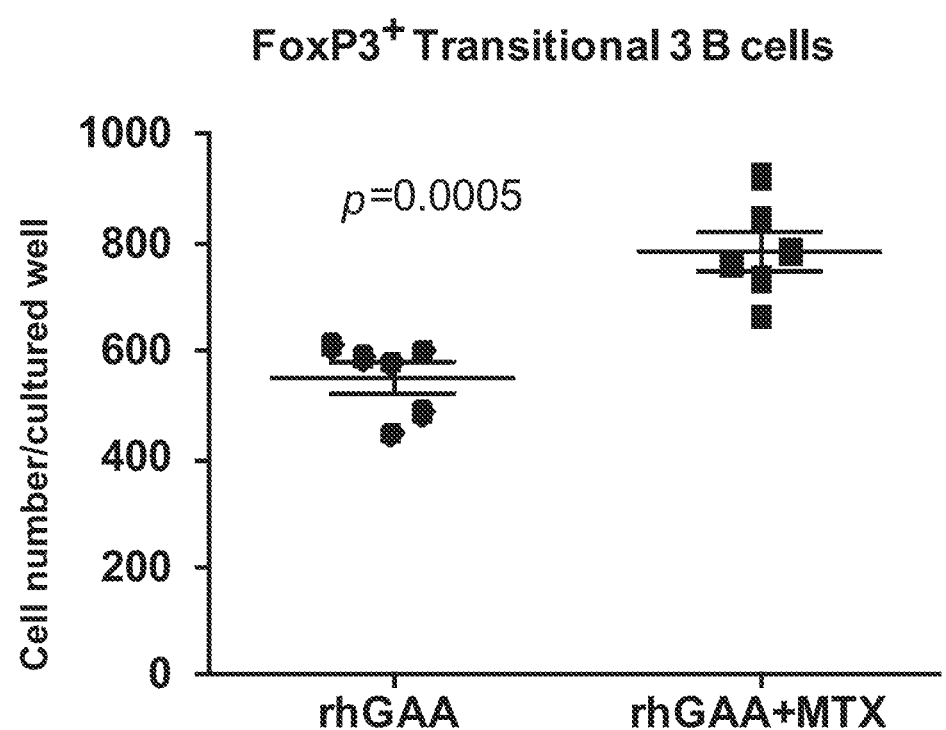
Figure 44C, cont'd

Figure 48B, cont'd
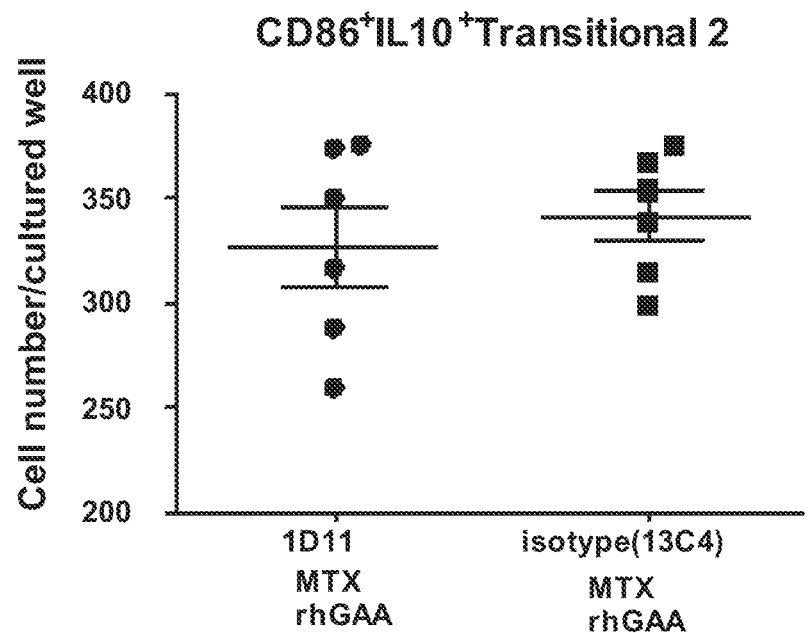
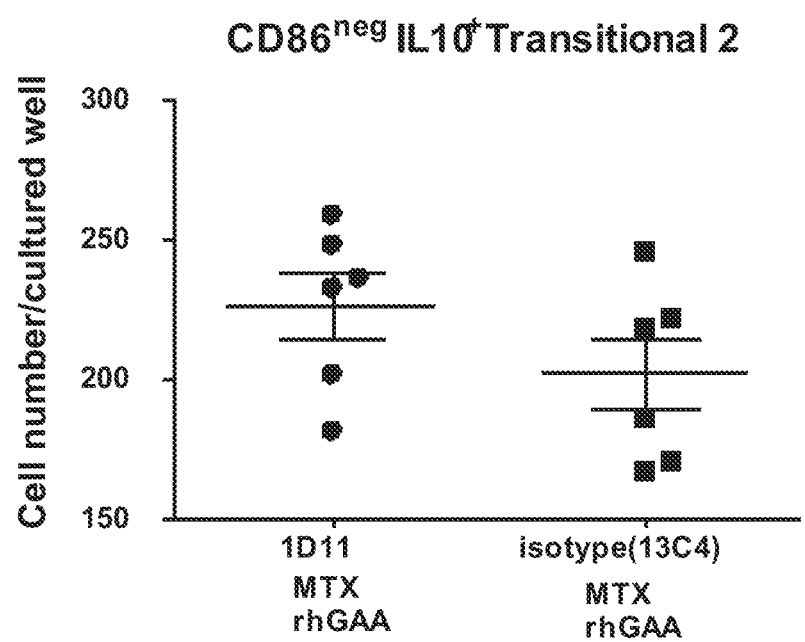

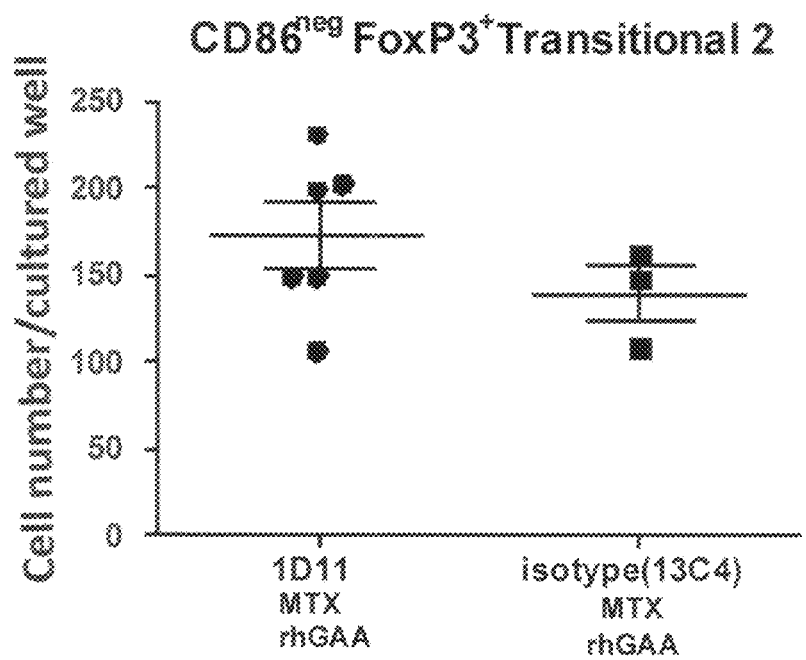
Figure 48C, cont'd

Figure 49A, cont'd
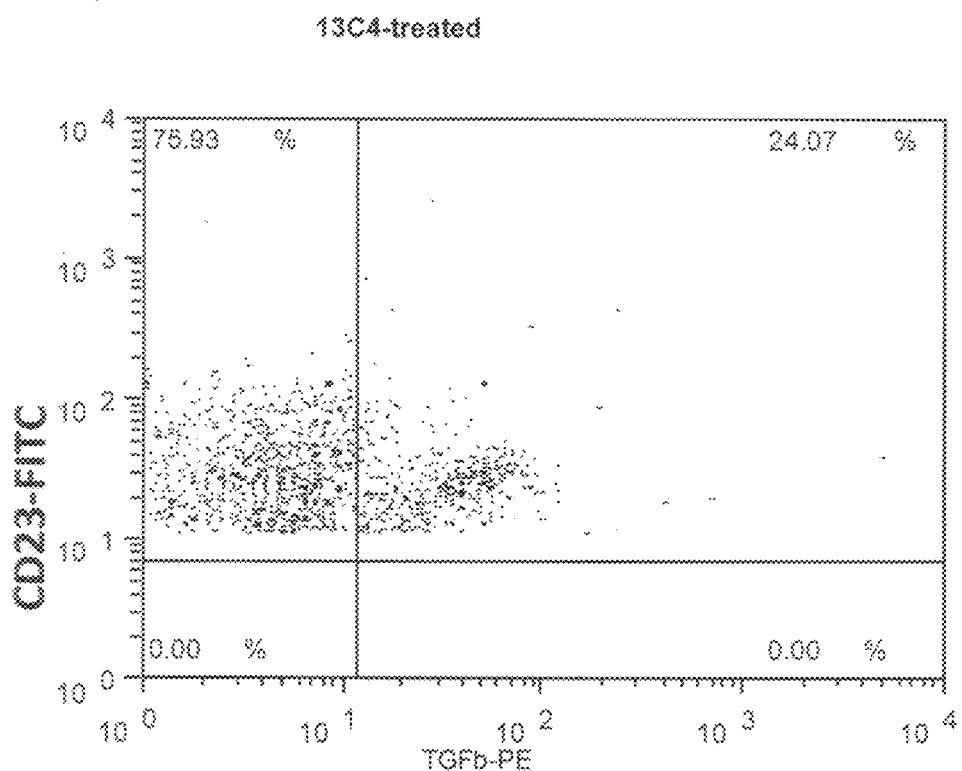
Figure 49B
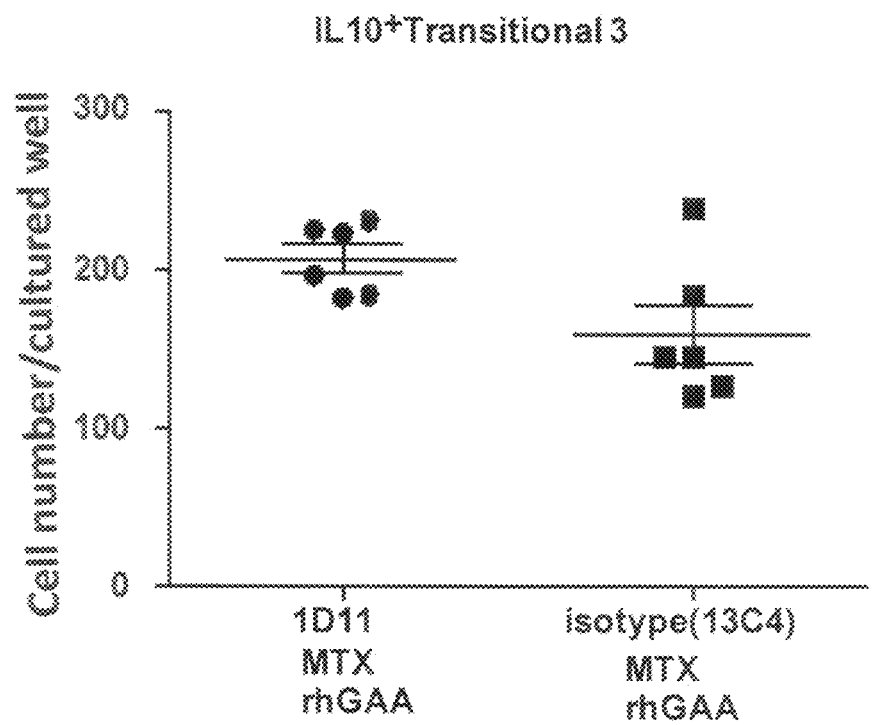

Figure 49B, cont'd
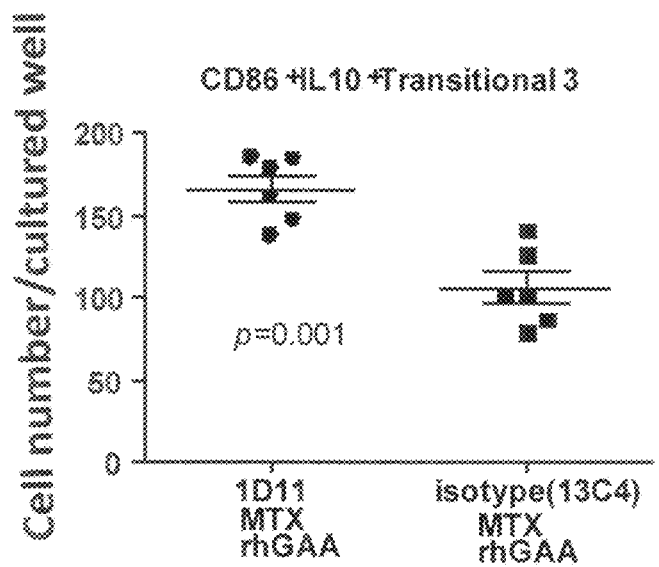
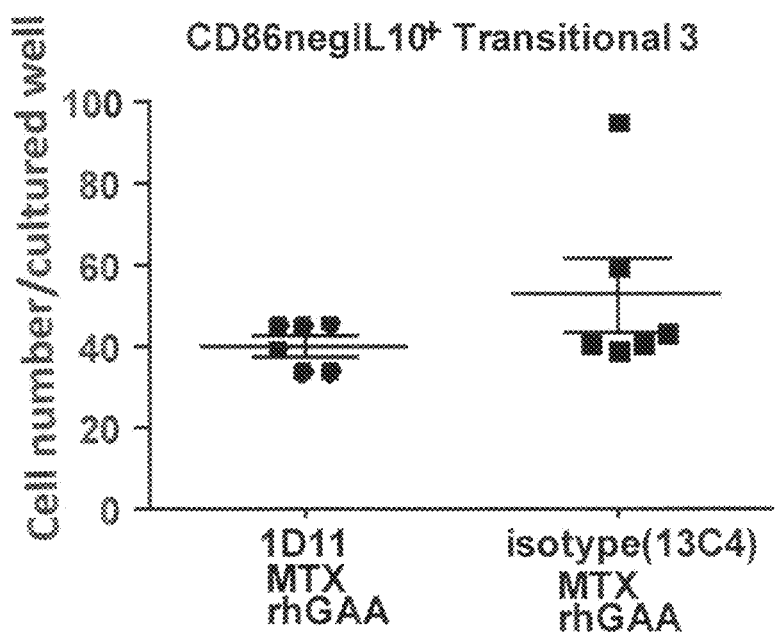

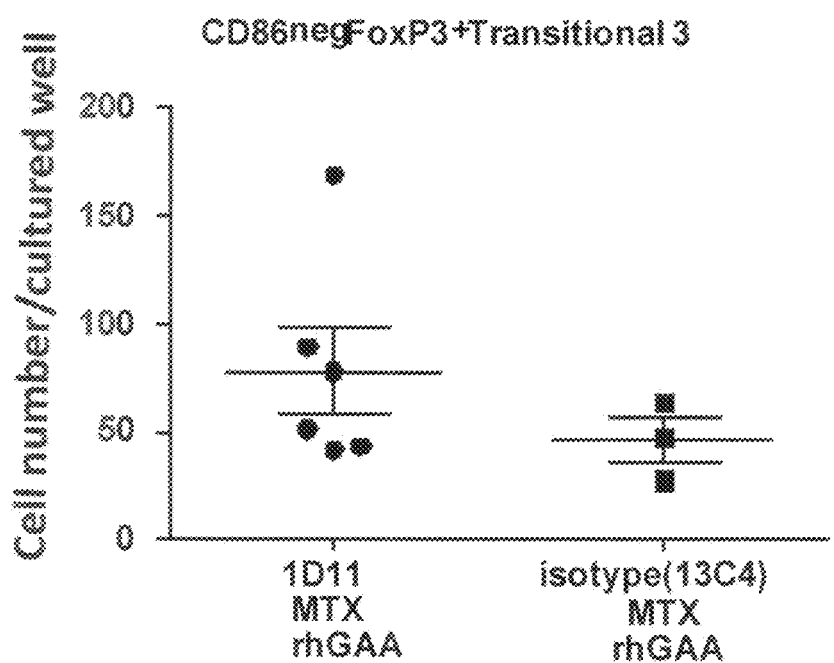
Figure 49C, cont'd

Figure 50A, cont'd
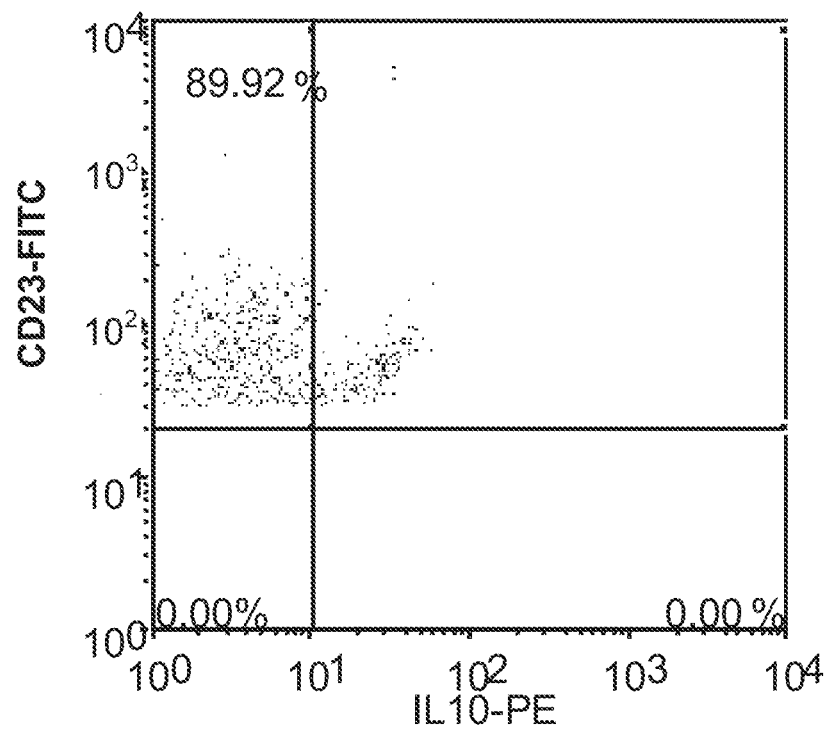
Figure 50B
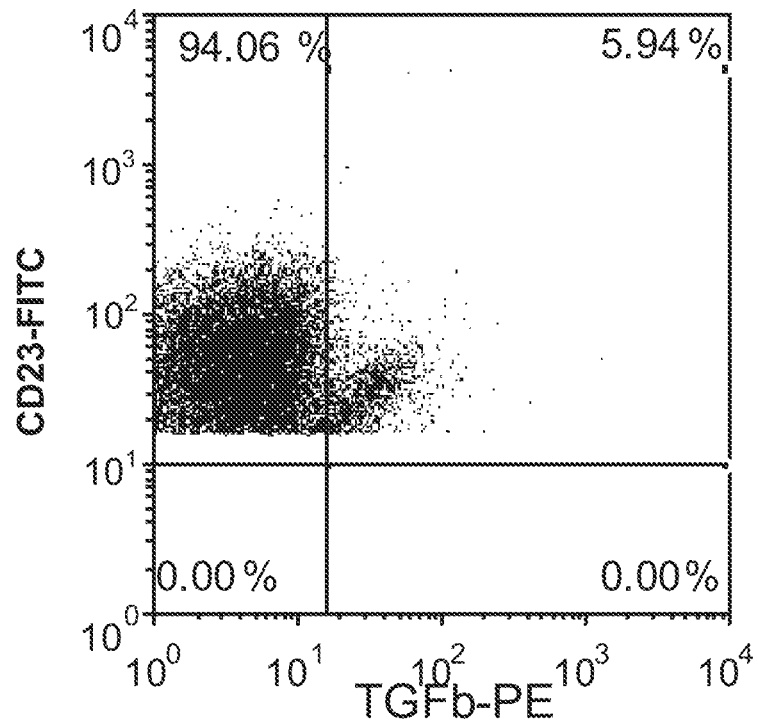

Figure 50B, cont'd
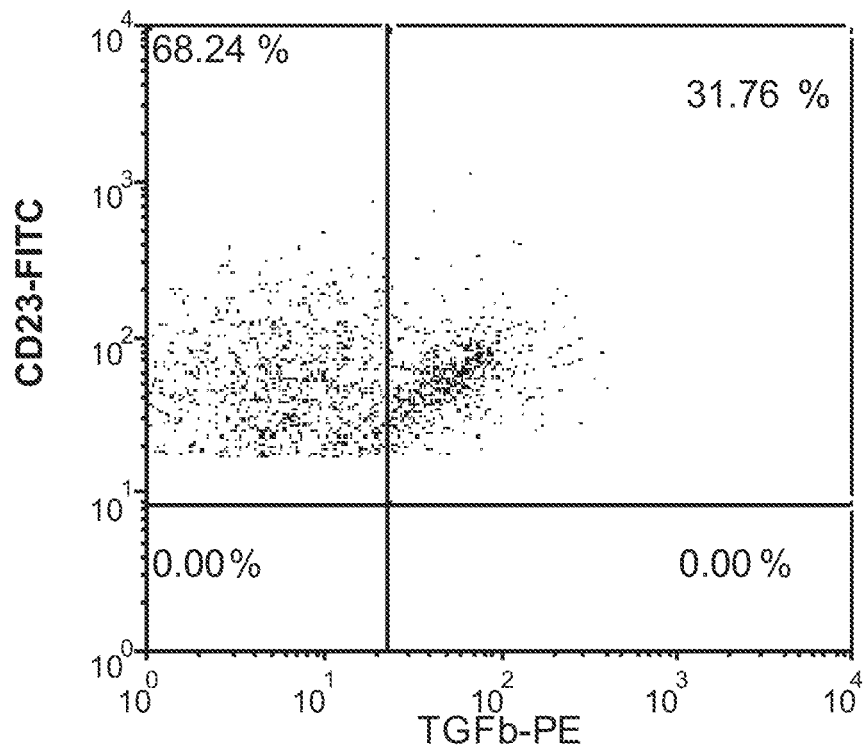
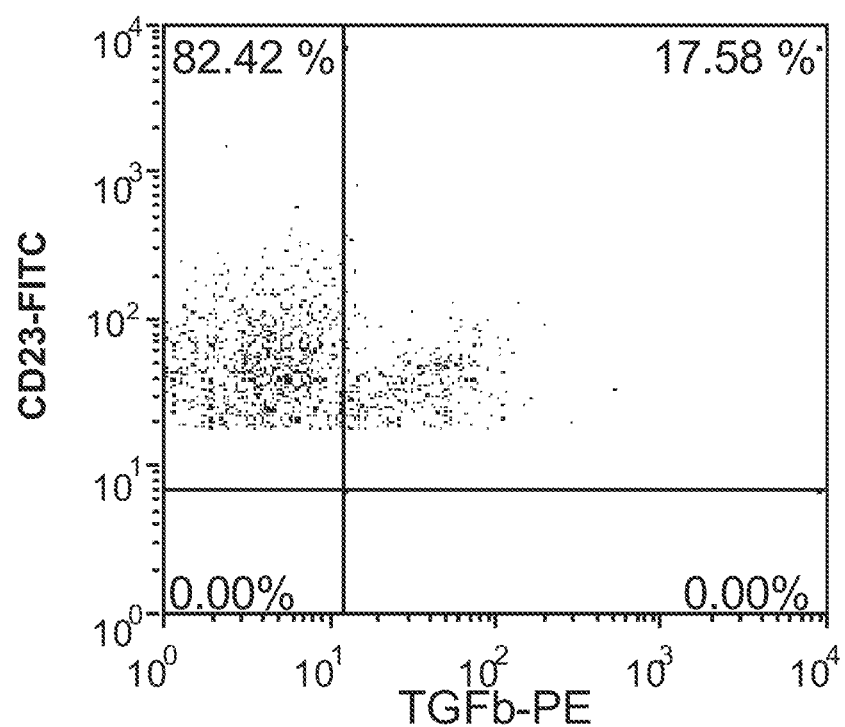

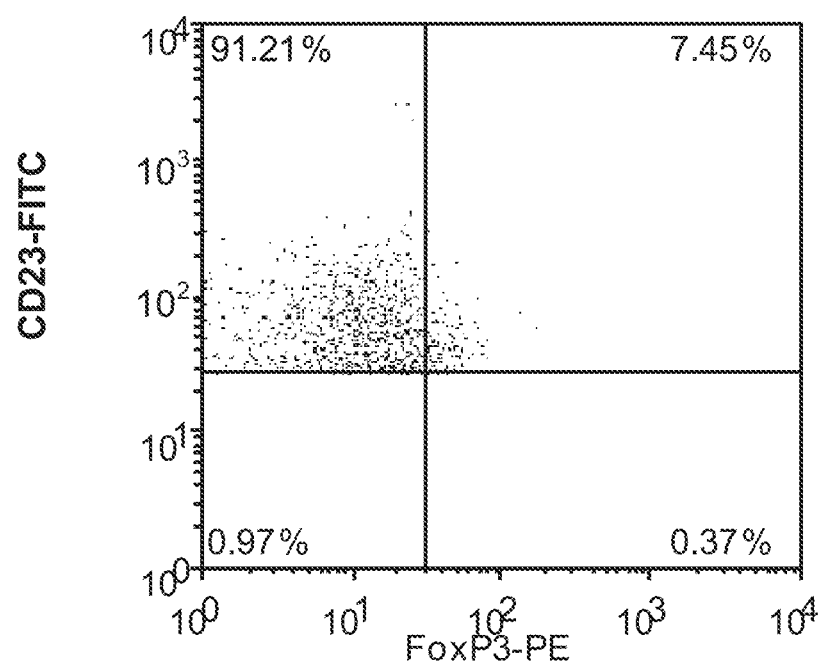
Figure 50C, cont'd

Figure 52, cont'd
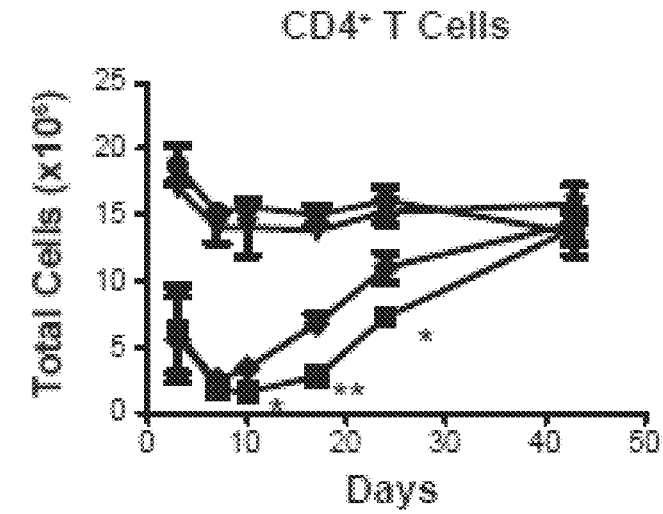
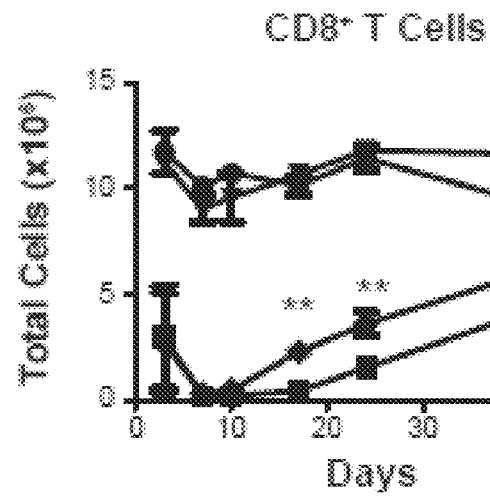
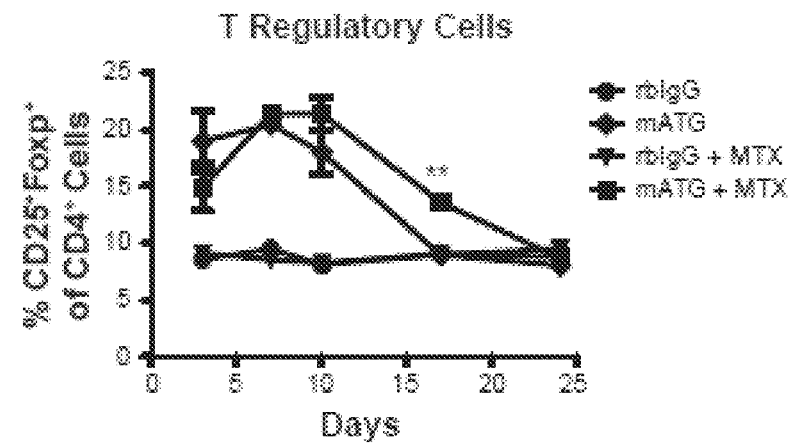

Figure 53, cont'd
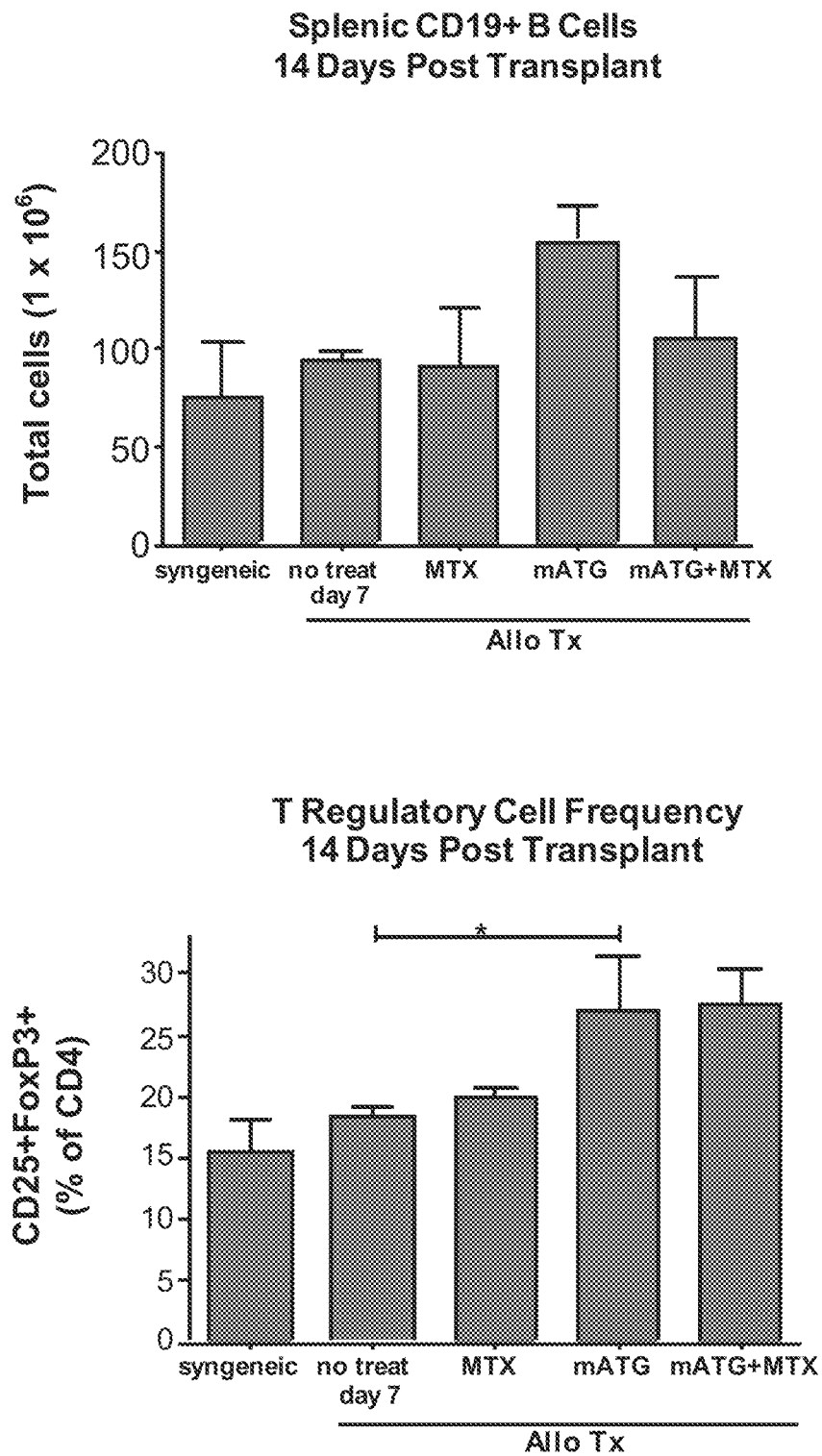

Figure 55, cont'd
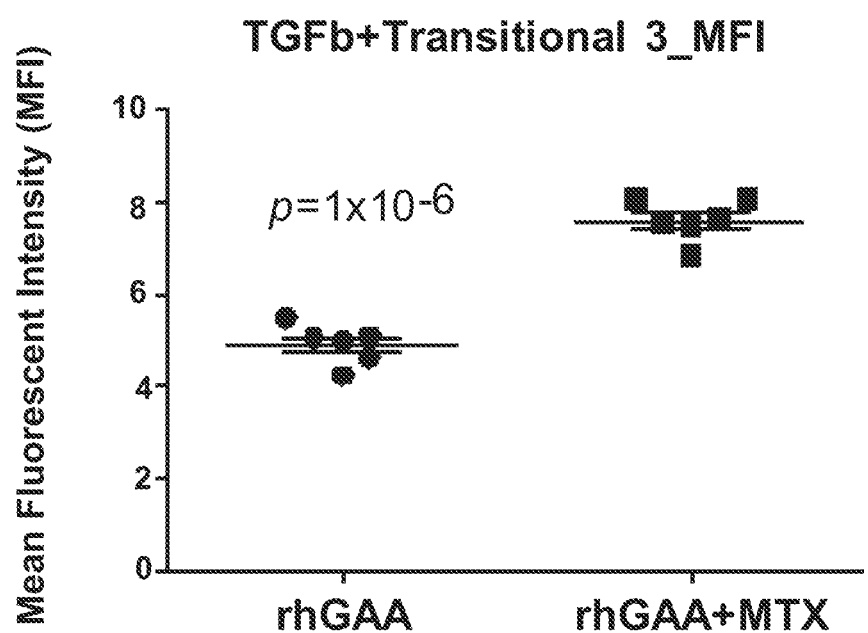

Figure 56, cont'd
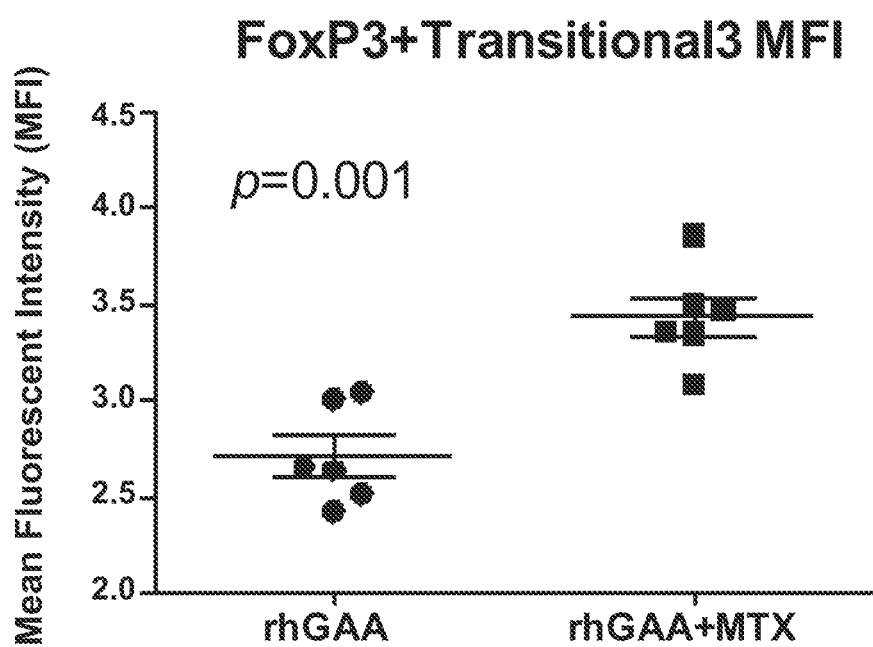

INDUCTION OF IMMUNE TOLERANCE BY USING METHOTREXATE

CROSS REFERENCE TO OTHER APPLICATIONS

This application is a continuation of U.S. patent application Ser. No. 14/116,486, which adopts the international filing date of May 3, 2012, which is a National Phase application under U.S.C. § 371 of International Application No. PCT/US2012/036405, filed May 3, 2012, which claims priority from U.S. Provisional Application No. 61/486,697, filed May 16, 2011, each of which is hereby incorporated by reference in its entirety.

FIELD OF THE INVENTION

This invention relates generally to immunology, and more specifically to the use of methotrexate to reduce undesired immune responses in patients.

BACKGROUND OF THE INVENTION

Currently, the U.S. Food and Drug Administration (FDA) has approved more than 130 protein therapeutics for clinical use (Leader et al., Nat Rev Drug Discov, 7(1):21-39 (2008)). These therapeutics include peptides, recombinant human proteins, protein vaccines, polyclonal antibody preparations derived from a variety of animal species, and monoclonal antibodies. Depending upon their sequence and conformational homology to endogenous self-antigens, glycosylation status, dose level, route of administration, localization, and manufacturing process-related characteristics, the therapeutic proteins may elicit antibody responses in the patient (Schellekens, Nat Rev Drug Discov, 1(6):457-62 (2002); Zinkernagel, Semin Immunol, 12(3):163-71 (2000), discussion 257-344; Thorland et al., Haemophilia, 5(2):101-5 (1999); Goodeve, Blood Coagul Fibrinolysis, 14 Suppl 1:S17-21 (2003)). These responses, referred to as anti-drug antibody (ADA) responses, can impact patient safety and drug efficacy sometimes.

In the case of the lysosomal storage disorder, Pompe disease, ADA can develop in the enzyme-replacement therapy (ERT) against recombinant human acid alpha-glucosidase. In patients who do not express measurable amounts of the endogenous enzyme, sustained levels of high antibody titer correlate with patient decline (CRIM-Pompe patients) (Kishnani et al., Mol Genet Metab., 99(1):26-33 (2010); Hunley et al., Pediatrics, 114(4):e532-5 (2004); Amalfitano et al., Genet Med, 3(2): 132-8 (2001)). Similar compromise in drug safety and efficacy has been observed in hemophilia patients who develop ADA to factor IX (Thorland et al., Haemophilia, 5(2):101-5 (1999); Ewenstein et al., Blood, 89(3):1115-6 (1997)). In rare instances, ADA can also induce autoimmune disease as in the case of recombinant human erythropoietin (Schellekens, Clin Ther, 24(11): 1720-40 (2002), discussion 1719; Locatelli et al., Pent Dial Int, 27 Suppl 2:S303-7 (2007)).

ADA responses can also occur with antibody therapeutics regardless of whether the therapeutics are non-human derived, humanized or even fully human. The immunogenicity of both monoclonal and polyclonal antibody therapeutics can influence patient safety and drug efficacy. Antibodies that develop against therapeutic monoclonal antibodies such as infliximab, adalimumab, rituximab and natalizumab have been associated with decreased serum levels and efficacy of the therapeutic antibodies (Bendtzen et al., Arthritis Rheum, 54(12):3782-9 (2006); Schmidt et al., Clin Immunol, 132(3):334-41 (2009); Bartelds et al., Ann Rheum Dis, 66(7):921-6 (2007); Baert et al., N Engl J Med, 348(7):601-8 (2003); Tahir et al., Rheumatology (Oxford), 44(4):561-2 (2005); Maini et al., Arthritis Rheum, 41(9): 1552-63 (1998)). Allergic reactions have been associated with anti-infliximab antibodies (Baert et al., N Engl J Med, 348(7):601-8 (2003)). Infusion-related hypersensitivity reactions have been observed in a small percentage of relapsing-remitting multiple sclerosis patients treated with natalizumab (Phillips et al., Neurology, 67(9):1717-8 (2006)).

Alemtuzumab is another antibody therapeutic that can generate ADA in relapsing-remitting multiple sclerosis patients (Coles et al., N Engl J Med, 2008. 359(17):1786-801 (2008)). Alemtuzumab is a lymphocyte-depleting monoclonal antibody that interacts with CD52, a cell surface antigen expressed on immune cells. Alemtuzumab is in late-stage clinical trials for treating relapsing-remitting multiple sclerosis and has also been evaluated in rheumatoid arthritis. A group of researchers have shown that anti-alemtuzumab antibodies developed in 63% of rheumatoid arthritis patients treated in a single dose escalation study (Weinblatt et al., Arthritis Rheum, 1995. 38(11):1589-94 (1995)). In that study, the efficacy of alemtuzumab appeared to be altered by the presence of ADA (Id.).

The polyclonal antibody therapeutic Thymoglobulin® is also associated with deleterious ADA in a small subset of patients. Serum sickness, acute renal failure and cardiovascular reactions have been observed in Thymoglobulin®-treated transplant recipients (Boothpur et al., Am J Kidney Dis., 55(1):141-3 (2009); Lundquist et al., Liver Transpl, 13(5):647-50 (2007); Busani et al., Minerva Anestesiol, 72(4):243-8 (2006); Tanriover et al., Transplantation, 80(2): 279-81 (2005); Buchler et al., Clin Transplant, 17(6):539-45 (2003)).

Researches have tried to find ways to minimize the deleterious effects of ADA. Tools that have been tested for their ability to induce immunotolerance and reduce ADA in protein therapies include, for example, non-depleting anti-CD4 antibodies (Cobbold et al., Semin Immunol, 2(6):377-87 (1990); Winsor-Hines et al., J Immunol, 173(7): 4715-23 (2004)), non-cell-binding minimal mutants of alemtuzumab (Gilliland et al., J Immunol, 162(6):3663-71 (1999); Somerfield et al., J Immunol., 185(1):763-8 (2010)), immunosuppressive therapies (Bennett et al., Blood, 106(10):3343-7 (2005); Dickson et al., J Clin Invest, 118(8):2868-76 (2008)), phosphatidylinositol-containing lipidic particles binding to Factor VIII (Peng et al., AAPS. J., 12(3):473-81 (2010)), and liver-specific administration of recombinant acid alpha-glucosidase via adeno-associated virus infection (Sun et al., Am J Human Genet, 81(5):1042-9 (2007); Sun et al., Mol Ther 18(2):353-60 (2009); Ziegler et al., Hum Gene Ther, 19(6):609-21 (2008)). There remains a need, however, to develop improved methods for reducing undesired antibody responses in protein therapies and other settings.

SUMMARY OF THE INVENTION

The invention provides a method of inducing immune tolerance in a subject in need of treatment with a therapeutic. In this method, one administers to the subject an effective amount of methotrexate in a single cycle, thereby inducing immune tolerance toward the therapeutic in the subject.

The invention also provides a method of inhibiting antibody responses to a therapeutic in a subject in need of treatment with the therapeutic. In this method, one administers to the subject an effective amount of methotrexate in a single cycle, thereby inhibiting antibody responses to the therapeutic in the subject.

The invention also provides a method of alleviating an infusion reaction to a therapeutic in a subject in need of treatment with the therapeutic. In this method, one administers to the subject an effective amount of methotrexate, thereby alleviating an infusion reaction to the protein therapeutic in the subject.

The invention also provides a method of reducing secondary autoimmunity in an autoimmune subject in need of treatment with a therapeutic. In this method, one administers to the subject an effective amount of methotrexate, thereby reducing secondary autoimmunity in the subject.

The invention also provides a method of increasing the efficacy of a therapeutic in a subject in need of treatment with the therapeutic. In this method, one administers to the subject an effective amount of methtrexate, thereby increasing the efficacy of the protein therapeutic in the subject.

The invention also provides a method of increasing the percentage of T regulatory cells in the T cell population in a subject treated with a lymphocyte-depleting therapy, e.g., an alemtuzumab therapy or a Thymoglobulin® therapy. In this method, one administers to the subject an effective amount of methotrexate, thereby increasing said percentage in said subject.

The invention also provides a method of increasing the percentage of B regulatory cells in the B cell population in a subject in need of treatment with a protein therapeutic such as an antibody therapeutic. In this method, one administers to the subject an effective amount of methotrexate, thereby increasing said percentage in said subject. In some embodiments, the effective amount of methotrexate is administered in a single cycle. In related embodiments, the invention provides a method of increasing TGF-beta-, IL-10-, and/or FoxP3-expressing B cells in a subject in need of treatment with a protein therapeutic, comprising administering an effective amount of methotrexate in a single cycle.

The invention also provides a method of prolonging the pharmacokinetics of a therapeutic agent in a subject. In this method, one administers methotrexate to the subject, before or during or after administration of the therapeutic agent, in an amount effective to prolong the pharmacokinetics of the therapeutic agent.

The invention further provides a method of depleting lymphocytes in a human patient in need thereof. In this method, one treats the patient with a lymphocyte-depleting agent and administers methotrexate to the patient, before or during or after the treatment with the lymphocyte-depleting agent, in an amount effective to induce immune tolerance in the patient toward the lymphocyte-depleting agent or to reduce secondary autoimmunity. In some embodiments, the effective amount of methotrexate is administered in a single cycle. In some embodiments, the lymphocyte-depleting agent may be a monoclonal antibody therapeutic (e.g., alemtuzumab or rituximab). In certain of these embodiments, the patient may be a multiple sclerosis patient (e.g., a remitting-relapsing multiple sclerosis patient). In some embodiments, the lymphocyte-depleting agent may be a polyclonal antibody therapeutic (e.g., anti-thymocyte globulin polyclonal antibody).

The invention also provides a method of inducing immune tolerance in a subject in need of tissue transplantation. In this method, one administers to the subject an effective amount of methotrexate, thereby inducing immune tolerance toward the transplanted tissue in the subject. In some embodiments, the effective amount of methotrexate is administered in a single cycle. In some embodiments, the transplanted tissue is renal tissue or cardiac tissue. In some embodiments, the subject also receives an agent for immune-modulation (e.g., an immunosuppressant), such as polyclonal anti-thymocyte globulin antibody).

The invention also provides a method of inhibiting T cell responses in a subject in need of a therapeutic or tissue transplantation. In this method, one administers to the subject an effective amount of methotrexate prior to, concurrently with, or after, treating the subject with the therapeutic or tissue transplantation, thereby inhibiting T cell responses in the subject.

In some embodiments of the methods of the invention, the therapeutic is a protein therapeutic.

In some embodiments of the methods of the invention, the therapeutic is an antibody therapeutic. For example, the antibody therapeutic may be a monoclonal antibody therapeutic and/or a lymphocyte-depleting agent (e.g., alemtuzumab), or a polyclonal antibody therapeutic (e.g., polyclonal rabbit anti-thymocyte globulin antibody). In further embodiments wherein the antibody therapeutic is alemtuzumab, the subject may be a multiple sclerosis patient. In further embodiments wherein the antibody therapeutic is polyclonal rabbit anti-thymocyte globulin antibody, the subject may be a human patient who is in need of organ transplantation, has aplastic anemia, and/or has or is at risk of having graft-versus-host disease. In other embodiments of the methods of the invention, the therapeutic is an enzyme. For example, the enzyme may be human alpha-galactosidase A or human acid alpha-glucosidase.

In some embodiments of the methods of the invention, the subject is a human.

In some embodiments of the methods of the invention, the effective amount of methotrexate may be 0.1 mg/kg to 5 mg/kg. In some embodiments, the single cycle of methotrexate may consist of 1 day of methotrexate administration, or 2, 3, 4, 5, 6, 7, 8, 9, 10, or 11 consecutive days of methotrexate administration. In some embodiments, the single cycle of methotrexate may be administered between 48 hours prior to and 48 hours after the onset of the therapeutic treatment.

BRIEF DESCRIPTION OF THE FIGURES

In each of the Figures described below, asterisks or stars indicate measurements with statistically significant differences (*, $p<0.05$; , $p \leq 0.001$; *, $p \leq 0.0001$).

FIG. 1A shows responses to a single course of mATG over an 8 week period. FIG. 1B shows responses to multiple courses of mATG over a 20 week period. Arrows indicate time points at which mATG or rbIgG were administered.

FIG. 4A shows that three cycles of methotrexate significantly reduce average anti-rabbit IgG titers. FIG. 4B shows that a single course of methotrexate significantly reduces average anti-rabbit IgG titers. FIG. 4C compares the average anti-rabbit IgG titers of mice treated with mATG alone, mATG and a single cycle of methotrexate, or mATG and three cycles of methotrexate. A single cycle of methotrexate reduces anti-rabbit IgG titers more significantly than three cycles of methotrexate.

FIG. 7A: Anti-alemtuzumab titers are lower in mice treated with a single cycle of 1 mg/kg or 5 mg/kg of methotrexate than in mice treated with 0.5 mg/kg or no methotrexate. Mice were treated with alemtuzumab alone, or alemtuzumab and a single cycle of methotrexate at 0.5 mg/kg, 1 mg/kg, or 5 mg/kg. FIG. 7B: Study design to test anti-alemtuzumab titers. Titer data was determined at 24 hours following the fifth dose of alemtuzumab, as indicated by the star. FIG. 7C: Methotrexate reduced anti-alemtuzumab antibody titers in mice receiving alemtuzumab and methotrexate, compared to mice receiving only alemtuzumab, 24 hours after the fifth dose of alemtuzumab.

FIG. 8A shows that total T cells ($CD3^+$) were reduced two, three, and four weeks post-treatment. FIG. 8B shows that total B cells ($CD19^+$) were reduced three weeks post-treatment. FIG. 8C shows that T helper cells ($CD4^+$) were reduced at two, three, and four weeks post-treatment, and FIG. 8D shows that cytotoxic T cells ($CD8^+$) were reduced at two, three, and four weeks post-treatment.

FIG. 9A shows responses following three cycles of treatment with alemtuzumab at 0.5 mg/kg, and one cycle of treatment with methotrexate at 0.5 mg/kg, 1 mg/kg, or 2 mg/kg. The first cycle of alemtuzumab treatment consisted of five consecutive days of dosing, and the second and third cycles each consisted of three consecutive days of dosing. FIG. 9B shows anti-alemtuzumab IgG titers of each animal per group at week 14.

FIG. 12A shows T regulatory cell levels in the spleen. FIG. 12B shows T regulatory cell levels in the blood.

FIG. 18A shows recipient IgG binding to allogeneic fibroblasts on day 21. FIG. 18B shows alloantibody levels on day 21 in mice given syngeneic transplants (Syn Tx) or an allogeneic transplant (Allo Tx) with the indicated treatments. Shown is the binding of individual recipient mouse serum IgG to allogeneic fibroblasts and is expressed as a ratio of the mean fluorescence intensity (MFI) to unstained fibroblasts. FIG. 18C shows alloantibody levels on day 21 in mice given no treatment, mATG, methotrexate, or mATG and methotrexate. Alloantibody levels were significantly lower in mice treated with methotrexate or mATG and methotrexate ($p=0.0008$ and $p<0.0001$, respectively).

FIG. 24A: activated follicular B cells; FIG. 24B: activated transitional 3 B cells.

FIG. 25A: Methotrexate enhances depletion of total T cells ($CD3^+$), T helper cells ($CD4^+$), and T regulatory cells ($CD4^+CD25^+Foxp3^+$) by alemtuzumab (AZM). Black bars represent measurements in mice treated with alemtuzumab alone, while white bars represent measurements in mice treated with alemtuzumab and methotrexate. FIG. 25B: Methotrexate enhances depletion of B cells by alemtuzumab. Stars indicate measurements with statistically significant differences (*, $p<0.05$).

FIG. 28A: T cells and B cells are significantly depleted. Small checks represent PBS-treated control mice, and large checks represent alemtuzumab-treated mice. FIG. 28B: B cells (CD 191 are 92% depleted at 24 hours after treatment, and remain 36% depleted three days after treatment. The three graphs represent different group of animals, each of which was bled at different time points. Stars indicate measurements with statistically significant differences (*, $p<0.05$; , $p\leq0.001$; *, $p\leq0.0001$).

FIG. 29A shows a study design for a six month study to assess cytokine levels in the spleen and lymph nodes. The star indicates that data were collected 24 hours after the fifth treatment with alemtuzumab. Arrows indicate time points at which alemtuzumab or methotrexate were administered, or terminal sacrifices were performed, as indicated. FIG. 29B shows levels of B cell activating factor belonging to the TNF family (BAFF) in mice treated with alemtuzumab alone or with alemtuzumab and methotrexate.

FIG. 30A shows a study design for a four month study. The star indicates that data were collected one week after the second cycle of methotrexate. Arrows indicate time points at which alemtuzumab or methotrexate were administered, or terminal sacrifices were performed, as indicated. FIG. 30B shows the levels of various cytokines in mice treated with alemtuzumab (AZM) alone or with 0.5 mg/kg, 1.0 mg/kg, or 2.0 mg/kg of methotrexate.

FIG. 37A shows rhGAA titers at weeks 2 and 6. From left to right, week 2 measurements in control mice treated with saline, mice treated with rhGAA, and mice treated with rhGAA and methotrexate, followed by week 6 measurements in control mice treated with saline, mice treated with rhGAA, and mice treated with rhGAA and methotrexate. FIG. 37B shows week 12 measurements in, from left to right, nu/nu mice treated with rhGAA alone (Myo), nu/nu mice treated with methotrexate and rhGAA, BL6 mice treated with rhGAA alone, and BL6 treated with methotrexate and rhGAA.

FIGS. 38A-B show that the numbers and percentages of IL-10 expressing B10 B cells is increased in mice tolerized to rhGAA with methotrexate. B10 B cells isolated from animals treated with rhGAA or rhGAA and methotrexate were assessed for IL-10 protein expression by flow cytometry.

FIG. 39A depicts a FACS plot of B10 B cells stained with CD86, while FIG. 39B depicts the numbers of CD86$^+$L10$^+$ B10 B cells and CD86$^-$IL10$^+$ B10 B cells in response to treatment with rhGAA or rhGAA and methotrexate.

FIG. 40B depicts CD86$^+$TGF-beta$^+$ B10 B cell and CD86$^-$TGF-beta$^+$ B10 B cell counts.

FIGS. 49A-C show that in transitional 3 B cells there is detectable TGF-beta, IL-10 and FoxP3, but no apparent effect of 1D11 treatment on the cells. Spleens were isolated from animals treated with rhGAA or rhGAA and methotrexate that also were co-administered 1D11 or 13C4 seven days following a single rhGAA treatment or a single rhGAA and methotrexate treatment, and cells were counted using flow cytometry.

FIGS. 50A-C show that 1D11 treatment does not affect basal levels of IL-10, TGF-beta, and FoxP3 in follicular B cells, transitional 2 B cells, and transitional 3 B cells (top to bottom).

DETAILED DESCRIPTION OF THE INVENTION

Figure 1A:
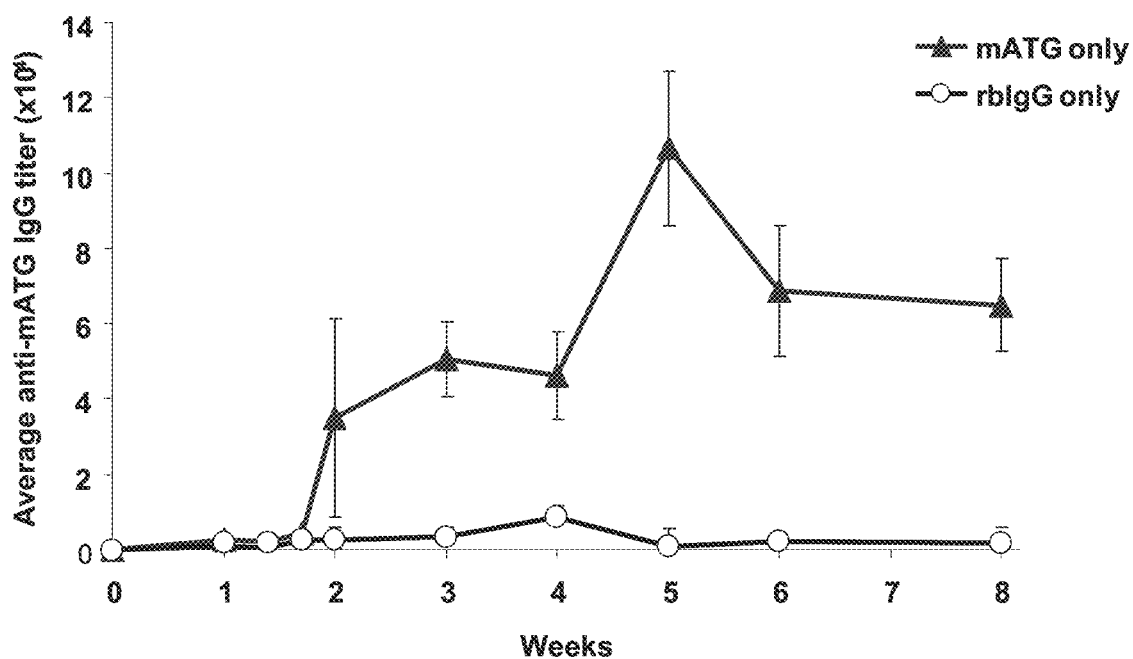
FIGS. 1A-B show anti-rabbit IgG responses to a single and multiple courses of mATG, a rabbit anti-murine thymocyte globulin polyclonal antibody. Average anti-rabbit IgG titers were measured, and mice treated with rabbit IgG (rbIgG) only were used as a control.

The present invention is based on our surprising discovery that a single cycle or short course of methotrexate administration reduces undesired immune responses (such as ADA responses, and other undesired T- and/or B-cell mediated immune responses) in patients receiving protein therapeutics such as replacement enzymes or therapeutic antibodies, and anti-graft antibody responses in tissue transplantation. This discovery leads to new methods for increasing both safety and efficacy of protein therapies and organ transplantation.

More specifically, our studies have shown that a single cycle of methotrexate reduces ADA against antibody therapeutics. As detailed below, one set of studies was done with a murine version of a polyclonal antibody therapeutic, Thymoglobulin®. Thymoglobulin® is a rabbit anti-human thymocyte globulin polyclonal antibody used for immunosuppression in the setting of solid organ transplantation, aplastic anemia and in prevention of graft-versus-host disease. A rabbit anti-murine thymocyte globulin polyclonal antibody (mATG) has been developed. It maintains similar characteristics to Thymoglobulin® (Ruzek, et al., Transplantation, 88(2):170-9 (2009)). We have demonstrated that a single course of methotrexate can reduce anti-mATG IgG titers by >95%. In fact, we have surprisingly found that a single cycle of methotrexate works better in reducing ADA than three cycles of methotrexate. In addition, this reduction in ADA maintains the levels of circulating mATG and enhances mATG-mediated cell depletion and T regulatory cell percentages upon repeat mATG dosing. Another set of our studies was done with a monoclonal antibody therapeutic, alemtuzumab. We have found that a single course of methotrexate can similarly control anti-alemtuzumab responses and enhance alemtuzumab-mediated lymphocyte depletion.

We have discovered that this single cycle regimen of methotrexate also reduces ADA where the protein therapeutic is an enzyme. In two of our studies, we demonstrated that a single cycle of methotrexate could effectively control anti-Myozyme® (recombinant human alglucosidase alpha or "rhGAA") responses where originally multiple cycles were thought to be required to reduce ADA.

We have discovered that methotrexate is also useful in organ transplantation. In our studies, we found that a single cycle of methotrexate could control anti-allograft antibody responses in heart allograft transplantation. When combined with mATG, the survival of a heart allograft was significantly longer.

Our studies show that a single cycle of methotrexate given within the first week of a protein therapy can provide a long-lived reduction of greater than 95% in ADA over many months of dosing. This reduction in antibody titers was long-lived despite the absence of methotrexate throughout the majority of the studies. Furthermore, we have found that a single cycle of methotrexate can control anti-allograft responses (e.g., in a murine allogeneic heart transplant model), showing control over antibody responses directed towards multiple antigens simultaneously. Methotrexate is classically known as a dihydrofolate reductase antagonist that is thought to kill proliferating cells by inhibiting purine metabolism and interfering with de novo DNA synthesis (Kremer, Arthritis Rheum, 50(5):1370-82 (2004)). It could be easily assumed that methotrexate may simply kill the reactive cells through this well-described mechanism, but this seems unlikely with the single cycle regimen that we have discovered. Methotrexate has a short half-life and is not likely to be in cells or circulation long enough to actively kill cells three to four months following treatment (Walling, Invest New Drugs, 24(1):37-77 (2006); Slavikova et al., Neoplasma, 25(2):211-6 (1978)). Moreover, we find no evidence of lymphocyte depletion following methotrexate treatment. Rather, we have surprisingly found that a single cycle regimen of methotrexate reduces undesired antibody responses by inducing an active mechanism of immune control, not by indiscriminately depleting lymphocytes.

Our studies show that a single cycle of methotrexate increases B10 regulatory B cells as well as activated marginal zone B cells, activated follicular B cells and activated transitional 3 B cells. Our studies also show that a single cycle of methotrexate increase the number of IL-10-expressing, TGF-beta-expressing, and FoxP3-expressing B10, follicular, transitional 2 and transitional B cells, and that this expansion is mediated by TGF-beta. These studies also show that methotrexate increases the expression levels of IL-10, TGF-beta, and FoxP3. The expansion of splenic B cell populations is surprising given the current understanding of the mechanism of action of methotrexate, and suggests that in this dosing paradigm, methotrexate is working in a unique, previously unknown way. Low, continual doses of methotrexate in infliximab-treated rheumatoid arthritis patients have been shown to reduce anti-infliximab antibody responses; yet as exposure is continuous, this regimen is more likely to involve constant immunosuppression, rather than tolerance induction. Methotrexate treatment alone has been shown to reduce disease activity in rheumatoid arthritis when given weekly in low doses. A recent publication suggests that upon continual administration of low dose methotrexate (every other day), autoantigen-specific T regulatory cells appear, which may help account for the efficacy of methotrexate treatment in rheumatoid arthritis (Xinqiang et al., Biomed Pharmacother, 64(7):463-471 (2010)). In contrast, the dosing paradigm described herein for methotrexate is truly unique in that it involves a short course of methotrexate treatment that can provide long-lasting control of undesired immunological responses.

Altogether, we have identified a unique dosing regimen of methotrexate that can yield long-lasting control over several different types of ADA responses and anti-allograft antibody responses in tissue transplantation, as well as T cell and B cell responses. We have found that the immune tolerance developed by methotrexate can be transferred from one animal to another, for example, by transplanting B cells from a tolerized animal to a non-tolerized animal. Our data suggest that methotrexate acts through a unique mechanism of action that involves the expansion of activated B cell subsets that may represent regulatory B cells active in suppressing immune responses. Furthermore, methotrexate also may act through a mechanism of T regulatory cell expansion.

Undesired Immune Responses in Bio-Therapy

The methods of this invention can control undesired immunological responses (e.g., ADA responses, and other undesired T- and/or B-cell mediated immune responses) in a variety of biological therapies (e.g., therapy using a biologic such as proteins, nucleic acids, carbohydrates, lipids, and metabolites). Protein therapy refers to therapy in which the therapeutic agent is a proteinaceous substance, including peptides and proteins. Protein therapeutics can, for example, be enzymes, cytokines, growth factors, immunomodulators, thrombolytics, antibodies (including polyclonal and monoclonal antibodies), antibody fragments or modified antibodies (e.g., Fab, F(ab')$_2$, Fv, Fd, scFv, and dAb). For example, many enzyme replacement therapies have been developed for patients with certain genetic diseases, including Fabrazyme® (recombinant human alpha-galactosidase) for Fabry disease, Cerezyme® (imiglucerase) for Gaucher disease, Aldurazyme® (laronidase) for Mucopolysaccharidosis I (MPS I), and Myozyme® and Lumizyme® (alglucosidase alpha) for Pompe disease. Examples of antibody therapeutics include Campath® (alemtuzumab), Thymoglobulin®, Avastin® (bevacizumab), Lucentis® (ranibizumab), Remicade® (infliximab), Humira® (adalimumab), Rituxan® (rituximab), Tysabri® (natalizumab), Simulect® (basiliximab), Zenapax® (daclizumab), OKT3® (muromonab-CD3), Erbitux® (Cetuximab), Mylotarg® (gemtuzumab), Herceptin® (trastuzumab), and Benlysta® (belimumab). Examples of other protein therapeutics include Enbrel® (etanercep), and other fusion proteins.

In many cases, undesired immune responses can be generated in a patient against the protein therapeutic, causing variable effects on patient outcome. Such responses occur because biologic therapeutics often contain sequences and conformations that are foreign to a human patient. For example, ADA interferes with therapeutic efficacy and/or increases safety risks. ADA may cause hypersensitivy reactions, anaphylaxis, serum sickness, immune complex disease, acute renal failure. ADA can be monitored in patients receiving protein therapy by a clinician using well established methods, including ELISA and immunohistochemistry.

In some instances, a "protein therapy" as used herein refers to a viral therapy where a viral vector is used to deliver a nucleic acid therapeutic. Exemplary viruses used in such therapies include, but are not limited to, adenoviruses, adeno-associated viruses, and retroviruses. Antibodies may develop against the capsid proteins of the virus, reducing the efficacy and increasing the safety risks of such therapies. The methods of this invention are useful to control undesired immunological responses (e.g., ADA responses, and other undesired T- and/or B-cell mediated immune responses) in viral therapies as well. The methods of this invention also may control undesired immunological responses in non-protein biological therapies. Exemplary non-protein bio-therapies include, but are not limited to, nucleic acid therapies, (e.g., antisense therapies, siRNA therapies, and miRNA therapies).

Anti-Graft Response in Transplantation

The methods of this invention can also be used to induce immune tolerance in a patient receiving tissue transplantation such as renal transplantation, liver transplantation, cardiac transplantation, and stem cell transplantation. Host versus graft and graft versus host rejections often occur in tissue transplantation, especially allograft and xenograft transplantation. A single cycle of methotrexate can be used alone or together with another immune-modulating agent, (e.g., an immunosuppressant such as Thymoglobulin®) to manage anti-graft antibody response. In addition, the combination of Thymoglobulin® and methotrexate in transplantation may act to prolong graft survival. Finally, in a case where Thymoglobulin® would be investigated in the settings of chronic autoimmune disease such as rheumatoid arthritis and multiple sclerosis, methotrexate may allow for safer re-treatment of Thymoglobulin®, protecting the patient from developing significant anti-rabbit antibodies (such as IgG and/or IgM) and/or infusion-related reactions.

Managing Undesired Immunological Responses with Methotrexate

We have found that that a single, short cycle of methotrexate can significantly reduce undesired immunological responses such as ADA in subjects receiving biologic therapeutics (e.g., protein therapeutics) and anti-allograft responses in patients receiving tissue transplantation. Reducing undesired ADA may not only improve patient safety, but also may improve the efficacy of a protein therapeutic through improving the protein therapeutic's pharmacodynamics and/or pharmacokinetics.

Methotrexate, a small molecule compound, has been used to treat patients with severe active rheumatoid arthritis, severe psoriasis, and certain types of cancer including cancers that begin in the tissues that form around a fertilized egg in the uterus, breast cancer, lung cancer, certain cancers of the head and neck, certain types of lymphoma, and leukemia (cancer that begins in the white blood cells). Methotrexate treats cancer by slowing the growth of cancer cells. Methotrexate treats psoriasis by slowing the growth of skin cells to stop scales from forming. Methotrexate may treat rheumatoid arthritis by decreasing the activity of the immune system.

Methotrexate has been studied in the context of controlling ADA responses elicited against a-galactosidase A and a-glucosidase. However, those studies were done with multiple cycles of methotrexate treatment (Garman et al. Clin Exp Immunol, 137(3):496-502 (2004); Joseph et al., Clin Exp Immunol, 152(1):138-46 (2008); Mendelsohn et al., N Engl J Med, 360(2):194-5 (2009)), rather than a single cycle of methotrexate.

Our studies surprisingly show that a single cycle of methotrexate suffices to reduce ADA and anti-allograft antibodies significantly. In fact, in studies involving antibody therapeutics (e.g., mATG), we show that single-cycled treatment of methotrexate is more effective in reducing ADA than multi-cycled treatment of methotrexate. Previous studies using methotrexate gave no indication that a single cycle of methotrexate would be sufficient to reduce ADA, much less that it would be more effective than multi-cycle treatment. Methotrexate is known to be cytotoxic. Therefore, if one had hypothesized that a mechanism for reduction of ADA by methotrexate relied upon this property, then reducing the number of cycles of treatment actually would have been predicted to reduce the beneficial effects of methotrexate. Furthermore, those previously published studies do not demonstrate the benefits of methotrexate treatment on pharmacokinetics, pharmacodynamics, efficacy, or safety, as surprisingly have been demonstrated herein with a single course of methotrexate. Nor do they disclose that methotrexate can reduce ADA in antibody therapy.

As used herein, a single cycle regimen refers to a treatment regimen, or a treatment unit, of consecutive or non-consecutive days and are started at preferably no more than five (e.g., no more than three) days following the dosing of the primary protein therapeutic or transplantation. If the primary protein therapeutic is dosed in multiple periods, a single cycle of treatment of methotrexate preferably does not extend past the first period of protein therapeutic dosing. By way of example, in a weekly, monthly, or annual protein therapy, a single cycle of methotrexate consists of three consecutive days of methotrexate intake (e.g., orally), starting on day 0, the day when the primary protein therapeutic is given to the patient for the first time, or when the patient receives a tissue transplant. Then the patient receives a single dose of methotrexate on day 1 (24 hours later) and on day 2 (48 hours later). A single cycle of methotrexate may also consist of, for example, 2, 3, 4, 5, 6, 7, or 8 consecutive daily doses of methotrexate, starting on day 0. Methotrexate also can be administered at other times as deemed appropriate, e.g., when managing secondary autoimmunity in e.g., a lymphocyte-depleting therapy. A single cycle of methotrexate preferably does not last longer than 8 days. In some embodiments, a single cycle of methotrexate begins between 48 hours prior to and 48 hours after the onset of the primary therapeutic treatment (i.e., the treatment with the biologic therapeutic). For example, a single cycle of methotrexate may begin 48 hours prior to, 36 hours prior to, 24 hours prior to, 12 hours prior to, concurrently with, 12 hours after, 24 hours after, 36 hours after, or 48 hours after, the onset of the primary therapeutic treatment.

Our studies also surprisingly show that a low dosage of methotrexate suffices to manage undesired immunological responses (e.g., ADA responses, and other undesired T-and/or B-cell mediated immune responses) in protein therapies and transplantation. Accordingly, in embodiments of the invention, methotrexate may be administered in more than one cycle, but at a low total dosage. For instance, the methotrexate can be administered in two or more (e.g., 3, 4, 5, 6, etc.) cycles, but with a total combined dosage of no more than 5 mg/kg in a patient.

The dosage of methotrexate will be an effective amount of methotrexate in reducing undesired immunological responses, such as antibody or cellular responses, when given in a single cycle. An effective amount of methotrexate in human patients may be in the range of 0.05 mg/kg to 5 mg/kg. In some embodiments, the effective amount is 0.1 mg/kg to 1.5 mg/kg. In some embodiments, the effective amount is 0.12 mg/kg to 1.28 mg/kg. In certain embodiments, the effective amount is 0.12 mg/kg. In certain embodiments, the effective amount is 1.28 mg/kg. The recommended dosage of methotrexate may pose minimal safety risks because the dosing regimen involves only a brief course of methotrexate at dose levels that are more similar to doses for rheumatoid arthritis than low neoplastic doses. In our studies, the total amount of methotrexate tested in each cycle in mice was 14 or 15 mg/kg. 14 mg/kg of methotrexate in mice is equivalent to approximately 68 mg or 5.92 mg/m$^2$ in an average adult weighing 60 kg. Rheumatoid arthritis patients can receive up to 25 mg of methotrexate per week without suffering from significant toxicities. The low neoplastic dose of methotrexate is considered to be 30 mg/m$^2$, significantly higher than 5.92 mg/m$^2$. Thus, the above recommended doses, combined with the transient nature of this methotrexate regimen, is likely to be well-tolerated in adults. The exact dosage and regimen of methotrexate should of course be established by a clinician, taking into account the patient's physical condition, age, weight, gender, other medications he/she is taking and their known side-effects, and any other relevant factors. The effect of methotrexate on managing undesired antibody responses in the patient can be monitored by well known methods, including clinical examination of the patient, symptoms, blood tests assaying ADA or anti-allograft antibody titers, immunohistochemical assays (e.g., C4 deposition assays and other solid-phase antibody detection methods such as the enzyme-linked immnuosorbent assay (ELISA) and bead-based flurometric assays). The effect also can be monitored by measuring levels of biomarkers such as MCP-1, IL-13, IL-6, and IL-12, which we have shown to be reduced in level by methotrexate treatment, and transitional 2 B cells, transitional 3 B cells, follicular B cells, marginal zone B cells, B10 B cells, and B1 B cells, which we have shown to be increased in number by methotrexate treatment. Additionally, TGF-beta, FoxP3, IL-5, IL-10, IL-15, and GM-CSF may be used as biomarkers to monitor the effects of methotrexate on undesired immune responses as needed. The levels of biomarkers also may be used to monitor the effects of methotrexate on T cell responsiveness to a therapeutic (e.g., a protein therapeutic). Biomarkers for T cell activation such as IL-2, interferon-y, and TNF-α, may also be monitored as readouts for methotrexate's effect on T cell responses.

Due to its ability to control undesired immune responses, the single cycle methotrexate regimen of this invention can expand the use of many protein therapeutics whose repeated uses in a given patient have been limited in the past due to safety and efficacy concerns. For example, the concomitant use of methotrexate with Thymoglobulin® may expand the utility of Thymoglobulin® to other disease settings where re-dosing is desired, such as T cell-mediated autoimmune diseases including, but not limited to, diabetes, lupus, scleroderma, rheumatoid arthritis, psoriasis and multiple sclerosis. In addition, methotrexate may expand upon the efficacy and safety of alemtuzumab, for example, in autoimmune diseases such as multiple sclerosis, wherein alemtuzumab is usually administered in repeated annual cycles, or in chronic B-cell lymphocytic leukemia, wherein alemtuzumab is administered in a 12-week cycle, dosing starting at 3 mg/day (until the infusion reactions are equal to or less than grade 2), then scaling up to 10 mg/day (until the infusion reactions are equal to or less than grade 2), and finally moving up to 30 mg/day (on alternate days, 3 times weekly). These types of dosing regimens may potentiate inhibitory ADA responses. Methotrexate may thus be used to control ADA and any other undesired immune responses.

Improving Lymphocyte-Depleting Therapy with Methotrexate

An exemplary application of this invention is to use methotrexate to improve lymphocyte-depletion therapy such as alemtuzumab therapy in treating multiple sclerosis (MS), such as relapsing-remitting MS. "Lymphocyte depletion" is a type of immunosuppression by reduction of circulating lymphocytes, e.g., T cells and/or B cells, resulting in lymphopenia. Therapeutically, lymphocyte depletion can be achieved by a protein therapeutic such as Thymoglobulin®, humanized anti-CD52 monoclonal antibody CAMPATH-1H® (alemtuzumab), and rituximab. Lymphocyte depletion is desired in treatment of a number of autoimmune conditions, including multiple sclerosis (Coles et al., Ann. Neurol. 46, 296-304 (1999); Coles et al., 2008), rheumatoid arthritis, vasculitis, and lupus.

Lymphocyte depletion therapy may cause secondary autoimmunity. Autoimmunity is referred to herein as "secondary autoimmunity" when it arises subsequent to the onset of a first ("primary") disease, for example, a "primary" autoimmune disease. Secondary autoimmunity sometimes arises in MS patients having, or having had, lymphopenia following, e.g., lymphocyte depleting therapy. In some individuals, secondary autoimmunity arises soon after lymphocyte depleting therapy (e.g., treatment with alemtuzumab). In other individuals, secondary autoimmunity may not arise until months or years after lymphocyte depleting therapy; in some of those individuals, by the time they develop secondary immunity, substantial lymphocyte recovery (total lymphocyte count) may have occurred so that they may no longer be lymphopenic. Lymphocyte depletion may occur in the context of treatment with antibody therapeutics or small molecule therapeutics.

Secondary autoimmunity arising in lymphopenic MS patients can be any type of autoimmune condition other than MS, including but not limited to thyroid autoimmunity (e.g., Graves' disease), thrombocytopenic purpura, immune thrombocytopenia (ITP), Goodpasture's disease, autoimmune neutropenia, autoimmune hemolytic anemia, and autoimmune lymphopenia. In some embodiments, the secondary autoimmunity is B cell mediated, i.e., B cell responses and auto-antibodies are directly linked with disease development and pathology.

Techniques for diagnosing and monitoring these autoimmune diseases are well known to those skilled in the art, including assessment of symptoms and medical examination such as blood analysis. The invention contemplates the use of any known methods. For example, autoantibody levels in a patient's body fluid (e.g., blood) can be determined as a means of detecting signs of autoimmunity. Specifically, anti-nuclear antibodies, anti-smooth muscle antibodies, and anti-mitochrondrial antibodies can be measured. In the event anti-nuclear antibodies are detected, additional assays can be performed to measure anti-double-stranded DNA antibodies, anti-ribonucleoprotein antibodies, and anti-La antibodies. Anti-thyroid peroxidase (TPO) and anti-thyroid stimulating hormone (TSH) receptor antibodies can be measured to detect autoimmune thyroid diseases; if anti-TPO or anti-TSH receptor antibodies are detected, one can measure whether thyroid function is affected by measuring free T3, free T4 and TSH levels. Anti-platelet antibodies can be measured to detect autoimmune thrombocytopenia, and a measurement of blood platelet levels may serve to determine if the presence of anti-platelet antibodies is causing a reduction in platelet number. See also WO 2010/041149.

The single cycle methotrexate regimen of this invention can be used to improve the safety and efficacy of lymphocyte-depleting therapy by reducing ADA as well as minimizing secondary autoimmunity. Without wishing to be bound by theory, we believe that methotrexate may reduce secondary autoimmunity by tolerizing multiple autoantigens simultaneously.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. The materials, methods, and examples are illustrative only and not intended to be limiting.

EXAMPLES

Further details of the invention will be described in the following non-limiting examples. It should be understood that these examples, while indicating preferred embodiments of the invention, are given by way of illustration only, and should not be construed as limiting the appended embodiments. From the present disclosure and these examples, one skilled in the art can ascertain certain characteristics of this invention, and without departing from the spirit and scope thereof, can make various changes and modifications of the invention to adapt it to various usages and conditions. Materials and methods used in these working examples are described as follows.

Mice

Normal female C57BL/6 mice between 6 and 12 weeks of age were used for the in vivo studies of rabbit anti-murine thymocyte globulin polyclonal antibody (mATG) and were obtained from Jackson Laboratories (Bar Harbor, Me.) or Taconic Laboratories (Hudson, N.Y.). Alemtuzumab-related studies employed human CD52 (huCD52) transgenic (Tg) mice between 6-12 weeks of age that were obtained from Charles River Laboratories/Genzyme Corp. Mice were housed and maintained in accordance with the Guide for Care and Use of Laboratory Animals and under American Association for Accreditation of Laboratory Animals Care I accreditation and all animal protocols used in these studies were approved by the Institutional Animals Care and Use Committee.

The huCD52 Tg mouse used for nonclinical pharmacology studies were generated by Xenogen (Cranbury, N.J., USA). To generate the mouse, a bacmid construct containing approximately 145 kilobases of genomic DNA from human chromosome 1 was randomly integrated into the mouse genome of CD-1 embryonic stem cells. By virtue of the span of human genomic DNA that this bacmid contained, the construct included a total of 5 partial or full genes of unknown function in addition to human CD52. The 5 partial or full gene segments contained in the bacmid were as follows: the human CD52 gene, the 3' end of a novel gene (DKFZP434L0117), the SH3BGRL3 gene (SH3 domain binding glutamic acid-rich protein like 3), the gene for socius (SOC), the AIM1L (absent in melanoma 1-like) gene, and the zinc finger protein 683 gene. Three founder lines were generated and line 107 was established at Genzyme.

Antibody Administration

Polyclonal antibodies mATG and rbIgG were prepared as described in Ruzek et al., Transplantation, 88(2):170-9 (2009), and administered by intraperitoneal injection in various regimens depending upon the experiment. Monoclonal antibody alemtuzumab was administered intravenously as either a single injection of 0.5 mg/kg or in either a three or five day cycle of 0.5 mg/kg/day.

Myozyme® Ttreatment

Recombinant human alglucosidase alfa (rhGAA, marketed by Genzyme Corp. as Myozyme®) was used as a formulated drug product. Mice were treated weekly with 20 mg/kg of rhGAA by bolus tail vein injection unless stated differently. All mice were treated prophylactically with 5 to 30 mg/kg diphenhydramine (Baxter Healthcare Corporation, Deerfield, Ill.) intraperitoneally prior to rhGAA administration. Control animals were treated intravenously with either sterile 0.9% saline or rhGAA-formulation buffer. Methotrexate treatment Methotrexate (Calbiochem catalog #454125) was administered at 0.5, 1.0, 2.0 or 5 mg/kg by intraperitoneal injection for 1-3 cycles, where each cycle equals either three, six or seven consecutive days of injection depending upon the experiment. In studies that involved monthly mATG treatment, methotrexate was administered intraperitoneally at 5 mg/kg at 0, 24, and 48 hours following either the initial mATG treatment or the first three mATG treatments. In transplant studies where mATG was dosed at days 0 and 4, methotrexate was given daily at 2 mg/kg from days 0 to 6, daily at 0.5 mg/kg from days 0 to 6, or daily at 0.5 mg/kg from days 0 to 11.

mATG Treatment

Polyclonal antibody mATG was administered as an intraperitoneal injection of 5 mg/kg every four weeks or as two 20 mg/kg doses given four days apart when in the transplant setting with the first dose given on the day of transplant (day 0).

Cell Preparations from Various Tissues

For splenocyte and lymph node cell preparations single-cell suspensions were generated from harvested mouse spleens or inguinal and mesenteric lymph nodes by homogenization between frosted glass slides into PBS containing 2% FCS. For splenocyte preparations, red blood cells were lysed by 1-2 minute incubation with a red blood cell lysis solution (BD Biosciences, San Diego, Calif.). Blood was isolated by retro-orbital bleeding and cell preparations were performed by lysing red blood cells with red blood cell lysing solution (BD Biosciences) for 20-30 minutes. For all tissue preparations, live cells were enumerated using the ViCell automated counter (Beckman Coulter, Fullerton, Calif.). Following isolation, all cell preparations were washed with PBS/2% FCS prior to use in the assays described below.

Flow Cytometry

For evaluation of cell populations within different tissues, single cell suspensions of the tissues were incubated with fluorochrome-conjugated antibodies that included anti-mouse CD4, CD8, CD25, CD44, CD62L (all antibodies from BD Biosciences or eBioscience, San Diego, Calif.). Intracellular Foxp3 expression analysis was performed according to the anti-Foxp3 manufacturer's protocol (eBiosciences, San Diego, Calif.). Following incubation with the antibodies, cells were washed and analyzed by flow cytometry (FACSCanto, BD Biosciences and FCS Express software, De Novo Software, Los Angeles, Calif.).

Cell populations evaluated were defined as follows:
total CD4 T cells: $CD4^+CD8^-$,
total CD8 T cells: $CD8^+CD4^-$,
CD4 naïve cells: $CD4^+CD25^-CD62L^+CD44^-$,
CD4 memory cells: $CD4^+CD25^+CD62L^-CD44^+$,
naïve CD8 T cells: $CD8^+CD44^-CD62L^+$,
CD8 memory cells: $CD8^+CD44^+CD62L^-$,
regulatory T cells: $CD4^+CD25^+Foxp3^+$,
total B cells: $CD19^+$,
B2/follicular B cells: $CD19^+CD21^{int}CD23^{hi}$,
B1 B cells: $CD19^+CD43^+CD11b^+$,
transitional 1 B cells: $CD19^+CD93^+CD23^-IgM^{hi}$,
transitional 2 B cells: $CD19^+CD93^+CD23^+IgM^{hi}$,
transitional 3 B cells: $CD19^+CD93^+CD23^+IgM^{lo}$,
marginal zone B cells: $CD19^+CD21^{hi}CD23^{lo}$, and
B10 B cells: $CD19^+CD5^+CD1d^+$.

In vitro blocking studies determined that up to 100 μg/ml mATG did not prevent detection of these populations.

Anti-mATG IgG ELISA

The levels of anti-mATG IgG in mouse serum were analyzed by enzyme linked immunosorbent assay (ELISA). Briefly, 96-well plates (Corning Inc., Corning, N.Y., USA) were coated overnight with 1 μg/ml of rabbit IgG in phosphate buffered saline (PBS). Following blocking with Super Block Blocking Buffer (Thermo Scientific, Rockford, Ill., USA) serial dilutions of serum were added in duplicate to rabbit IgG-coated plates and incubated at 37° C. for 1 h. The plates were washed and horseradish peroxidase-conjugated goat anti-mouse IgG secondary antibody (Southern Biotechnology Associates, Birmingham, Ala., USA) was added and allowed to incubate for 1 h at 37° C. Following a final wash, 3,3',5,5'-tetramethylbenzidine substrate (BioFx, Owings Mills, Md., USA) was added and allowed to develop for 15 min at room temperature. The reaction was stopped by the addition of 1 N HCl and absorbance values were read at 450/650 nm on an ELISA plate reader (Molecular Devices, Sunnyvale, Calif., USA). End-point titers were defined as the lowest dilution that averages above an absorbance of 0.100 using Softmax software (Molecular Devices, Sunnyvale, Calif., USA).

mATG-specific IgG ELISA

Mouse serum was determined by ELISA. Briefly, 96-well plates (Corning Inc., Corning, N.Y., USA) were coated overnight with 1 μg/ml of goat anti-rabbit IgG-Fc fragment antibody (Bethyl Laboratories, Tex., USA). Following blocking with 0.5% BSA (high purity), standard controls and serum samples were diluted as necessary and added in duplicate to the wells of the coated plates and incubated at 36-38° C. for 1 hour with gentle shaking. The plates were washed and horseradish peroxidase-conjugated goat anti-rabbit IgG-Fc fragment antibody (Bethyl Laboratories, Tex., USA) was added as appropriate and incubated for 1 hour at 36-38° C. with gentle shaking. Following a final wash, 3,3',5,5'-tetramethylbenzidine substrate (BioFx, Owings Mills, Md., USA) was added and allowed to develop for 15 min at 23-25° C. The reaction was stopped by adding 1 N HCL and absorbance values were read at 450/650 nm on an ELISA plate reader (Molecular Devices, Sunnyvale, Calif., USA). Final concentrations were interpolated off the standard curve. It was predetermined that the measurement of mATG-specific IgG by this method were only modestly affected by titers of anti-mATG IgG that were greater than 218,000.

Anti-alemtuzumab IgG ELISA

Mice were bled 4-6 days following alemtuzumab treatment and specific anti-alemtuzumab IgG was measured by ELISA. Briefly, 96-well plates (Corning Inc., Corning, N.Y., USA) were coated overnight with 3 μg/ml of alemtuzumab in PBS (pH 7.2). Following blocking with 0.1% BSA in PBS, serial dilutions of serum were added in duplicate to alemtuzumab-coated plates and incubated at 37° C. for 1 h. The plates were washed, and horseradish peroxidase-conjugated goat anti-mouse IgG secondary antibody (Southern Biotechnology Associates, Birmingham, Ala., USA) was added and allowed to incubate for 1 h at 37° C. Following a final wash, TMB substrate (BioFx, Owings Mills, Md., USA) was added and allowed to develop for 15 min at room temperature. The reaction was stopped by the addition of 1 N HCl and absorbance values were read at 450/650 nm on an ELISA plate reader (Molecular Devices, Sunnyvale, Calif., USA). End-point titers were defined as the antilog of the logarithmically transformed sample dilution interpolated at an absorbance value of 0.2 using Excel software (Microsoft, Redmond, Wash., USA).

Anti-rhGAA IgG ELISA

Mice were bled 4-6 days following rhGAA treatment and specific IgG was measured by ELISA. Briefly, 96 well plates (Corning Inc., Corning, N.Y., USA) were coated overnight with 5 μg/ml of rhGAA in sodium acetate buffer (pH 5.0). Following blocking with 0.1% BSA in PBS, serial dilutions of serum were added in duplicate to rhGAA-coated plates and incubated at 37° C. for 1 hour. The plates were washed, and HRP-conjugated goat anti-mouse IgG secondary antibody (Southern Biotechnology Associates, Birmingham, Ala.) was added and allowed to incubate for 1 hour at 37° C. Following a final wash, 3,3',5,5'-tetramethylbenzidine substrate (TMB, KPL, Gaithersburg, Md.) was added and allowed to develop for 15 minutes at room temperature. The reaction was stopped by the addition of 1N HCl and absorbance values were read at 450/650 nm on an ELISA plate reader (Molecular Devices, Sunnyvale, Calif.). Endpoint titers were defined as the reciprocal of the sample dilution resulting in an absorbance value of 0.2 using Softmax software (Molecular Devices, Sunnyvale, Calif.).

Ex Vivo Studies

C57BL/6 (Jackson Laboratories) or E4GAAKO (Charles River) mice 8-12 weeks old were given 5 mg/kg of methotrexate (Calbiochem catalog #454125) by intraperitoneal injection for 1-3 cycles, where 1 cycle equals 3 consecutive injection days. 20 mg/kg of Myozyme® (Genzyme Corporation) was given by tail vein injection once or for 2-6 weekly doses, commencing with the first methotrexate dose. Animals were sacrificed weekly or daily after initiation of treatment. Spleen, mesenteric, and inguinal lymph nodes were collected for flow cytometric analysis of T and B cell subsets and sera was collected for ELISA assays. Spleens were processed between glass slides and red blood cells (RBC) was lysed with lysing buffer purchased from BD Biosciences (catalog#555899) according to the manufacturer's instructions. Lymph nodes were processed between glass slides and washed with phosphate buffered saline (PBS) containing 2% fetal calf serum (FCS). Cells were resuspended in 200 μL of PBS containing 4% fetal bovine serum and 25 μg/mL of total mouse IgG and blocked for 30 minutes at 4° C. Approximately 3 million spleens cells and 1 million lymph node cells were stained with different antibody cocktails and analyzed with a high through put sampler (HTS) on a Becton Dickinson CANTOII flow cytometer. At least 100,000 cell events were acquired within the lymphocyte gate. Anti-mouse antibody cocktails consisted of PE-CD21/35 catalog #552957, FITC-catalog #553138, PE-CD138 catalog #553714, PE-PE-Cy7-CD4 catalog #552775, FITC-CD3e catalog #553062, APC-CD11b catalog #553312, PE-Cy7-IgM catalog #552867, APC-Cy7-CD8 catalog #557654, PE-CD273 (PD-L2) catalog #557796, APC-CD138 catalog #558626, PE-Cy7-CD11b catalog #552850, PE-CD93 (early B lineage) catalog #558039, APC-CD69 catalog #560689, Pe-Cy7-CD24 catalog #560536, FITC-CD1d catalog #553845, APC-CD5 catalog #550035, and Percp-Cy5-7AAD catalog #559925, all purchased from BD Pharmingen. FITC-FoxP3 intracellular staining kit was purchased from eBioscience. Pacific Blue (PB)-CD25 catalog #102022, PB-CD23 catalog #101616 and PB-CD86 catalog #105022 were purchased from BioLegend. Analysis of lymphocyte subsets was performed with FCS express version 3 software provided by De Novo Software. Percentages were generated with the batch processing option and absolute numbers were calculated according to the cell counts obtained. Spleen and lymph node cell counts were obtained with a Beckman Coulter Vi-cell XR cell viability analyzer according to the manufacturer's instructions.

In Vitro and Cytokine Analysis

C57BL/6 (Jackson Laboratories) or E4GAAKO (Charles River) mice 8-12 weeks old were given 5 mg/kg of methotrexate (Calbiochem catalog #454125) by intraperitoneal injection for 1 cycle (3 consecutive daily doses) commencing with treatment with 20 mg/kg of rhGAA. For the 1D11 studies, animals were treated with intraperitoneal injections of 5 mg/kg of either 1D11 or 13C4 (Genzyme Corporation) 3 time per week, every other day, commencing with rhGAA and methotrexate treatment. Animals were sacrificed on day 6 or 7 post rhGAA initiation depending on the mouse strain. Spleens were prepared in single cell suspension and loaded onto the RoboSep (STEMCELL technologies) instrument according to the manufacturer's instructions and subjected to B cell negative selection. Purified B cells were seeded at 500,000 cells per well in 96 well round bottom plates (Costar catalog #3799) and either incubated with no stimulation or with 10 μg/mL of LPS (Sigma catalog #L5014) for 48 hours at 37° C. All wells received Monensin (BD Bioscience catalog #554724) according to the manufacturer's instructions. Cells were allowed to incubate for at least 4 hours at 37° C. Samples were transferred to V bottom wells (USA Scientific catalog #651201) and spun at 1200 rpm for 5 minutes at 4° C. Cells were resuspended in 200 μL of PBS containing 4% fetal bovine serum and 25 μg/ml of total mouse IgG and blocked for 30 minutes at 4° C. Plates were spun again and resuspended in 90 μL of PBS/2% FCS with the addition of 10 μL of antibody cocktail as described above, and incubated for 20 minutes at 4° C. with the addition of 5 μL 7AAD for the last 10 minutes of the staining procedure. Addition of 100 μL of buffer to the samples with subsequent spin was used as a wash. Samples could be resuspended in buffer for surface analysis of protein and immediate acquisition or resuspended in Fix/Perm (eBioscience catalog #11-5773) for intracellular staining of IL-10 (BioLegend catalog #505008), TGF-beta (BioLegend catalog #141404) and FoxP3 (eBioscience catalog #11-5773-82) according to the manufacturer's instructions. Additional surface staining included TGF-beta and Tim-1 (BioLegend catalog #119506) antibodies. All samples were acquired and analyzed as described above.

Animals and Cardiac Allograft Model

C57BL/6 and BALB/c mice were obtained from Charles River (Kingston, N.Y. or Raleigh, N.C.) and used in these experiments between 8 and 13 weeks of age. The donor allogenic C57BL/6 mice were first anesthetized with an intraperitoneal injection of Ketamine (Fort Dodge Animal Health/Pfizer, Fort Dodge, Iowa) and Xylazine (Lloyd, Shenandoah, Iowa) and a median sternotomy was performed. The donor heart was slowly perfused in situ with 1 ml of cold heparinized Ringer's lactate solution (Baxter Healthcare, Deerfield, Ill.) through the inferior vena cava and aorta before the superior vena cava and pulmonary veins were ligated and divided. The ascending aorta and pulmonary artery were then transected, the graft removed from the donor and the heart was stored in ice-cold saline until engraftment. A recipient mouse (Balb/c) was similarly anesthetized and prepped as described above for donor mice, except that the abdominal cavity was opened. Using a surgical microscope to view the opened abdominal cavity, the abdominal aorta (AA) and the inferior vena cava (IVC) was isolated. The donor heart was placed into the recipient abdomen (upside down) and the grafts revascularized with end-to-side anastomoses between the donor pulmonary artery and the recipient inferior vena cava, as well as the donor's aorta and the recipient abdominal aorta. After hemostasis was confirmed, the abdominal muscle was closed with a running 5-O Vicryl suture (Ethicon, Johnson & Johnson, Somerville, N.J.), and the skin closed with running 5-0 Ethilon suture (Ethicon). Standard post-op pain assessment and management was performed. Grafts were assessed by palpation 5-7 times per week for the first 30 day, and then 3-4 times per week until the end of the study.

C57Bl/6 mice were treated with one 20 mg/kg intravenous dose of rhGAA (Genzyme Corporation), 3 consecutive intraperitoneal doses of 5 mg/kg methotrexate (APP Pharmaceuticals, LLC), and either 1D11 or 13C4 at 5 mg/kg (Genzyme Corporation) for 3 doses every other day. Methotrexate, 1D11, and 13C4 treatment commenced with rhGAA injections. Spleens were collected 7 days after treatment initiation and were processed as described above for B cells, culture and flow analysis. Additionally, rhGAA titer data was obtained by treating animals as described above, with rhGAA dosed weekly over 12 weeks, methotrexate dosed for either 1 or 3 cycles, and 1D11 or 13C4 dosed 3 times a week every other day for 12 weeks. Serum samples were collected every 2 weeks for ELISA analysis.

Histopathology and Immunohistochemistry

Cardiac grafts were fixed in 10% neutral buffered formalin, bisected along the longitudinal axis to expose the right and left ventricles and the outflow tract, and routinely processed for paraffin embedding. Sections were cut at 5 microns and were stained with hematoxylin and eosin (H&E) or Masson's trichrome. Serial sections were also immunostained as described below. Each H&E-stained section was evaluated qualitatively for various features of allograft rejection pathology (e.g., vasculitis, myocardial degeneration and necrosis, myocarditis) using a histologic grading scheme. Immunohistochemistry was performed using a Bond-Max automated immunostaining system (Leica Microsystems Inc., Buffalo Grove, Ill.). To detect CD3 and Foxp3 dual immunopositive cells, graft tissue sections were subjected to double immunostaining with anti-CD3 and anti-Foxp3 antibodies using Bond Polymer Refine Detection kit and Bond Polymer AP Red kit (Leica, Buffalo Grove, Ill.) following manufacturer's guidelines. Briefly, deparaffinized sections of paraffin-embedded grafts were subjected to heat-induced epitope retrieval (25 min at 99° C.), incubated with serum free protein block (Dako, Carpentaria, Calif.), rabbit monoclonal anti-CD3 antibody (Lab Vision/Neo Marker), peroxidase-conjugated polymer, peroxidase block, and diamino benizidene detection reagent followed by rat anti-mouse Foxp3 antibody (eBioscience Inc., San Diego, Calif.) and then a rabbit anti-rat antibody (Vector Laboratories, Inc., Burlingame, Calif.). Slides were then incubated with Bond Polymer AP and mixed red detection reagent and finally counterstained with hematoxylin. In negative control slides, primary anti-CD3 and anti-Foxp3 antibodies were replaced with Chromepure whole rabbit IgG (Jackson ImmunoResearch Laboratories, Inc., West Grove, Pa.) and rat IgG2a (AbD Serotec, Raleigh, N.C.), respectively.

Serum Alloantibody Levels

Serum alloantibody levels were determined by incubating serum from cardiac transplanted or normal mice at 1:50 dilutions with an SV40 transformed C57BL/6 fibroblast line (SVB6) followed by detection of fibrobast bound antibodies (alloantibodies) using FITC rabbit anti-mouse IgG (Dako, Carpinteria, Calif.) and by flow cytometric analysis. Geometric mean fluorescent intensities of serum stained fibroblasts were divided by isotype control stained fibroblasts to normalize alloantibody levels between experiments. The binding of serum antibodies to allogenic fibroblasts were specifically alloantibodies because the same serum samples did not bind to a SV40 transformed BALB/c fibroblast line (SVBalb) (data not shown).

Adoptive Transfer Mouse Model

C57BL/6 mice were obtained from Jackson Laboratories and were housed under specific pathogen free conditions. Control mice were given a single intravenous injection of rhGAA at 20 mg/kg. Tolerized mice were given a single intravenous injection of rhGAA at 20 mg/kg, in addition to three daily consecutive methotrexate intraperitoneal injections of 0.5 mg. Spleens were harvested on day six after the initial rhGAA injection, from both donor groups, and processed into pooled single cell suspensions. Cells were washed and filtered through a 0.22 μM filter. Cells were then enriched for B cells using a StemCell Technologies RoboSep cell separation system, and resuspended to allow for a 200 μl intravenous injection. Tolerized and non-tolerized recipient groups received either a high cell $10 \times 10^6$ or a low cell $5 \times 10^6$ concentration via intravenous injections. Control groups were given rhGAA only, or rhGAA and methotrexate (single cycle of three consecutive daily MTX injections). All groups received weekly intravenous rhGAA 20 mg/kg injections, and were retro-orbitally bled biweekly for 16 weeks, into BD Vacutainer serum separator tubes. Serum was removed and stored below −20° C. until used for ELISA. Anti-rhGAA antibody titers were determined using ELISA, read on a SpectraMax M2, and calculated using Softmax to extrapolate titer value. Raw data Softmax files and EXCEL spreadsheets containing control and titer information were stored on network servers. All graphs and statistics were generated using GraphPad Prism software.

Example 1

Anti-Drug Antibodies are Produced in Response to Antibody Therapeutics

Figure 1B:
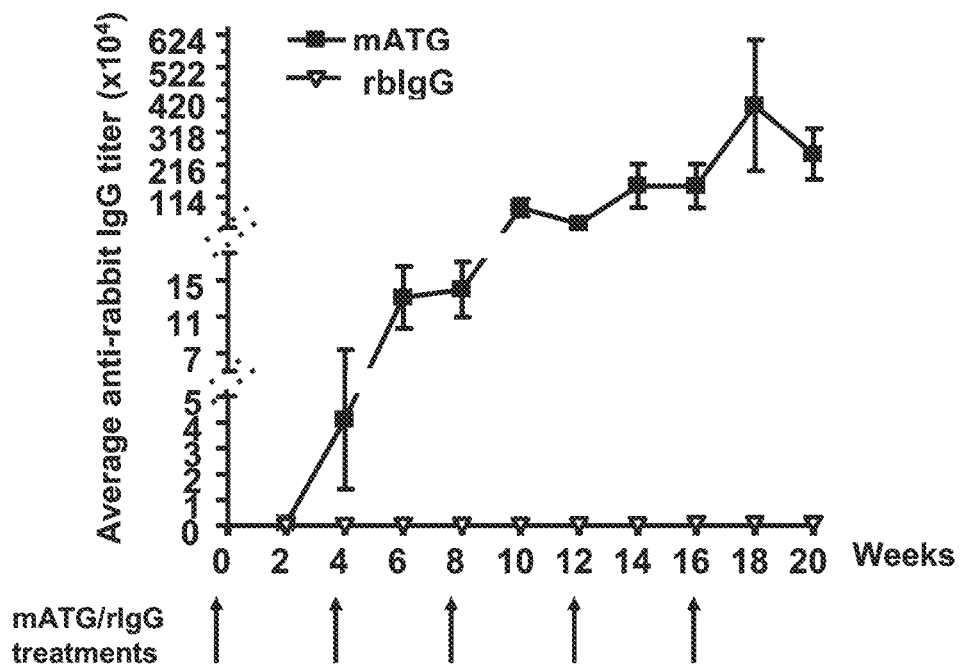

Polycloncal antibody mATG binds to a variety of immune cell types, including antigen-presenting cells. Our data show that a single course of mATG (two doses of 25 mg/kg given three days apart, administered intraperitoneally) could generate anti-mATG IgG titers as high as 100,000 (FIG. 1A) in mice. When given as successive monthly injections (5 mg/kg, every 4 weeks), anti-mATG titers were further increased with titers up to $5 \times 10^6$ after five monthly injections (FIG. 1B). For both the single course and the monthly injections, rabbit IgG (rbIgG) was used as a control.

Figure 2:
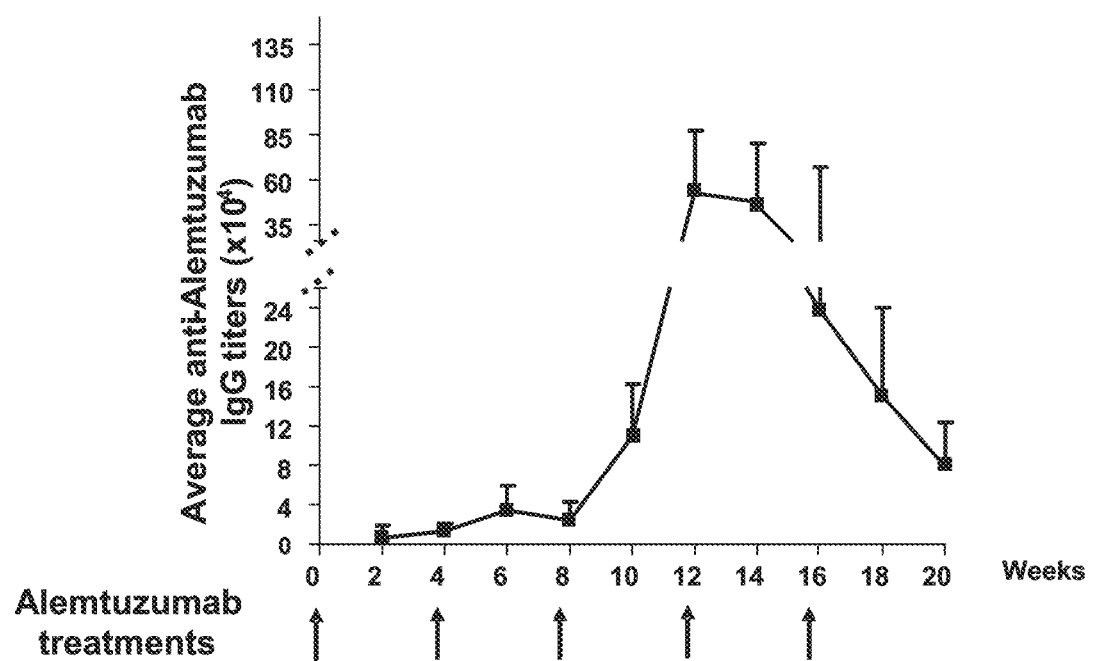
FIG. 2 shows average alemtuzumab-specific IgG titers following five monthly treatments with alemtuzumab. Arrows indicate time points at which alemtuzumab was administered.

As alemtuzumab does not cross-react with murine CD52, preclnical studies with alemtuzumab must be done in huCD52 Tg mice where the transgene expression pattern is similar to CD52 expression in humans. Similar to mATG, intravenous administration of alemtuzumab (0.5 mg/kg) elicited significant ADA responses in huCD52 Tg mice. These responses increased through the first four treatments and then declined such that following the fifth dose of alemtuzumab, huCD52 Tg mice no longer generated anti-alemtuzumab antibodies (FIG. 2). This non-responsiveness suggests that natural tolerance had occurred (Rosenberg et al., Blood, 93(6):2081-8 (1999)).

The data show that the ADA titers against mATG in the C57BL/6 mice and the ADA titers against alemtuzumab in the huCD52 Tg CD1 mice were high (>100,000). This high level of immunogenicity may be attributed to the ability of mATG and alemtuzumab to bind antigen-presenting cells, thereby enhancing antigen processing and presentation for inducing immune responses against them.

Example 2

Figure 3:
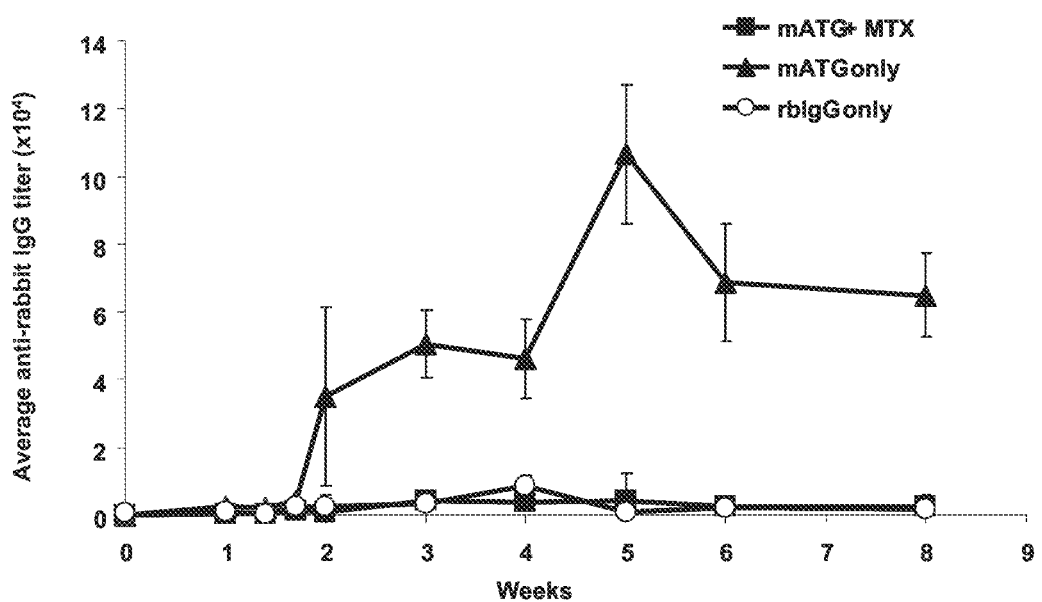
FIG. 3 shows suppression of anti-mATG IgG responses by methotrexate (MTX) following a single course of mATG. Mice were treated with mATG only, rbIgG only, or mATG and methotrexate.

Methotrexate Controls Anti-mATG IgG Responses with a Single Cycle of Administration Elevated antibody titers have been reported following Thymoglobulin® treatment, and case reports of serum sickness, acute renal failure and cardiovascular reactions have been described in patients treated with Thymoglobulin® (Boothpur et al., supra; Lundquist et al., Liver Transpl, 13(5):647-50 (2007); Busani et al., Minerva Anestesiol, 72(4):243-8 (2006); Tanriover et al., Transplantation, 80(2): 279-81 (2005); Buchler et al., Clin Transplant, 17(6):539-45 (2003)). To determine if methotrexate could reduce anti-ATG responses, and thus, mitigate these safety concerns, a three-day regimen of methotrexate, given only as a single cycle, was evaluated as a means of controlling anti-mATG IgG responses in mice. This is distinct from the regimen that was previously published in that only a single cycle of methotrexate was administered with mATG as opposed to at least three cycles that were given in the context of ERTs. Methotrexate (Calbiochem catalog #454125) administered intraperitoneally at 5 mg/kg for six consecutive days starting on the first of two mATG administrations (25 mg/kg, 3 days apart) could suppress anti-mATG IgG responses through at least eight weeks following treatment by 95% when comparing area under the effect curves (FIG. 3).

Figure 4A:
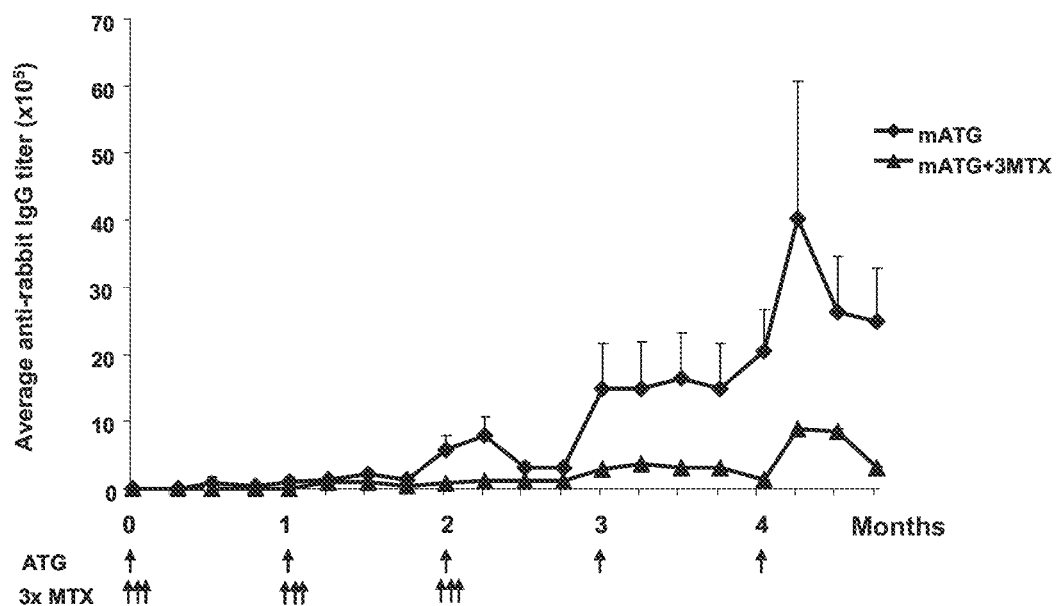
FIGS. 4A-C show the effects of methotrexate on anti-rabbit IgG responses throughout a course of five monthly treatments with mATG. Arrows indicate time points at which mATG or methotrexate were administered.

Next, the effect of methotrexate on anti-mATG titers following five monthly injections of mATG at 5 mg/kg/injection was evaluated. Monthly injections of mATG treatment were performed because lymphocyte repopulation is near complete one month following mATG treatment (Ruzek, supra). Anti-drug antibody responses were then quantified weekly through 20 weeks of monthly treatments. During this period, despite CD4+ T cell depletion by mATG, antibody titers reached as high as 5 million (FIG. 1B). Interestingly, animals that received non-specific rabbit IgG at the same dose level and schedule as mATG showed low anti-rabbit IgG responses (FIG. 1B). One possibility for the enhanced immunogenicity of mATG may be the specific binding of mATG to antigen presenting cells (APCs) such as follicular dendritic cells, which when in the presence of complement may significantly enhance B cell responses. Two treatment regimens of methotrexate also were evaluated. In previous work with enzyme-replacement therapy (ERT), three cycles of methotrexate given during the first three doses of acid alpha-glucosidase provided a sustained reduction in antibody titer through at least eight months of weekly ERT dosing (Joseph et al., Clin Exp Immunol, 152(1):138-46 (2008)). A similar course of methotrexate was evaluated in the context of mATG where 5 mg/kg of methotrexate was given within 15 minutes of mATG administration as well as 24 and 48 hours following each of the first three monthly mATG treatments. This regimen successfully decreased anti-mATG antibody responses from titers of approximately 4 million to titers of 816,000, yielding a reduction of 79% comparing area under the effect curves (FIG. 4A).

Figure 4B:
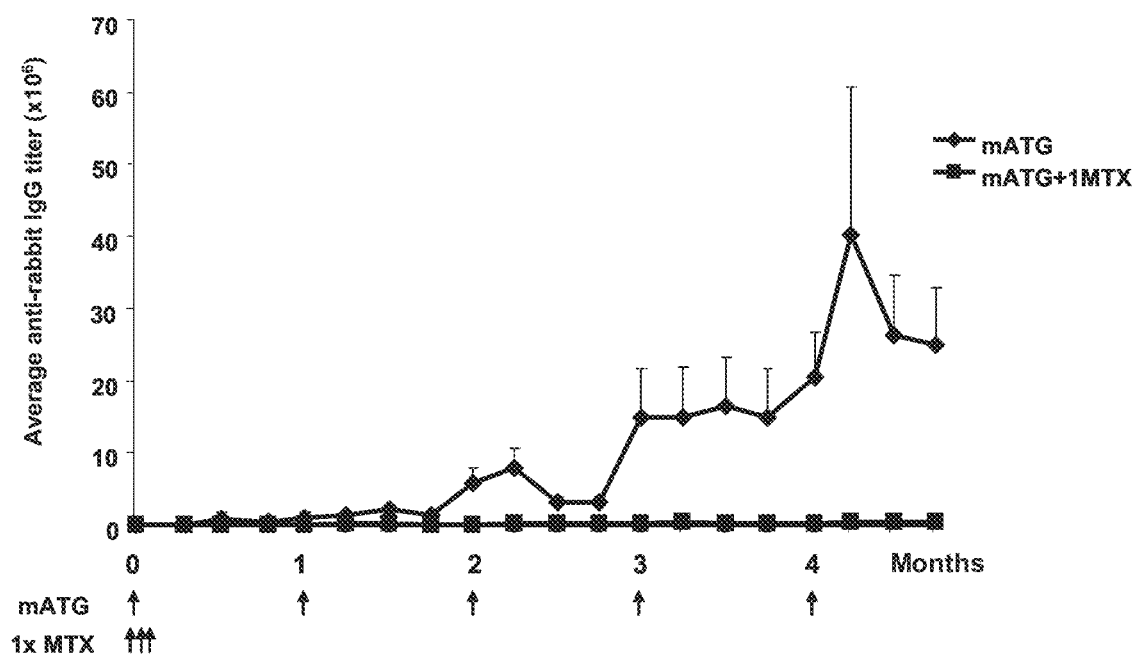
Figure 4C:
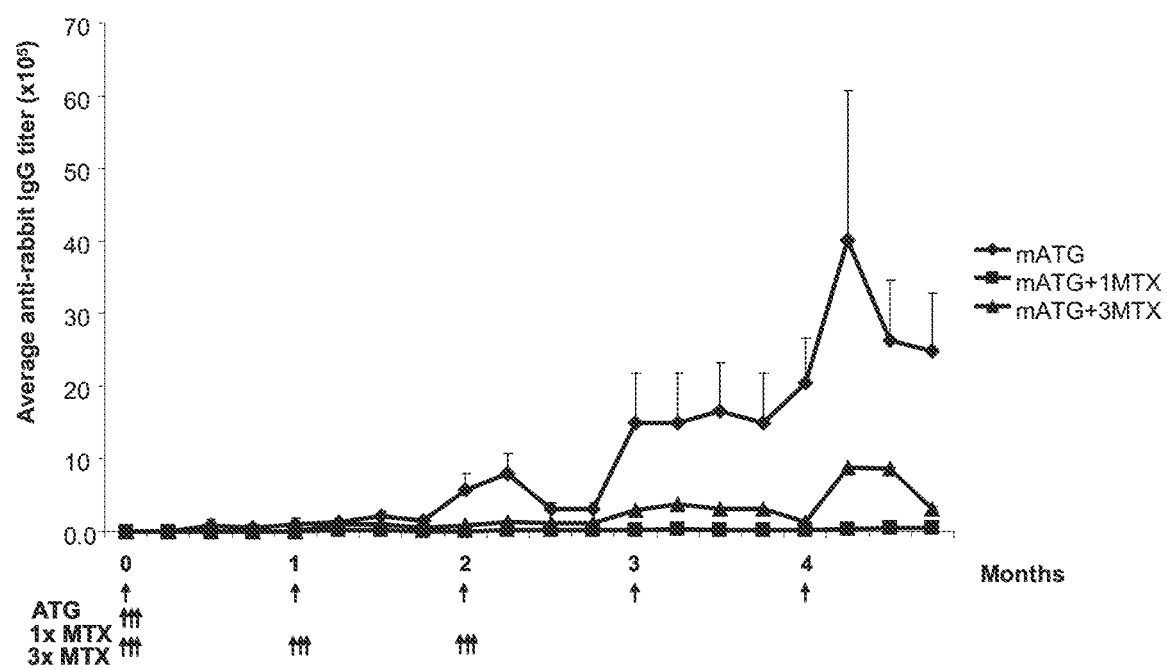

Additionally, the effect of a single course of methotrexate given around only the first of five monthly mATG treatments on anti-mATG IgG responses was evaluated and compared directly with a three-cycle regimen. Surprisingly, this single cycle regimen reduced anti-mATG IgG titers even further than the three-cycle regimen, to a titer of approximately 50,000 (FIG. 4B). Comparing area under the effect curves, the single cycle regimen reduced anti-mATG IgG titers by 98%, while the three cycle regimen reduced titers by 69% (FIG. 4C). The increased effects of the single-cycle versus three-cycle regimen suggests that increasing methotrexate exposure may actually antagonize its tolerizing effects, perhaps by killing the cells that are mediating the control over antibody titer.

Example 3

Methotrexate Induces an Active Mechanism of Immune Tolerance

As shown above, a very brief course of methotrexate can significantly control antibody responses through multiple rounds of antigen challenge. In this context, the brief cycle was a single cycle of methotrexate that produced lasting effects (on both antibody titers and cytokine levels) over the course of months of testing. This long-lived control of the antibody response suggests that methotrexate can successfully induce immune tolerance. Methotrexate had thus far been evaluated in the context of five consecutive monthly doses of mATG. To further evaluate whether an immune tolerance mechanism had been activated, animals that originally received five monthly mATG injections were withheld from treatment for eight weeks. Following this rest period, the animals were given a final injection of mATG. If a mechanism of immune tolerance was employed, anti-mATG IgG titers should not increase significantly following the sixth mATG treatment.

Figure 5:
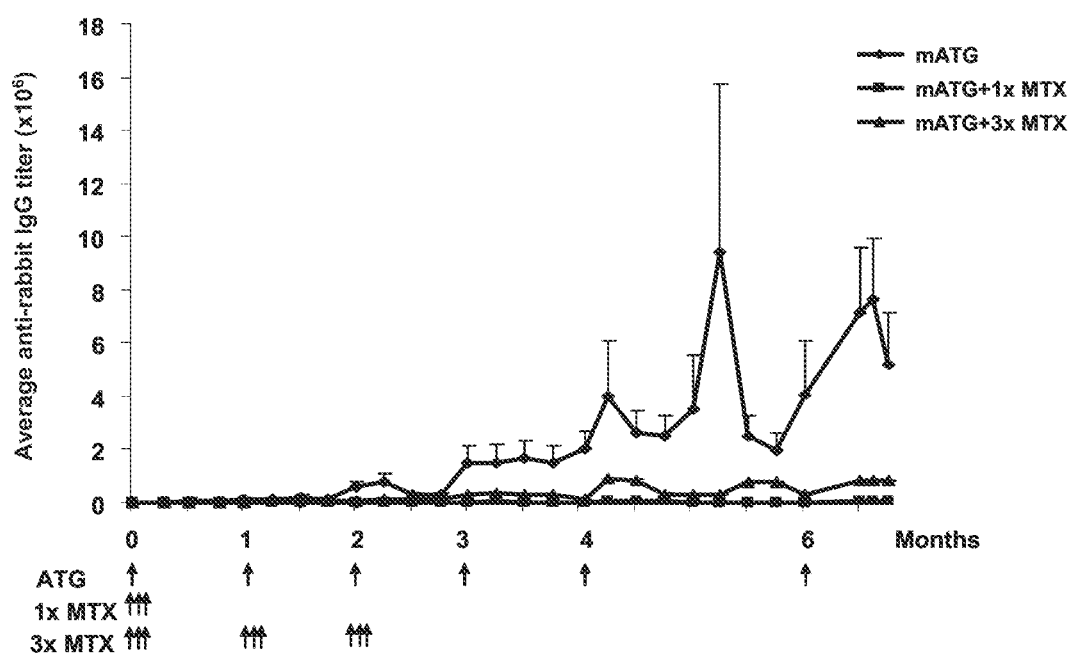
FIG. 5 shows that average anti-rabbit IgG titers are reduced after mATG re-challenge in methotrexate-treated mice (single and multiple methotrexate cycles), as compared to mice treated with mATG but not methotrexate. Arrows indicate time points at which mATG or methotrexate were administered.

Our data show that animals that were not dosed with methotrexate experienced an increase in anti-mATG IgG titers, as expected (FIG. 5). By contrast, animals that received just one cycle of methotrexate with the first injection of mATG did not generate significantly greater anti-mATG IgG titers (FIG. 5). A similar trend was observed in animals treated with three cycles of methotrexate, though the effect was not as dramatic (FIG. 5). When comparing area under the effect curves, the single course of methotrexate reduced titers by 99% while the three cycle regimen reduced titers by 85%. These data indicate that methotrexate can maintain control over recall responses, suggesting that the mice have developed tolerance against this antigen.

Figure 6:
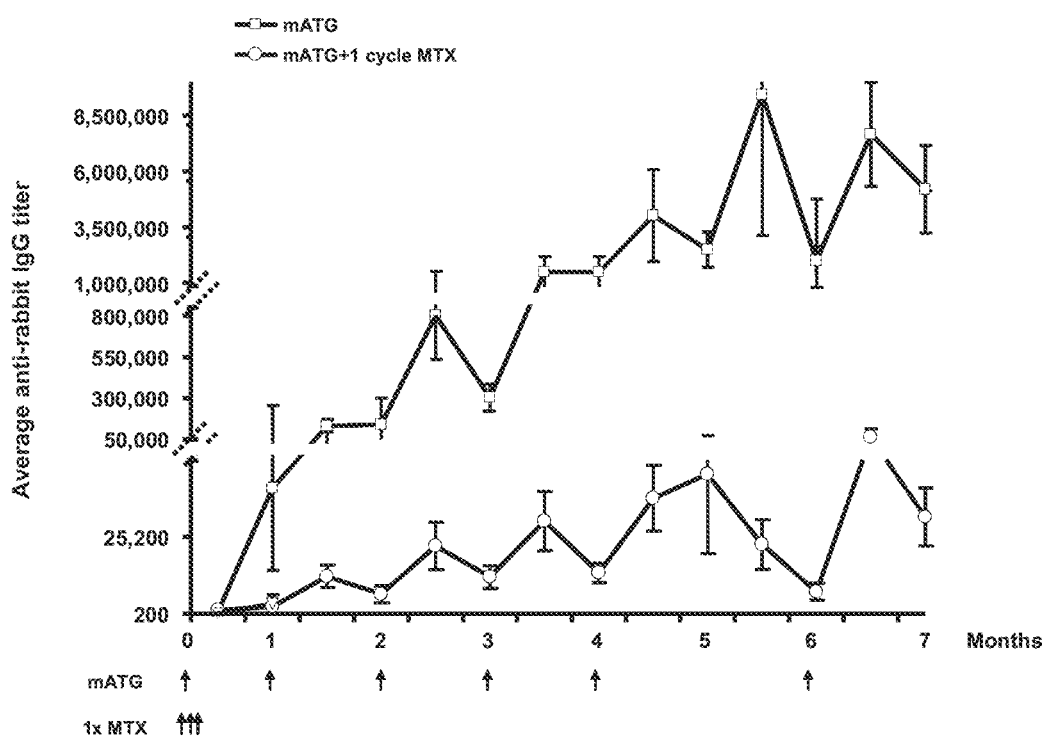
FIG. 6 shows that the average anti-rabbit IgG titer in mice treated with mATG and a single cycle of methotrexate is 100 fold less than that in mice treated with mATG alone. Arrows indicate time points at which mATG or methotrexate were administered.

Although methotrexate-treated animals generated measurable titers that increase with successive mATG treatments, overall, titer levels in methotrexate-treated animals were consistently 100-fold lower than those observed in animals treated with mATG alone (FIG. 6). The lower level of antibody titers should significantly reduce the potential for safety risks and efficacy effects. Although not wishing to be bound by theory, these data suggest that an active mechanism of control has been induced that can significantly reduce anti-mATG IgG responses, and is maintained long after methotrexate treatment.

Example 4

Figure 7A:
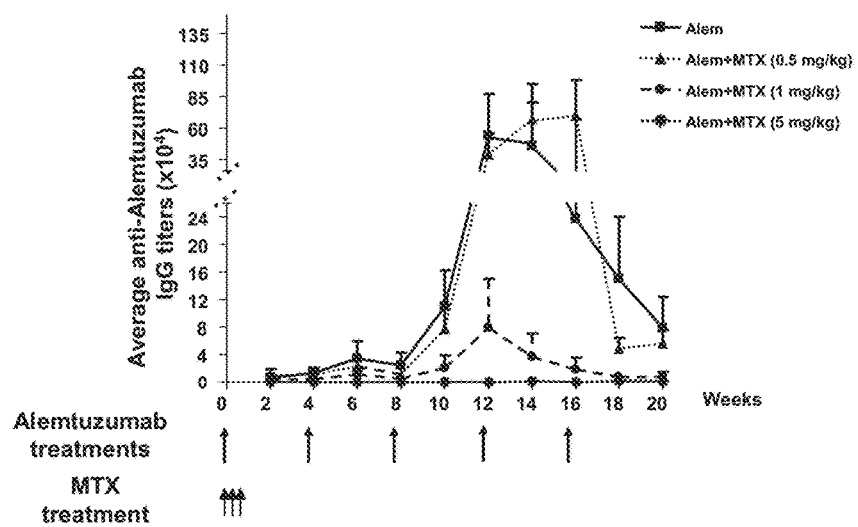
FIGS. 7A-C show that methotrexate can reduce average anti-alemtuzumab IgG titers in huCD52 Tg mice.

A Single Cycle of Methotrexate can Significantly Control Anti-Alemtuzumab Responses In relapsing-remitting multiple sclerosis, alemtuzumab is dosed in annual cycles and patients can generate ADA (Coles et al., N Engl J Med, 359(17):1786-801 (2008)). As immunogenicity and pharmacokinetic testing is ongoing in multiple phase III studies, it is unclear whether anti-alemtuzumab antibodies will impact exposure, efficacy, and/ or safety in a subset of patients. Thus, we evaluated whether a single cycle of methotrexate could control ADA titers following five monthly single injection cycles of alemtuzumab. HuCD52 Tg mice were given alemtuzumab (0.5 mg/kg) intravenously monthly for five consecutive months. Methotrexate was given at 0.5, 1 or 5 mg/kg 15 minutes prior to the first monthly alemtzumab dose as well as 24 and 48 hours after the dose. 1 mg/kg of methotrexate provided some benefit, as it reduced anti-alemtuzumab responses by 88% (FIG. 7A). 5 mg/kg of methotrexate successfully reduced anti-alemtuzumab IgG responses by 99% (FIG. 7A). Methotrexate appeared to have no effect on natural tolerance.

Figure 7B:
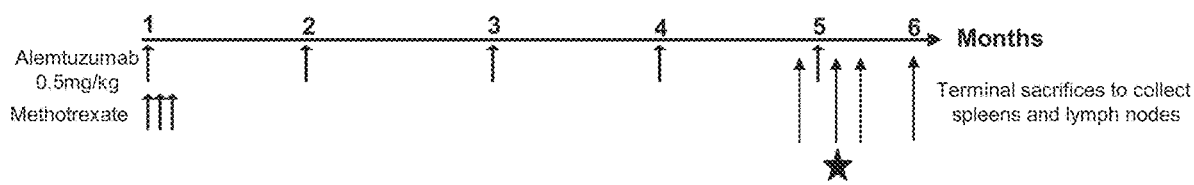
Figure 7C:
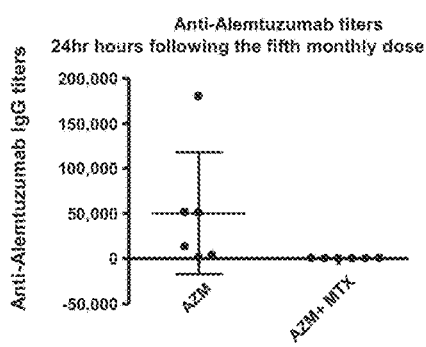
Figure 8A:
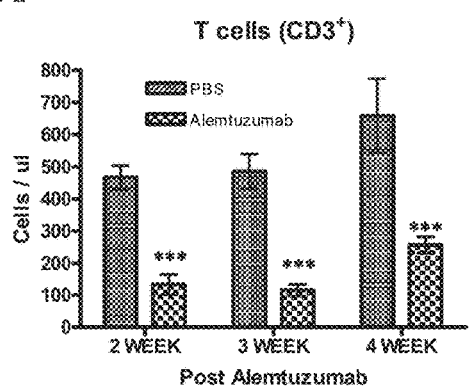
FIGS. 8A-D show the absolute cell number/µl of whole blood of circulating T cells in mice treated with five daily doses of 0.5 mg/kg alemtuzumab or phosphate-buffered saline (PBS).
Figure 8B:
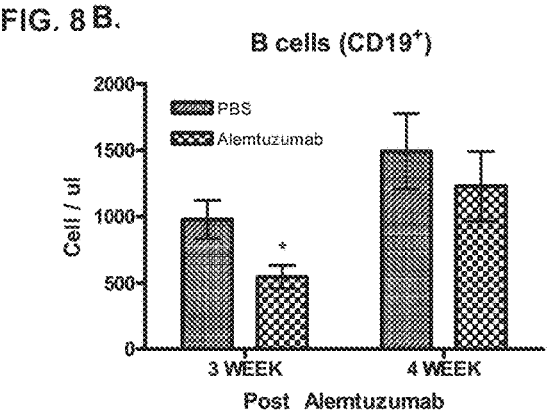
Figure 8C:
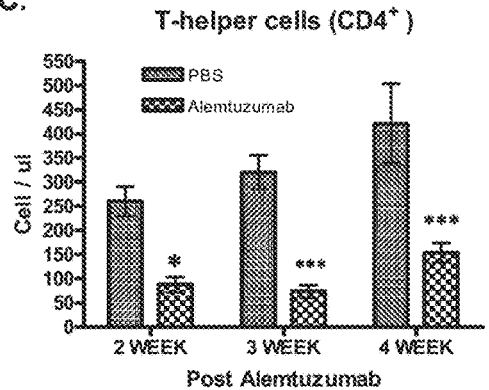
Figure 8D:
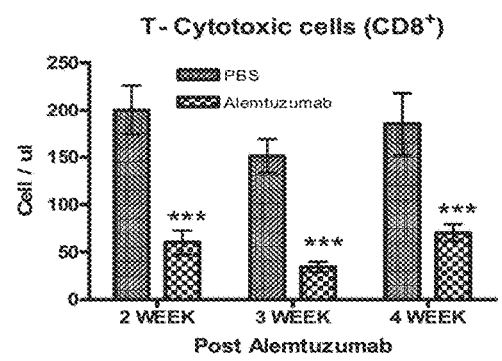

A second study confirmed the above findings. As above, huCD52 transgenic mice were treated with five monthly doses of 0.5 mg/kg alemtuzumab. The mice also were treated with or without three daily doses of 5 mg/kg/day of methotrexate in connection with the first administration of alemtuzumab (FIG. 7B). Serum samples were collected throughout the study to assess anti-alemtuzumab titers and confirm tolerance. Titer data were obtained at 24 hours after the fifth monthly dose. The data demonstrated that methotrexate reduced anti-alemtuzumab antibody titers (FIG. 7C).

Example 5

Methotrexate can Control Anti-Alemtuzumab Antibody Responses in the Context of a Clinically Relevant Alemtuzmab Dosing Regimen A series of experiments was conducted to evaluate if methotrexate could successfully control ADA in the context of a clinically-relevant dosing scheme of alemtuzumab in huCD52 Tg mice. In the clinic, alemtuzumab is dosed as an initial cycle of five daily treatments of 12 mg/day. Twelve months following the initial treatment cycle in patients, an additional cycle of three daily 12 mg doses of alemtuzumab is administered. At the time of the second treatment cycle, the levels of circulating $CD19^+$ B cells have recovered to baseline values; however, the levels of circulating $CD4^+$ T helper cells and $CD8^+$ T cytotoxic cells have not fully repopulated (Coles et al., N Engl J Med, 359(17):1786-801 (2008)).

Initially, the depletion and repopulation kinetics of circulating T and B cell subsets following five daily treatments of alemtuzumab was investigated in huCD52 Tg mice. In the peripheral blood of huCD52 Tg mice treated with alemtuzumab for five consecutive days with 0.5 mg/kg (equivalent to the 12 mg/kg human dosage) via intravenous injection, total $CD3^+$ T cells, $CD4^+$ T helper cells, and $CD8^+$ T cytotoxic cells did not recover to pre-treatment levels four weeks following treatment, while the numbers of $CD19^+$ B cells returned to control levels (FIGS. 8A-D).

Figure 9:
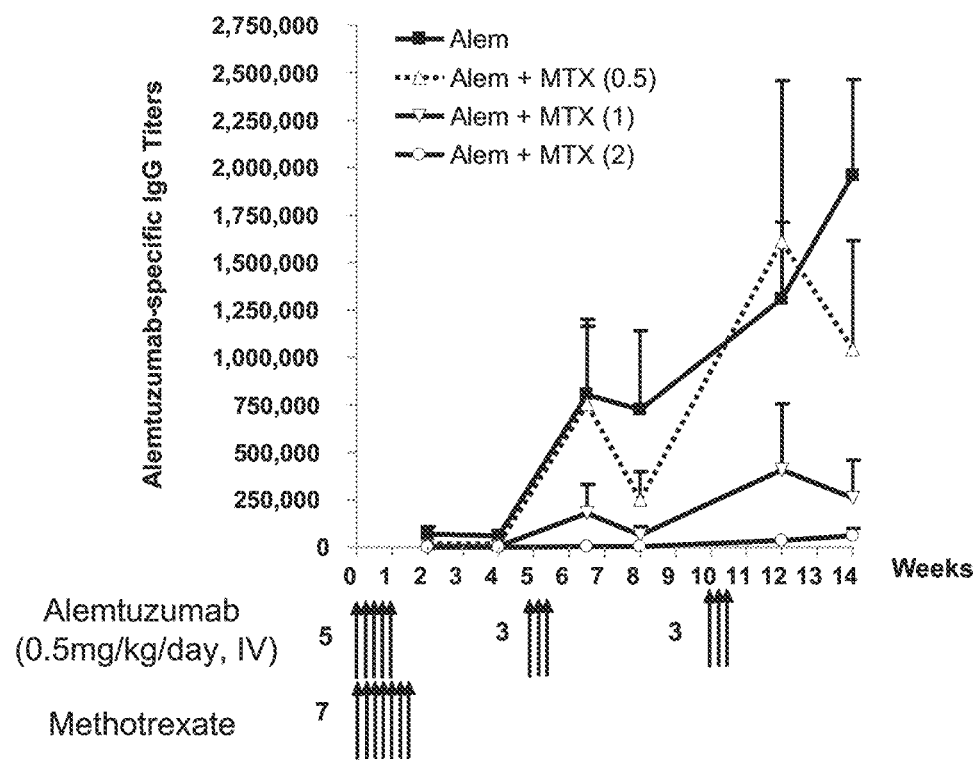
FIGS. 9A-B show alemtuzumab-specific IgG responses.
Figure 9:
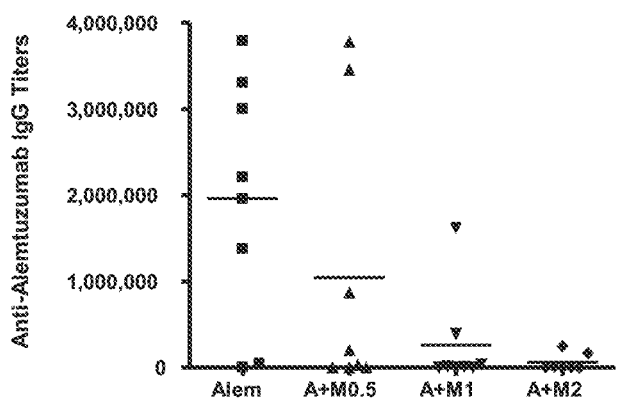

In order to simulate the cellular environment experienced by patients at the time of retreatment, alemtuzumab was re-administered in huCD52 Tg mice between 4 and 5 weeks following the first cycle. Since the initial course of alemtuzumab was a five-day cycle, methotrexate was administered 15 minutes prior to each daily alemtuzumab treatment and for two days afterwards. The maximal cumulative cycle dose of methotrexate given in this regimen is 14 mg/kg (2 mg/kg/day), which is very similar to the cumulative dose of 15 mg/kg when methotrexate is given as a three-day course of 5 mg/kg/day. We evaluated the effects of 2, 1 and 0.5 mg/kg/day administration of methotrexate on anti-alemtuzumab antibodies over three alemtuzumab treatment cycles. At 1 mg/kg, methotrexate appeared to control titers in 7 of the 8 mice tested and overall reduced titers by 79% (FIG. 9B). At 2 mg/kg, methotrexate successfully reduced ADA by 98% when comparing area under the effect curves (FIG. 9A).

Example 6

Methotrexate can Improve the Pharmacokinetics and Pharmacodynamics of mATG

Figure 10:
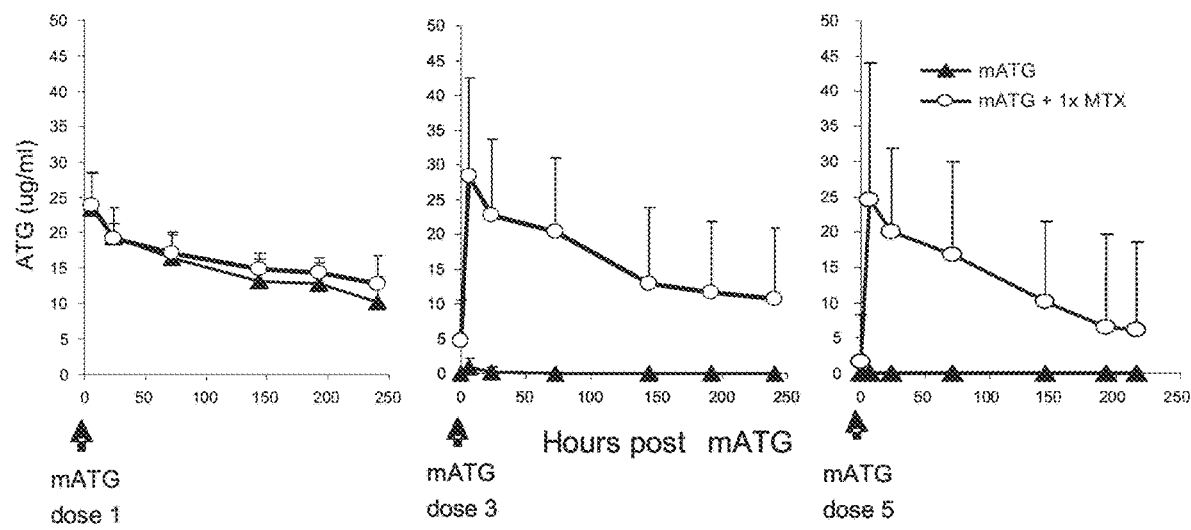
FIG. 10 shows that a single cycle of 5 mg/kg of methotrexate restores circulating mATG levels in mice treated with five monthly doses of mATG.

ADA can interfere with the pharmacokinetics and pharmacodynamics of protein therapeutics. We evaluated whether anti-mATG IgG ADA responses interfered with mATG pharmacokinetics. Mice were treated for five months with monthly injections of either mATG alone or mATG with a single cycle of methotrexate. Methotrexate was administered at 5 mg/kg daily for three doses. Blood was sampled at various times after month 1, month 3, and month 5 to assay the level of circulating mATG (FIG. 10).

At month 1, the levels of circulating mATG were similar among both treatments groups, but at months 3 and 5 only the methotrexate-treated group had measurable levels of circulating mATG. Without methotrexate administration, the levels of mATG measured following the third and fifth mATG doses were significantly lower than those measured after the first dose (FIG. 10). Previous studies have shown that methotrexate significantly reduces anti-mATG IgG responses. Thus, it appears that antibodies against mATG interfere with mATG exposure and pharmacokinetics.

As antibodies against mATG appear to significantly reduce the levels of circulating mATG following repeat dosing, it may be expected that the pharmacodynamics of mATG when redosed is negatively affected as well. Lymphocyte depletion in the blood, spleen and lymph nodes was evaluated after the fifth monthly mATG treatment, when titers were at their highest. As described above, animals treated with methotrexate were only given a single cycle of treatment.

Figure 11:
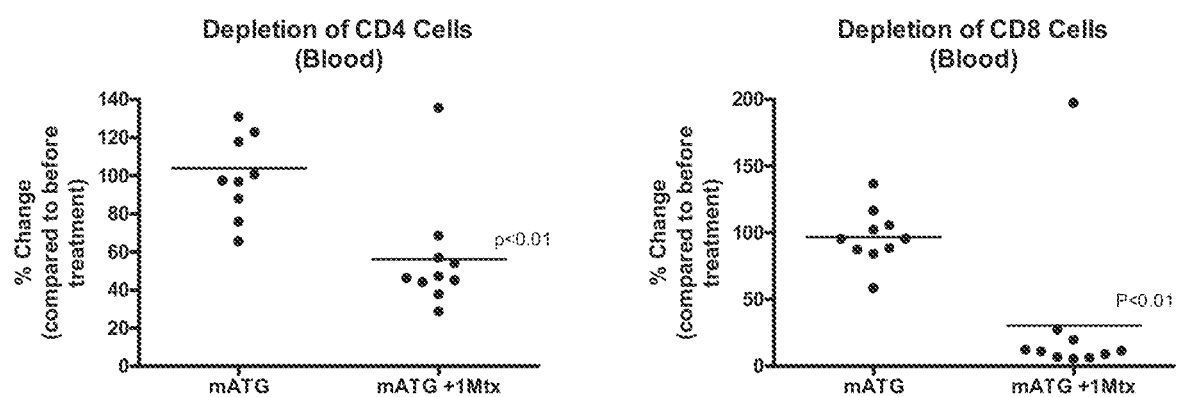
FIG. 11 shows that mice treated with five monthly treatments of mATG and a single cycle of methotrexate have enhanced mATG-mediated $CD4^+$ and $CD8^+$ T cell depletion in blood after the fifth dose of mATG. These data are pooled from two experiments.
Figure 12A:
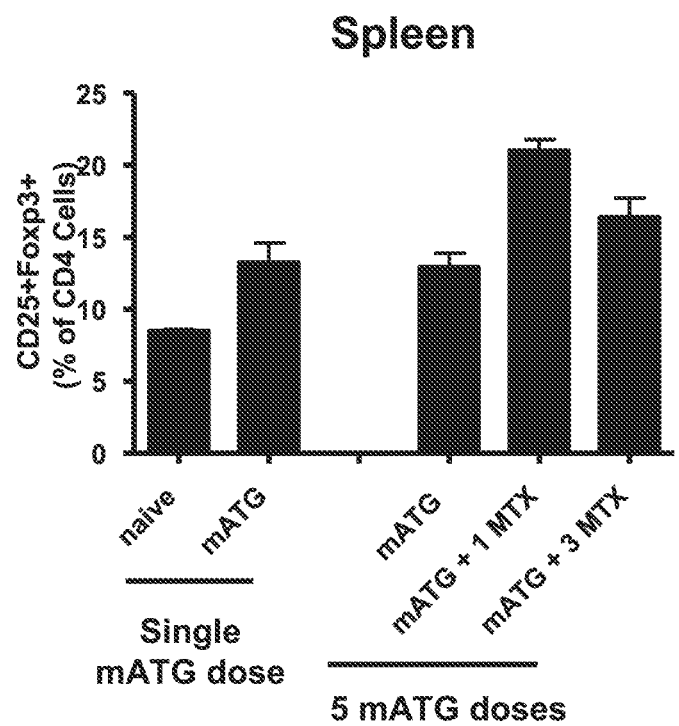
FIGS. 12A-B show that mice treated with a single cycle of methotrexate exhibit increased percentages of T regulatory ($CD25^+Foxp3^+$) cells following a fifth monthly mATG treatment. Mice were treated with five monthly treatments of mATG alone, or five monthly treatments of mATG and a single cycle of methotrexate, or five monthly treatments of mATG and three cycles of methotrexate.
Figure 12B:
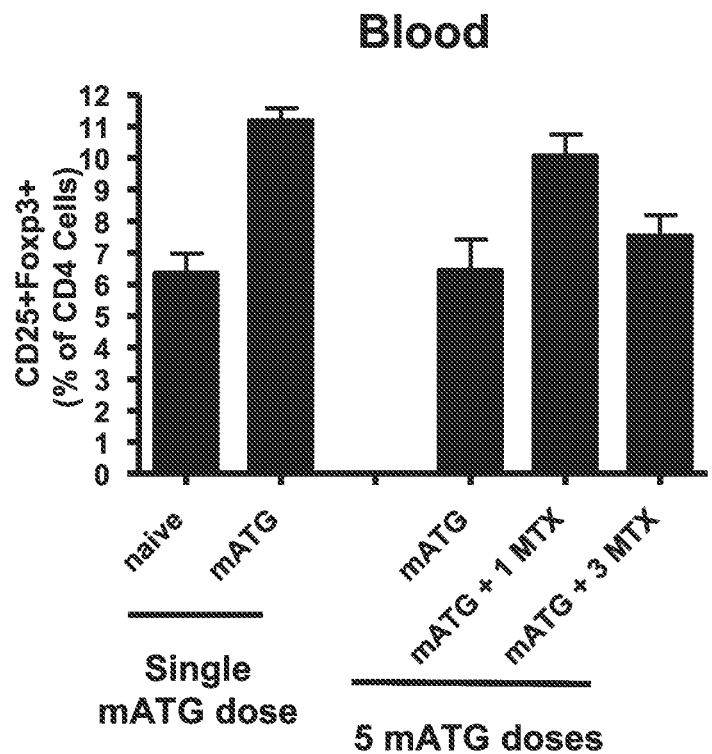

Levels of circulating $CD4^+$ and $CD8^+$ T cells were unchanged after the fifth mATG treatment in animals treated with mATG but not methotrexate. However, in animals treated with mATG and one cycle of methotrexate, circulating $CD4^+$ and $CD8^+$ T cells were significantly depleted (FIG. 11). This effect was similarly observed in spleen and lymph nodes as well. Methotrexate treatment enhanced the ability of mATG to increase the percentage of T regulatory cells in the spleen and blood (FIGS. 12A-B). A similar effect was observed in blood and lymph nodes. The enhanced presence of T regulatory cells following mATG and Thymoglobulin® treatment has been postulated to contribute to the efficacy of this therapeutic (Ruzek et al., Blood, 111(3): 1726-34 (2008)). The ability of methotrexate to help maintain this effect following successive courses of mATG is a potential added benefit of significantly reducing antibody anti-rabbit IgG titers.

Figure 13A:
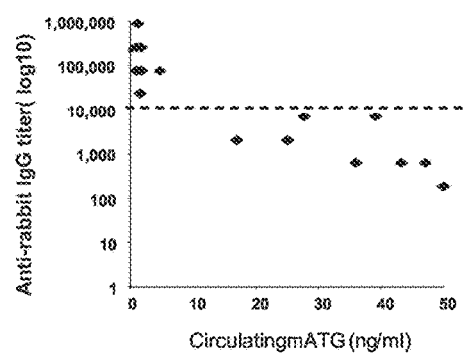
FIG. 13A shows that an anti-rabbit IgG titer greater than 10,000 can interfere with pharmacokinetics of mATG.
Figure 13B:
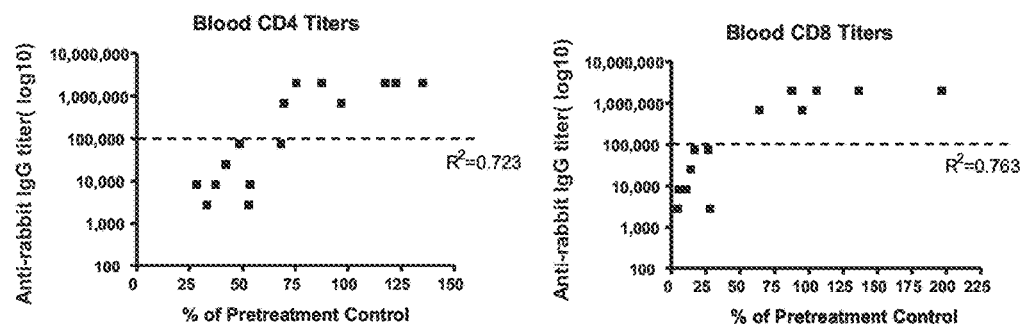
FIG. 13B shows that an anti-rabbit titer greater than 100,000 can interfere with CD4 and CD8 cell depletion. % of pretreatment control refers to the percent of CD4 and CD8 titers relative to their respective levels prior to mATG treatment.

Thus far, pharmacokinetic and efficacy studies suggest that anti-mATG antibodies interfere with the exposure and efficacy of mATG. A direct comparison between anti-mATG IgG titer and mATG exposure reveals that when end-point titers are greater than 10,000, the level of circulating mATG is significantly reduced (FIG. 13a). Moreover, when anti-mATG IgG titers are greater than 100,000, mATG-mediated cell depletion is inhibited (FIGS. 13b and 13c). The $R^2$ correlation between titer and cell depletion is >0.7.

Example 7

Methotrexate can Improve the Pharmacodynamics of Alemtuzumab

Methotrexate not only enhances the pharmacodynamics of mATG, but also restores alemtuzumab-mediated depletion of circulating T and B cells when anti-alemtuzumab responses appear to neutralize some of the depleting activity. In the studies described in this example, five monthly intravenous injections of alemtuzumab were given to huCD52 Tg mice with and without methotrexate. 5 mg/kg of methotrexate was administered daily for the first three days of the 6 month study. Blood was harvested from animals of both treatment groups two days prior to the fifth dose and one day after the fifth dose of alemtuzumab. Cell populations were assessed by flow cytometry as described in Example 6.

Figure 14:
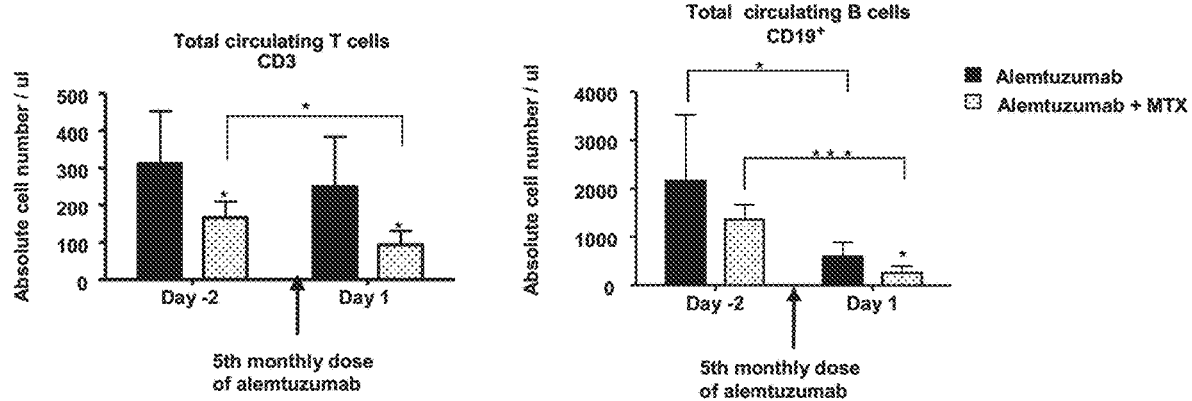
FIG. 14 shows that mice treated with 5 mg/kg of methotrexate exhibit enhanced alemtuzumab depletion of circulating $CD3^+$ T cells and $CD19^+$ B cells after a fifth monthly dose of alemtuzumab. Mice were treated with alemtuzumab alone, or alemtuzumab and a single cycle of methotrexate for the first three days of the study. Asterisks indicate measurements with statistically significant differences (*, $p<0.05$; ***, $p\leq0.0001$).

Our data show that the fifth monthly dose of alemtuzumab appeared to no longer deplete T cells, as the absolute number of circulating T cells seemed similar before and after treatment (FIG. 14 (each time point represents a different set of animals)). By contrast, methotrexate appeared to have restored the ability of alemtuzumab to deplete T cells (P=0.012). When comparing the absolute numbers of circulating T cells in animals treated with alemtuzumab alone and animals treated with both alemtuzumab and methotrexate at either two days prior to or one day following alemtuzumab dosing, the numbers of circulating T cells were significantly lower in methotrexate-treated animals (P=0.034 and 0.02; FIG. 14). Similarly, methotrexate treatment appeared to enhance the depletion of B cells by alemtuzumab (P=1.2× $10^{-5}$, P=0.02 respectively), and the number of circulating B cells was decreased further in methotrexate-treated animals one day following treatment (FIG. 14).

Example 8

Figure 15A:
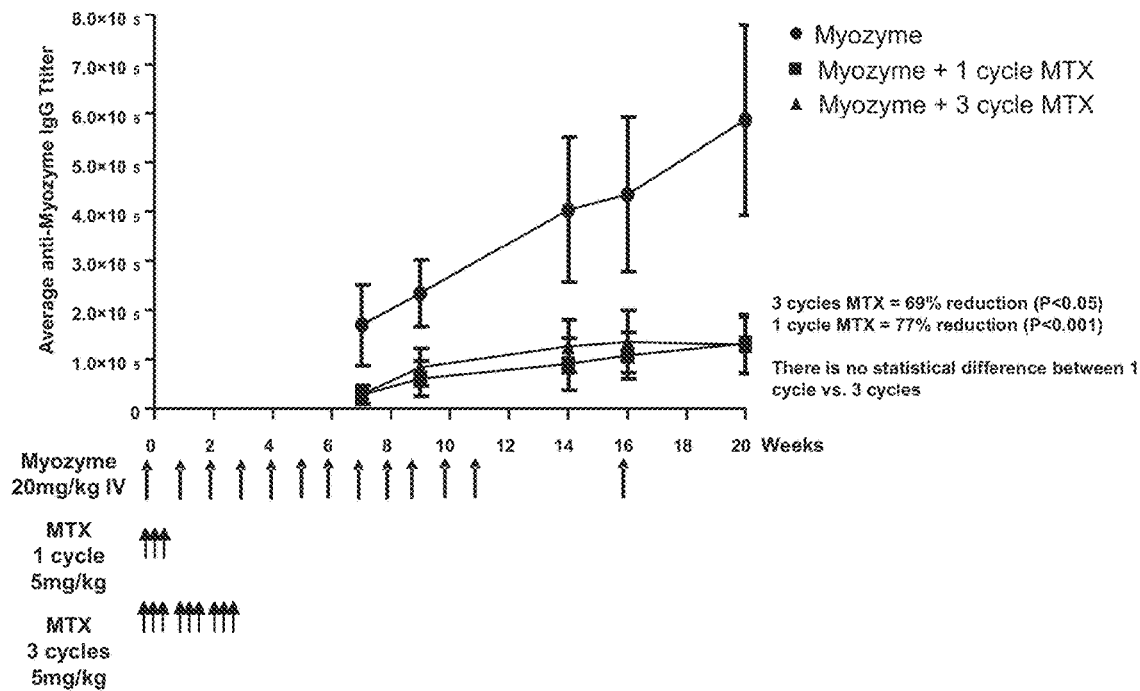
FIG. 15A shows that a single cycle of methotrexate can reduce recombinant human acid alpha-glucosidase (rhGAA)-specific IgG titers throughout treatment, and even four weeks after the last rhGAA treatment, in a 16-week study. Arrows indicate time points at which rhGAA and methotrexate were administered. Mice were treated with rhGAA alone, or rhGAA and a single cycle of methotrexate, or rhGAA and three cycles of methotrexate.
Figure 15B:
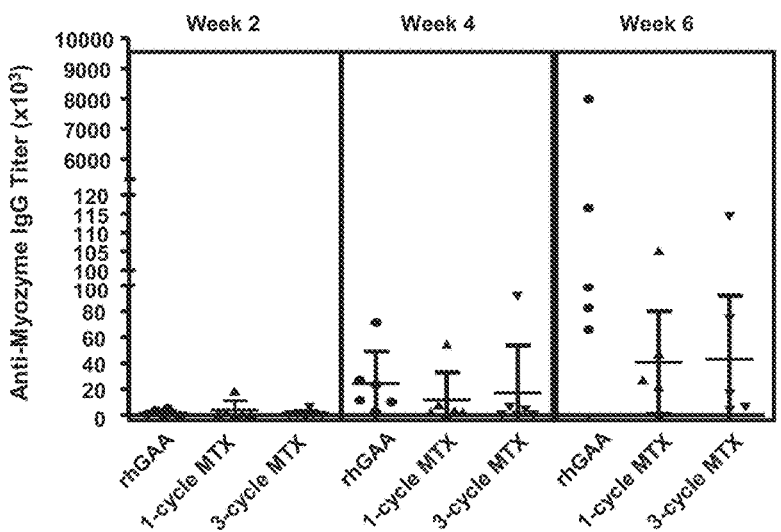
FIG. 15B shows that, in a six-week study, a single cycle of methotrexate reduces rhGAA-specific IgG titers.
Figure 15C:
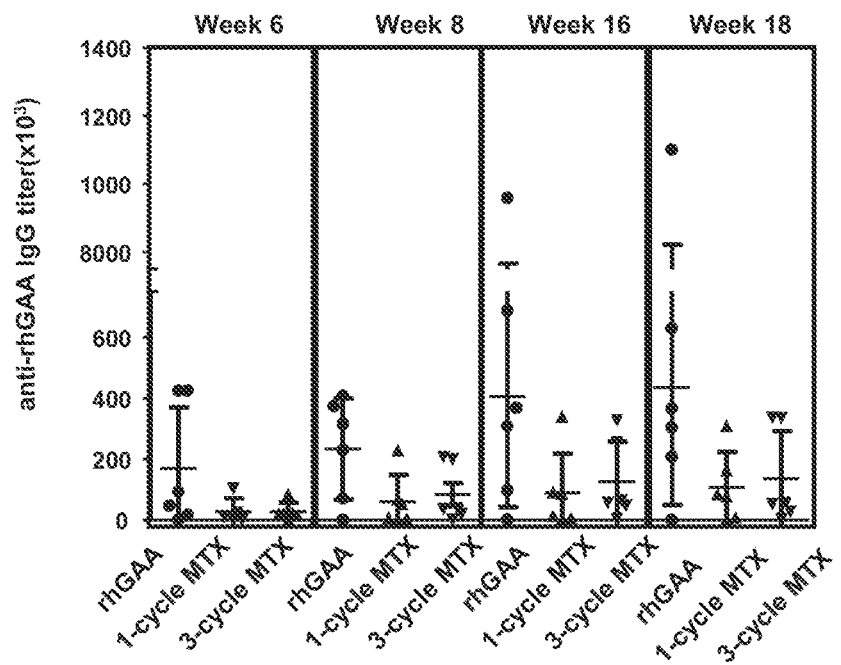
FIG. 15C shows that a single cycle of methotrexate reduces rhGAA-specific IgG titers in an 18 week study.

A Single Cycle of Methotrexate can Significantly Control Anti-rhGAA Antibody Responses We also studied the effect of methotrexate in rhGAA enzyme replacement therapy. In this study, the animals were injected weekly with rhGAA for twelve consecutive weeks, then rested for four weeks and then re-challenged with rhGAA at week 16. The animals were also given a single cycle of three consecutive daily doses of 5 mg/kg methotrexate at week 1, or given one cycle at each of weeks 1, 2, and 3 (with a total of three cycles). The rhGAA-specific IgG titers were measured in the animals at weeks 0 (prior to any treatment), 6, 8, 12, 16, 18, and 20. Our data show that a single cycle of methotrexate controlled anti-rhGAA responses through at least 20 weeks as well as the three cycle regimen (FIG. 15).

Figure 37A:
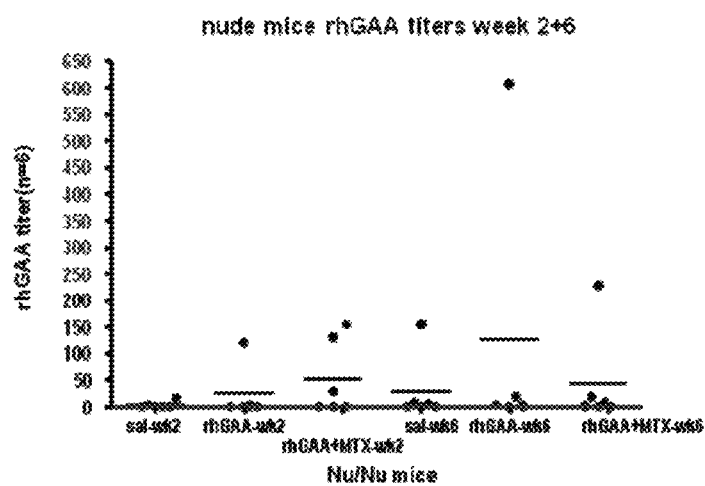
FIGS. 37A-B show rhGAA titers at weeks 2, 6, and 12 in nu/nu nude mice.
Figure 37B:
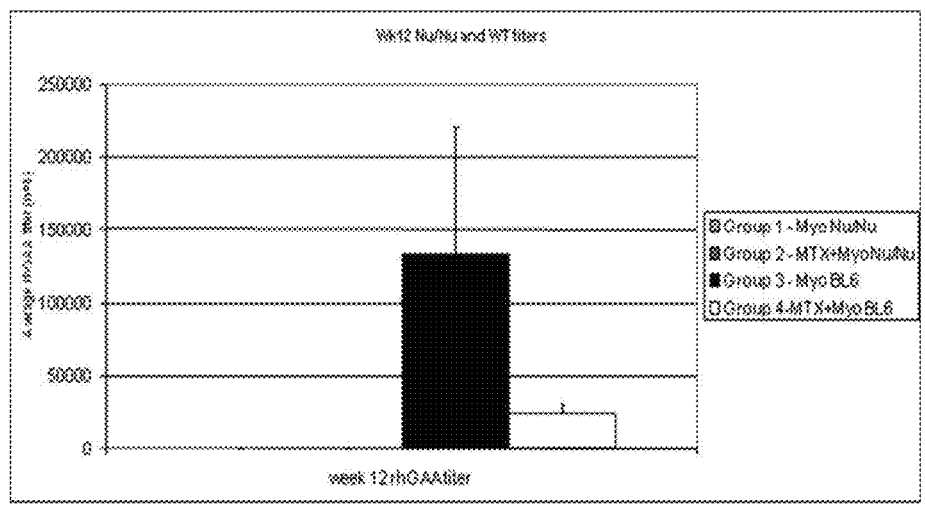

Studies also have been conducted in T cell deficient Nu/Nu mice to evaluate the role of T cells in generating anti-rhGAA titers. In these experiments, we have repeatedly observed that little to no ADA to rhGAA develop in these T cell deficient mice (FIGS. 37A-B). These data support the notion that T cells contribute to anti-rhGAA titers. Thus, as methotrexate can control ADA to rhGAA, it is also likely affecting T cell responses to rhGAA.

Example 9

Methotrexate Enhances mATG-Mediated Survival of Heart Allogeneic Transplants

In addition to evaluating whether methotrexate could enhance the efficacy of mATG in normal mice, we investigated whether mATG function could be augmented by methotrexate in a transplantation setting. Since Thymoglobulin® is used clinically as an induction therapy to prolong transplant survival, we evaluated whether the addition of methotrexate could augment the efficacy of mATG in a murine allogeneic heart transplant model. 20 mg/kg of mATG was administered on days 0 and 4, while 2 mg/kg methotrexate was administered as a single cycle of treatment on days 0-6.

Figure 16A:
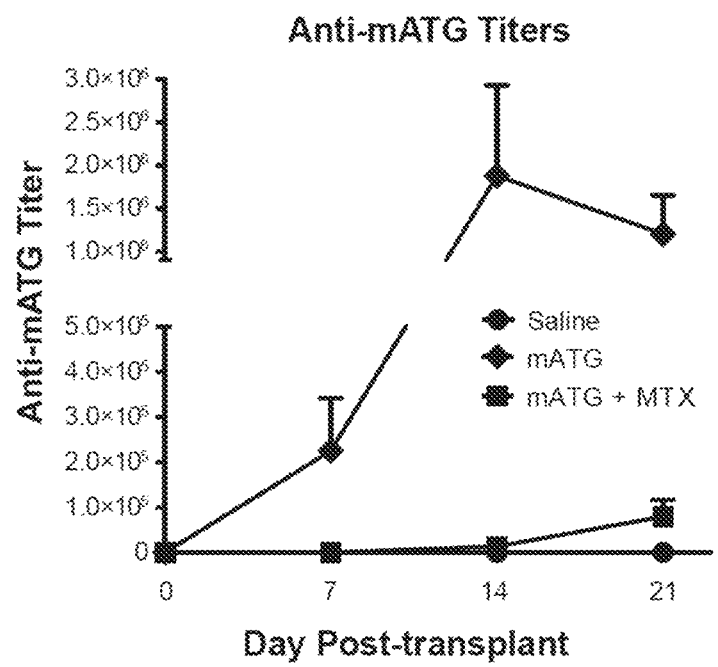
FIG. 16A shows that methotrexate decreases anti-rabbit IgG titers in a murine allogeneic heart transplant model when administered with mATG, as compared to mATG alone.
Figure 16B:
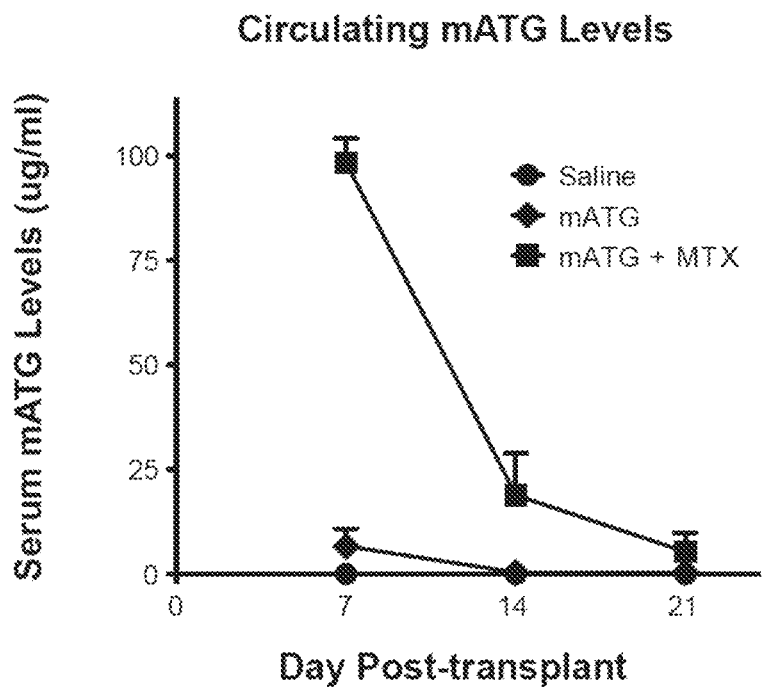
FIG. 16B shows that methotrexate increases circulating levels of mATG in a murine allogeneic heart transplant model. Mice were treated with saline, mATG alone, or mATG and a single cycle of methotrexate. mATG was administered at 20 mg/kg at days 0 and 4 of the study, while 2 mg/kg of methotrexate was administered on days 0-6 of the study.

In addition, we investigated four fold lower doses of methotrexate (0.5 mg/kg) given under the same regimen or with an extended regimen of 12 consecutive days. Groups of mice either received no treatment (saline control), mATG alone, or a combination of the mATG and methotrexate regimens. Similar to studies in normal mice, methotrexate coadministered with mATG reduced anti-drug antibody titers to mATG regardless of regimen used (FIG. 16A and Table 1). Moreover, coincidental to the reduction in antibody titers was an observed increase in mATG exposure in this transplant setting (FIG. 16). Given the likely adjuvant effect under the conditions of a potent, coincident immune response against the transplanted tissue, the anti-drug antibody titers increased even faster than in a normal mouse setting and resulted in mATG levels being near undetectable within 7 days of the first mATG administration (FIG. 16B). By contrast, by seven days following transplant, anti-rabbit IgG antibody titers were significantly lower in mice treated with methotrexate, and circulating mATG levels were significantly higher in those mice. This emphasizes that under conditions of an ongoing inflammatory response, anti-drug antibody responses can be accelerated and perhaps have an even greater impact on pharmacodynamics and efficacy. Importantly, even under these conditions, methotrexate had a profound inhibitory effect on mATG anti-drug antibodies and enhanced mATG exposure. However, because circulating mATG levels were still low to undetectable by 21 days with combination mATG and methotrexate treatment, additional tolerance mechanisms are likely at play given the >100 day graft survival. These results demonstrate a remarkable synergy between mATG and methotrexate treatment on the survival of the allogenic grafts and show a similar level of reduction in mATG anti-drug antibodies and enhancement of mATG exposure as observed in normal mice.

TABLE 1

Methotrexate regimens reduce anti-mATG antibody titers in cardiac allograft transplant mice

| | | | Average anti-mATG Titers | | |
| | | | mATG + MTX | | |
| Days post-transplant | Saline | mATG | 2 m/kg MTX Days 0-6 | 0.5 mg/kg MTX Days 0-6 | 0.5 mg/kg MTX Days 0-11 |
| --- | --- | --- | --- | --- | --- |
| Day 14 | 0 | 1,880,820 | 13,500 | 43,740 | 5,400 |
| Day 21 | 0 | 1,202,850 | 79,380 | n/a | n/a |
| Day 28 | n/a | n/a | n/a | 72,900 | 92,340 |

*n/a = Not available

Figure 17:
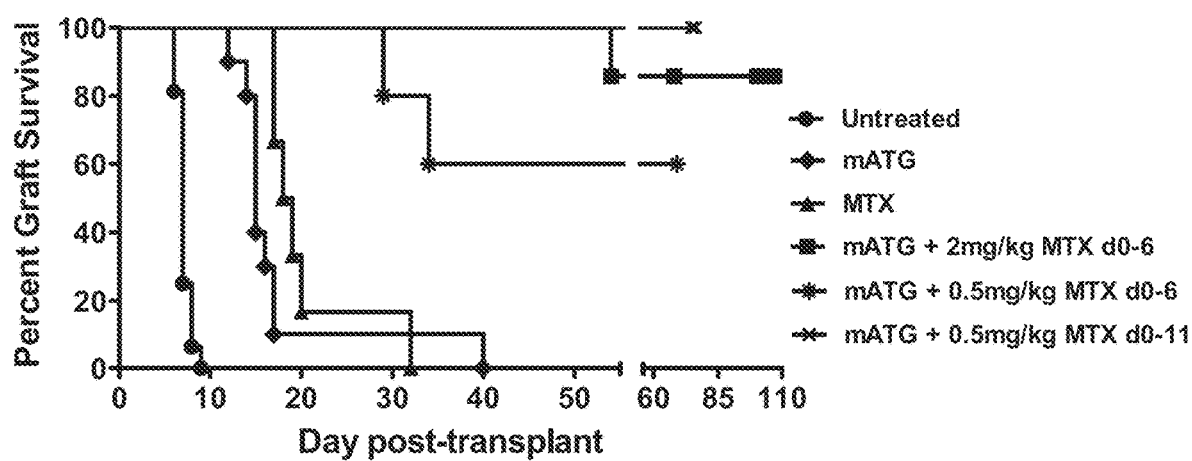
FIG. 17 shows a Kaplan-Meier plot indicating that a combined treatment of mATG and methotrexate prolongs the survival of allogeneic hearts transplanted into recipient mice. Mice were left untreated, or were treated with 20 mg/kg of mATG alone at days 0 and 4 of the study, or with 2 mg/kg of methotrexate alone on days 0-6 of the study, or with both mATG and 2 mg/kg of methotrexate on days 0-6, or with both mATG and 0.5 mg/kg of methotrexate on days 0-6 or days 0-11.
Figure 18A:
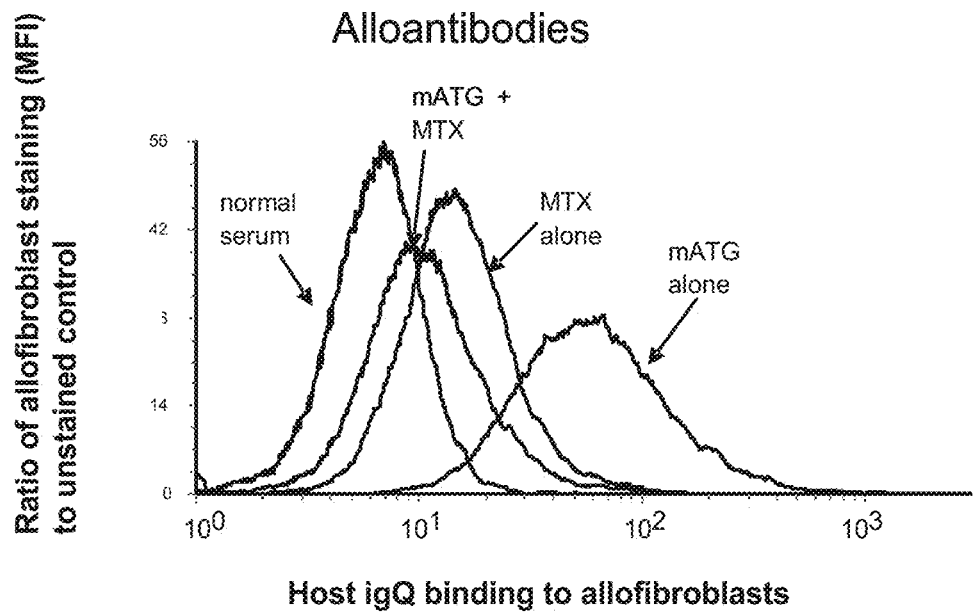
FIGS. 18A-C show that mice with an allogeneic heart transplanted treated with either methotrexate alone or methotrexate in combination with mATG experience a reduction in anti-allograft antibody responses.
Figure 18B:
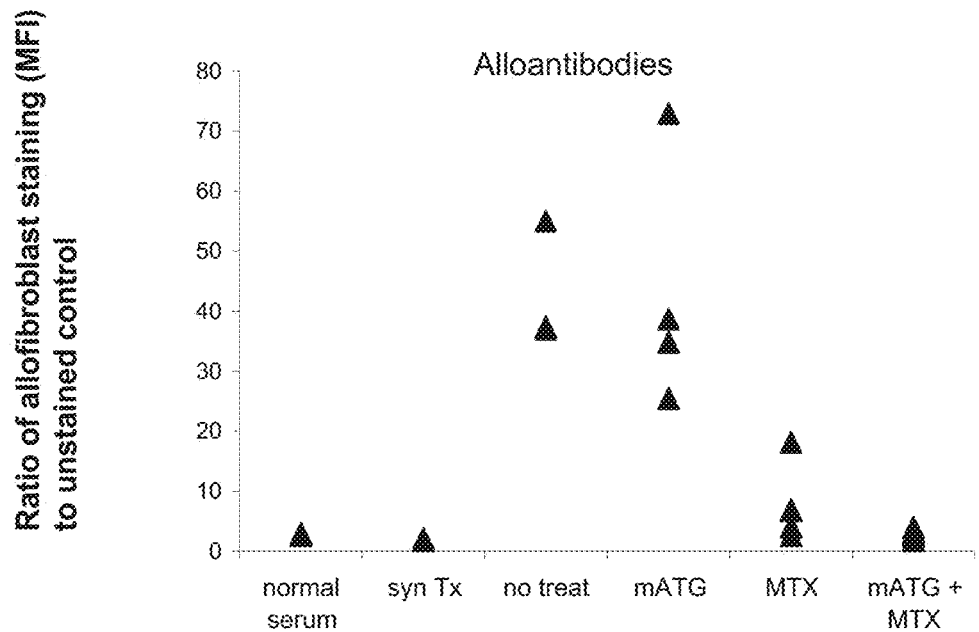
Figure 18C:
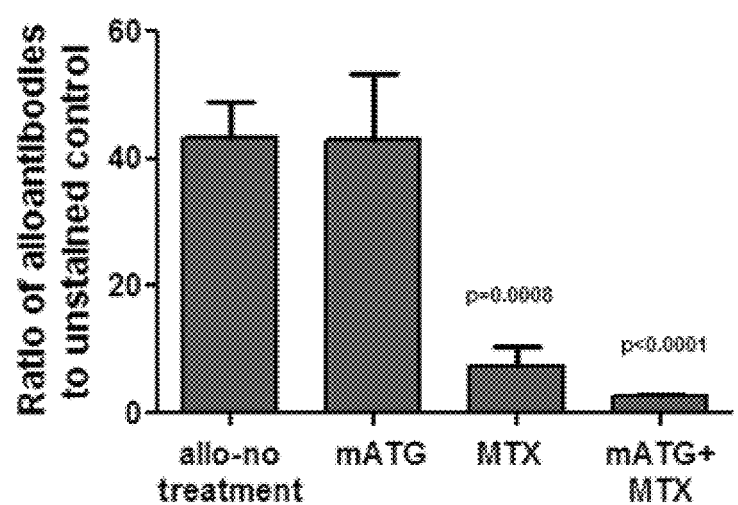

Additional data confirmed that the combination treatment of mATG and methotrexate significantly extended the survival of heart allografts in addition to reducing anti-allograft responses (FIGS. 17 and 18). Indeed, while both mATG or methotrexate treatment alone provided a modest benefit of an average extended survival to 15 and 20 days, respectively, the co-administration of mATG and any of the methotrexate regimens evaluated demonstrated a dramatic benefit in cardiac graft survival with the majority of mice retaining their grafts for up to over 100 days (FIG. 17). Since cardiac graft survival continues long after the early, brief induction treatments of mATG and methotrexate, this regimen appears to be tolerogenic rather than immunosuppressive. The effect was unique to the combination of mATG and methotrexate, as other immunosuppressive agents (e.g., mycophenolate mofetil, dexamethasone, rapamycin and cyclophosphamide) failed to significantly prolong graft survival when co-administered with mATG. Remarkably, methotrexate treatment alone was able to significantly reduce anti-allograft antibodies, further substantiating the effects of methotrexate on controlling antibody responses in general (FIG. 18). In this scenario, methotrexate appears to be able to control antibody responses against multiple antigens of the heart allograft simultaneously. A further reduction was induced by combining mATG with methotrexate treatment (FIG. 18C).

Example 10

Figure 19:
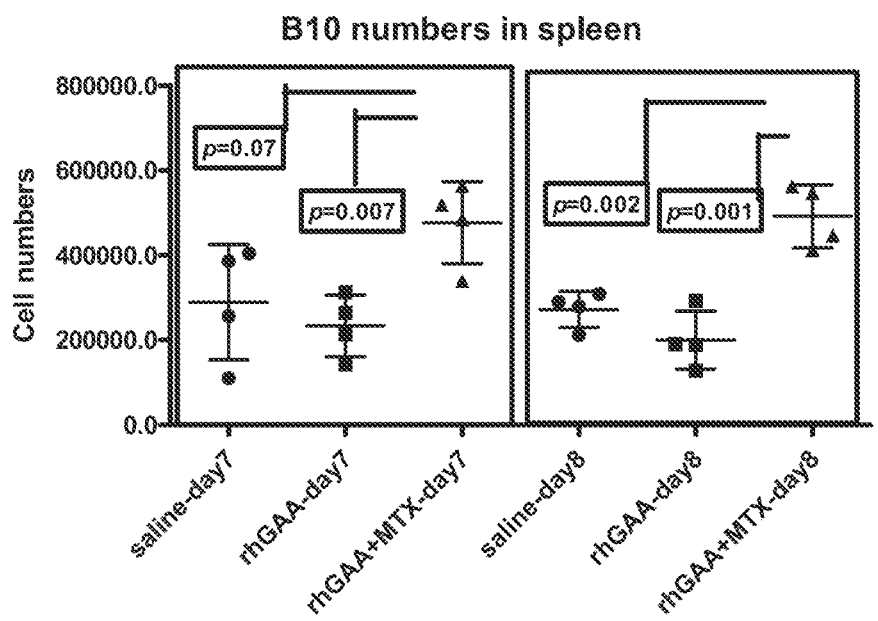
FIG. 19 shows that B10 regulatory B cells are significantly increased following methotrexate treatment. Mice were treated with rhGAA alone or rhGAA and a single three-day cycle of methotrexate or saline. Cell numbers were counted on day 7 and day 8 of the study.

The Mechanism of Methotrexate-Induced Tolerance is Unique from the Currently Known and Accepted Function of Methotrexate The dosing regimen of methotrexate described in the Examples above appears to invoke a mechanism that is unique from that previously described. Methotrexate is a folate antagonist that is thought to mediate its suppressive effects by inducing the death of proliferating cells. mATG data presented above demonstrates that antibody responses are induced but remain significantly decreased with each successive mATG treatment in methotrexate-treated animals. These data suggest that B cell responses are actively managed. Without wishing to be bound by theory, we hypothesize that methotrexate may induce a regulatory cell population(s) that controls these responses as they occur. We investigated the effect of methotrexate treatment on a variety of splenic B and T cell subsets in animals treated with Myozyme® and methotrexate compared with animals treated with Myozyme® alone. We observed significant increases in the B10 regulatory B cell population seven and eight days following Myozyme® treatment (four and five days after methotrexate treatment; FIG. 19).

Figure 20:
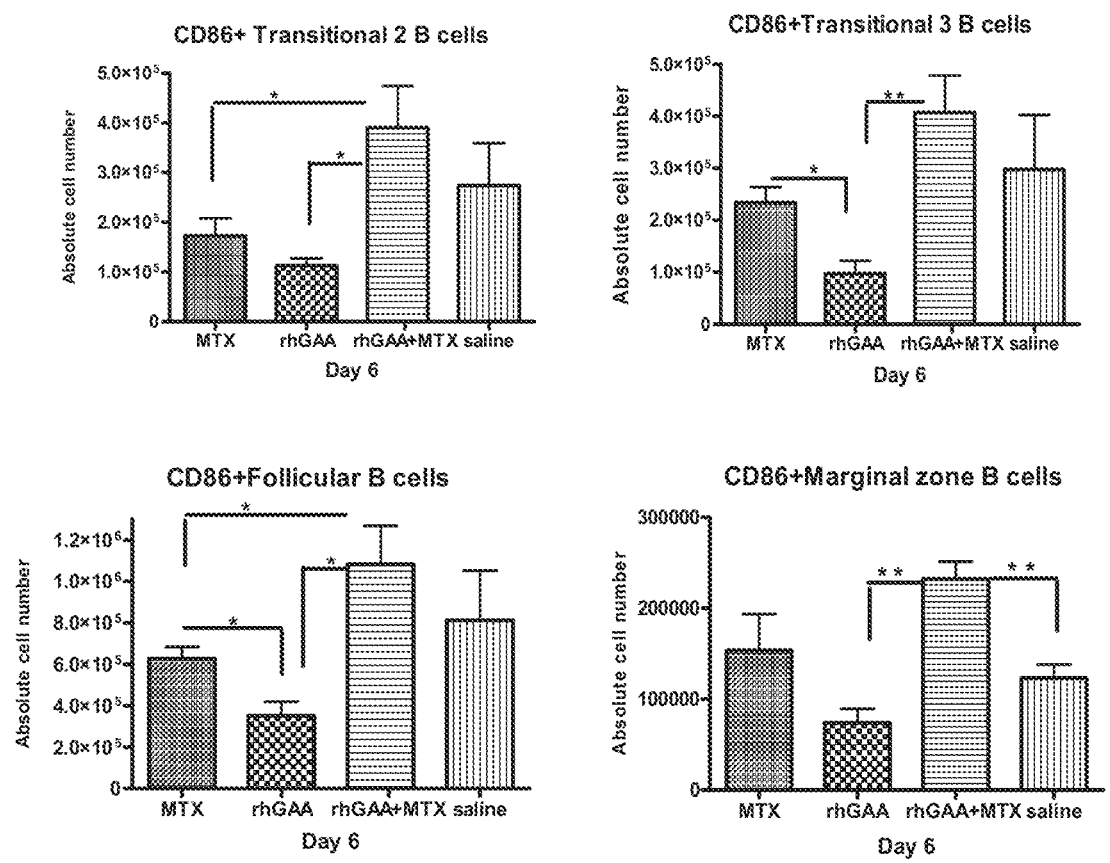
FIG. 20 shows that activated B cell subpopulations are significantly increased on day 6 following treatment with rhGAA and a single three-day cycle of methotrexate, as compared to treatment with rhGAA alone. Absolute cell numbers of CD86+ transitional 2 B cells, CD86+ transitional 3 B cells, CD86+ follicular B cells, and CD86+ marginal zone B cells were counted on day 6 of the study. Asterisks indicate measurements with statistically significant differences (*, $p<0.05$; **, $p\leq0.001$).
Figure 21:
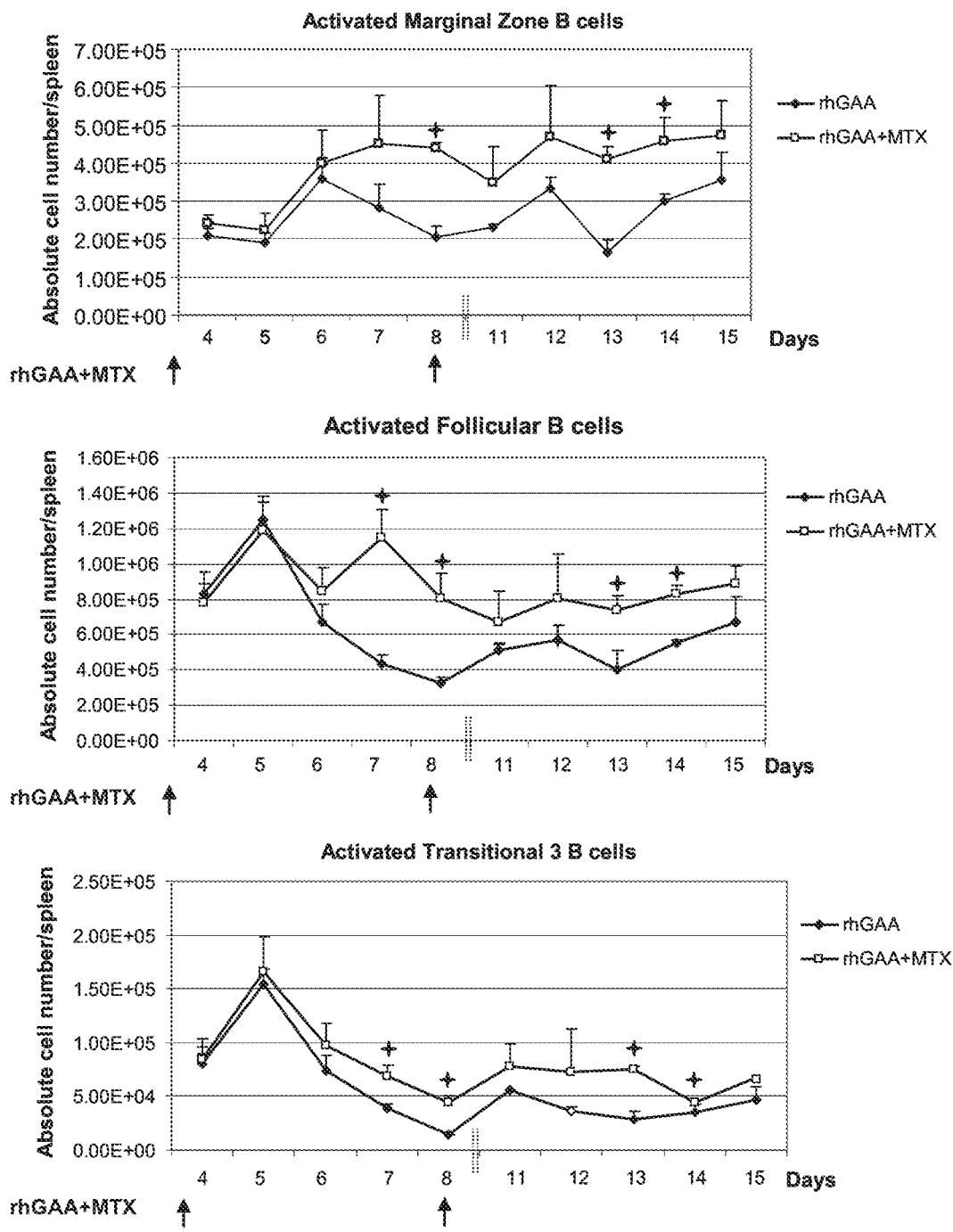
FIG. 21 shows that for activated splenic B cell subpopulations, such as activated marginal zone B cells, activated follicular B cells, and activated transitional 3 B cells, cell numbers remain enhanced even following treatment with rhGAA and methotrexate, as compared to treatment with rhGAA alone. Arrows represent the treatment with rhGAA and methotrexate. rhGAA was administered on day 1 and day 8. Methotrexate was administered on days 1, 2, and 3, and days 8, 9, and 10. Significant differences are represented by stars (*, $p<0.05$). Data not shown for days 8 and 9 (indicated by vertical dotted lines).
Figure 22:
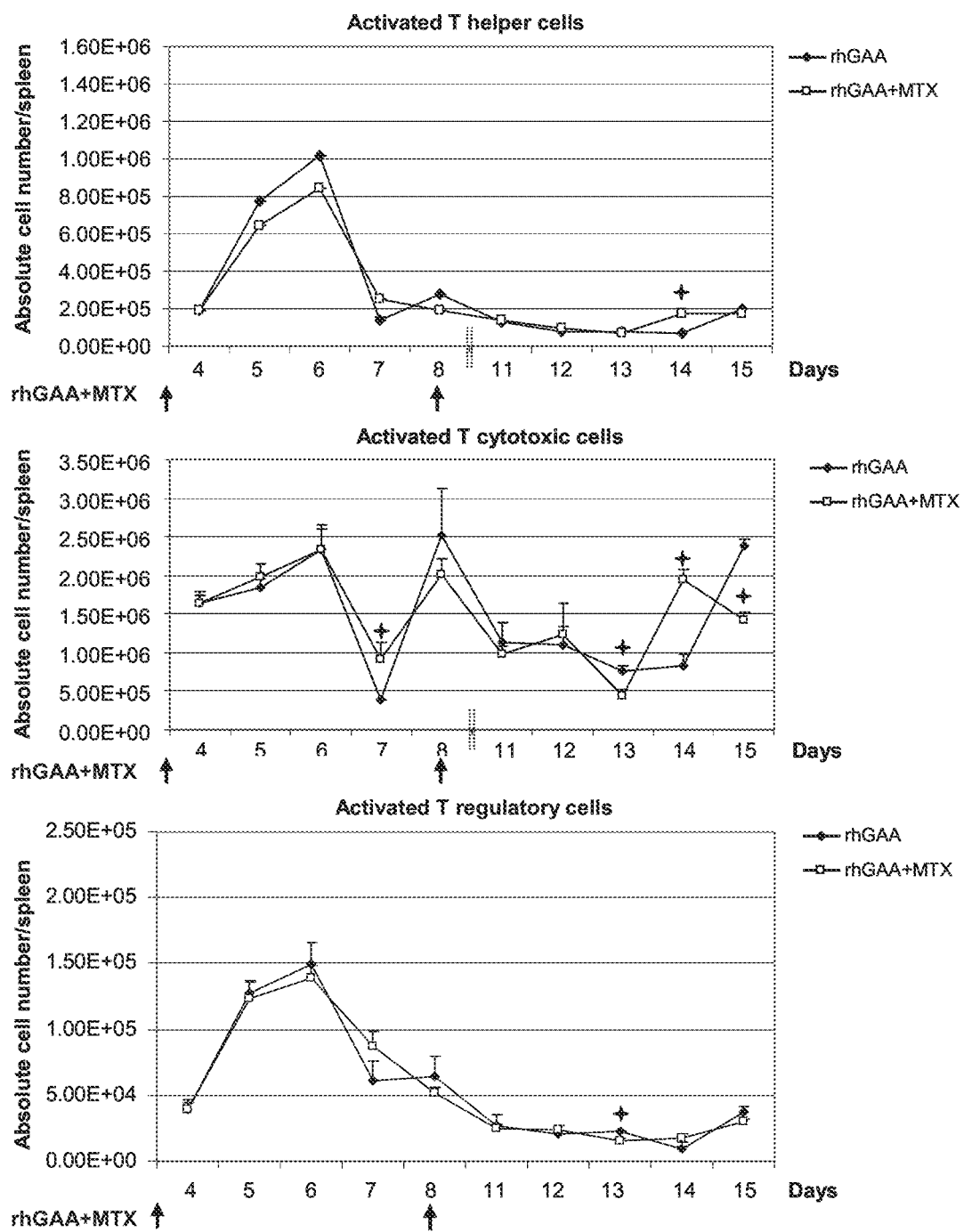
FIG. 22 shows that activated splenic T cell populations, such as activated T helper cells, activated T cytotoxic cells, and activated T regulatory cells, remain largely unchanged following treatment with rhGAA and methotrexate, as compared to treatment with rhGAA alone. Arrows represent the treatment with rhGAA and methotrexate. rhGAA was administered on day 1 and day 8. Methotrexate was administered on days 1, 2, and 3, and days 8, 9, and 10. Significant differences are represented by stars (*, $p<0.05$). Data not shown for days 8 and 9 (indicated by vertical dotted lines).

In addition, a number of activated B cell subsets were significantly increased following methotrexate treatment (FIG. 20). These populations included activated marginal zone B cells, activated follicular B cells and activated transitional 2 and 3 B cells. Cell populations were defined as follows: B2/follicular B cells: $CD19^+CD21^{int}CD23^{hi}$; transitional 2 B cells: $CD19^+CD93^+CD23^+IgM^{hi}$; and transitional 3 B cells: $CD19^+CD93^+CD23^+IgM^{lo}$; marginal zone B cells: $CD19^+CD21^{hi}CD23^{lo}$. A daily assessment of splenic cell populations in animals given two cycles of Myozyme® and methotrexate, where Myozyme® was administered days 1 and 8 and 5 mg/kg of methotrexate was given days 1-3 and 8-10, demonstrated that these activated B cell populations remained increased (FIG. 21). This result is surprising because the expected response after methotrexate treatment would be death of activated, proliferating cells. In contrast, activated T helper, T cytotoxic and T regulatory cell populations remained largely unchanged (FIG. 22). T helper cells were defined as CD4+, T cytotoxic were defined as CD8+, and T regulatory cells were defined as CD4+CD25+ and FoxP3+. These findings suggest that the increased B cell populations may help mediate methotrexate-induced immune tolerance.

Example 11

Methotrexate Increases Selected B Cell Populations in Combination with mATG

In the above examples, after each mATG treatment, ADA titers in both the mice treated with mATG alone and the mice treated with mATG and methotrexate increased, suggesting that both sets of animals contain B cells that are capable of contributing to an antibody response (FIG. 6). If that is the case, at least two hypotheses can be drawn. A first hypothesis is that methotrexate may have killed the vast majority of B cells capable of responding to Myozyme®, and the few that remain are responsible for this slight response. Although this is possible, flow cytometry data from multiple experiments have not indicated a decrease in B cell populations following Myozyme® and methotrexate treatment. A second hypothesis is that B cell populations that can respond to Myozyme® are not killed by this brief course of methotrexate, but remain and are controlled by regulatory cells following each exposure to Myozyme®. Thus far, phenotypic data describe an enhancement of B cell subsets following methotrexate and Myozyme® treatment. The phenotype of these B cells seems similar to regulatory B cell subsets which have been described in animal studies and in tolerant transplant patients. We therefore sought to test this second hypothesis in the context of different treatments.

Figure 23:
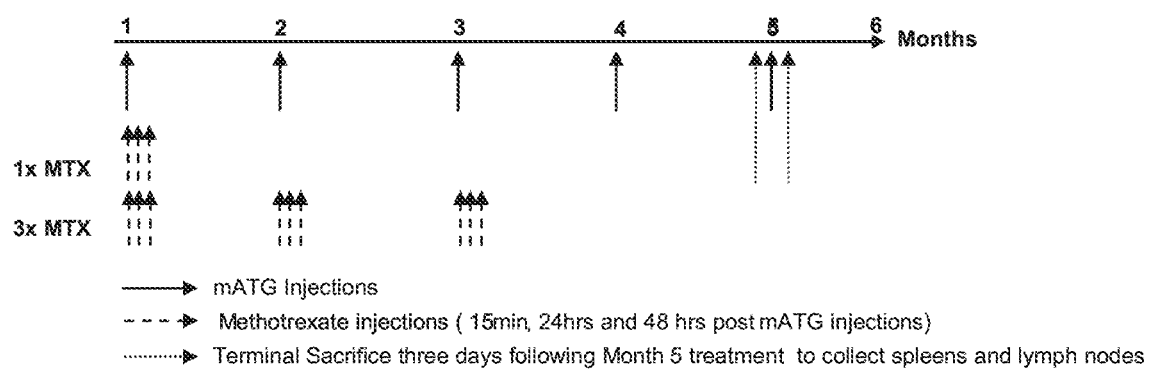
FIG. 23 shows a six month-long study design for examining methotrexate treatment in combination with mATG. Solid arrows represent 5 mg/kg mATG injections, dashed arrows represent 5 mg/kg methotrexate injections, and dotted arrows represent terminal sacrifices.

Animals were treated with mATG monthly for five months and received either a single cycle of 5 mg/kg of methotrexate on the first three days of the study, three cycles of 5 mg/kg of methotrexate, or no methotrexate (FIG. 23). Differences in cell populations among the three treatment groups were then assessed by comparing the populations in animals one day prior to the fifth mATG dose and two days after the fifth mATG dose.

Figure 24A:
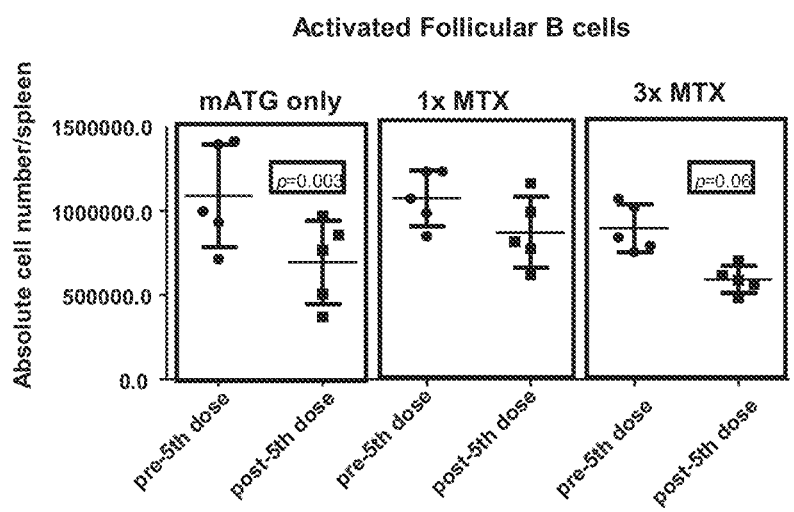
FIGS. 24A-B show that a single cycle of methotrexate in connection with mATG enriches splenic B cells, as compared to mATG alone or three cycles of methotrexate.
Figure 24B:
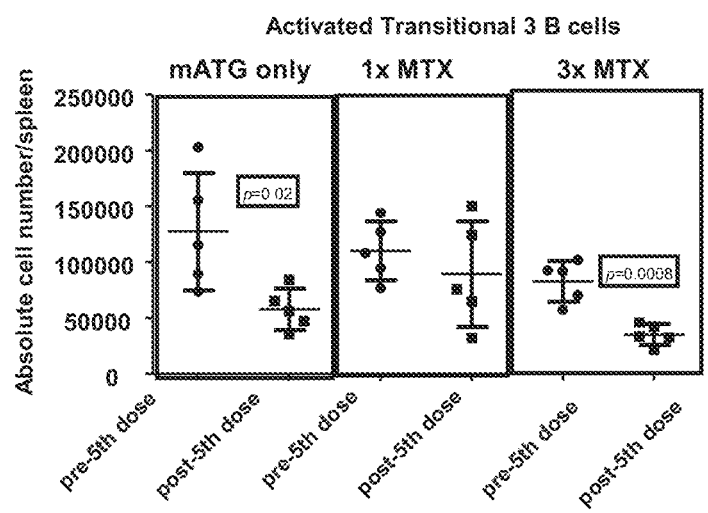

Surprisingly, five months after treatment with a single cycle of methotrexate, differences were observed between mice that received a single cycle of methotrexate and mATG and mice that received either mATG alone or mATG with three cycles of methotrexate. Two cell populations that unexpectedly demonstrated effects were activated follicular B cells and activated transitional 3 B cells (FIGS. 24A-B, respectively). In mice treated with either mATG alone or in combination with three cycles of methotrexate, decreases were observed in the absolute cell number of these cell populations. However, in mice that received only a single cycle of methotrexate, no statistically significant decreases in these populations observed, suggesting that this dosing regimen of methotrexate induced some enrichment of these populations. Interestingly, both of these cell populations were also shown to be enriched directly following methotrexate treatment in combination with in Myozyme (FIG. 21). Similar subsets also have been identified in tolerant transplant patients. It is possible that a single cycle of methotrexate treatment can induce these B cell subsets which, upon antigen exposure, become activated and suppressive.

Example 12

Methotrexate Increases Selected B Cell Populations in Combination with Alemtuzumab

As described in Example 4, huCD52 transgenic mice were treated with single monthly doses of 0.5 mg/kg alemtuzumab for five months, either with or without three daily doses of 5 mg/kg/day of methotrexate in connection with the first administration of alemtuzumab. Cell populations were evaluated in the blood and spleen of the mice 2 days prior to, and 1, 7 and/or 28 days following, the fifth dose of alemtuzumab by flow cytometry.

Figure 25A:
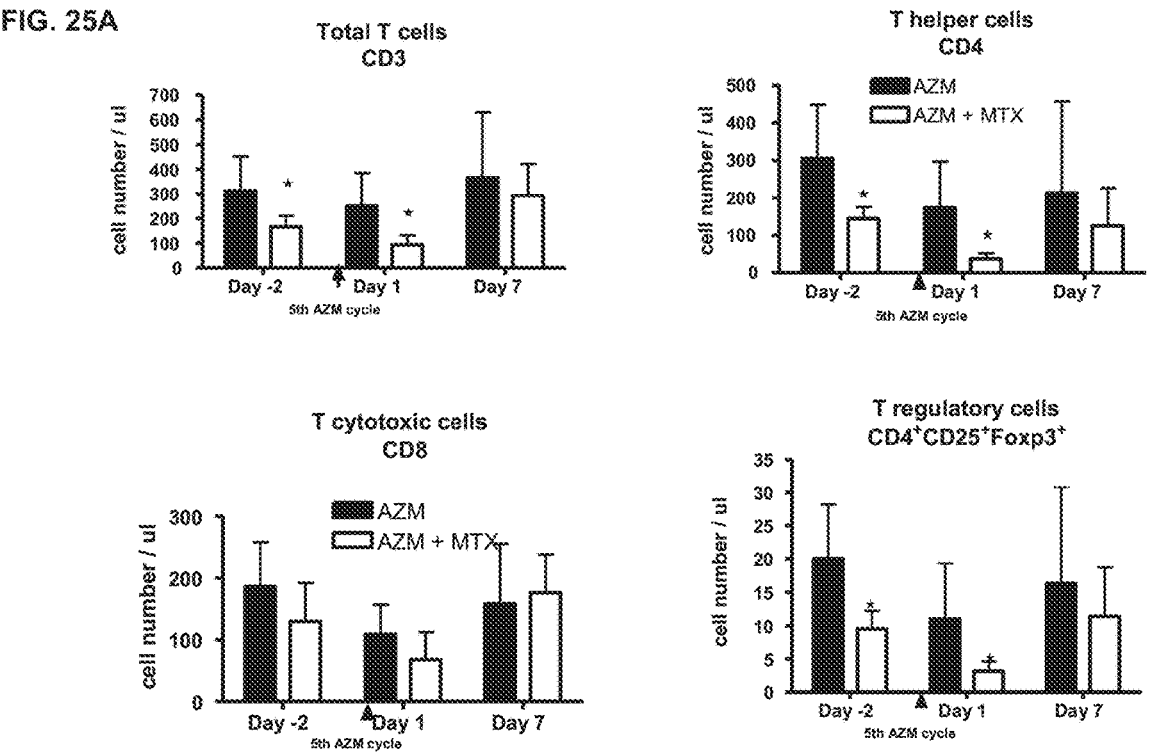
FIGS. 25A-B show the effects of methotrexate on alemtuzumab's pharmacodynamics in the blood. Mice were treated with 0.5 mg/kg of alemtuzumab for five months, either with or without three daily doses of 5 mg/kg/day of methotrexate in connection with the first administration of alemtuzumab.
Figure 25B:
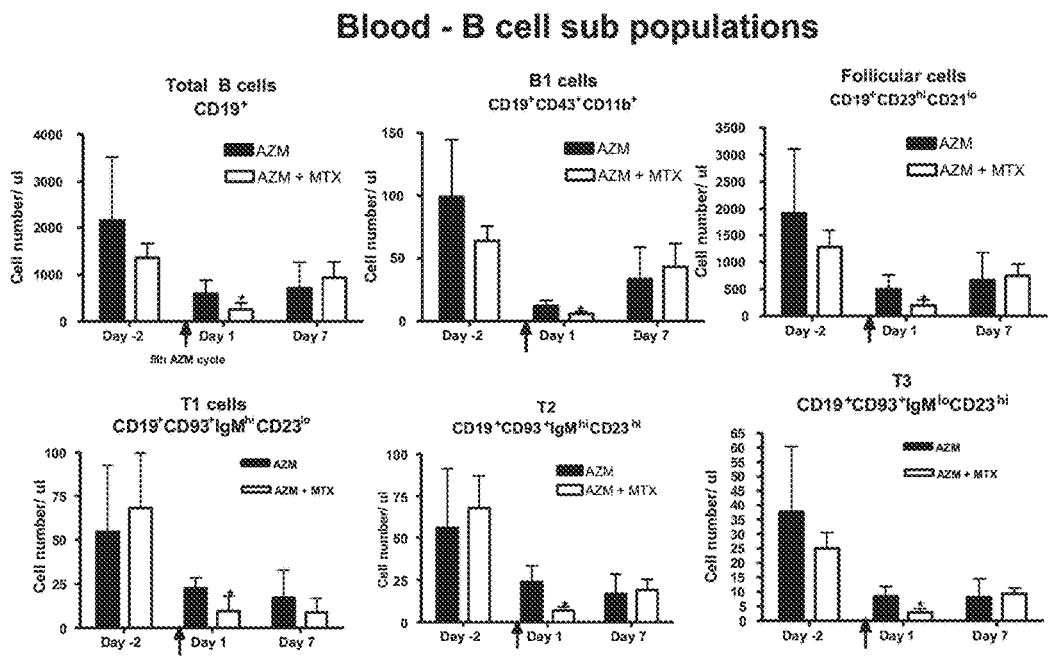
Figure 26:
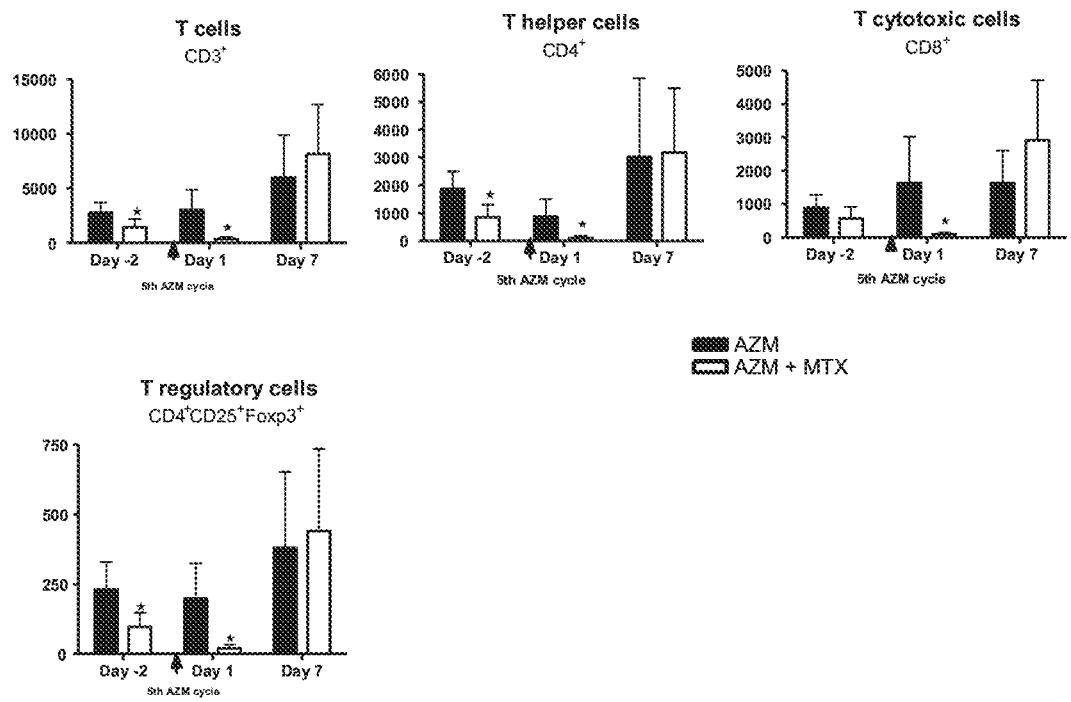
FIG. 26 shows the effects of methotrexate on alemtuzumab's pharmacodynamics in the spleen. Mice were treated with 0.5 mg/kg of alemtuzumab for five months, either with or without three daily doses of 5 mg/kg/day of methotrexate in connection with the first administration of alemtuzumab. T cells are depleted following the fifth treatment with alemtuzumab. CD8 CEN: $CD8^+$ central memory T cells; CD8 EFF MEM: $CD8^+$ effector memory T cells; CD4 CEN MEM: $CD4^+$ central memory T cells; CD4 EFF MEM: $CD4^+$ effector memory T cells. Stars indicate measurements with statistically significant differences (*, $p<0.05$).
Figure 26:
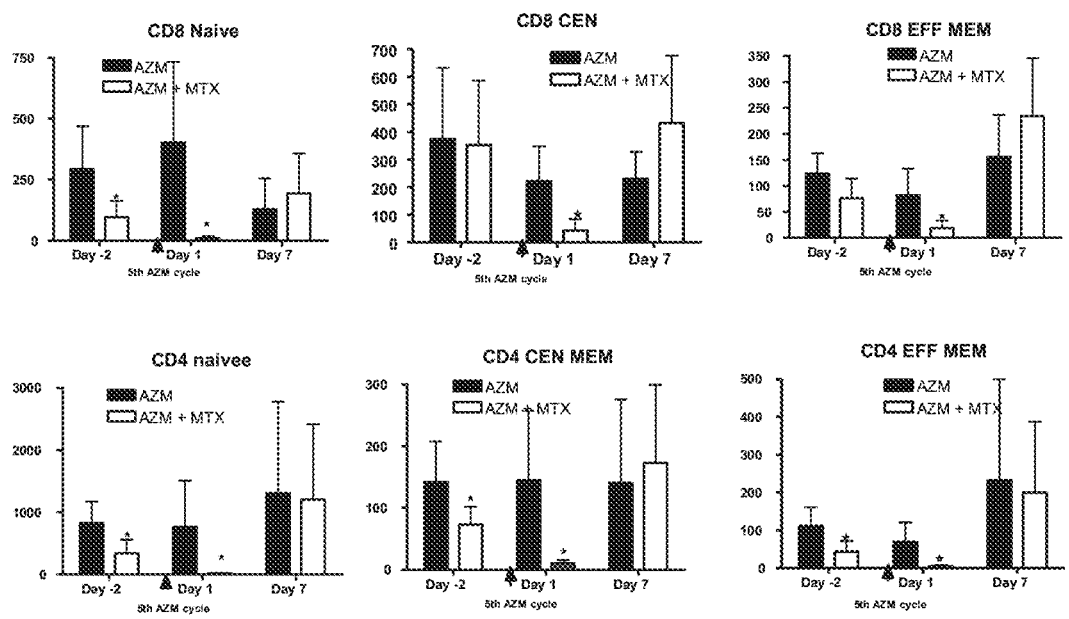

In blood, the pharmacodynamic effect of alemtuzumab was enhanced in methotrexate-treated animals 24 hours following the fifth dose of alemtuzumab. Statistically significant cell depletion was observed in both T cell and B cell subsets one day after the fifth dose, consistent with previous data indicating that anti-alemtuzumab titers are low in these animals and would not be likely to interfere with alemtuzumab-mediated depletion. By contrast, mice treated with alemtuzumab alone may have more alemtuzumab-neutralizing antibodies that interfere with alemtuzumab pharmacodynamics. As shown in FIG. 25A, there was no significant depletion of T cell subsets in alemtuzumab-treated mice, but mice treated with alemtuzumab and methotrexate exhibit significant alemtuzumab-mediated depletion in total T cells, T helper cells and T regulatory cells one day following alemtuzumab dosing. Similar findings were observed in circulating B cell subsets (FIG. 25B), although trends towards decreasing cell numbers were also observed in animals treated with alemtuzumab alone As with circulating T cell populations, splenic T cell populations were significantly depleted in methotrexate-treated animals one day following the fifth alemtuzumab treatment (FIGS. 26A-B).

Figure 27A:
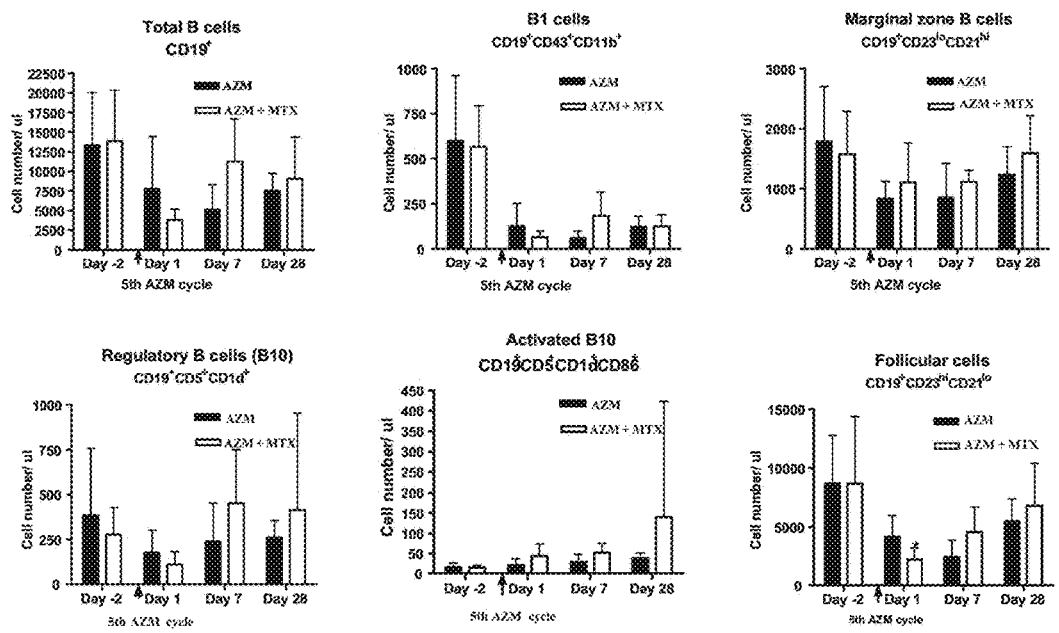
FIGS. 27A-B show the effects of methotrexate on B cell numbers in the spleen. Mice were treated with 0.5 mg/kg of alemtuzumab for five months, either with or without three daily doses of 5 mg/kg/day of methotrexate in connection with the first administration of alemtuzumab. Stars indicate measurements with statistically significant differences (*, $p<0.05$).
Figure 27B:
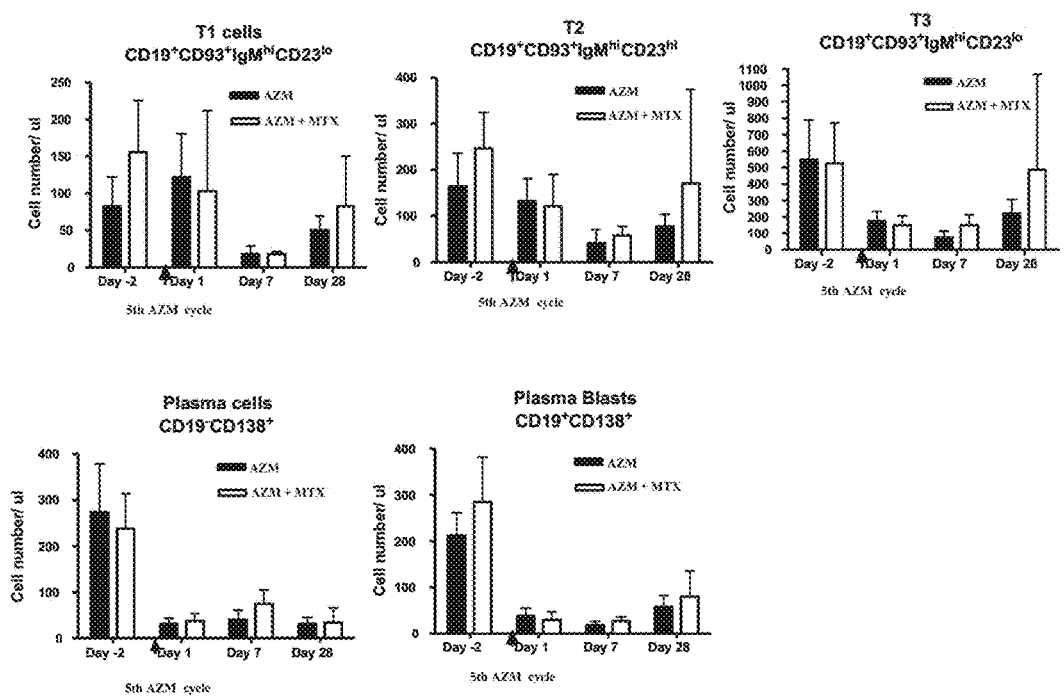

In contrast to T cell depletion in mice treated with alemtuzumab and methotrexate, each of the splenic B cell populations that were analyzed, except for follicular B cells, were not significantly depleted (FIG. 27). This assessment includes the regulatory B cell population, B10 B cells. Without wishing to be bound by theory, we hypothesize that methotrexate may enrich some or all of these B cell populations, which counters their alemtuzumab-mediated depletion. This enrichment is not expected to occur in the fast, fluid environment of the blood because immune cells do not differentiate in blood. Instead, immune responses occur in the spleen and other peripheral lymphoid tissue where cell/cell interactions and cytokine/chemokine-initiated responses can occur in the diverse niches of the tissue. This may explain the differential effects of the alemtuzumab-mediated depletion of B cells observed in blood and spleen. These data are similar to data generated with mATG, wherein splenic B cells appeared to be enriched in mice treated with a single cycle of methotrexate in combination with mATG (FIG. 24A-B). Indeed, in all of the studies described herein, enrichment following methotrexate treatment has been observed when assessing specific populations of activated cells. However, when assessing total numbers of a cell population that includes both activated and non-activated cells, such as total follicular B cells, significant enrichment in methotrexate-treated animals was not observed.

Figure 28A:
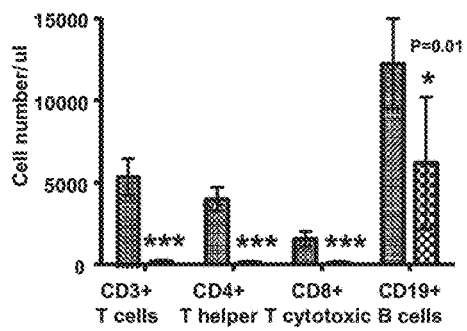
FIGS. 28A-B show depletion of splenic lymphocytes three days after a single dose of alemtuzumab.
Figure 28B:
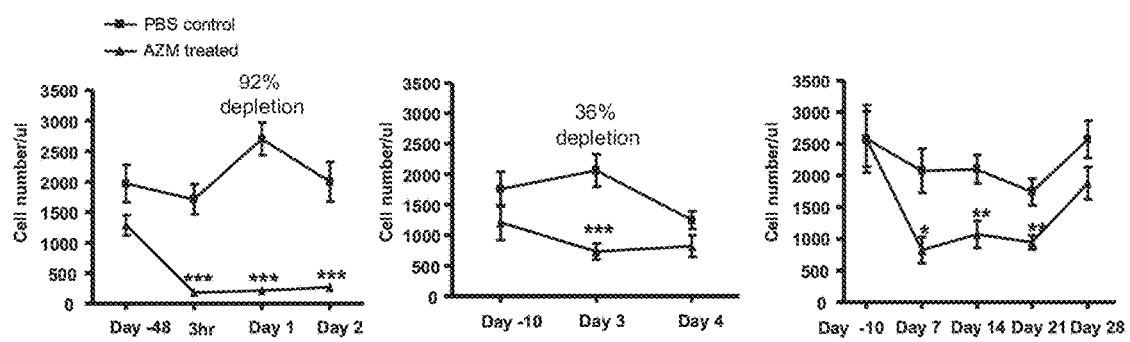

In contrast to splenic cell populations 24 hours after alemtuzumab treatment, three days after treatment with a single dose of alemtuzumab (and not methotrexate), splenic cell subsets were significantly depleted (FIG. 28A). It is possible that at 24 hours, B cell depletion may be greater in alemtuzumab-treated animals than at three days following alemtuzumab treatment, as B cell repopulation may have begun by the three-day mark. This has been demonstrated in several studies assessing these populations in peripheral blood. Depletion was observed as early as three hours post-dosing in the peripheral blood. By three days following treatment, circulating B cell pools were still significantly lower in alemtuzumab-treated mice than in control mice treated with phosphate buffered saline (PBS), although the percent depletion was not as great as that at 24 hours. The percent depletion at 24 hours was 92%, whereas the depletion at three days was 36% (FIG. 28B). B cell reconstitution seems to occur rapidly following a single dose.

In conclusion, five months after animals received methotrexate and directly after antigen exposure, it appears that methotrexate may have enriched B cell populations that potentially help mediate tolerance induction. The populations that appear enriched are similar to those that are increased directly after methotrexate treatment (FIG. 21). Taken together, this suggests that methotrexate may induce an environment that allows immune responses to be actively controlled at the time of antigen exposure, even long after the treatment with methotrexate.

Example 13

The Effects of Methotrexate on Cytokine Levels

Cytokines play a dual role in B cell responses. For instance, B-cell activating cytokines IL-6 and BAFF are also required for B cell differentiation. Since methotrexate seems to increase B cell populations, one may expect these cytokines to be increased. However, IL-6 is also pro-inflammatory, and therefore, elevated levels may interfere with methotrexate-induced effects. Like IL-6, IL-10 is involved in B cell differentiation into plasma cells and immunosuppression as well.

Figure 29A:
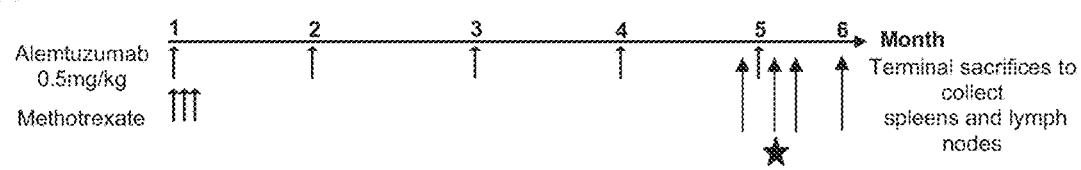
FIGS. 29A-B show the effects of methotrexate on cytokine levels.
Figure 29B:
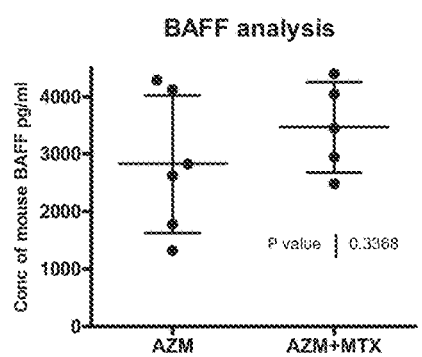

BAFF data were generated from serum samples taken 24 hours after the $5^{th}$ dose of alemtuzumab (FIG. 29A). This is a continuation of cellular data from this study presented above. At this time point no difference in BAFF levels were observed (FIG. 29B).

TABLE 2

Study design in mice treated with alemtuzumab and/or methotrexate

| Grp # | Treatment | Animals |
|---|---|---|
| 1 | PBS | 4M/4F |
| 2 | 0.5 mg/kg alemtuzumab (× 5 days) | 4M/4F |
| 3 | 0.5 mg/kg alemtuzumab + methotrexate (0.5 mg/kg for 8 days) | 4M/4F |
| 4 | 0.5 mg/kg alemtuzumab + methotrexate (1 mg/kg for 8 days) | 4M/4F |
| 5 | 0.5 mg/kg alemtuzumab + methotrexate (2 mg/kg for 8 days) | 4M/4F |

Figure 30A:
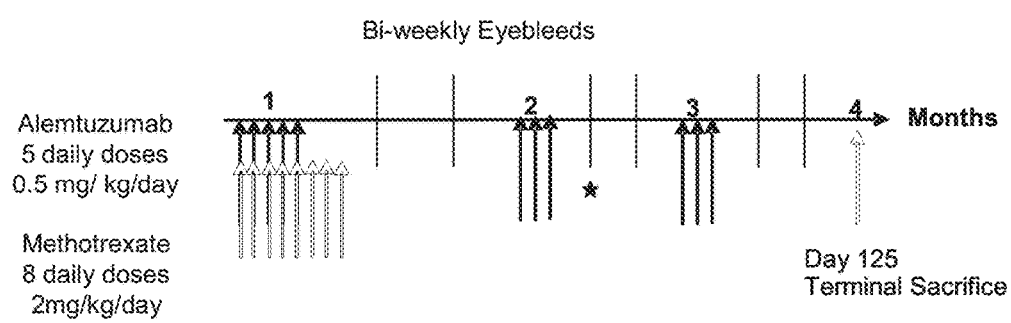
FIGS. 30A-B show the levels of cytokines after treatment with alemtuzumab and methotrexate.
Figure 30B:
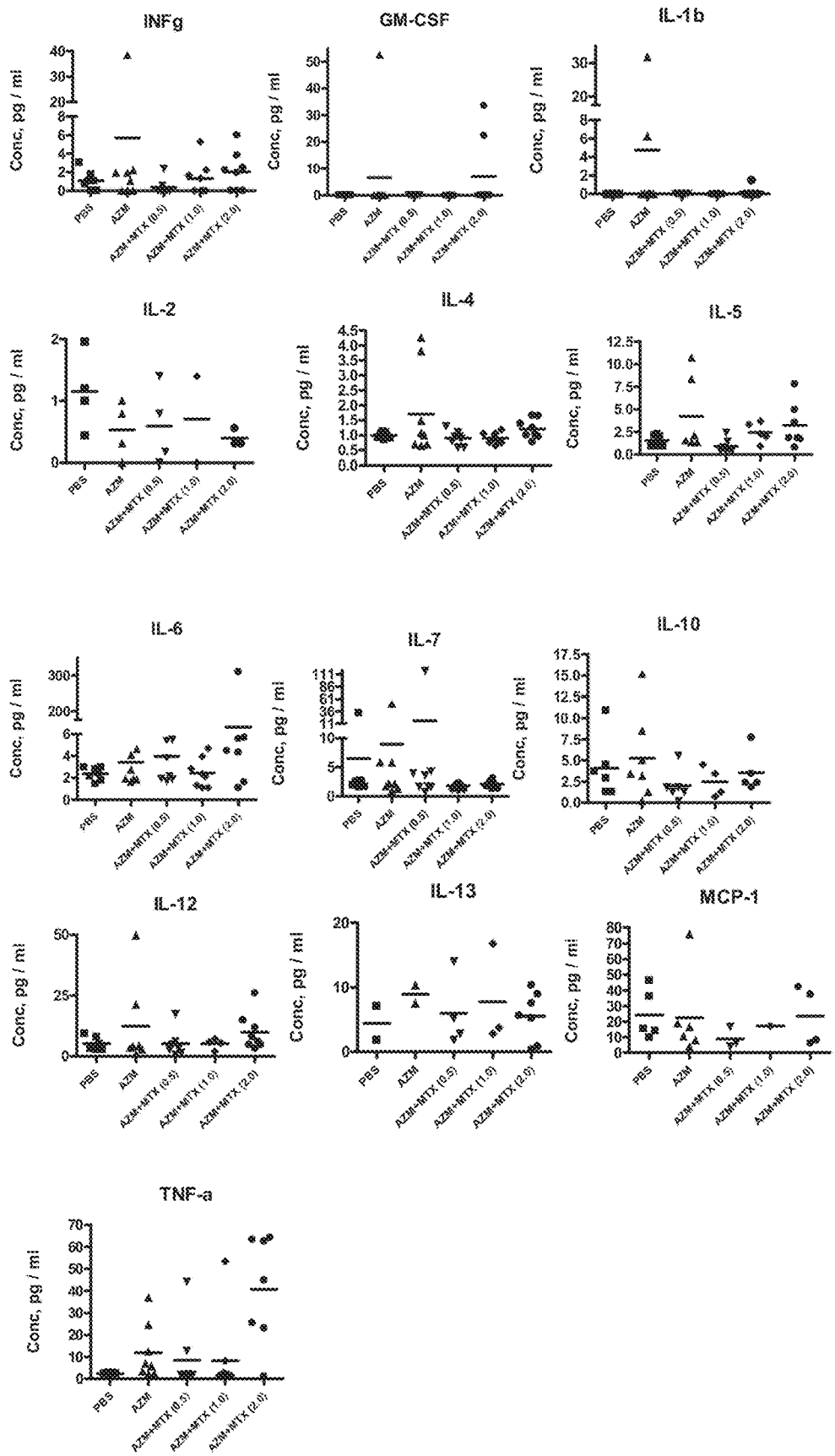

Cytokine levels were assessed one week after the second cycle of alemtuzumab (FIG. 29B). Generally, one week after the second cycle of alemtuzumab, cytokine levels appeared low. At this time point, a statistically significant increase was observed in TNF-alpha levels in animals treated with 2 mg/kg of methotrexate. This increase may reflect a change that is related to methotrexate-induced tolerance, or that is a sign of an inflammatory response. Trends observed in other cytokines, such as apparent increases in IL-6 and potentially slight decreases in IL-7, also were noted (FIG. 30).

Regulatory B cells have been associated with IL-10 secretion. One way to assess whether IL-10-secreting regulatory B cells play a role in methotrexate-induced tolerance is to evaluate whether methotrexate can control antibody responses in IL-10 deficient animals. This type of assessment may be challenging in that, as mentioned above, IL-10 is necessary for plasma cell differentiation and therefore antibody responses may be lower in these animals. With this caveat in mind, we observed interesting trends suggesting that IL-10 may play a role in methotrexate-induced tolerance.

Figure 31:
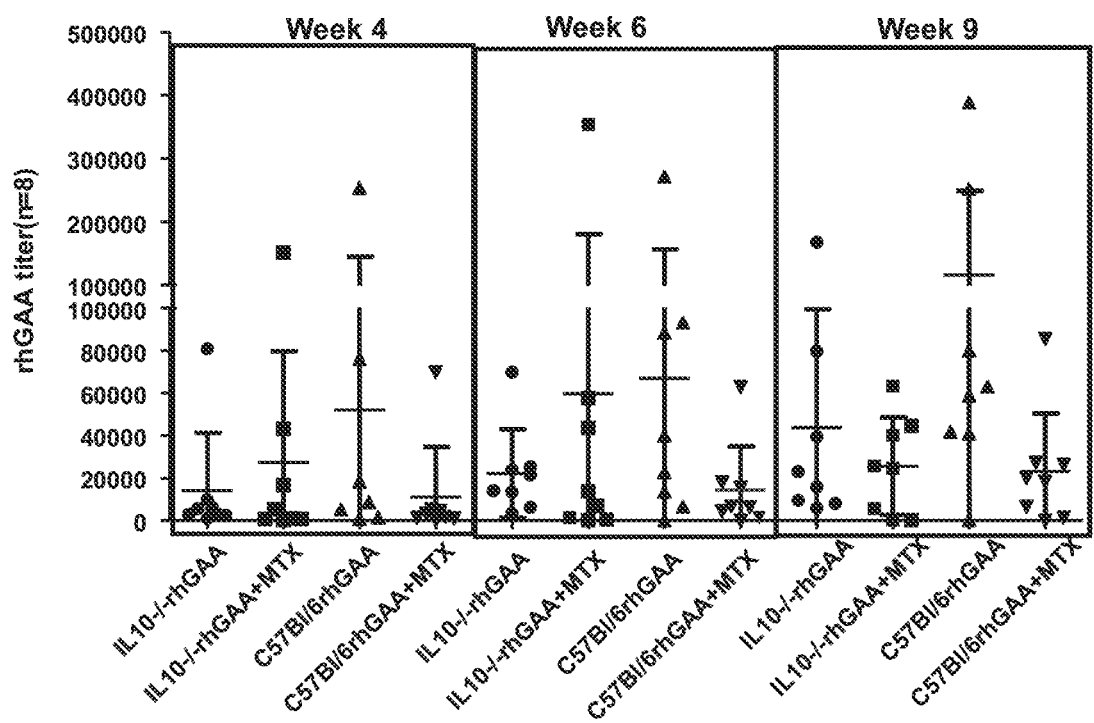
FIG. 31 shows the effects of methotrexate on anti-rhGAA titers in IL10−/− (knockout) and C57BL/6 mice. 20 mg/kg of rhGAA was administered weekly for nine weeks in IL10−/− knockout and C57BL/6 wild-type mice, with or without 5 mg/kg/day of methotrexate at 0, 24, and 48 hours after the first three weekly treatments of rhGAA.

In this study, animals received 20 mg/kg of intravenous Myozyme® weekly for nine weeks. Three cycles of methotrexate were administered at 5 mg/kg/day 0, 24, and 48 hours after the first three weekly treatments of Myozyme®. Anti-Myozyme® titers were assessed at weeks 4, 6, and 9 (FIG. 31). Comparing the average titer values in rhGAA- and rhGAA/methotrexate-treated IL-10 knockout mice, a significant decrease in titer was not observed, although a slight trend was observed at week 9. As expected, antibody titers were not as high in the IL-10 knockout animals as in the C57BL/6 wild-type animals. Anti-rhGAA responses in C57BL/6 wild-type animals treated with rhGAA and methotrexate were decreased at 4, 6 and 9 weeks. By contrast, anti-rhGAA titers at weeks 4 and 6 were not decreased in IL-10 knockout animals that were treated with rhGAA and methotrexate. At week 9, there was a slight decrease, which may indicate a delayed induction of tolerance in IL-10 deficient mice. This would be consistent with reports that IL-10 is not the only suppressive cytokine secreted by regulatory B cells (Sagoo et al., J. Clin. Investigation; 120(6):1848-1861 (2010)). TGF-beta also has been associated with the regulatory B cell response. If there is such a delay, other cytokines such as TGF-beta may be able to help mediate the methotrexate-tolerizing effect. These data thus far suggest that IL-10 may play a role in methotrexate-induced tolerance.

Example 14

A Role for Methotrexate in the Treatment of Alemtumzab-Associated Secondary Autoimmunity Alemtuzumab-treated multiple sclerosis patients can develop secondary autoimmunity. The most common autoimmune disorders that develop following alemtuzumb treatment are those related to thyroid autoimmunity. In addition, immune thrombocytopenic purpura and Good Pasture's syndrome also have been observed in multiple sclerosis patients treated with alemtuzumab. All three types of autoimmunity are B cell mediated in that B cell responses and auto-antibodies are directly linked with disease development and pathology. The association of alemtuzumab treatment with the development of these secondary diseases is not well understood.

Following alemtuzumab treatment, T cells and B cells are depleted. A large percentage of these depleted T and B cells are likely to be auto-reactive cells that interact with antigens expressed in the central nervous system. As a result, their subsequent depletion by alemtuzumab is thought to contribute to the therapeutic benefit of this monoclonal antibody therapy. Patients suffering from autoimmune disease have been described to contain autoreactivities (i.e., autoreactive B cells and autoreactive antibodies) against multiple antigens that are associated with a variety of autoimmune diseases. Environmental, physiological, and genetic factors all contribute to the determination of whether autoimmune disease will likely ensue and influence which autoimmune disease will present in the patient. It is not uncommon for patients who suffer from one type of autoimmune disease to also develop another.

In the context of alemtuzumab, one hypothesis is that inherent autoreactivities that were not as prominent as those related to multiple sclerosis are allowed to expand in the lymphocyte-depleted environment following alemtuzumab treatment. People that develop an autoimmune disease typically have autoreactivites to a number of different antigens and therefore a predisposition to develop other autoimmunities (i.e., "inherent autoreactivity"). In support of this idea are data in huCD52 Tg mice which show that alemtuzumab does not equivalently deplete all B cell populations (FIG. 27). In fact, there appears to be an imbalance in the B cell repertoire that favors a constituency of low affinity autoreactive B cells, particularly marginal zone B cells. Importantly, marginal zone B cells have been associated with thyroid autoimmunity (Segundo et al., Thyroid, 11(6):525-530 (2001). Additionally, the regulatory B cell subset, B10 B cells, which have been shown to help quell autoimmunity in the murine model of multiple sclerosis, EAE (Matsushita et al., J. Clin. Investigation, 118:3420-3430 (2008)), and have been shown to exist in humans (Iwata et al., Blood, 117:530-541 (2011)) is depleted for longer periods of time than marginal zone B cells. A short course of methotrexate treatment during the first cycle of alemtuzumab may help increase the representation of regulatory B10 B cells, and to restore the B cell balance such that marginal zone B cells are more equally represented in the B cell repertoire following alemtuzumab treatment and/or differentiate the marginal zone B cells into regulatory marginal zone B cells (CD1d+ marginal zone cells).

Splenic B cell populations were studied to determine the effects of alemtuzumab on B cell depletion (FIG. 32). 0.5 mg/kg of alemtuzumab was administered intravenously for five consecutive days in huCD52 Tg mice. Specifically, populations of follicular B cells (which are typically not autoreactive), B1 B cells and marginal zone B cells (both of which are autoreactive), B10 B cells (which are regulatory), and transitional B cells and marginal zone B cells (which are thought to be able to differentiate into B regulatory cells) were examined.

Figure 32:
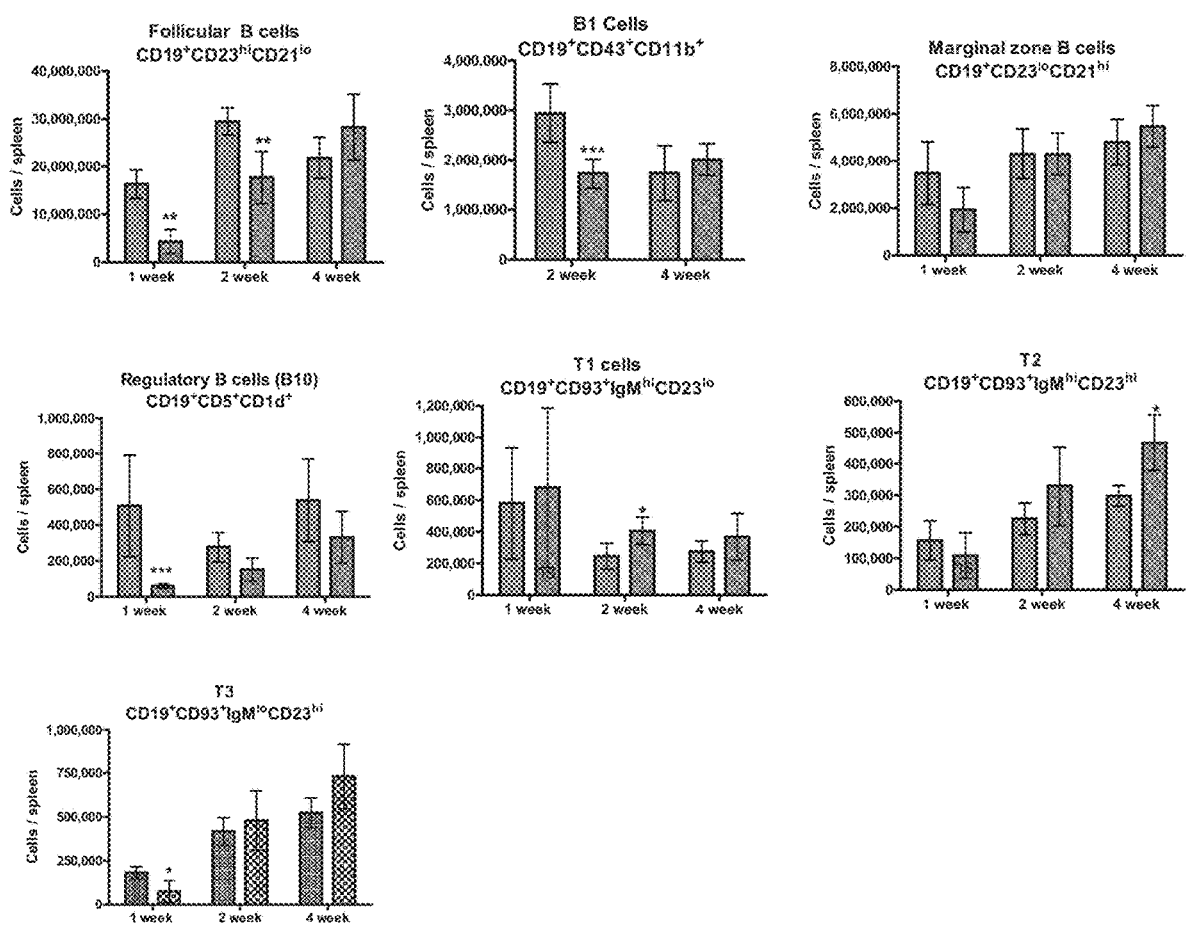
FIG. 32 shows that some, but not all, splenic B cell populations are depleted at one and/or two weeks following treatment with alemtuzumab. Small hatched bars represent phosphate buffered saline (PBS) treated huCD52 transgenic control mice; large hatched bars depict huCD52 transgenic mice treated with 0.5 mg/kg of alemtuzumab for five consecutive days. Asterisks indicate measurements with statistically significant differences (*, $p<0.05$; , $p\leq0.001$; *, $p\leq0.0001$).

While follicular, B1, and regulatory B cells were depleted at one and/or two weeks following treatment with alemtuzumab, marginal zone B cells and transitional 1 (T1) and transitional 2 (T2) B cells were not depleted at any of the time-points (FIG. 32). Transitional 3 B cells (T3) were only depleted after one week of treatment, and the numbers of regulatory B cells generally appear lower in alemtuzumab-treated mice than in control-treated animals, although statistical significance was not observed at weeks 2 and 4.

Figure 33:
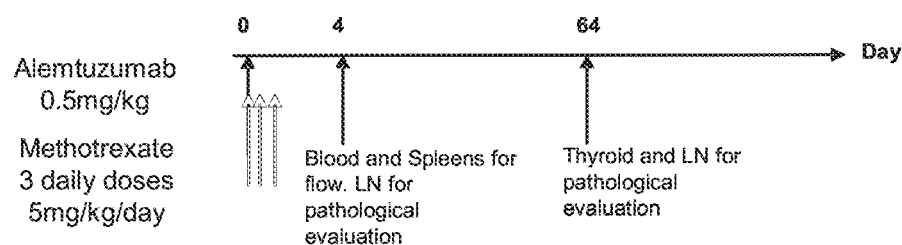
FIG. 33 shows a study design for examining the effects of methotrexate on B cell populations in the context of treatment with alemtuzumab. Thyroid and lymph nodes (LN) were used for pathological evaluation. Arrows indicate time points at which alemtuzumab and methotrexate were administered, or terminal sacrifices as indicated.

To examine the effects of methotrexate on B cell populations in the context of treatment with alemtuzumab, a second study was performed as indicated in Table 3 and FIG. 33. Surprisingly, co-treatment of methotrexate with alemtuzumab may allow for a stronger depletion of marginal zone B cells shortly following alemtuzumab treatment than depletion observed with alemtuzumab alone (FIG. 34), thereby promoting a balanced immune environment with the appropriate level of naturally occurring low-affinity self-reactive B cells necessary for proper early response to infection.

Figure 34:
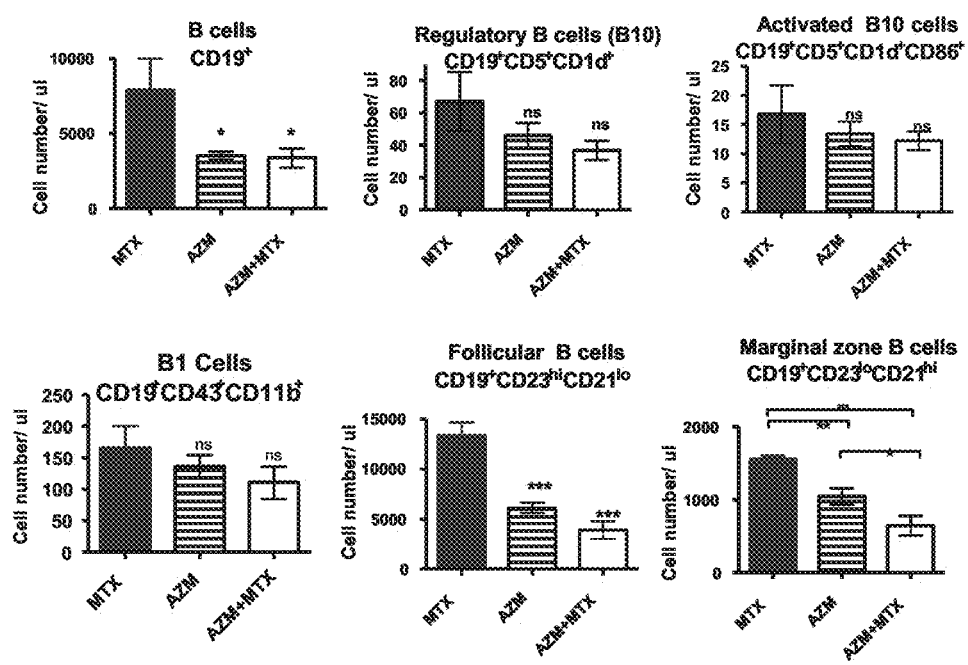
FIG. 34 shows the effects of three daily doses of 5 mg/kg/day methotrexate alone, 0.5 mg/kg alemtuzumab alone, and 0.5 mg/kg alemtuzumab and 5 mg/kg/day methotrexate in combination on the depletion of B cell populations. Asterisks indicate measurements with statistically significant differences (*, p<0.05; , p≤0.001; *, p≤0.0001); ns, not significant).

A group of mice treated with alemtuzumab alone was included in this study, and revealed that mice treated only with methotrexate in this short cycle regimen exhibited cellular effects in the absence of antigen stimulation, which can be different from the effects observed in control mice treated with methotrexate alone (FIG. 34). Data generated in this study, wherein splenic B cell populations were assessed two days following the last day of methotrexate treatment, suggest that methotrexate may enhance the depletion of marginal zone B cells. This supports the hypothesis that methotrexate, when delivered with alemtuzumab, may result in a cellular environment wherein naturally occurring B cell subsets are appropriately in balance with non-autoreactive B cell subsets.

TABLE 3

Study design in mice treated with alemtuzumab and/or methotrexate

| Grp # | Treatment | Animals Per Group | Sacrifice time points | Flow data | Pathology |
|---|---|---|---|---|---|
| 1 | 0.5 mg/kg alemtuzumab | 5 | Day 4 | Blood, spleen | Lymph node (LN) |
| 2 | 0.5 mg/kg alemtuzumab + methotrexate (5 mg/kg) | 5 | Day 4 | Blood, spleen | LN |
| 3 | 0.5 mg/kg alemtuzumab | 5 | Day 64 | — | LN, thyroid |
| 4 | 0.5 mg/kg alemtuzumab + methotrexate (5 mg/kg) | 5 | Day 64 | — | LN, thyroid |
| 5 | 0.5 mg/kg alemtuzumab | 5 | Day 64 | — | LN, thyroid |
| 6 | 0.5 mg/kg alemtuzumab + methotrexate (5 mg/kg) | 5 | Day 64 | — | LN, thyroid |
| 7 | Methotrexate | 5 | Day 4 | Blood, spleen | LN |

Figure 35:
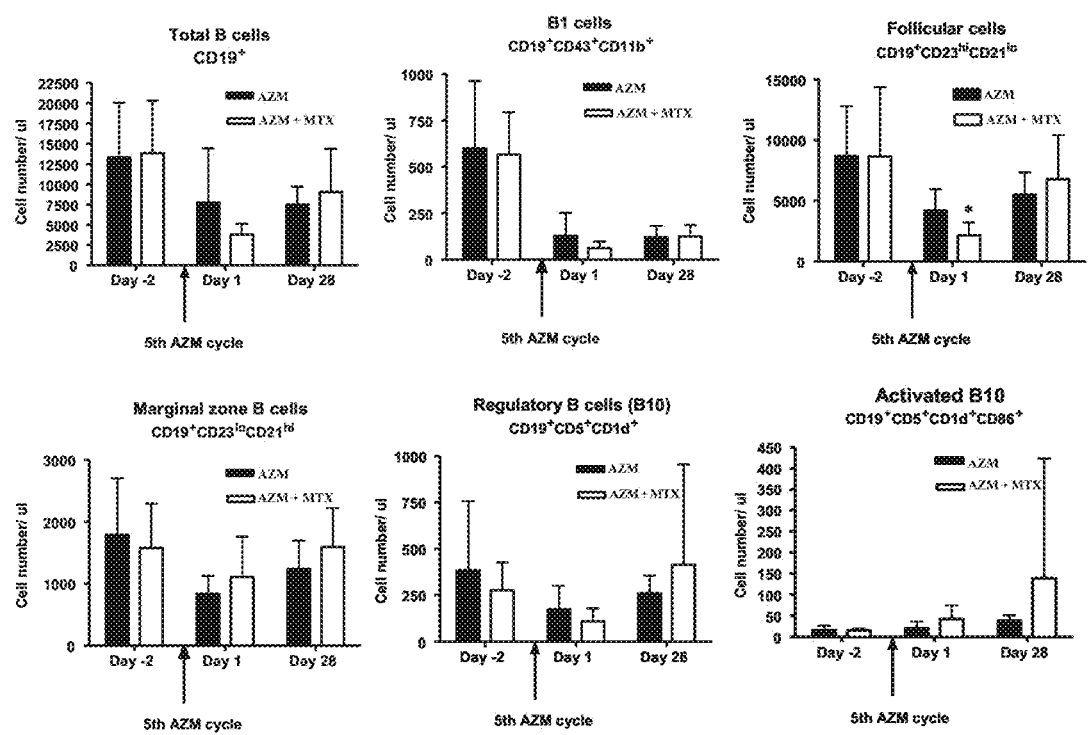
FIG. 35 shows the effects of methotrexate on B cell depletion after five cycles of treatment with 0.5 mg/kg alemtuzumab alone or three daily doses of 5 mg/kg/day methotrexate alone or 0.5 mg/kg alemtuzumab and 5 mg/kg/day methotrexate in combination. Asterisks indicate measurements with statistically significant differences (*, p<0.05).

Based on the daily assessment of cell populations that followed directly after methotrexate treatment with Myozyme®, we hypothesize that in the context of alemtuzumab, B10 B cell populations and other potentially regulatory B cell populations will be enriched by methotrexate no earlier than 5-6 days following methotrexate treatment. We have not observed such populations to be enriched as early as two days after methotrexate treatment, which is consistent with this hypothesis. By contrast, the effects seem to be different at longer time periods after methotrexate treatment, as seen in the context of mATG and alemtuzumab treatment. In both of those scenarios, five months after methotrexate treatment, B cell subsets appeared enriched in methotrexate-treated mice one and two days following mATG and alemtuzumab dosing (see FIG. 35 for alemtuzumab data). Interestingly, marginal zone B cells at this time point also appeared increased (although this is not statistically significant).

Methotrexate induces tolerance to protein therapies and transplanted cardiac tissue antigens, thereby abrogating B cell immune responses that relate to the production and secretion of ADA and anti-allograft antibodies. We therefore hypothesize that methotrexate may not only help control the cellular environment following alemtuzumab treatment, but that it also may induce tolerance to self-proteins and mitigate the B cell immune responses that relate to the generation of auto-antibodies that contribute to the development and pathology of B cell-mediated autoimmune diseases.

Figure 36:
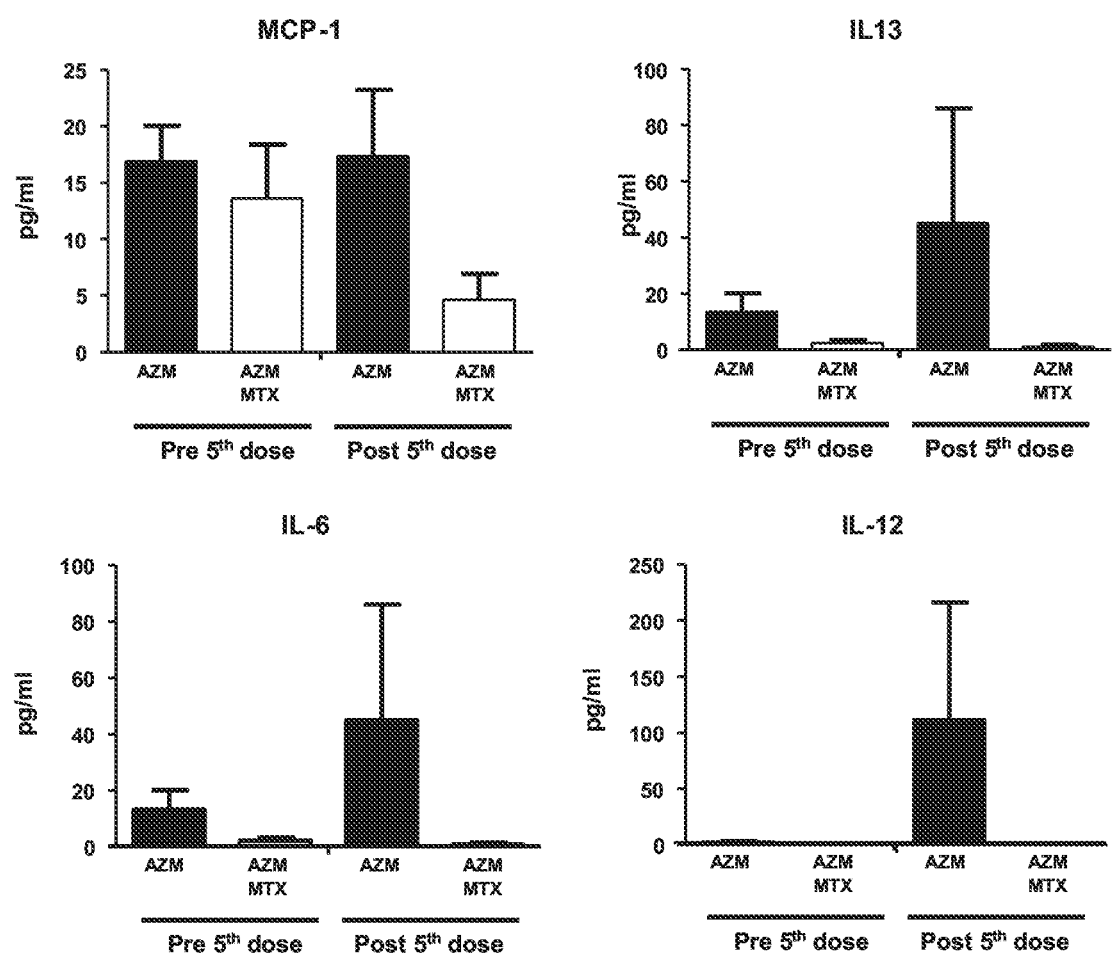
FIG. 36 shows that levels of the cytokines MCP-1, IL-13, IL-6, and IL-12 are decreased in mice treated with a single cycle of three days of 5 mg/kg of methotrexate administered on the first day of alemtuzumab treatment. Data were collected 24 hours after a fifth dose of alemtuzumab, four months after treatment with methotrexate.

To test this hypothesis, animals were dosed monthly for five months with alemtuzumab. Methotrexate was given to a group of animals at 5 mg/kg for three consecutive days following only the first alemtuzumab treatment. Two days prior to and one day following the fifth dose of alemtuzumab treatment, animals were sacrificed for analysis. Serum cytokine levels were assessed before and after alemtuzumab treatment. Surprisingly, these results suggest that the levels of the pro-inflammatory cytokines MCP-1, IL-13, IL-6, and IL-12 were decreased in animals treated with methotrexate 24 hours after the fifth dose of alemtuzumab, five months after being dosed with any methotrexate (FIG. 36). These cytokines not only promote B cell responses and immune cell recruitment, but they also can play a role in hypersensitivity reactions. These data suggest that methotrexate may help deter infusion associated reactions.

Example 15

Methotrexate Induces Immune Tolerance Through Specific Induction of Regulatory B Cell Populations Our data surprisingly show that methotrexate induces immune tolerance not by the expected means of killing proliferating cells as suggested by others (Messinger et al., Genetics in Medicine 14:135-142 (2012) and Lacané et al., Am J Med Genet Part C Semin Med Genet 160C:30-39 (2012)), but through the specific induction of regulatory B cells populations that express TGF-beta, IL-10 and FoxP3. B cells from mice tolerized to Myozyme® by a single cycle of methotrexate appeared to transfer immune tolerance to naive animals. Moreover, both IL-10 and TGF-beta appeared to be necessary for methotrexate-induced immune tolerance. In some cell subsets it also appeared that methotrexate induced TGF-beta, which in turn induced IL-10 and FoxP3. This mechanism is novel and unexpected, and questions the value of a current clinical immune tolerance protocol that involves co-treatment with three cycles of methotrexate, Rituximab® (a B cell-depleting agent), and optionally, intravenous immunoglobulin (IVIG) (Messinger et al., supra). Although this combination treatment appears to be successful, our data suggest 1) that a single cycle of methotrexate may potentially generate even lower ADA titers than those currently observed, and 2) that if too much methotrexate and rituximab are administered, immune tolerance may not be maintained. The initial doses of rituximab may not be too harmful as rituximab-mediated B cell depletion is not thought to comprehensively deplete all B cells in the blood and tissues. As seen with the studies described herein, although alemtuzumab actively depletes B10 B cells, treatment with methotrexate still is able to access those cells that seem to help maintain alemtuzumab tolerance for many months following the initial cycle of methotrexate. Moreover, rituximab treatment is rapidly followed by increased representation of transitional B cells, which, as shown herein, seem influenced by methotrexate to induce and mediate immune tolerance. As these mechanistic data are counterintuitive and unexpected, a single cycle of low dose methotrexate is a surprising and effective method of inducing immune tolerance to, inter alia, lymphocyte-depleting protein therapies.

As described above, several B cell subsets are significantly increased in cell percentage and/or cell numbers soon after co-administration of methotrexate with a protein therapeutic. Moreover, these subsets appear increased in methotrexate-tolerized mice long after a single cycle treatment of methotrexate (see, e.g., FIGS. 24, 27, and 35). Together, these data suggest that these cell populations may actively mediate both the induction and maintenance of immune tolerance induction. To further substantiate this hypothesis, we investigated whether these cell populations expressed cytokines and other proteins often associated with immune regulation.

Figure 38A:
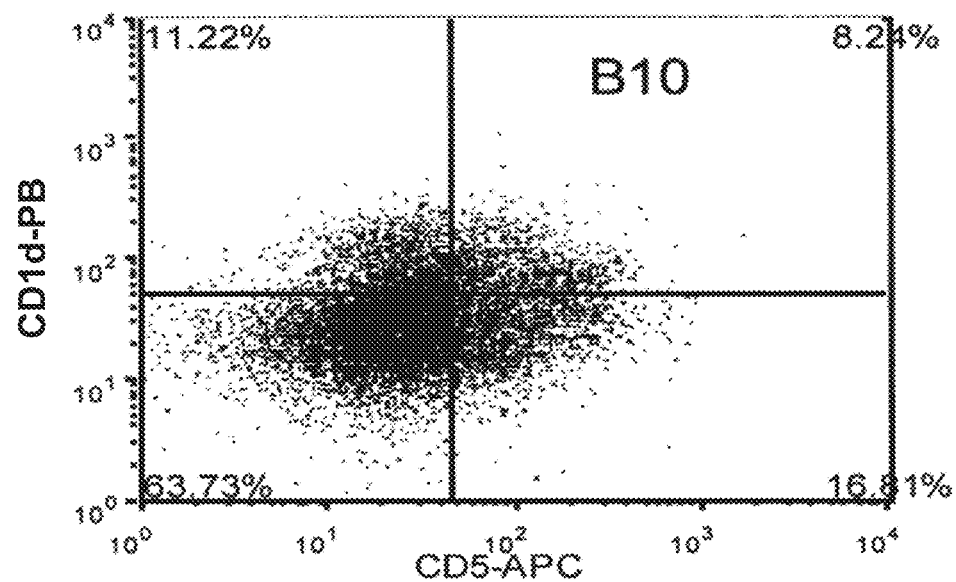
Figure 38A:
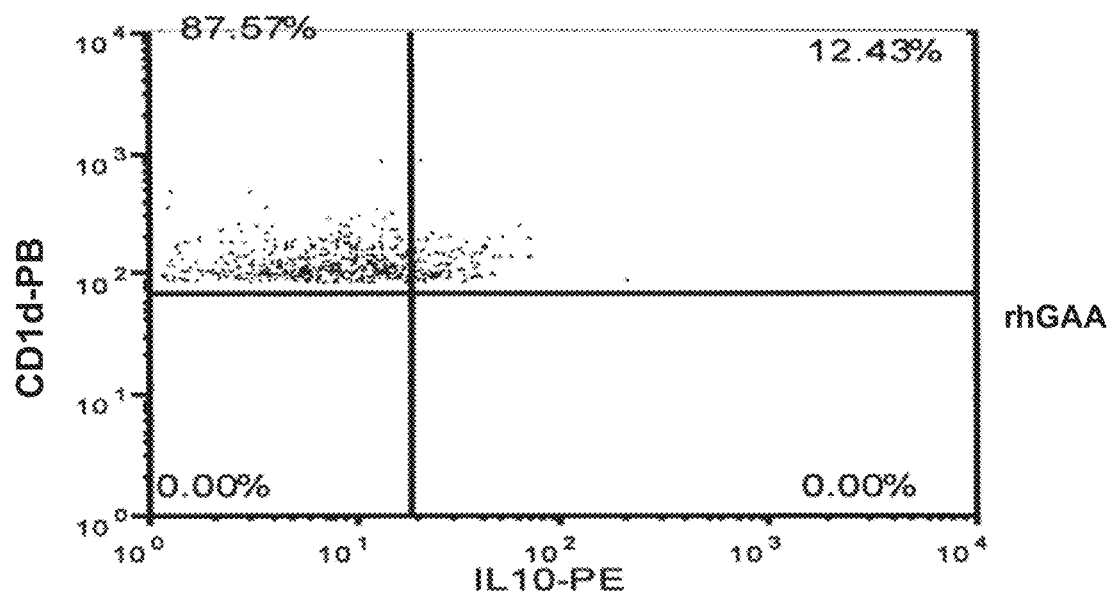
Figure 39A:
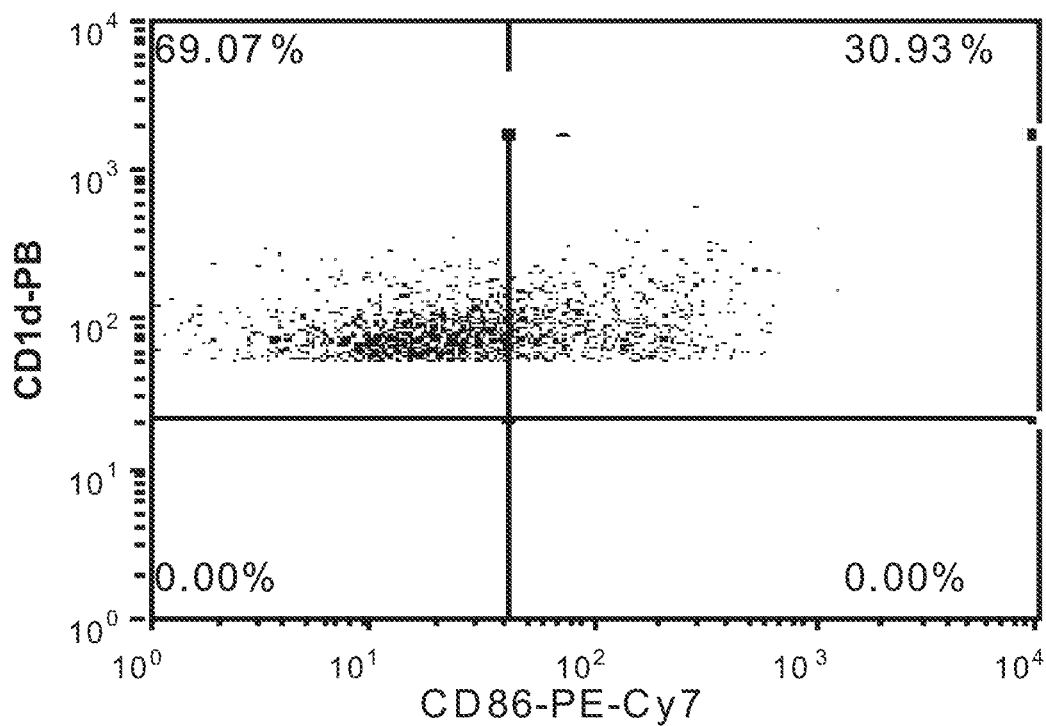
FIGS. 39A-B show that IL-10 is expressed in both activated (CD86+) and non-activated (CD86−) B10 B cells.
Figure 39B:
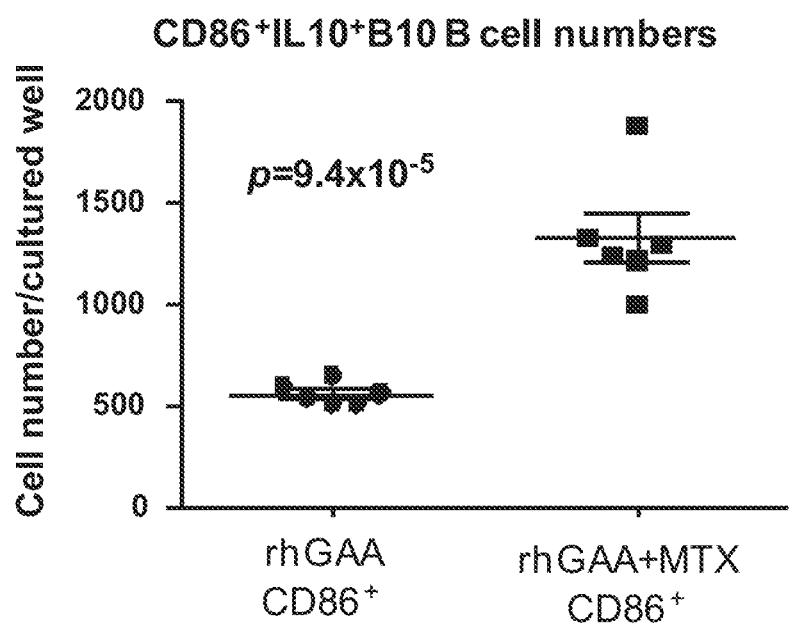
Figure 54:
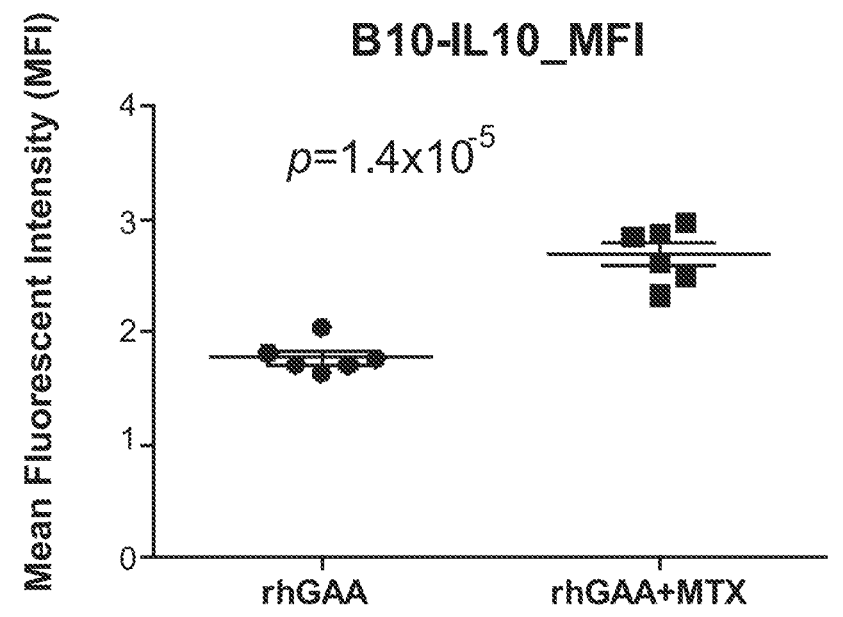
FIG. 54 shows that methotrexate treatment induces statistically significant increases in IL-10 in multiple cell subsets as viewed by a shift in mean fluorescence intensity (MFI) of these proteins in animals treated with rhGAA or rhGAA and methotrexate.
Figure 54:
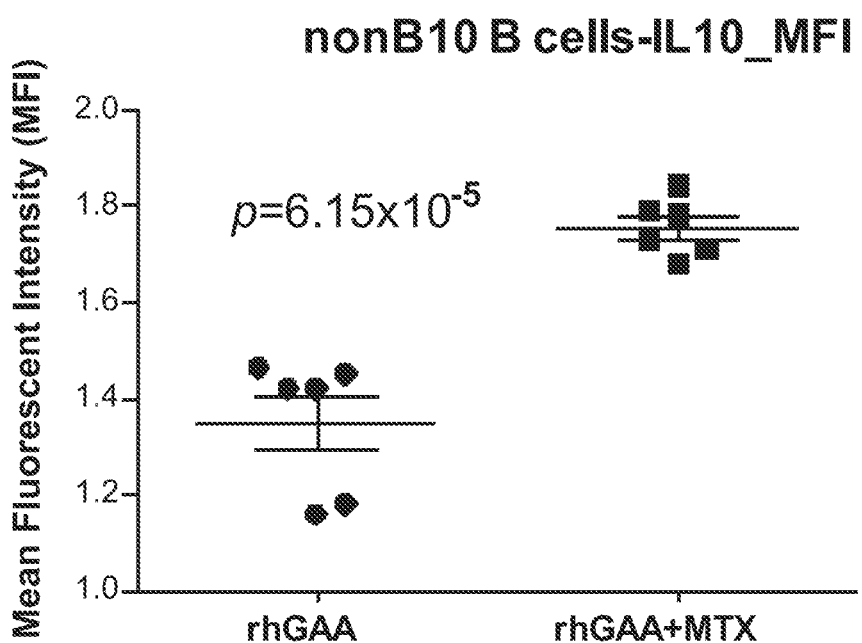

One cell type associated with immune regulation is B10 B cells. B10 B cells in both human and mouse are characterized by their expression of IL-10 (Matsushita et al., J. Clin. Invest. 118:3420-3430 (2008), Iwata et al., Blood 117:530-541 (2011)), and can only suppress immune responses in IL-10 competent mice. B10 B cells were increased in methotrexate-tolerized mice (FIG. 19), and IL-10 knockout animals were unresponsive to methotrexate-induced immune tolerance (FIG. 31). B10 B cells isolated from animals treated with Myozyme® or Myozyme® and methotrexate were assessed for IL-10 protein expression by flow cytometry. Although IL-10 was expressed in B10 cells from both treatment groups, the number of B10 B cells expressing IL-10 was increased in animals treated with Myozyme® and methotrexate (FIG. 38). IL-10 was expressed in both activated, CD86+ and non-activated, CD86-B10 B cells following two days of culture (FIG. 39). Previous studies appear to show that IL-10 expression is measured only following in vitro stimulation of cells by stimulants such as PMA/Ionomycin or LPS (Carter et al., J Immunol 186:5569-5579 (2011); Yanaba et al., J Immunol 182:7459-7472 (2009)). Surprisingly, in our studies, the cultured splenic B cells did not need any stimulation or manipulation to allow for the measurement of IL-10, more directly suggesting that these B10 B cells express IL-10 in vivo. The data provided herein were generated in non-stimulated cultures. In addition, we believe that we have demonstrated for the first time that methotrexate can specifically expand cell populations that express IL-10. Moreover, these cell populations appear to express more IL-10 when isolated from animals treated with Myozyme® and methotrexate than from animals treated with Myozyme® alone (FIG. 54).

Figure 40A:
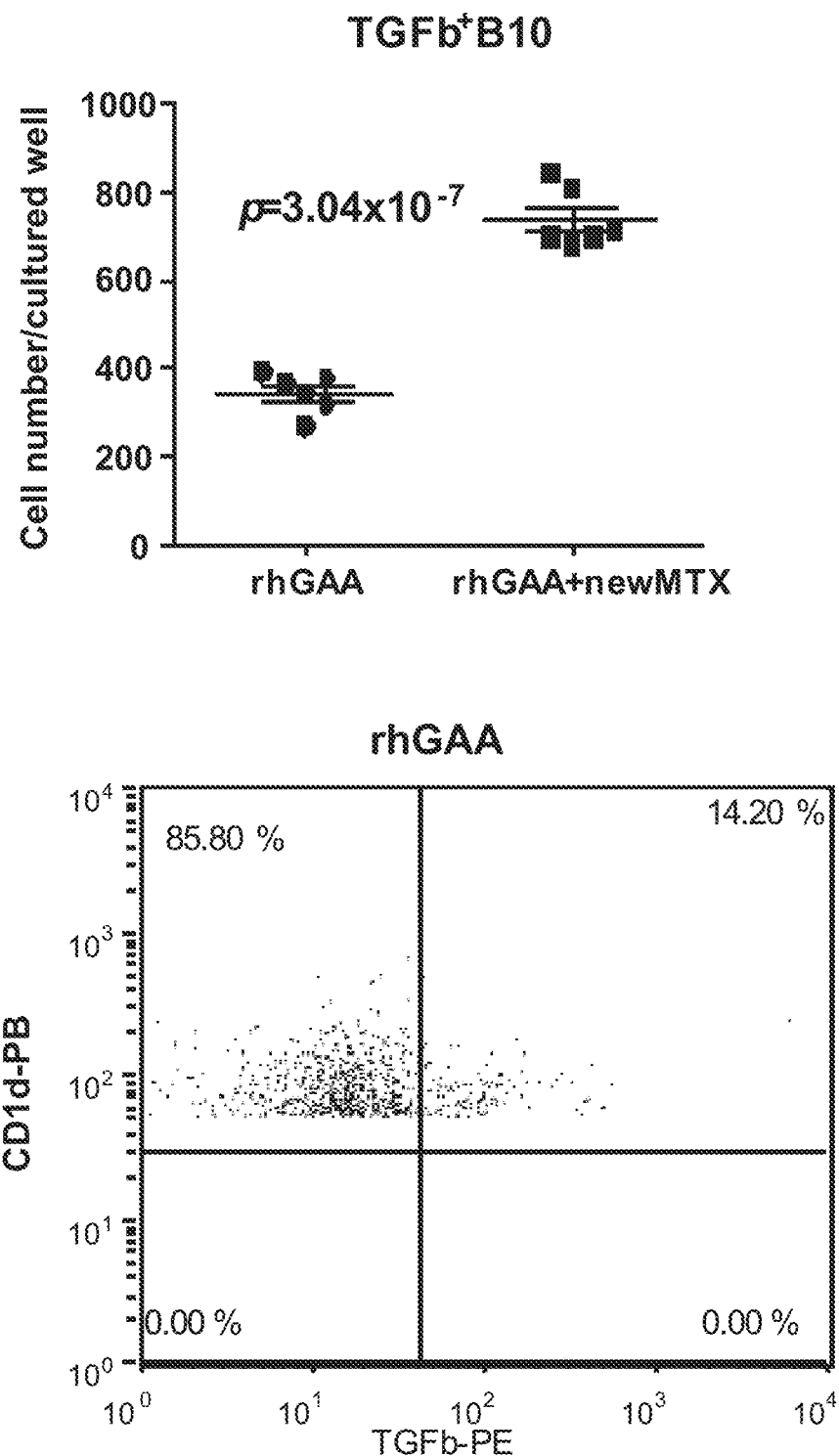
FIGS. 40A-B show that methotrexate treatment with rhGAA induces B10 B cells to increase their expression of TGF-beta. The second and third panels of FIG. 40A are FACS plots showing B10 B cells stained with TGF-beta and CD86 from animals treated with rhGAA or rhGAA and methotrexate. The first panel of FIG. 40A depicts the number of TGF-beta$^+$ B10 B cells in animals treated with rhGAA or rhGAA and methotrexate.
Figure 40B:
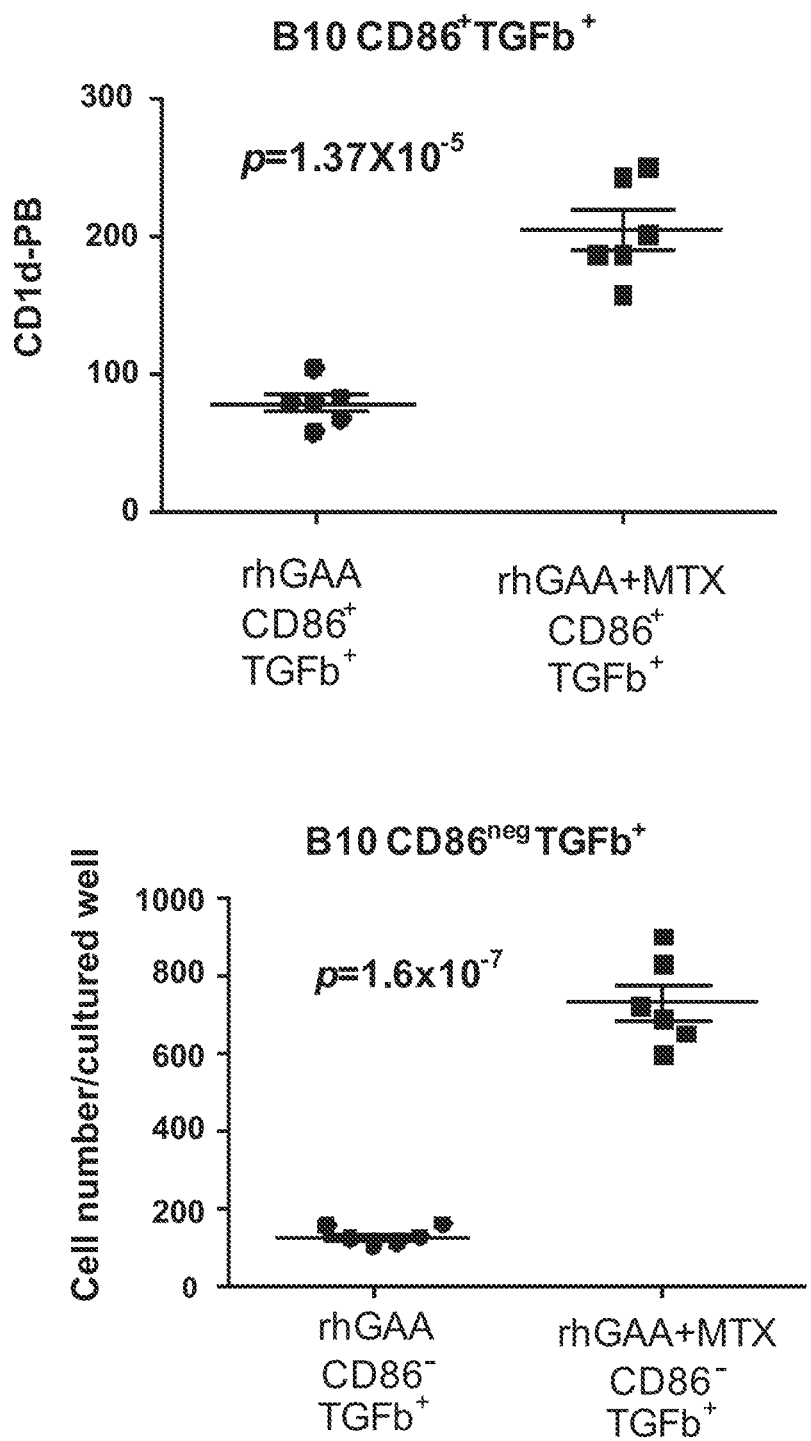
Figure 55:
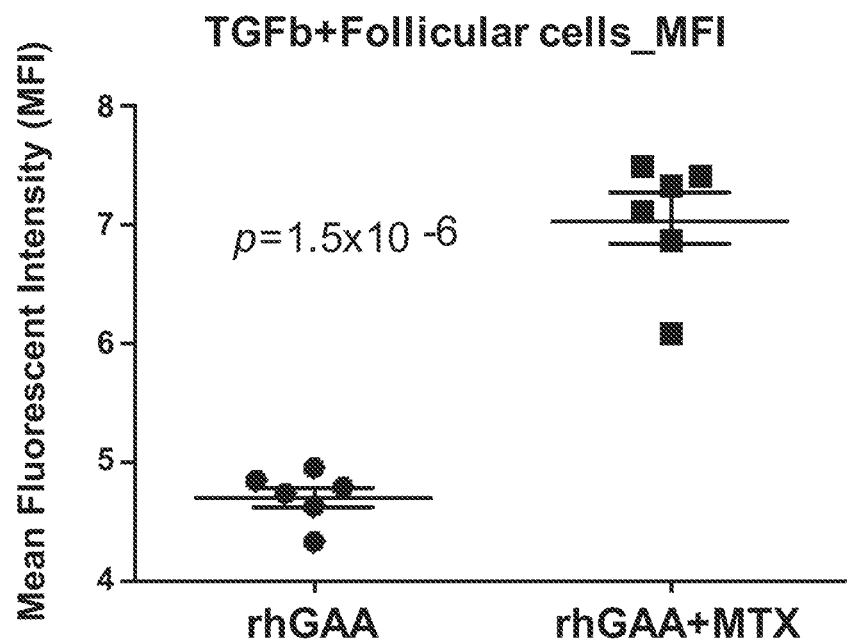
FIG. 55 shows that methotrexate treatment induces statistically significant increases in TGF-beta in multiple cell subsets as viewed by a shift in mean fluorescence intensity (MFI) of these proteins in animals treated with rhGAA or rhGAA and methotrexate.
Figure 55:
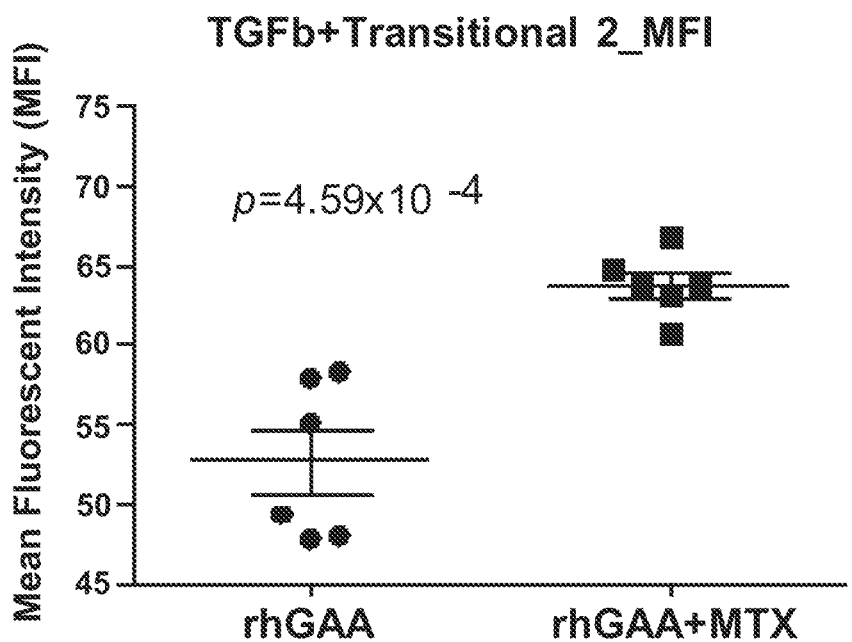

TGF-beta expression is associated with immune regulation in T regulatory cells and is often linked with IL-10 expression in T regulatory cells. Moreover, some reports seem to indicate that regulatory B cells can express TGF-beta. Although B10 B cells have never been reported to express TGF-beta, we decided to assess TGF-beta expression in B10 B cells of mice treated with Myozyme® alone or with Myozyme® and methotrexate using flow cytometry. Unexpectedly, we found that B10 B cells express TGF-beta, and that the numbers of TGF-beta-expressing cells is increased in methotrexate-tolerized animals (FIG. 40A). Moreover, in these cultured cells, TGF-beta is expressed in both activated (CD86+) and non-activated (CD86-) B10 B cells (FIG. 40B). This is an additional novel observation that methotrexate treatment increases the numbers of cells that express TGF-beta. Additionally, methotrexate increases the expression level of TGF-beta (FIG. 55).

Figure 41A:
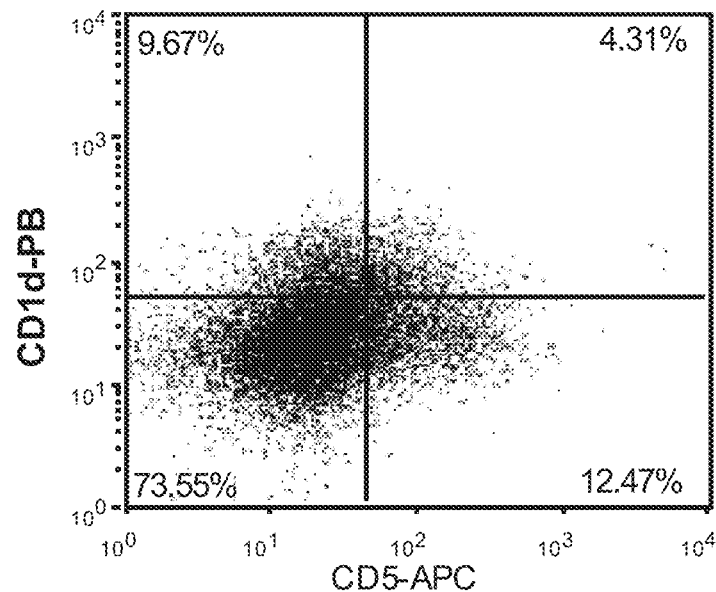
FIG. 41A depicts that B10 B cells appear to express FoxP3 in animals treated with rhGAA (FIG. 41A).
Figure 41A:
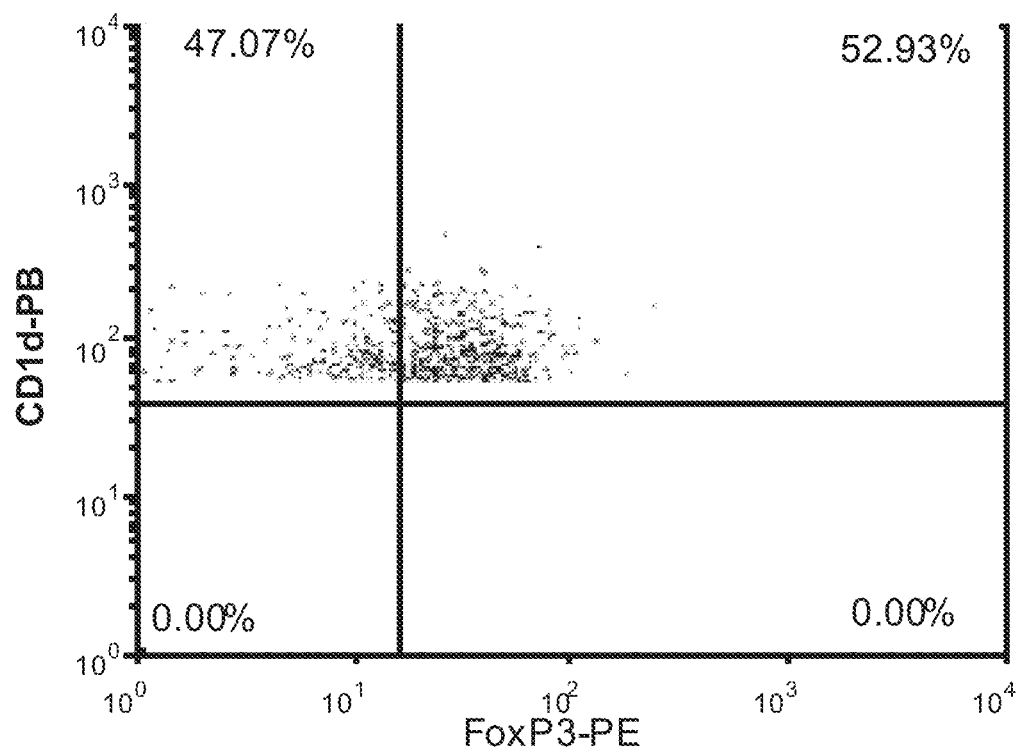
Figure 41B:
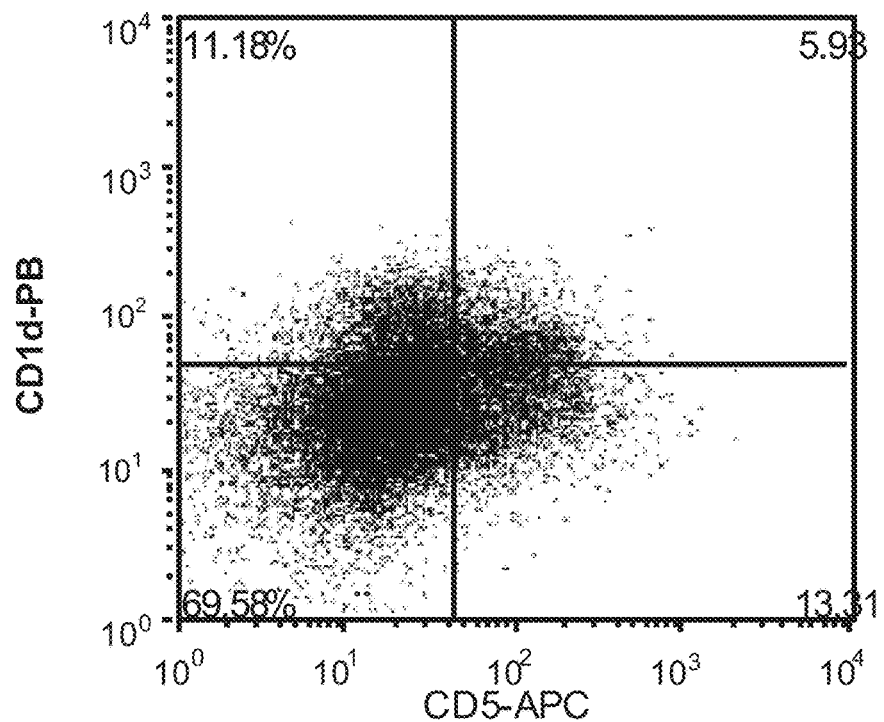
FIG. 41B depicts that the numbers of FoxP3+ B cells increase with treatment with both methotrexate and rhGAA.
Figure 41B:
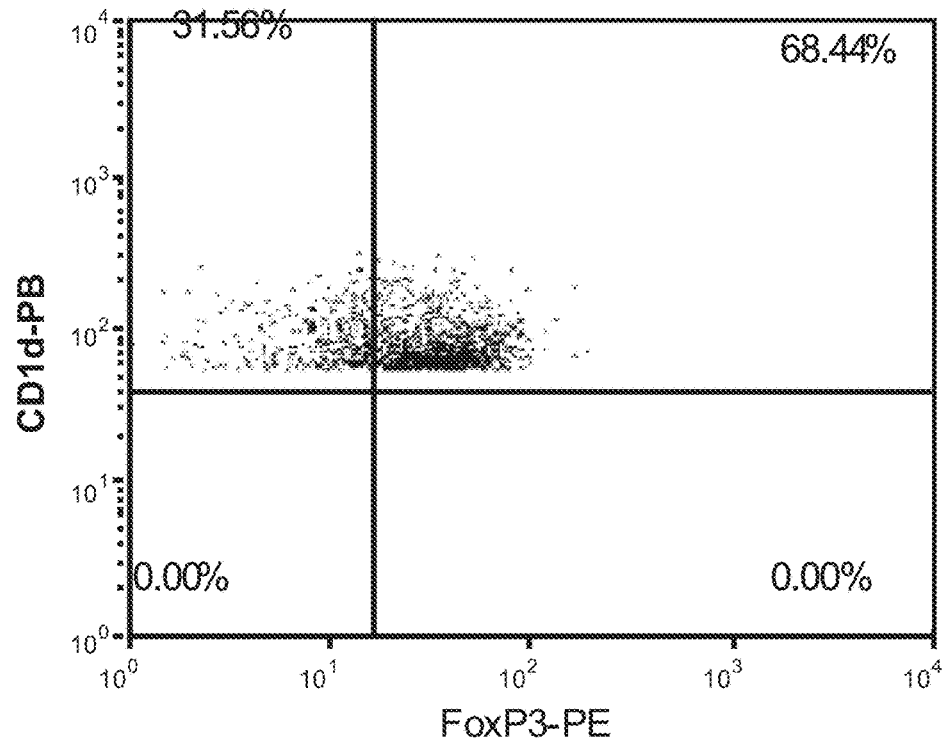
Figure 41C:
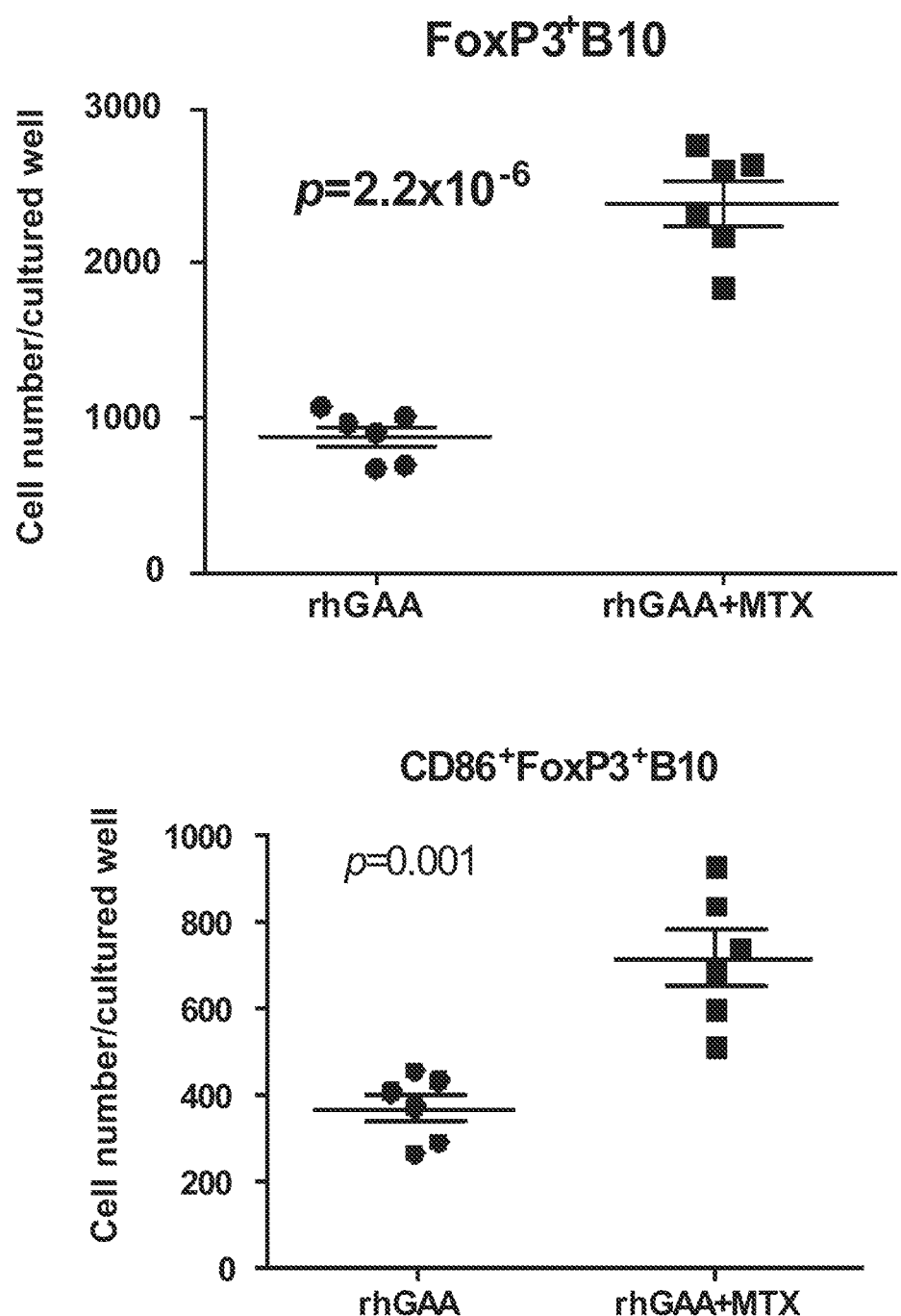
FIG. 41C depicts that both activated (CD86+) and non-activated (CD86−) B10 B cells express FoxP3.
Figure 42A:
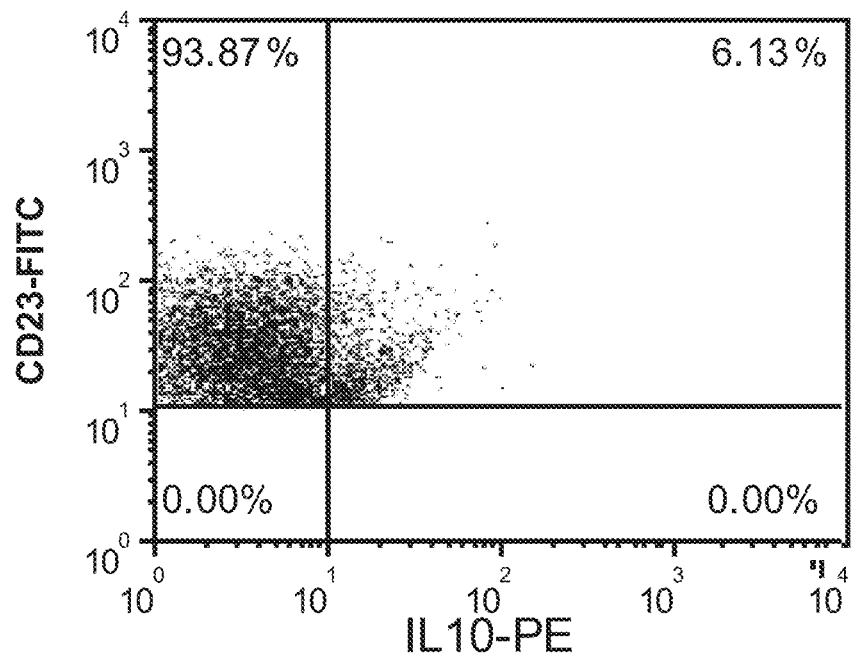
FIGS. 42A-C show that follicular, transitional 2, and transitional 3 B cells (top to bottom) express IL-10 and that the cell numbers of the IL-10-expressing B cell subsets increase with methotrexate as compared to mice treated with rhGAA alone.
Figure 42A:
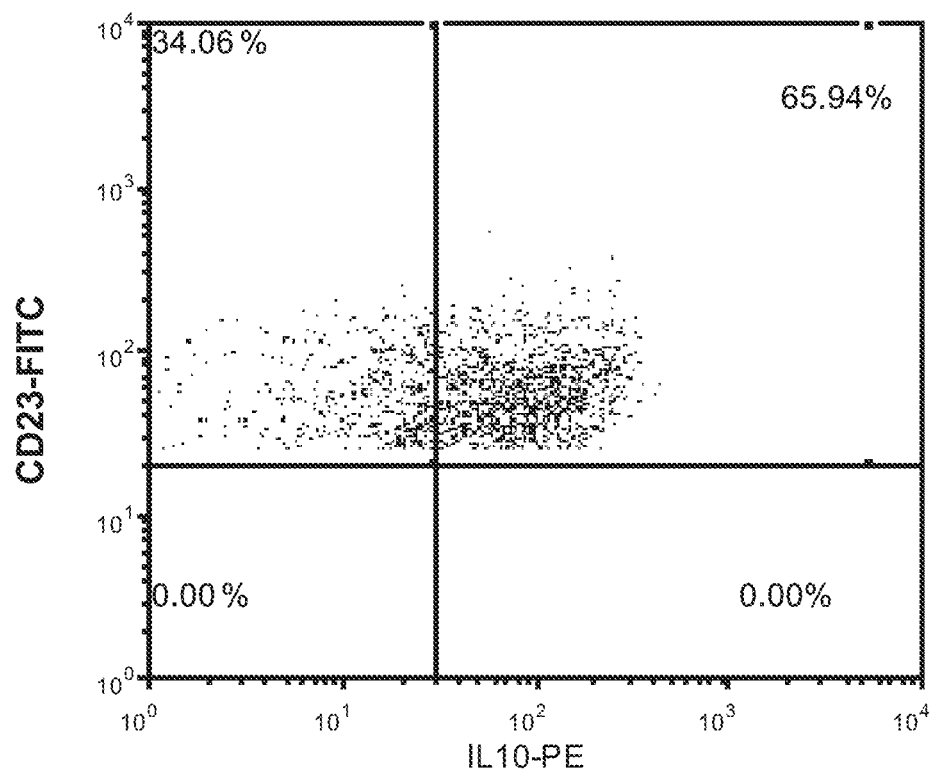
Figure 42B:
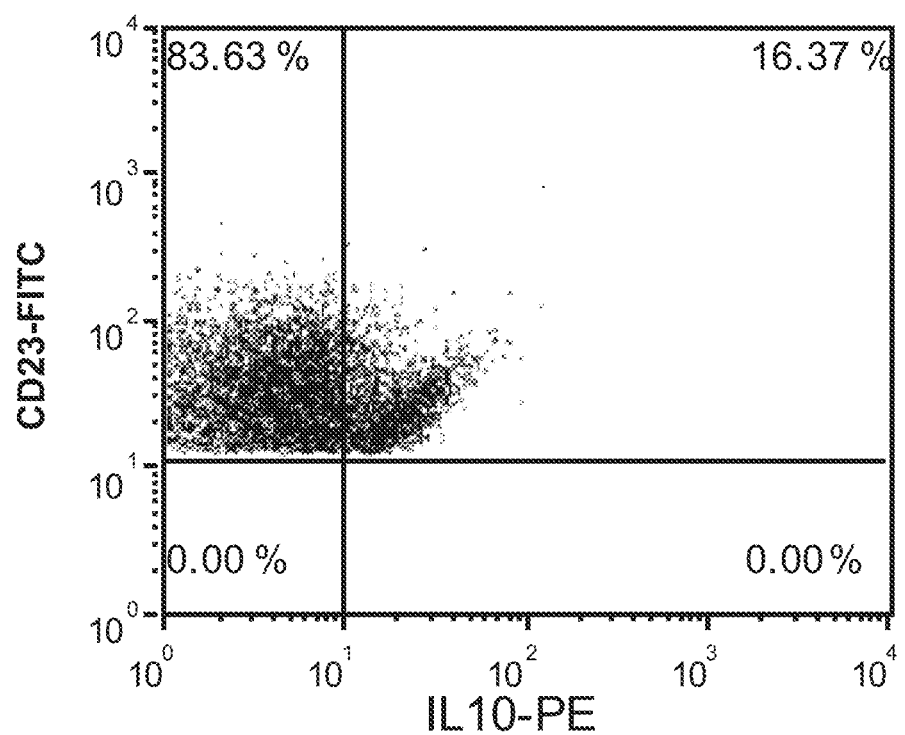
Figure 42B:
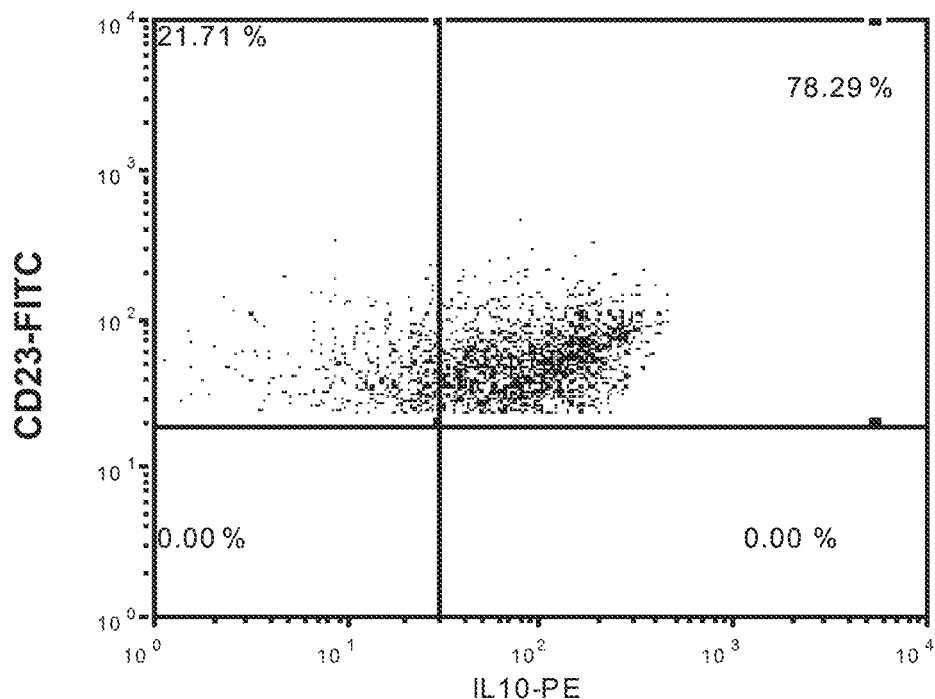
Figure 42C:
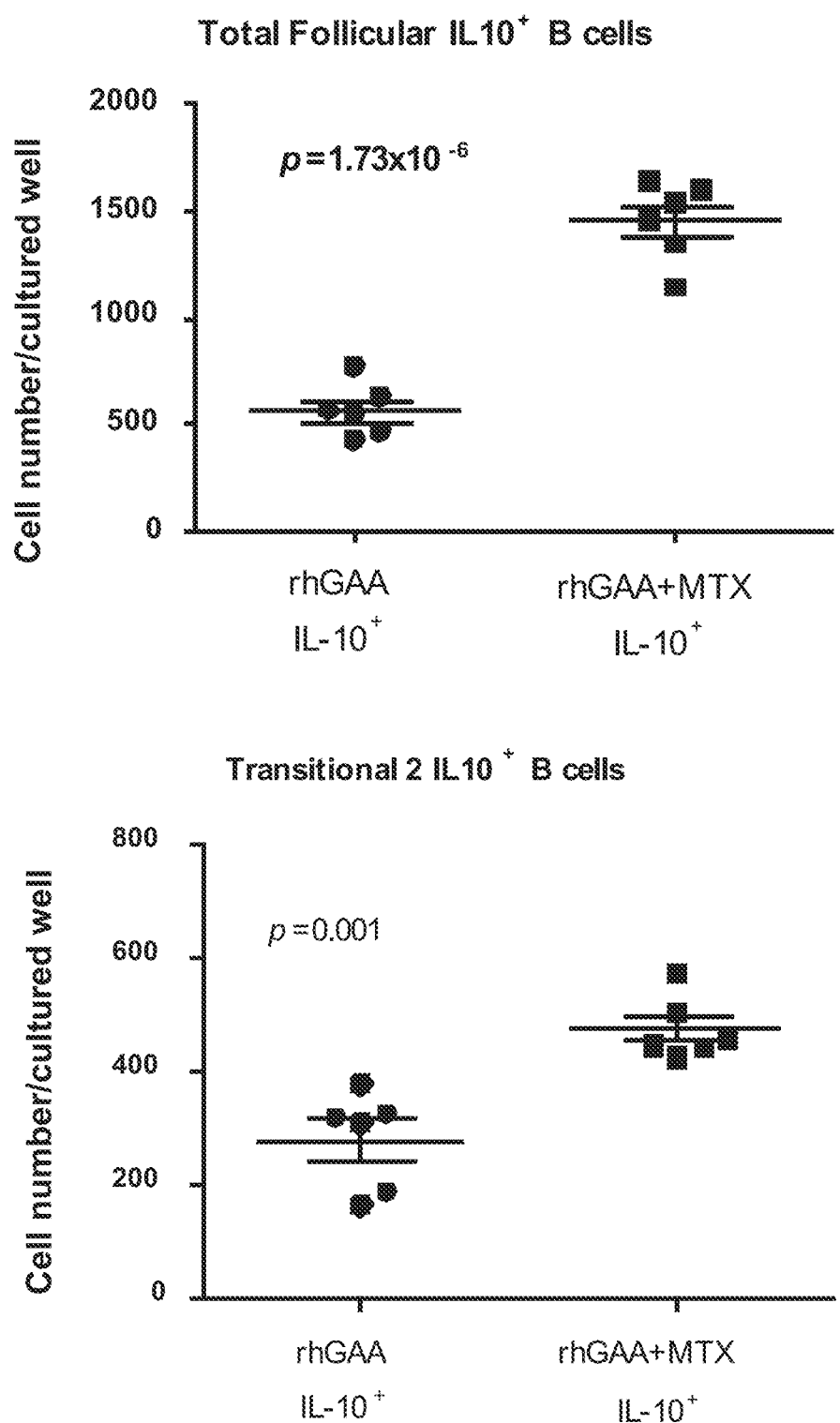
Figure 56:
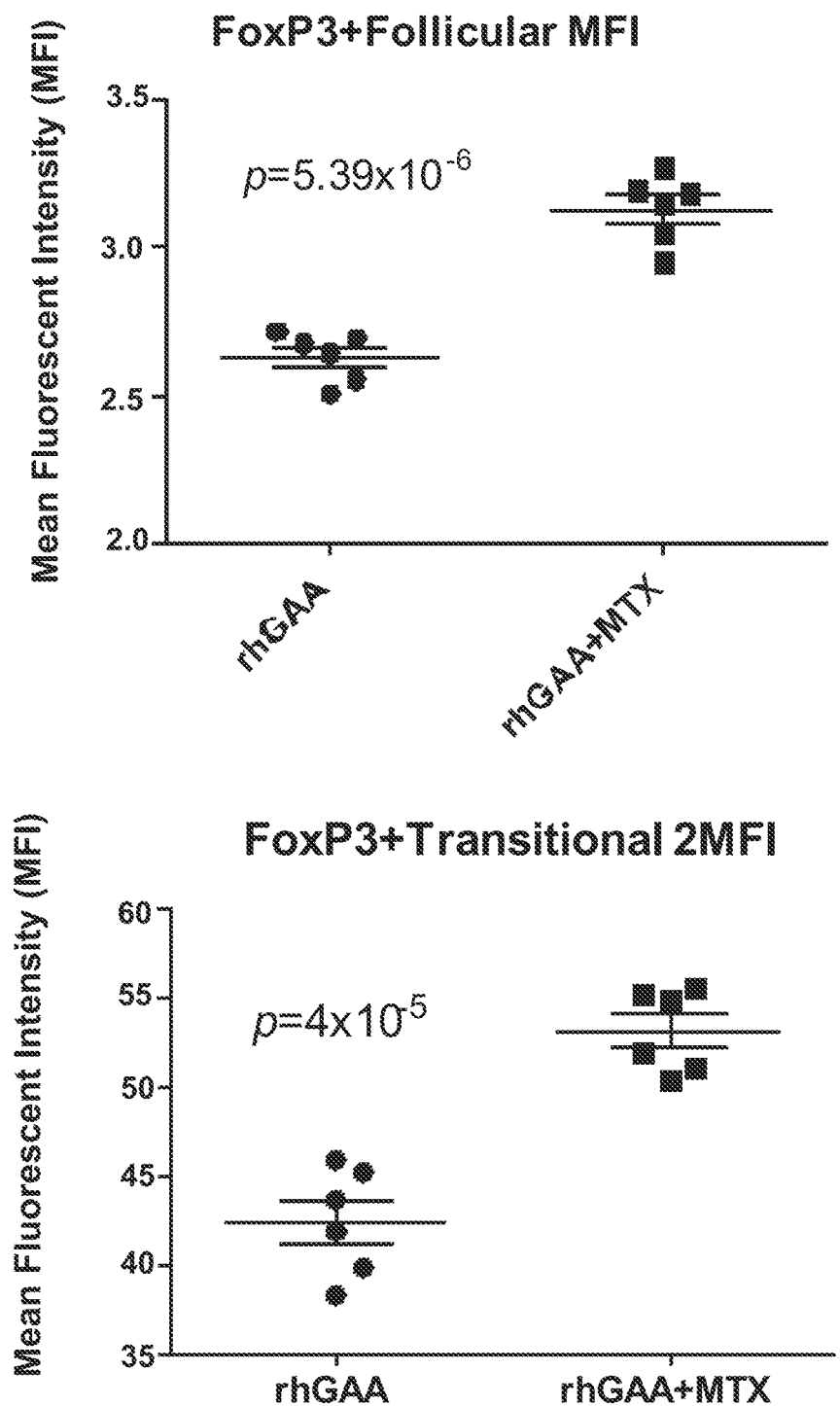
FIG. 56 shows that methotrexate treatment induces statistically significant increases in FoxP3 in multiple cell subsets as viewed by a shift in mean fluorescence intensity (MFI) of these proteins in animals treated with rhGAA or rhGAA and methotrexate.

FoxP3 is another protein associated with immune regulation. FoxP3 is a marker for T regulatory cells. FoxP3 has not been reported to be expressed in B10 B cells in mice. We investigated FoxP3 expression in B10 B cells in the presence and absence of methotrexate-induced immune tolerance by using flow cytometry. B10 B cells appear to express FoxP3, as seen in animals treated with Myozyme® alone (FIG. 41A). The numbers of FoxP3+ B cells appear to increase with treatment with both methotrexate and Myozyme® (FIG. 41B). Additionally, both cultured activated (CD86+) and non-activated (CD86-) B10 B cells appear to express FoxP3 (FIG. 41). This was the first report that B10 B cells express FoxP3. We found that FoxP3 was expressed in both activated (CD86+) and unactivated (CD86-) B 10 B cells and the expression of FoxP3 is increased with methotrexate treatment (FIG. 56).

Figure 43A:
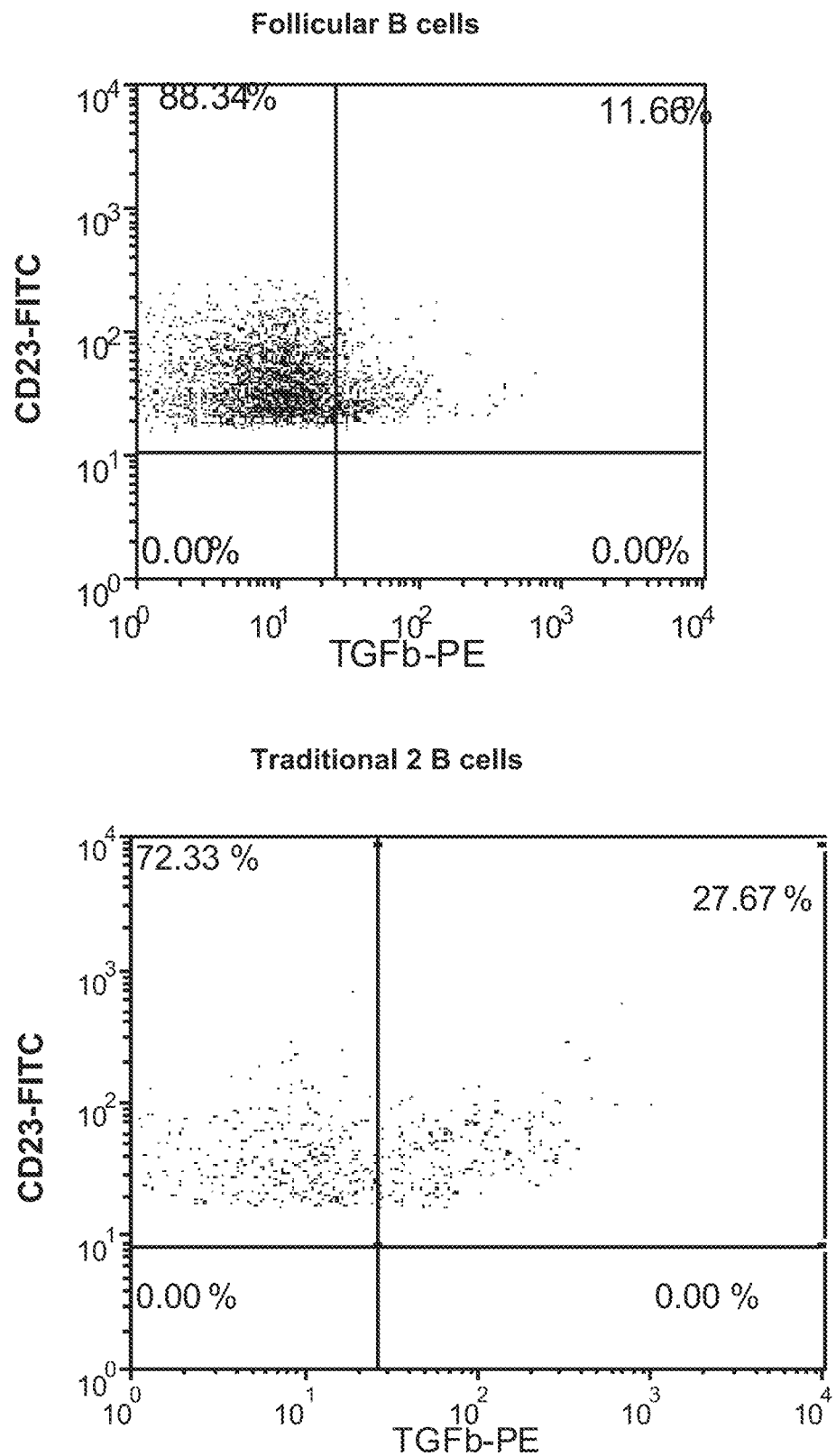
FIGS. 43A-C show that follicular, transitional 2, and transitional 3 B cells (top to bottom) express TGF-beta and that the cell numbers of the TGF-beta-expressing B cell subsets increase with methotrexate as compared to mice treated with rhGAA alone.
Figure 43B:
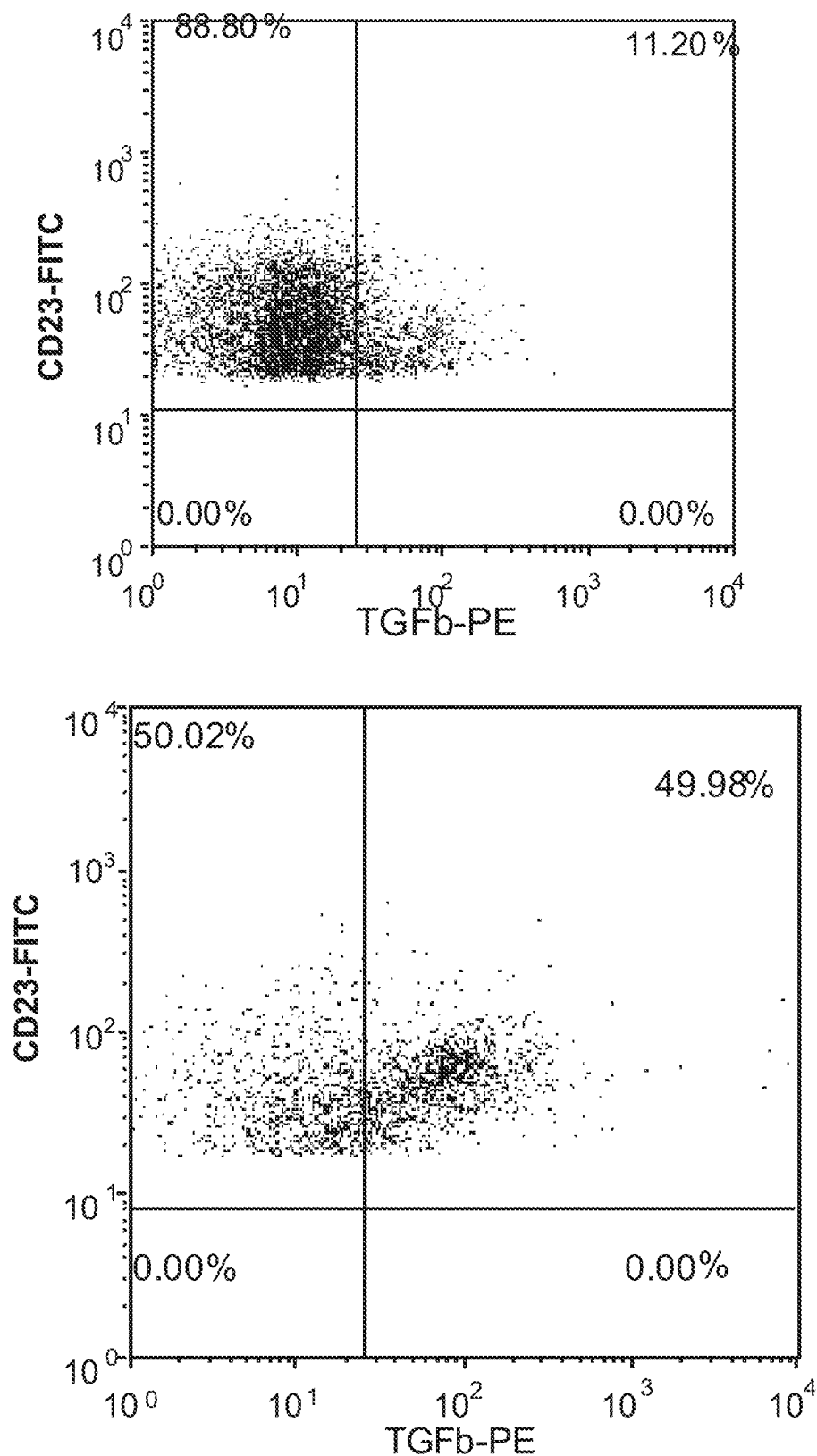
Figure 43C:
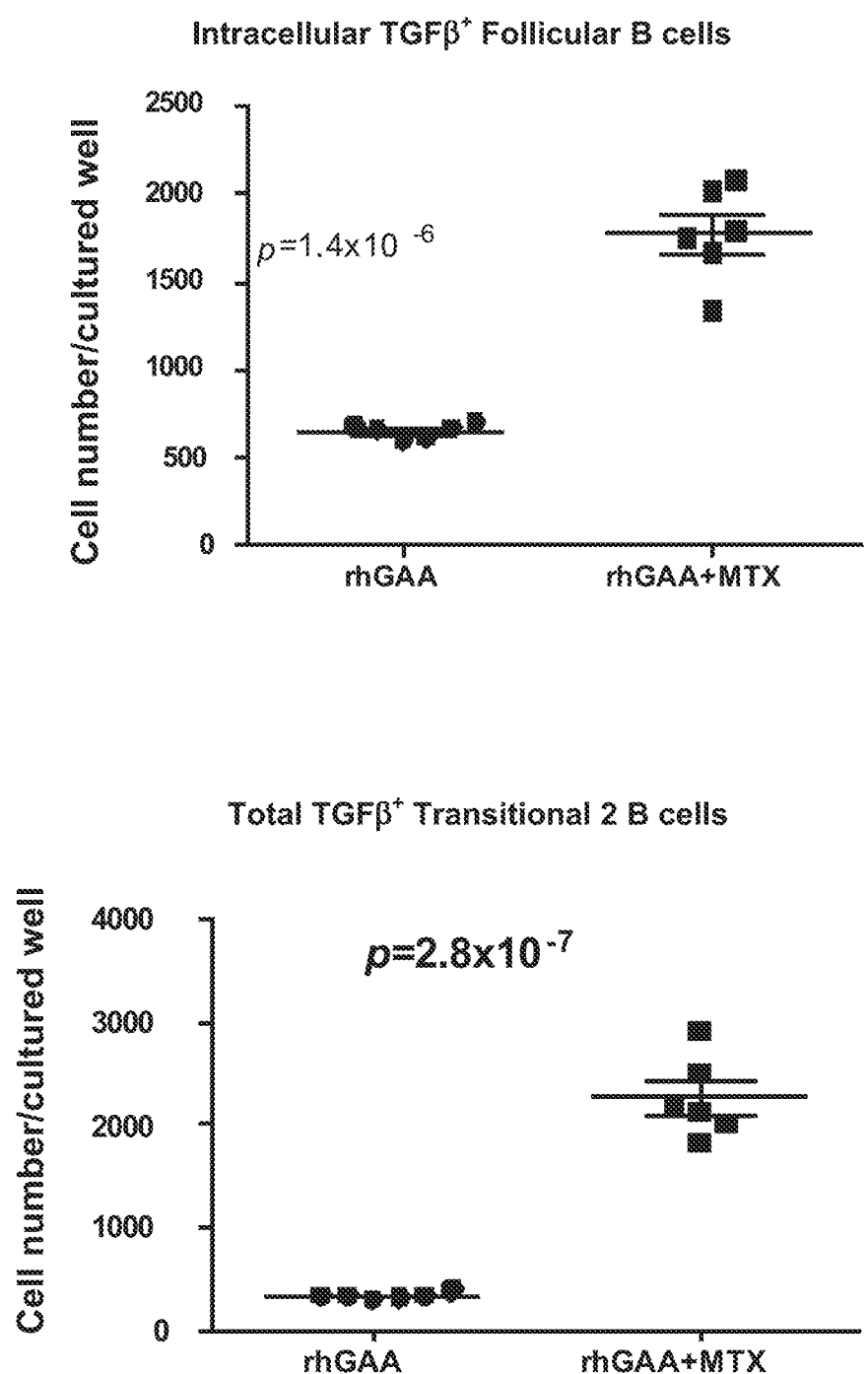
Figure 44A:
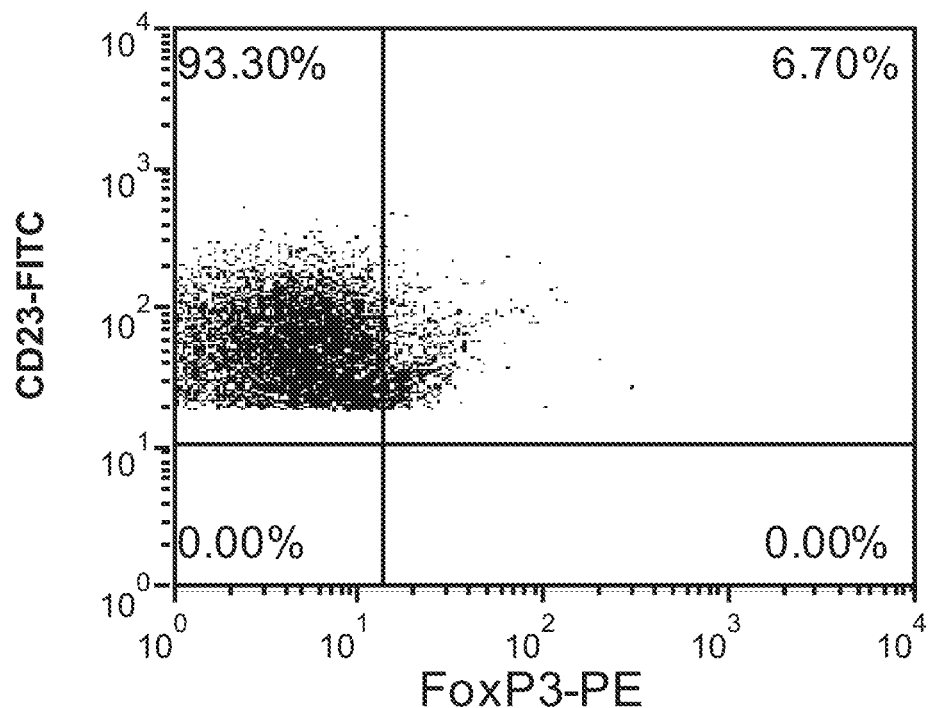
FIGS. 44A-C show that follicular, transitional 2, and transitional 3 B cells (top to bottom) express FoxP3 and that the cell numbers of the FoxP3-expressing B cell subsets increase with methotrexate as compared to mice treated with rhGAA alone.
Figure 44A:
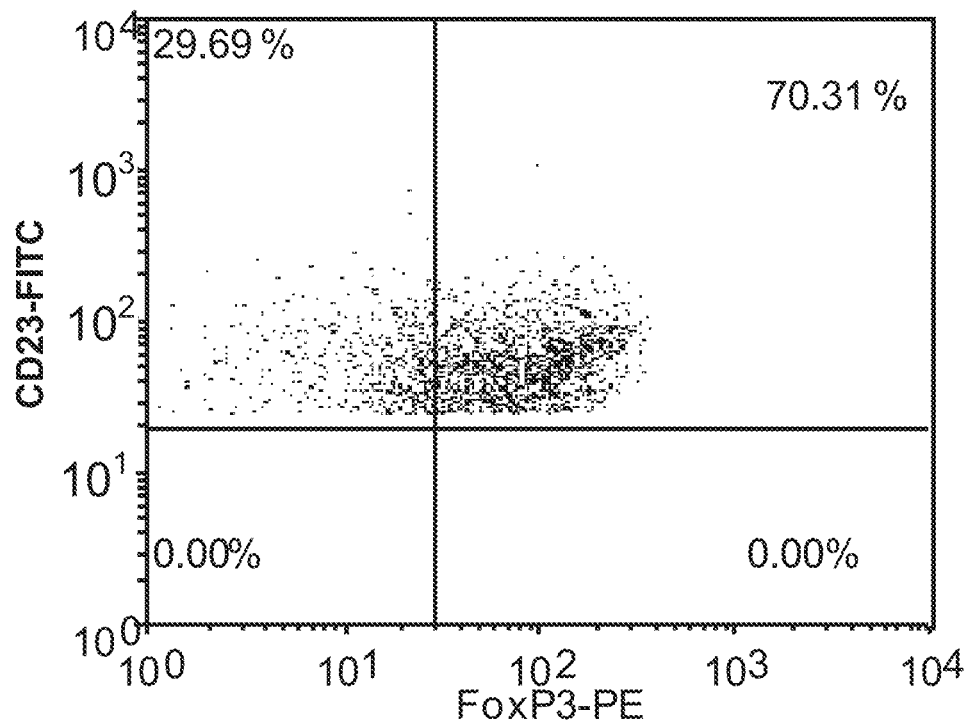
Figure 44B:
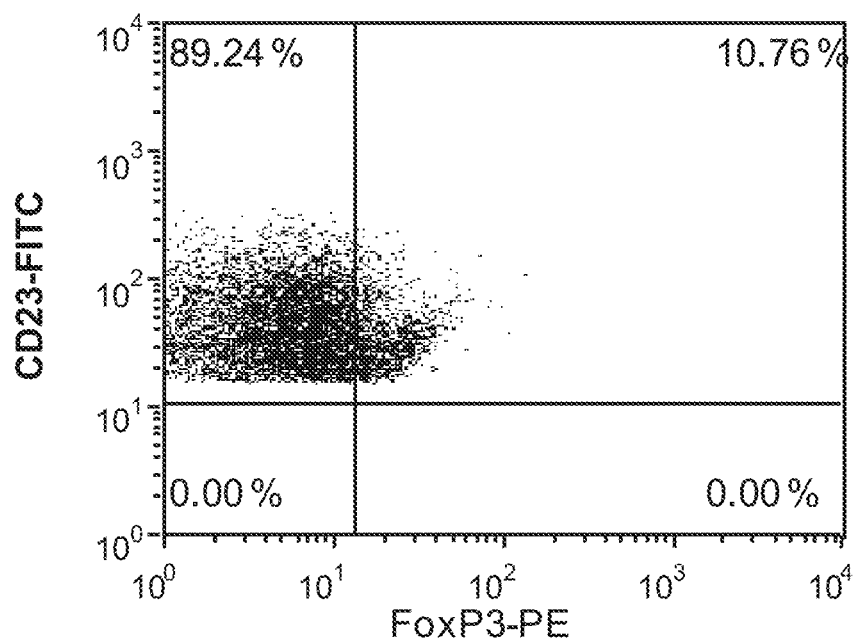
Figure 44B:
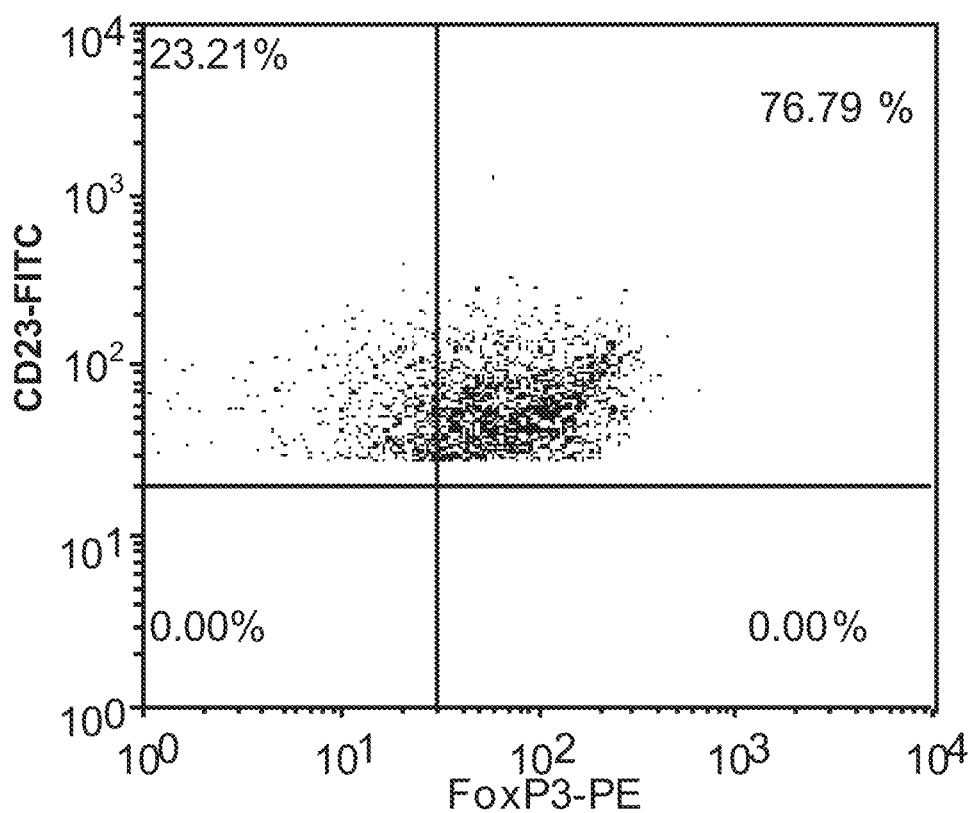
Figure 44C:
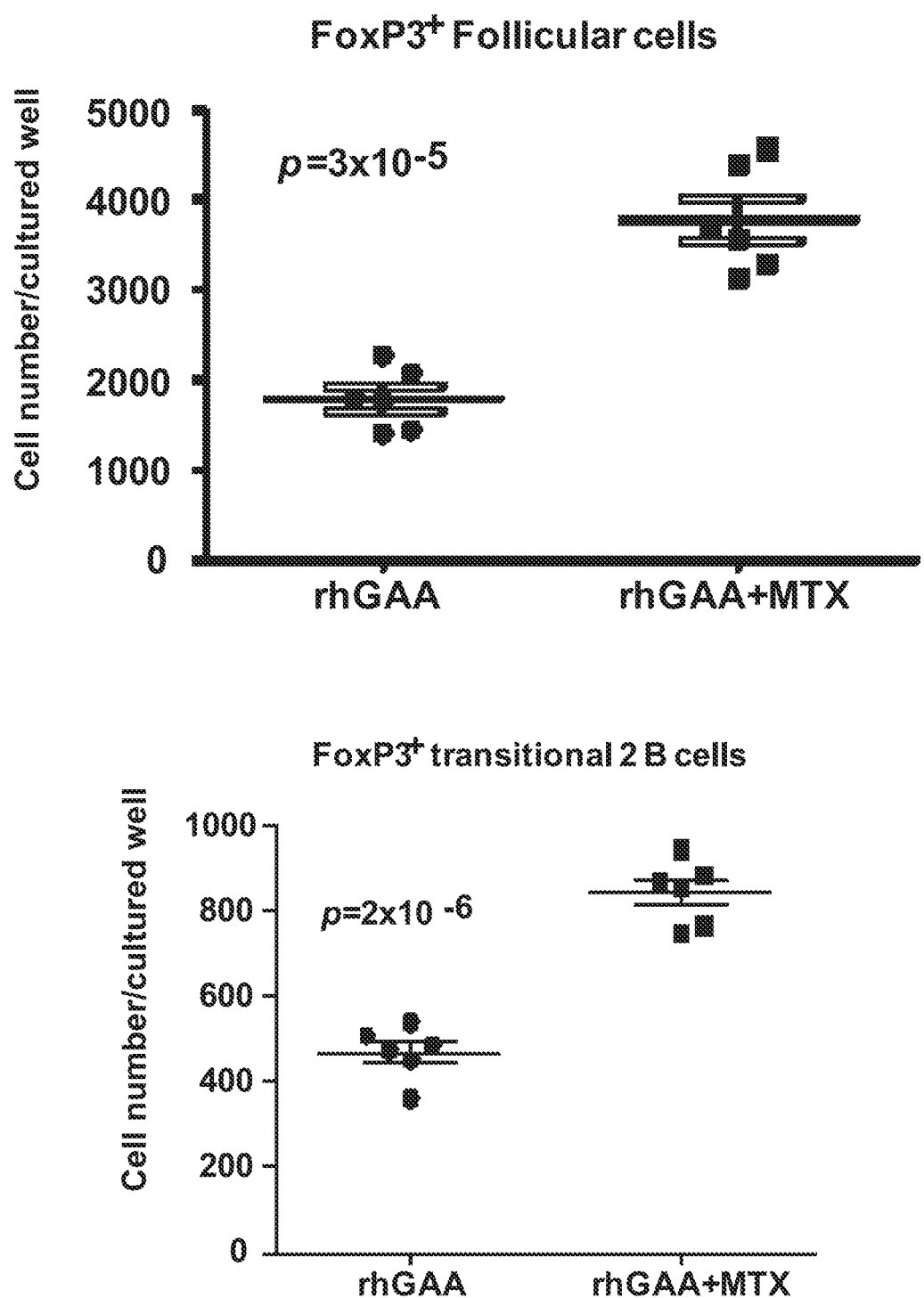

Because additional B cell-types are significantly increased with single cycle methotrexate-induced immune tolerance, we assessed whether some of these cell types expressed IL-10, TGF-beta and FoxP3. Transitional 2, transitional 3 and follicular B cells were found to express IL-10 (FIG. 42), TGF-beta (FIG. 43) and FoxP3 (FIG. 44), which was novel and unexpected for each of those B cell subsets. As observed with the B10 cells, the absolute cell numbers of the IL-10, TGF-beta, and FoxP3 B cell subsets were increased with methotrexate (FIGS. 42-44 B and C) as compared to mice treated with Myozyme® alone (FIGS. 42-44 A and C). Methotrexate treatment also induces statistically significant increases in IL-10, TGFbeta and FoxP3 in multiple cell subsets as viewed by the shift in mean fluorescence intensity of these proteins in animals treated with Myozyme® alone or Myozyme® and methotrexate (FIGS. 54-56).

Figure 45:
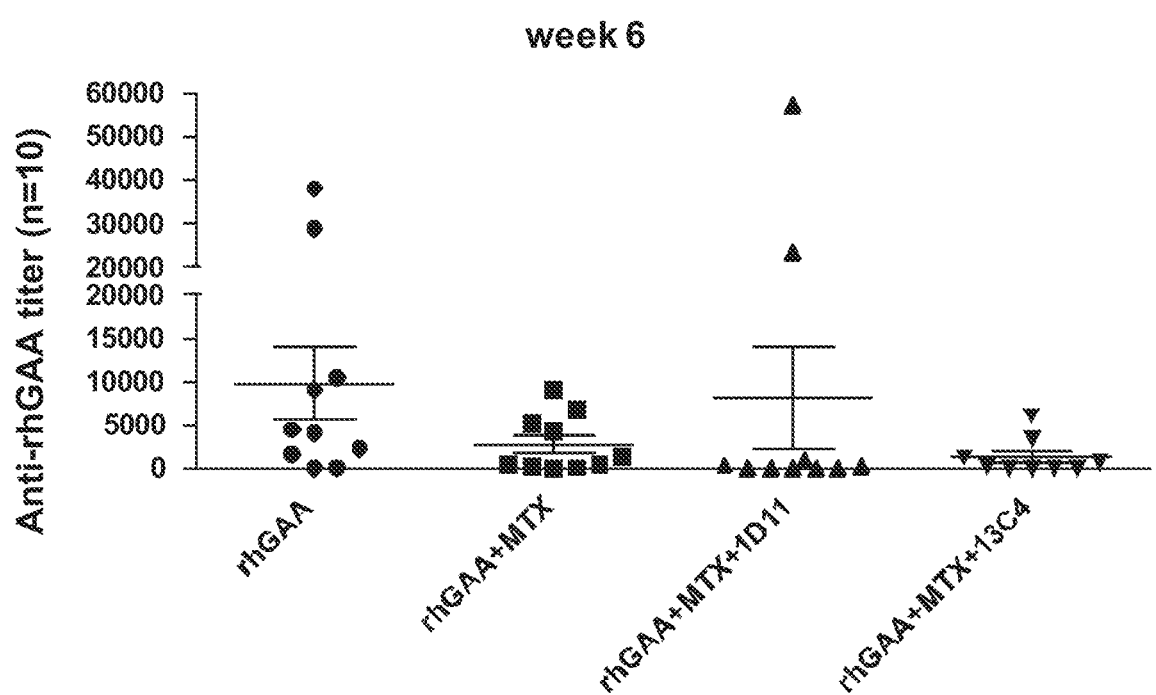
FIG. 45 shows anti-rhGAA titers at week 6 in animals treated with rhGAA or rhGAA and methotrexate, in the presence or absence of 5 mg/kg of anti-TGF-beta antibody (1D11, Genzyme) or the isotype control (13C4). Antibody titers were assessed bi-weekly in the four different groups of animals.

To further investigate the multiple TGF-beta expressing B cell populations enriched by treatment with methotrexate and Myozyme®, we next looked to determine whether TGF-beta is required for methotrexate-induced immune tolerance. Animals were treated with Myozyme® or Myozyme® and methotrexate with or without the presence of 5 mg/kg of anti-TGF-beta antibody (1D11, Genzyme) or the isotype control (13C4) given three times per week via intraperitoneal injection throughout the study. Antibody titers were assessed bi-weekly in four different groups of animals. If TGF-beta was required for methotrexate-induced immune tolerance, then we would expect that animals treated with the anti-TGF-beta antibody should not exhibit reduced anti-Myozyme titers. Week 6 titers are depicted in FIG. 45, and suggest that TGF-beta may be necessary for methotrexate-induced immune tolerance. Because this is an early time point, only some of the animals have had time to generate anti-Myozyme responses. Importantly, at this time point titers appear similar to those shown in FIG. 15C at week 6, where two animals in the rhGAA alone and the rhGAA- and methotrexate- and 1D11-treated animals exhibited high titers. In comparison, none of the animals treated with rhGAA and methotrexate or rhGAA and methotrexate and 13C4 exhibited high titers.

Additionally, spleens were isolated from animals treated with Myozyme® or Myozyme® and methotrexate that also were co-administered 1D11 or 13C4 seven days following a single Myozyme® treatment or a single Myozyme® and methotrexate treatment. At this time point, transitional 2, transitional 3, B10 and follicular B cells that expressed IL-10, TGF-beta, and FoxP3 were increased in animals treated with Myozyme® and methotrexate. Cells in each group were then pooled and cultured for two days and then assessed by flow cytometry to determine whether the anti-TGF-beta treatment with 1D11 interfered with the expansion of cells that expressed TGF-beta, IL-10, and FoxP3 in comparison to the isotype control antibody (13C4).

Figure 46A:
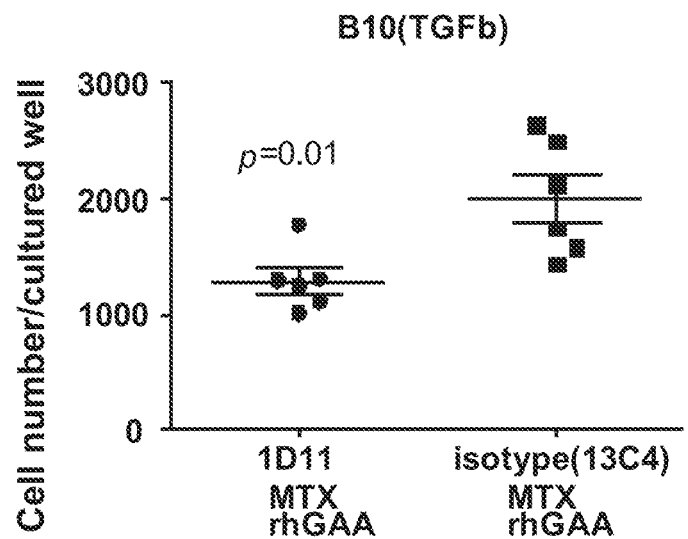
FIGS. 46A-C show that 1D11 treatment interfered with methotrexate-induced expansion of B10 B cells expressing TGF-beta, IL-10, or FoxP3. Spleens were isolated from animals treated with rhGAA or rhGAA and methotrexate that also were co-administered 1D11 or 13C4 seven days following a single rhGAA treatment or a single rhGAA and methotrexate treatment. Cells in each group were then pooled and cultured for two days and then counted using flow cytometry.
Figure 46B:
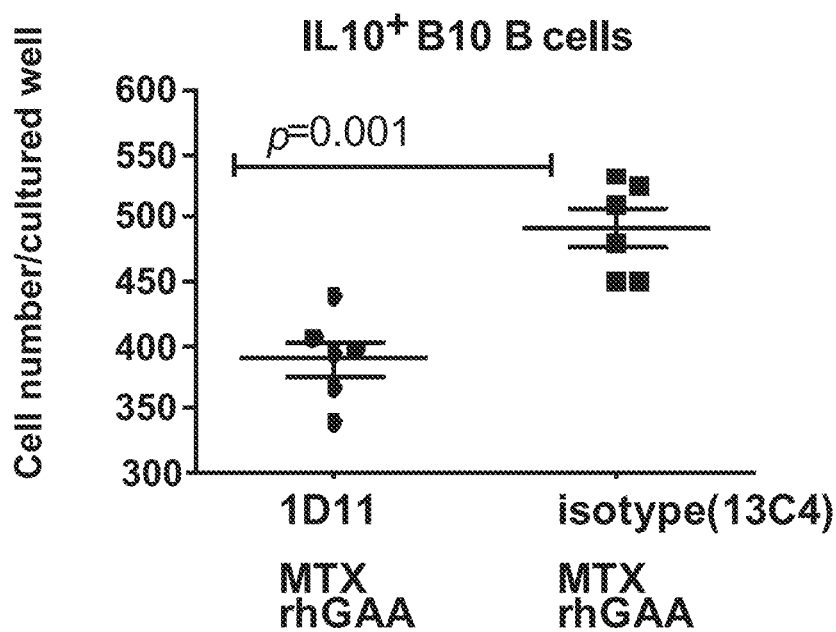
Figure 46C:
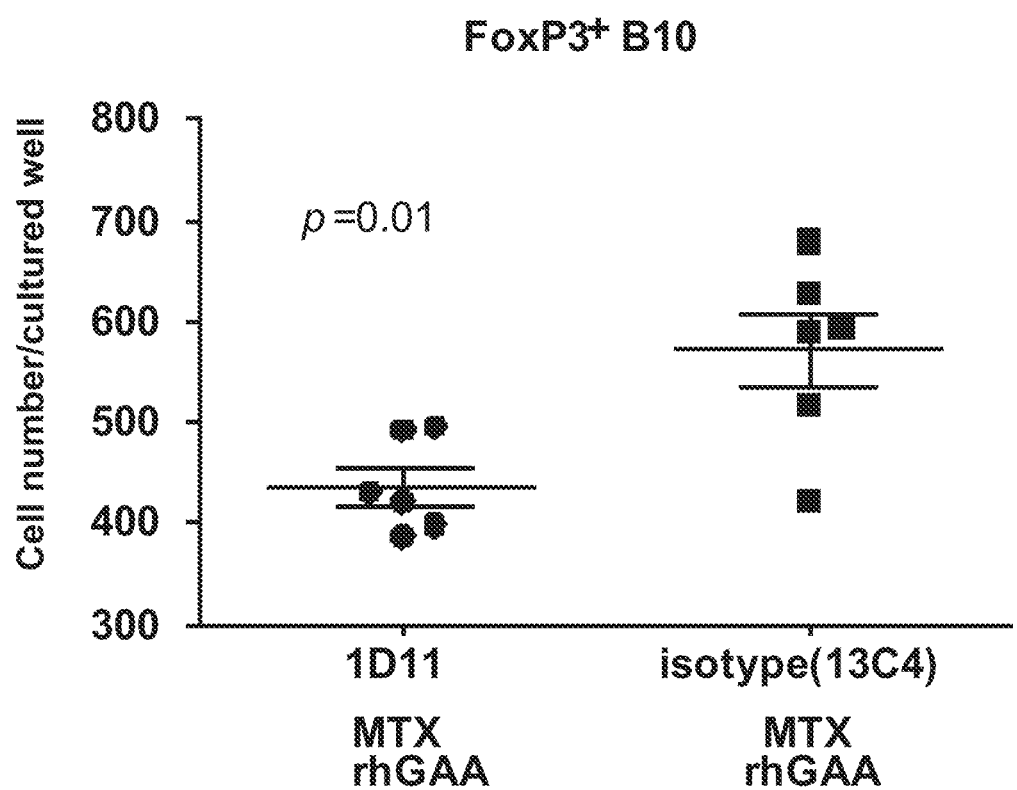
Figure 47A:
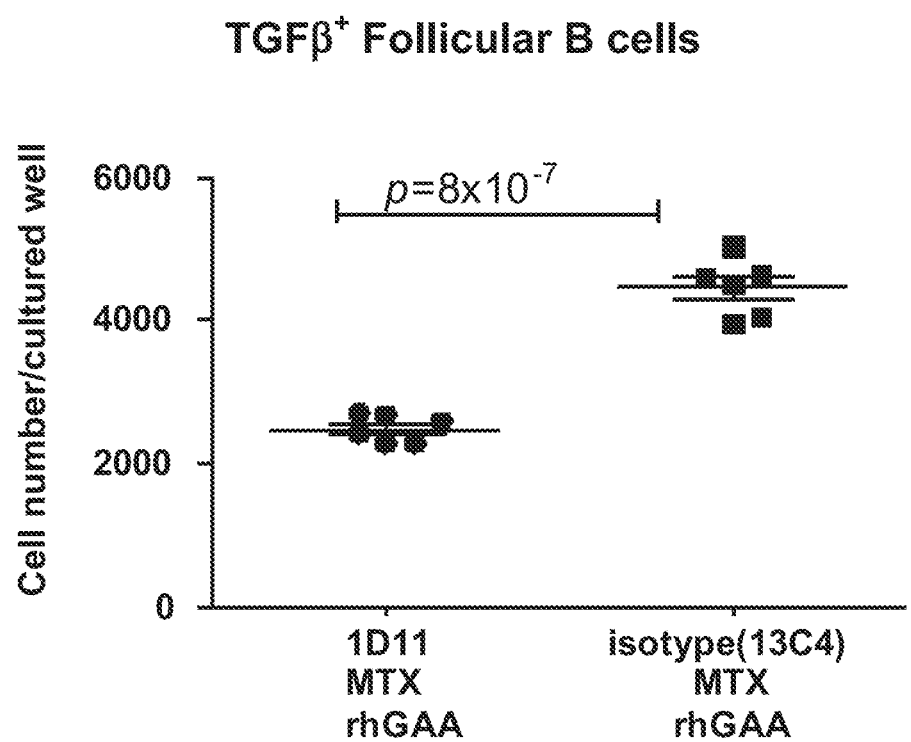
FIGS. 47A-C show that 1D11 treatment interfered with methotrexate-induced expansion of follicular B cells expressing TGF-beta or IL-10, although FoxP3+ Follicular B cells did not appear to experience 1D11 effects. Spleens were isolated from animals treated with rhGAA or rhGAA and methotrexate that also were co-administered 1D11 or 13C4 seven days following a single rhGAA treatment or a single rhGAA and methotrexate treatment. Cells in each group were then pooled and cultured for two days and then counted using flow cytometry.
Figure 47B:
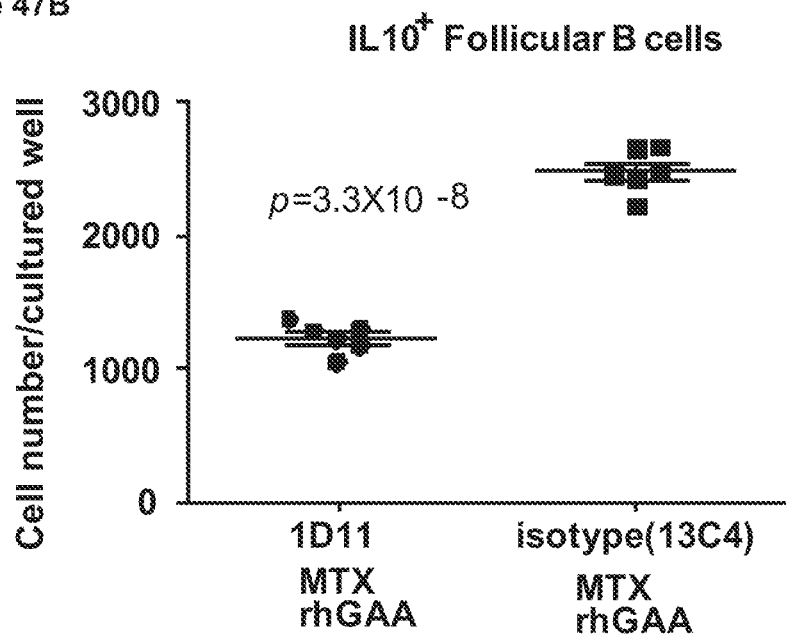
Figure 47C:
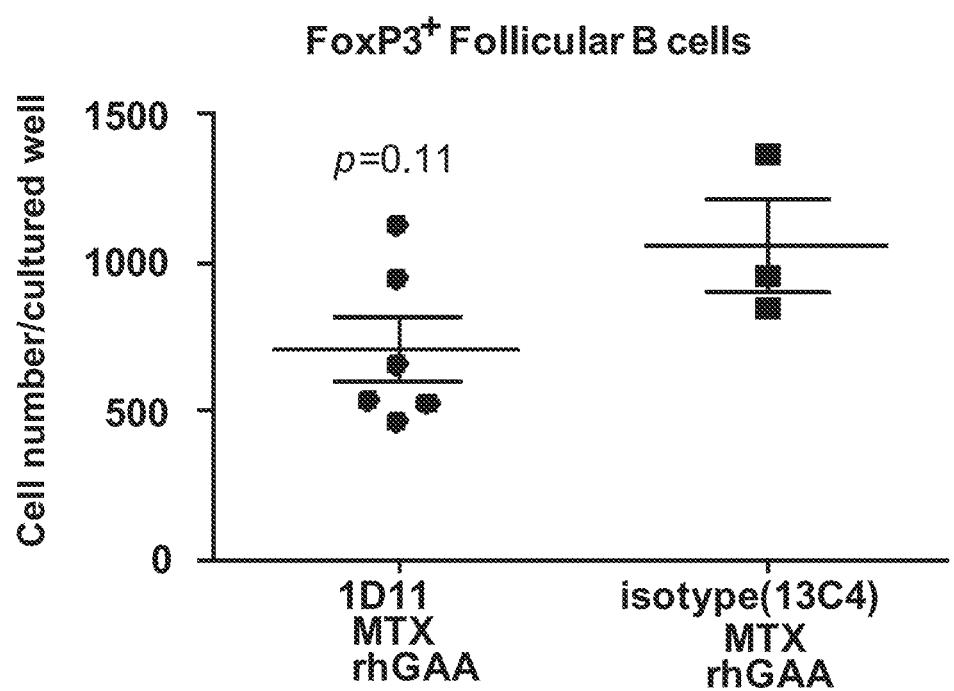
Figure 48A:
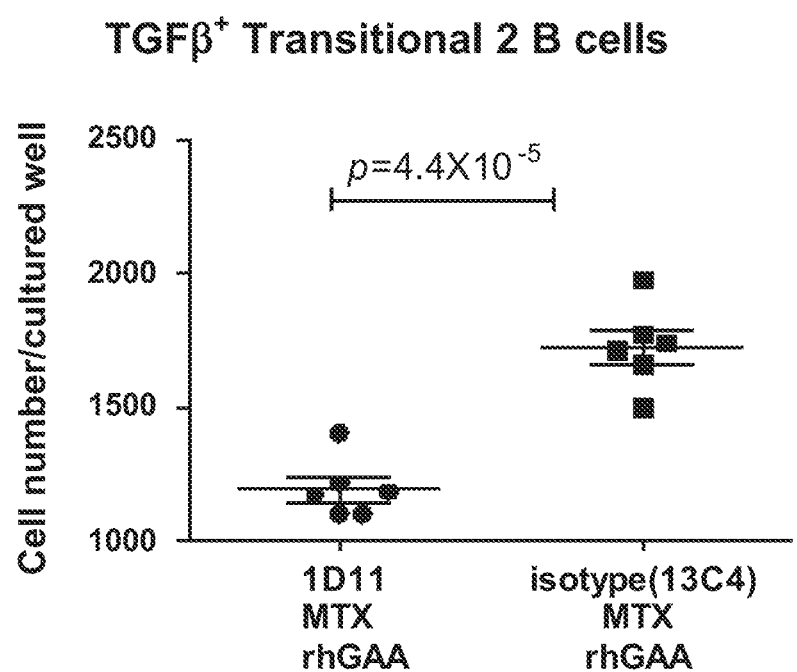
FIGS. 48A-C show that, in transitional 2 B cells, while 1D11 treatment interfered with methotrexate-induced expansion of TGF-beta-expressing transitional 2 B cells, no effects were seen on IL-10+ transitional 2 B cells. Spleens were isolated from animals treated with rhGAA or rhGAA and methotrexate that also were co-administered 1D11 or 13C4 seven days following a single rhGAA treatment or a single rhGAA and methotrexate treatment. Cells in each group were then pooled and cultured for two days and then counted using flow cytometry.
Figure 48B:
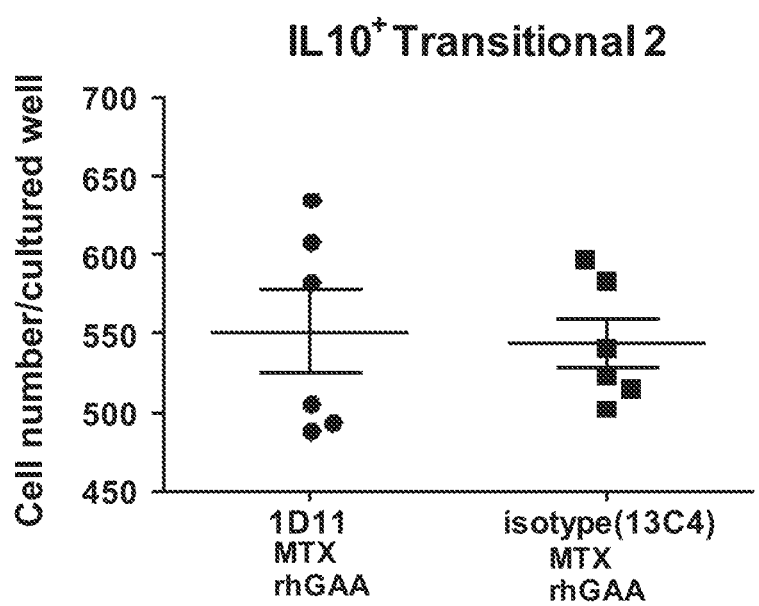
Figure 48C:
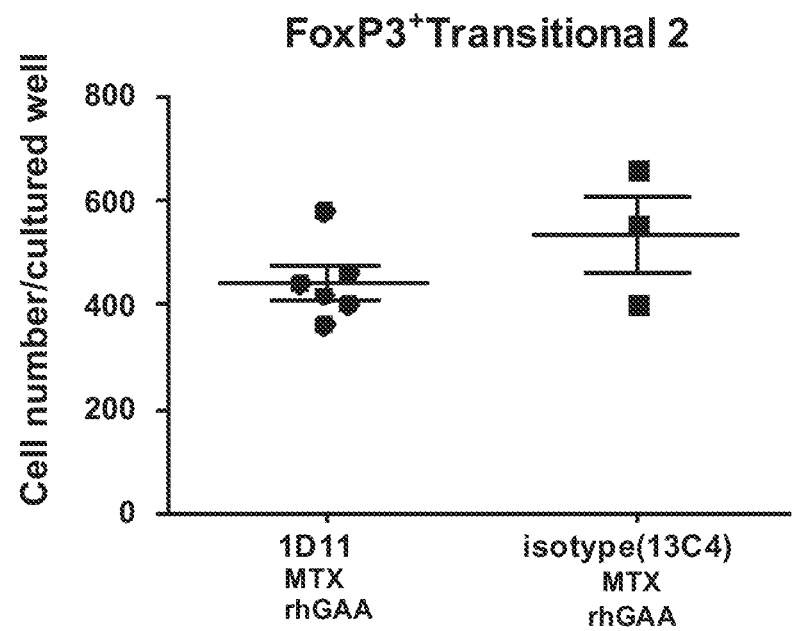
Figure 48C:
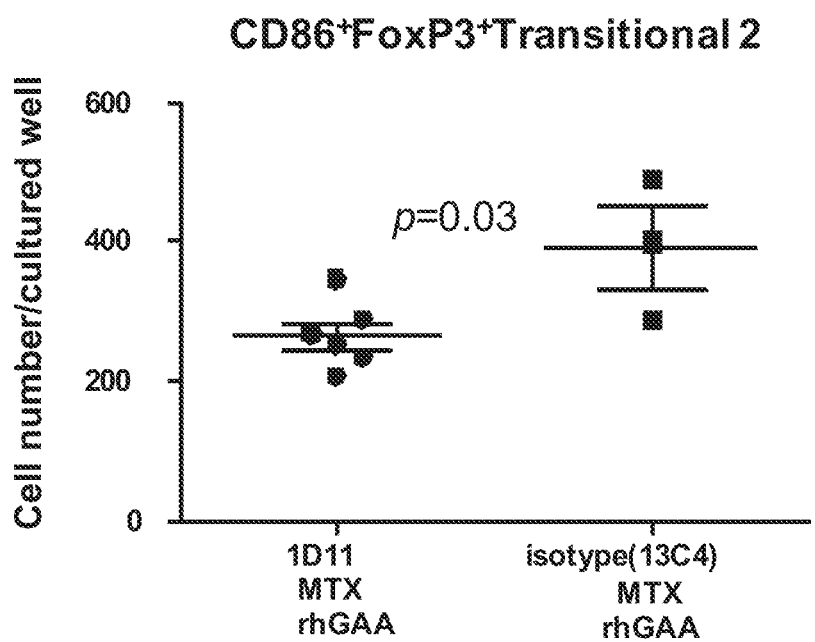
Figure 49A:
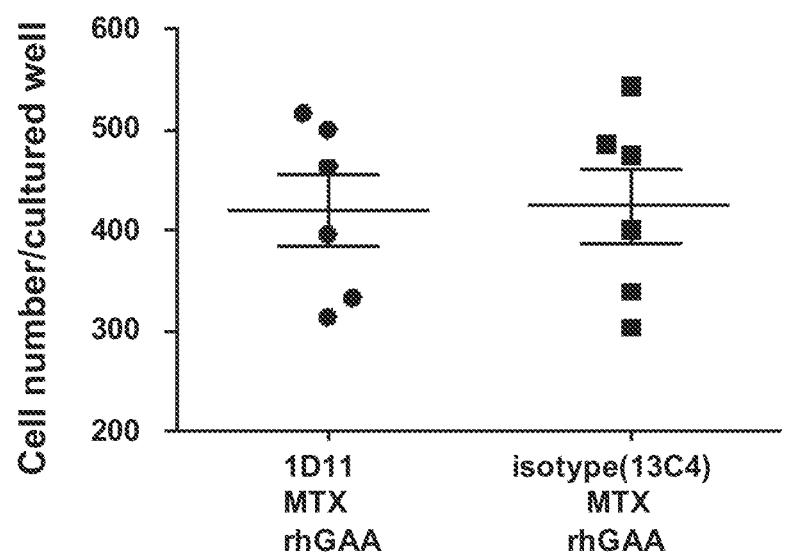
Figure 49A:
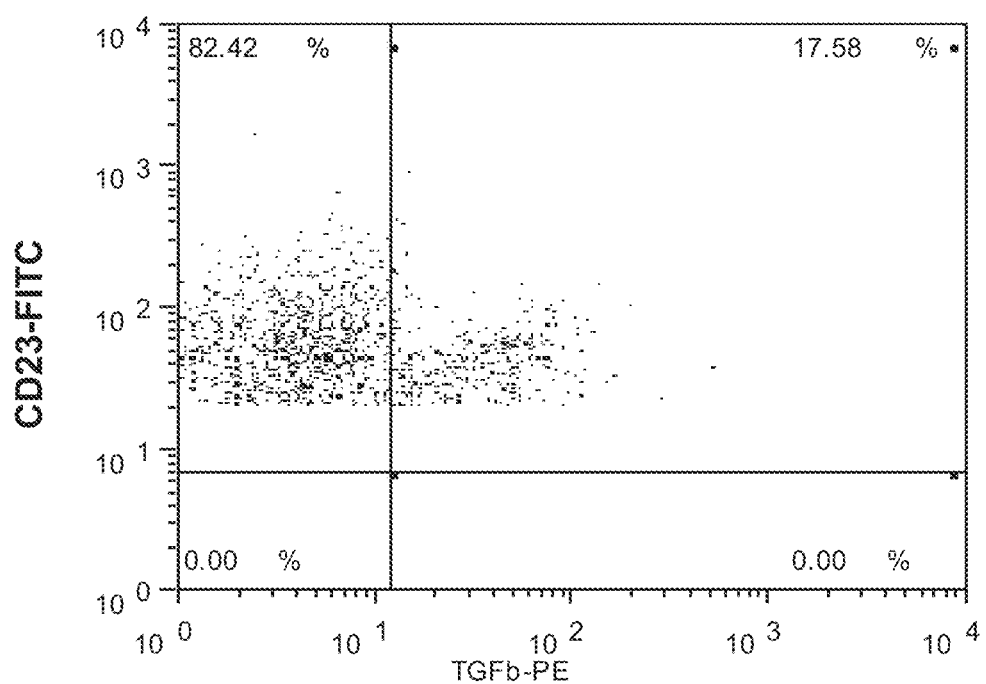
Figure 49C:
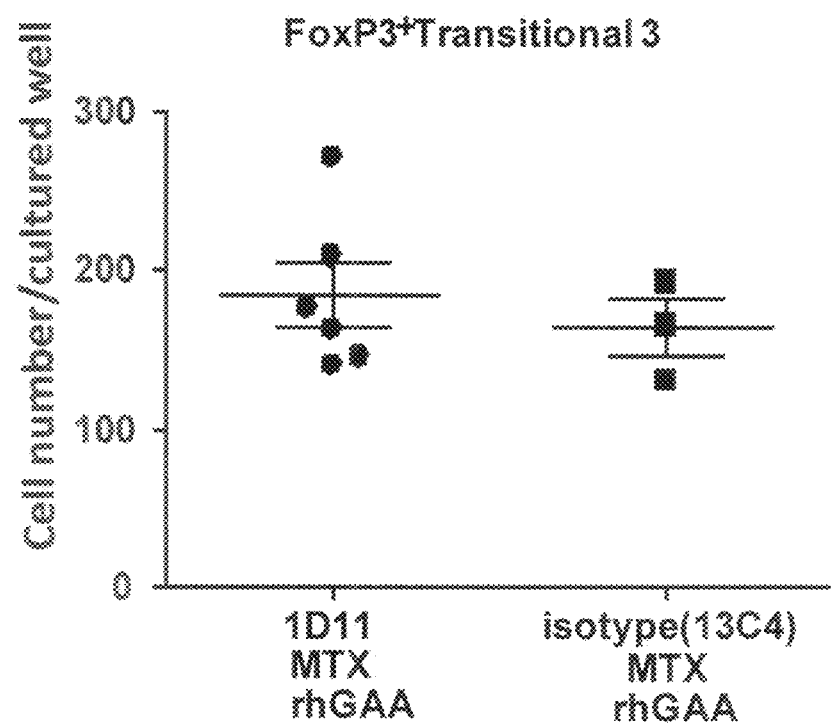
Figure 49C:
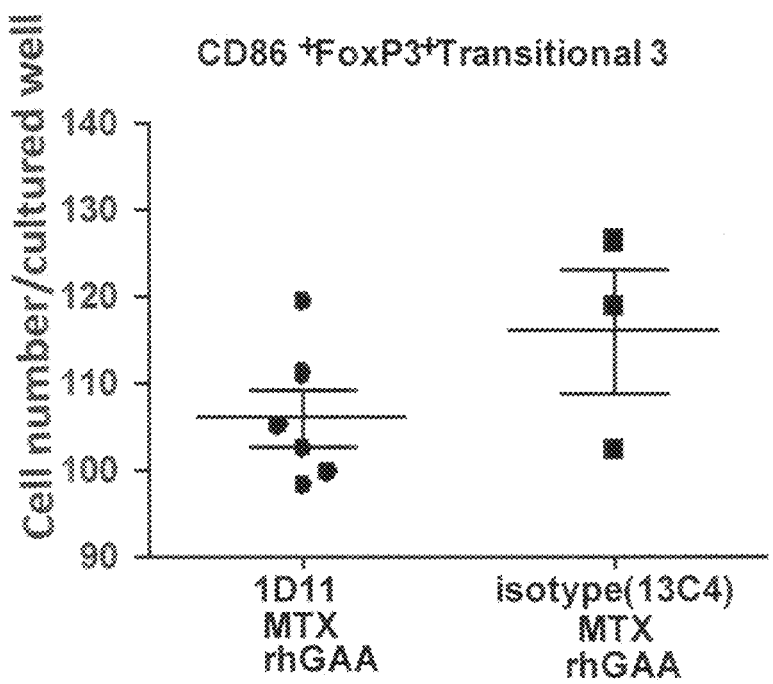
Figure 50A:
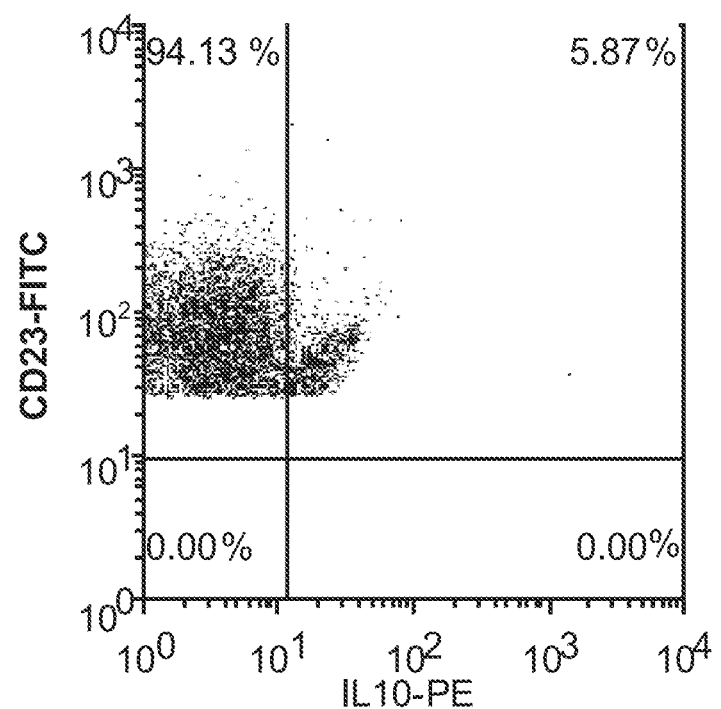
Figure 50A:
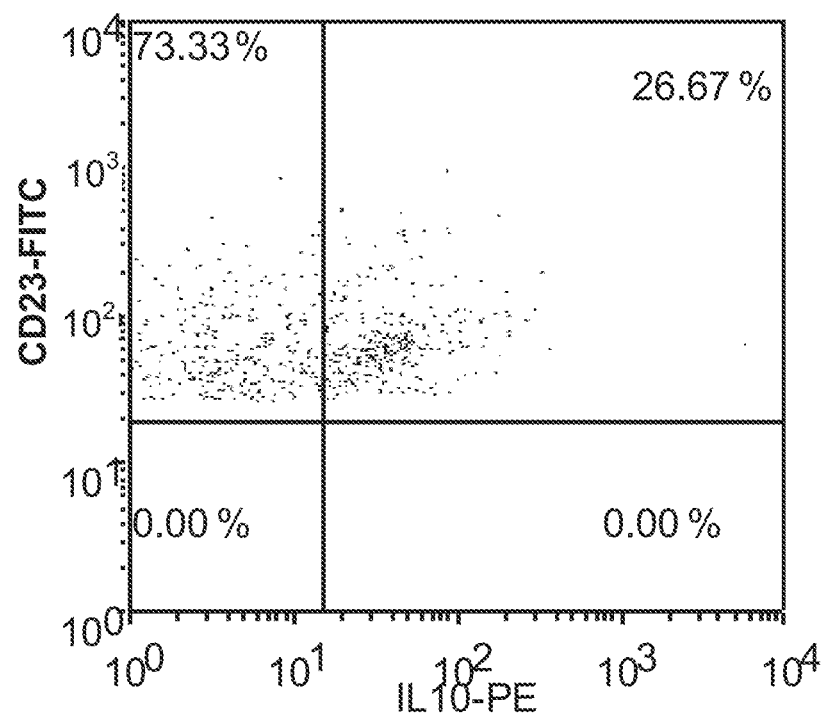
Figure 50C:
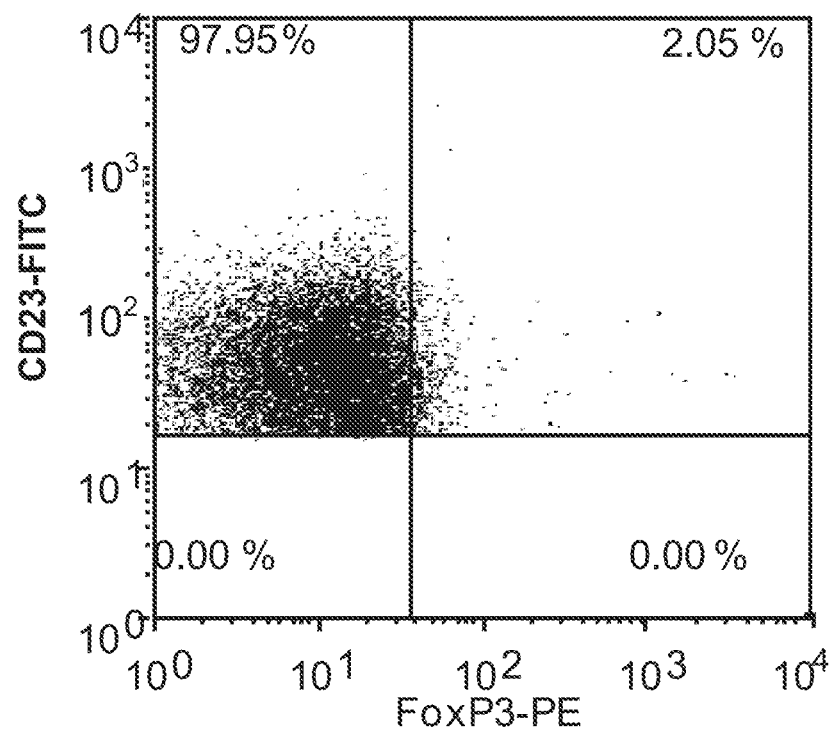
Figure 50C:
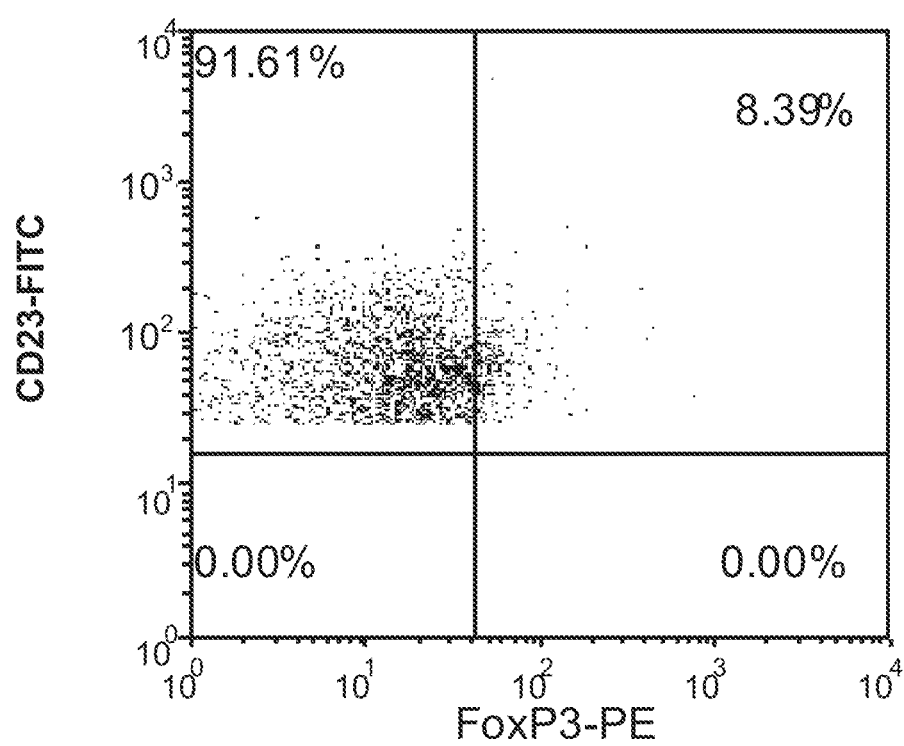

Quite unexpectedly, 1D11 treatment interfered with not only the methotrexate-induced expansion of cells expressing TGF-beta, but also with the expansion of some subsets expressing IL-10 and FoxP3. This was true specifically for B10 B cells (FIG. 46) and follicular B cells (FIG. 47), though FoxP3+ Follicular B cells did not appear to experience 1D11 effects. In transitional 2 B cells where 1D11 treatment interfered with TGF-beta-expressing transitional 2 B cells, no effects were seen with IL-10+ transitional 2 B cells (including activated transitional 2 B cells; FIG. 48). Moreover, effects in FoxP3+ transitional 2 B cells by 1D11 did not seem apparent in this small treatment group unless one looks at activated, CD86+ transitional 2 B cells. Importantly, these data suggest that methotrexate-induced TGF-beta is associated with IL-10 and FoxP3 in only some cell types. For transitional 3 B cells, even though there is detectable TGF-beta in the transitional 3 subset (FIG. 49), there is no apparent effect of 1D11 treatment on these cells ($P<0.05$; FIG. 49). Notably, in activated CD86+ transitional 3 B cells, there appear to be higher numbers of IL-10+ transitional 3 B cells in 1D11-treated mice. This may suggest that this population might be expanding to try to help compensate for losses in the numbers of other cell-types due to 1D11 treatment. Also of note is that 1D11 treatment did not affect basal levels of IL-10, TGF-beta, and FoxP3 in these cells (FIG. 50A-C, respectively), but it appeared to influence methotrexate effects on cells that express those cytokines.

In summary, interfering with TGF-beta by injecting a TGF-beta antibody during methotrexate-induced immune tolerance reduces the numbers of cells that are expressing TGF-beta in comparison to animals treated with the isotype control. Moreover, the typical increases observed with methotrexate-induced tolerance in IL-10 and FoxP3-expressing B10 B cells are inhibited by 1D11 treatment. 1D11 treatment appears to influence methotrexate effects on TGF-beta, IL-10, and/or FoxP3 in certain B cell types, but not all B cell types. These observations are surprising, and suggest that methotrexate induces TGF-beta, which in turn induces IL-10 and potentially FoxP3 in certain cells, such as B10 B cells. Although the association of TGF-beta with IL-10 and FoxP3 appears to have been reported before, it has not been shown in these cell types. Moreover, methotrexate has not been simultaneously associated with this complex signaling cascade.

Figure 51A:
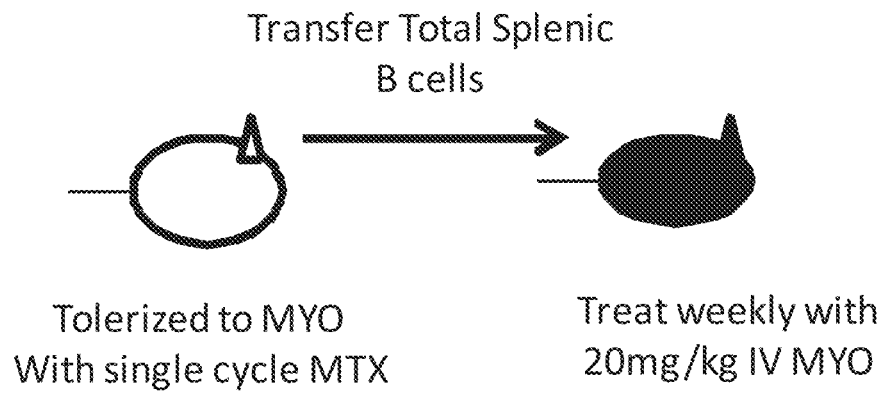
FIG. 51A is a schematic showing the transfer of total splenic B cells from a mouse tolerized to rhGAA (Myozyme® or "MYO") into an rhGAA-naive recipient mouse. After transfer, the recipients (along with non-transferred control animals treated with either rhGAA or rhGAA and methotrexate) were treated weekly with 20 mg/kg of rhGAA.
Figure 51B:
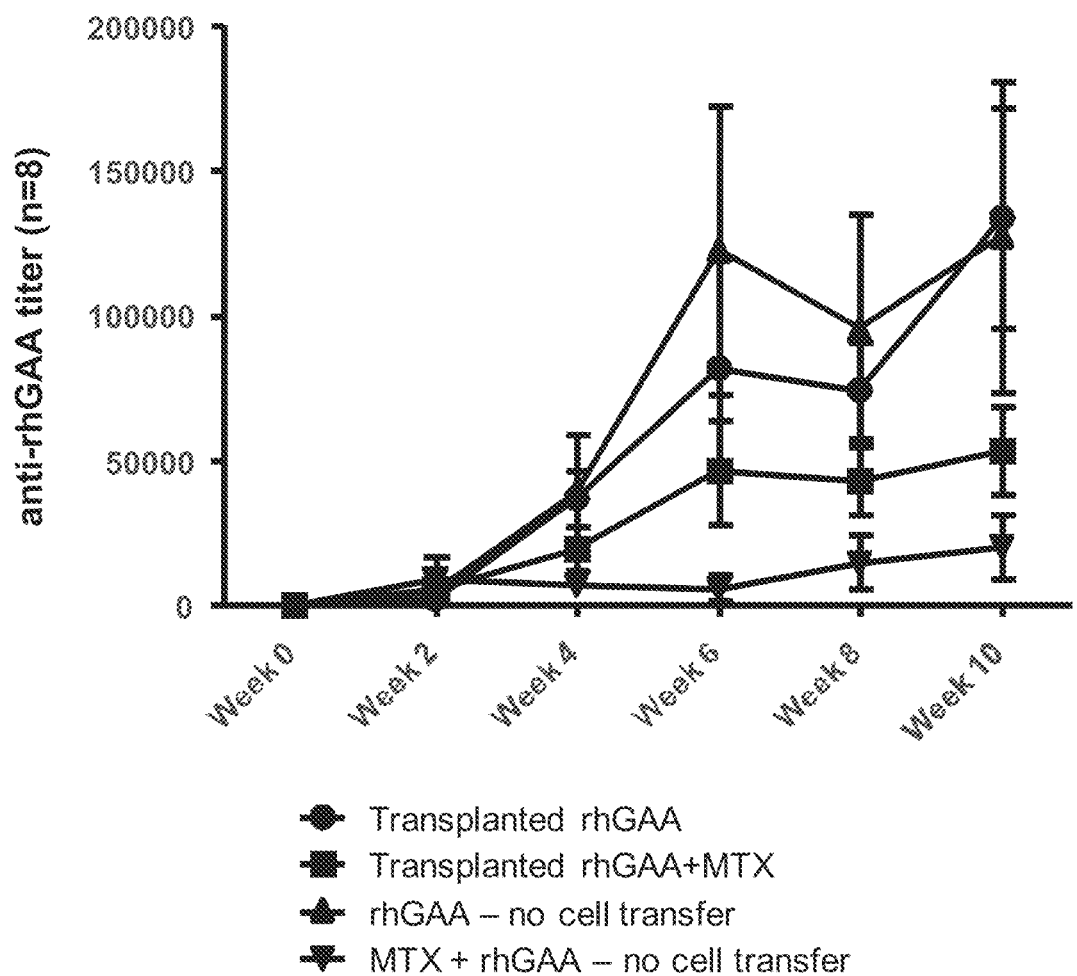
FIG. 51B shows titer analysis demonstrating that total splenic B cells isolated from animals treated with rhGAA and single cycle of methotrexate can transfer immune tolerance to rhGAA in naive hosts.

Thus far, we have demonstrated that certain B cells are significantly increased with methotrexate-induced tolerance, and that those B cells express proteins associated with immune-regulation (suppression). To more directly evaluate if the B cells themselves are mediating methotrexate-induced tolerance, we performed an adoptive transfer experiment assessing whether total splenic B cells from methotrexate-tolerized mice could transfer immune tolerance to naive hosts. We performed this experiment using Myozyme® and a single cycle of methotrexate treatment. We isolated spleens from animals treated with Myozyme® alone or with Myozyme® and methotrexate, 7 days after a single treatment of Myozyme® or Myozyme® and methotrexate, (when the above-mentioned B cell subsets were increased by methotrexate), and then purified all of the splenic B cells. Those cells were then transferred into Myozyme®-naive recipient mice (FIG. 51A). After transfer, the recipients (along with non-transferred control animals treated with either Myozyme® or Myozyme® and methotrexate) were treated weekly with 20 mg/kg of Myozyme®. Blood was collected every other week to assess anti-Myozyme antibody titers. At the time of harvesting spleens, a subset of B cells from each donor group was assessed by flow cytometry to confirm the expected increases in TGF-beta+, IL-10+ and/or FoxP3+ transitional 2, transitional 3, B10 and follicular B cells. Donor groups were confirmed to have the expected phenotype. Titer analysis suggested that total splenic B cells isolated from animals treated with Myozyme® and a single cycle of methotrexate could transfer immune tolerance to Myozyme® in naïve hosts (FIG. 51B). This supports that B cells can mediate methotrexate-induced immune tolerance, and was the first time that B cells have been described to be enriched (and not killed) by methotrexate to help mediate anti-inflammatory effects. These data also directly question the concomitant use of a B cell depleting agent with methotrexate to induce immune tolerance, which is currently being performed in patients (Messinger et al., supra and Lacaná et al., supra).

Example 16

Methotrexate Improves Graft Pathology

Figure 52:
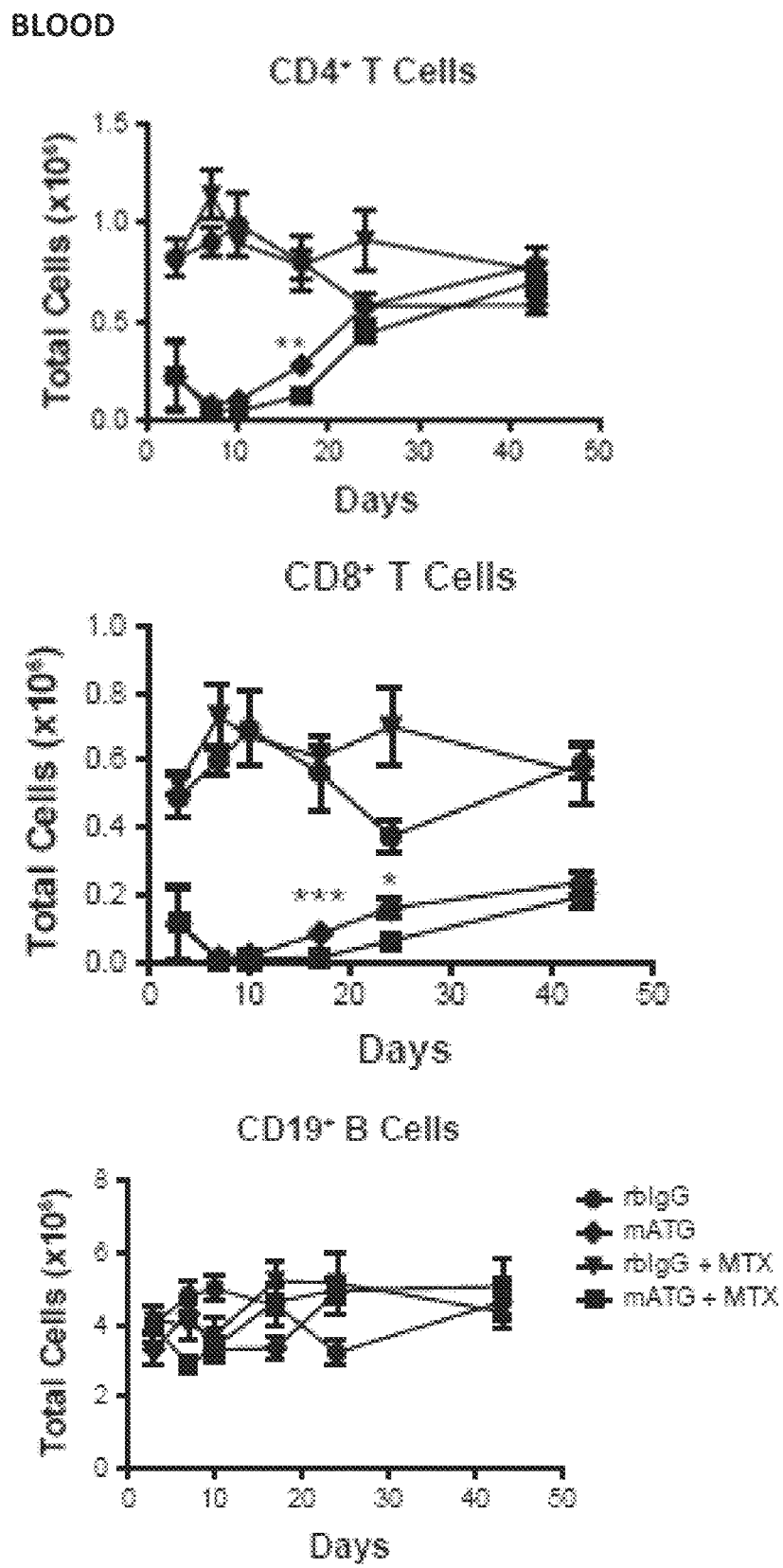
FIG. 52 depicts cell counts from the blood or spleen of normal mice treated with rabbit IgG (rbIgG), mATG alone, rbIgG and methotrexate, or mATG and methotrexate. Methotrexate does not deplete CD4+, CD8+, T regulatory (CD4+CD25+FoxP3+) T cells, or total CD19+ B cells in normal animals.
Figure 53:
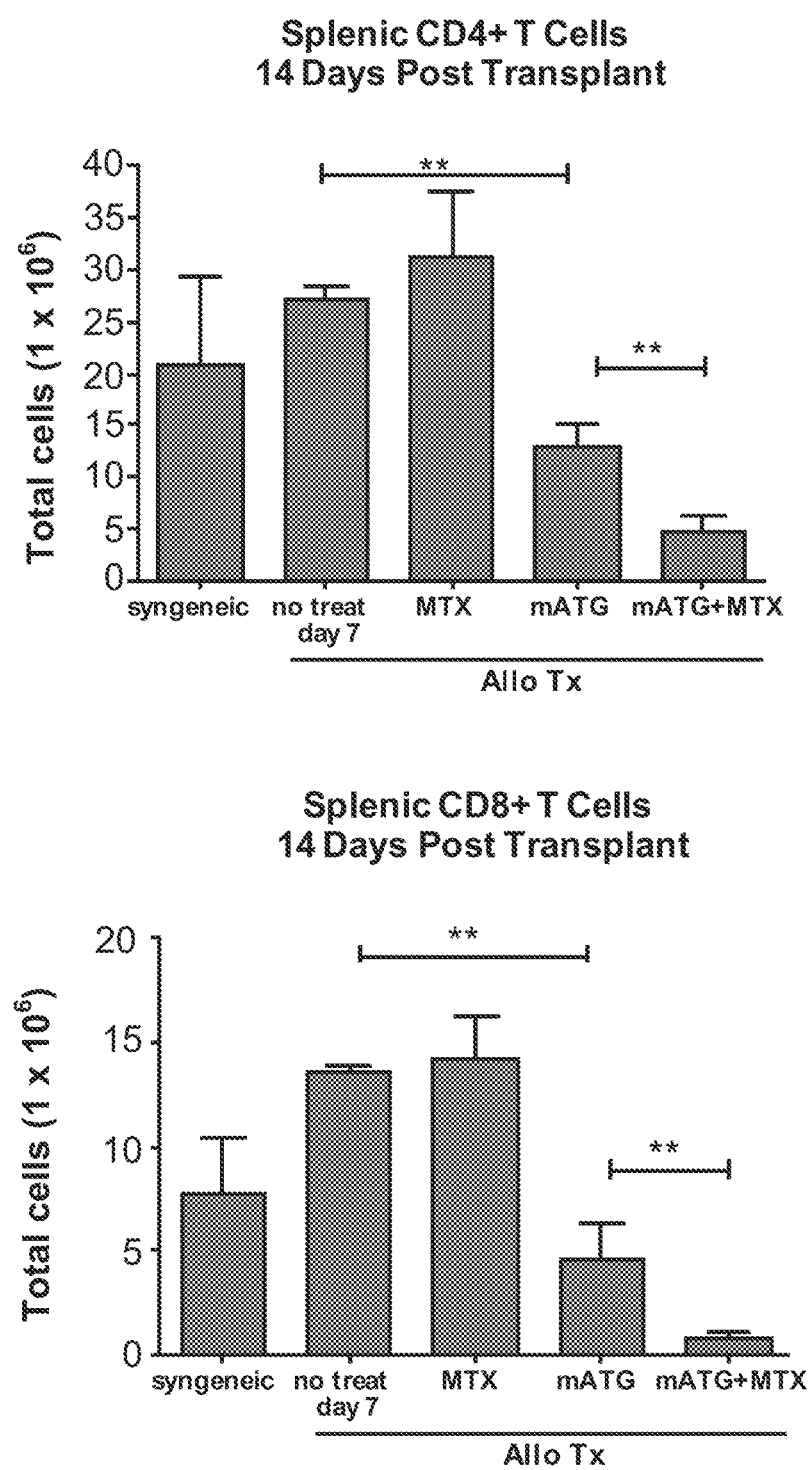
FIG. 53 depicts cell counts from the blood or spleen of transplant mice treated with rbIgG, mATG alone, rbIgG and methotrexate, or mATG and methotrexate 14 days after transplantation. Methotrexate does not deplete CD4+, CD8+, T regulatory (CD4+CD25+FoxP3+) T cells, and total CD19+ B cells in transplant animals.

We also have generated additional data in the context of murine anti-thymocyte globulin that demonstrates that methotrexate does not deplete CD4+, CD8+, T regulatory (CD4+CD25+FoxP3+) T cells, and total CD19+ B cells in normal animals (FIG. 52) and in transplant animals (FIG. 53). When comparing normal animals treated with non-specific rabbit IgG alone or in combination with methotrexate, there were no significant changes in the cell populations in the blood and spleen (FIG. 52). Moreover, when comparing those populations isolated from animals treated with mATG alone or with mATG and methotrexate, there was no enhanced depletion. Rather, we observed only an extension of mATG-mediated CD4+, CD8+, and T regulatory cell effects, which was most likely due to increased mATG exposure by methotrexate (FIG. 52). In addition, methotrexate treatment alone in animals receiving an allogeneic transplant did not deplete those particular cell subsets (FIG. 53). The lower numbers of CD4+ and CD8+ T cells in animals treated with mATG and methotrexate compared to animals treated with mATG alone can be explained by the prolonged effect of mATG when in the context of methotrexate treatment. Importantly, methotrexate did not induce decreases in B cells as would have been expected if methotrexate was killing activated B cells to reduce antibody responses in either normal or transplanted animals (FIGS. 52 and 53). These data suggest that methotrexate effects on anti-drug antibodies may not be mediated by anti-folate induced depletion of activated B cells. As expected, mATG treatment also did not impact total B cell numbers in this heterotopic cardiac allograft model model. Overall, the combined treatment of mATG and methotrexate attenuated the severity of graft rejection pathology and was associated with decreased T cell infiltrate in the graft, but not with increases in cells with a regulatory T cell phenotype. This is consistent with the results generated in the context of Myozyme® and alemtuzumab.

To both assess the histological changes in long-surviving grafts as well as to understand the mechanism of mATG and methotrexate combination on graft survival, cardiac grafts were collected and evaluated for pathology as well as cellular composition. In particular, because regulatory T cells have been associated with long-term graft survival in transplantation, are induced by Thymoglobulin® and mATG, and have been demonstrated to be responsible for delayed graft rejection following mATG treatment, CD3+ Foxp3+ cells, which bear a phenotype consistent with T regulatory cells, were evaluated. Specifically, cardiac grafts were collected from the mATG and methotrexate combination-treated group and the untreated syngeneic group at least 100 days after transplantation. Grafts from untreated mice and mice treated with mATG alone or methotrexate alone were taken after graft rejection for comparison. Tissue sections stained with H&E or Masson's trichrome or immunostained anti-CD3 and anti-Foxp3 antibodies were microscopically evaluated for histologic changes indicative of transplant rejection, e.g., mild to moderate myocarditis, myocardial degeneration and necrosis, cardiac allograft vasculopathy (CAV), and T cell infiltration. At day 100, allografts from animals co-treated with mATG and methotrexate revealed minimal to mild CAV lesions and no to minimal myocardial degeneration and myocarditis. Histological changes suggestive of graft rejection were not apparent in syngeneic grafts at this late time point (FIG. 54). Allografts from the combination treated group exhibited mild T cell infiltration in the myocardium with a few cells infiltrating the myocardial blood vessels. Syngeneic grafts contained rare T cells within the myocardium. Clusters of T cells with occasional dual CD3 and Foxp3 immunopositive cells were present in the epicardium of both syngeneic grafts and combination-treated allografts. Thus, long-surviving grafts showed minimal signs of graft rejection, which correlates with reduced inflammation.

Because the effects of mATG and methotrexate combination treatment were likely to more actively occur closer to the time of transplantation, we also evaluated pathology and characterized the cellular infiltrate of transplanted heart allografts at 7 (for untreated mice) or 14 (for all treatment groups) days after transplantation. Untreated allografts displayed graft rejection pathology including myocarditis, myocardial degeneration and necrosis in both epicardial and intramyocardial branches of coronary arteries. By contrast, allografts isolated from animals treated with both mATG and methotrexate revealed less severe CAV. This was in comparison to allografts from untreated animals as well as from animals treated with either mATG or methotrexate (FIG. 58). As expected, syngeneic grafts from untreated mice revealed little or no pathology at these time points. CD3+ T cell infiltration was observed in the myocardium and epicardium in allografts from untreated mice and those treated with mATG or methotrexate alone. A few CD3+ T cells also were present in the inflammatory cell infiltrate associated with the CAV lesions in these grafts. By contrast, allografts from animals treated with the combination of mATG and methotrexate exhibited substantially lower CD3+ T cell infiltration in the myocardium and only minimal CD3+ T cell infiltration in the epicardium. Syngeneic cardiac grafts showed minimal CD3+ T cell infiltration only in the epicardium. A small proportion of T cells within the inflammatory cell infiltrates in the epicardium appeared to have a T regulatory cell phenotype as indicated by dual CD3 and Foxp3 immunoreactivity, but this frequency appeared no greater within inflammatory infiltrates than in other groups. Therefore, reduced pathology also was observed early after treatment with mATG and methotrexate and was associated with both reduced and epicardium-restricted T cell infiltration.

What is claimed is:

1. A method of increasing the percentage of B regulatory cells in the B cell population in a subject in need of treatment with a therapeutic, comprising administering to the subject an effective amount of methotrexate, thereby increasing said percentage in said subject, wherein the subject is administered a therapeutic for more than one cycle of a dosing regimen, wherein the therapeutic is human acid alpha-glucosidase, wherein the effective amount of methotrexate is administered in a single cycle of the dosing regimen of the therapeutic, and wherein methotrexate is not administered in subsequent cycles of the dosing regimen of the therapeutic.

2. The method of claim 1, wherein the effective amount of methotrexate is 0.1 mg/kg to 5 mg/kg.

3. The method of claim 1, wherein the single cycle of methotrexate is administered between 48 hours prior to and 48 hours after the onset of the therapeutic treatment.

4. The method of claim 1, wherein the B regulatory cells are B 10 regulatory B cells.

5. The method of claim 1, wherein the B cell population is the splenic B cell population.

6. The method of claim 1, wherein the B regulatory cells express IL-10, TGF-β and FoxP3.

* * * * *

UNITED STATES PATENT AND TRADEMARK OFFICE
CERTIFICATE OF CORRECTION

| | | |
|---|---|---|
| PATENT NO. | : 11,672,802 B2 | Page 1 of 1 |
| APPLICATION NO. | : 16/828407 | |
| DATED | : June 13, 2023 | |
| INVENTOR(S) | : Alexandra Joseph et al. | |

It is certified that error appears in the above-identified patent and that said Letters Patent is hereby corrected as shown below:

In the Claims

In Claim 4, Column 44, Line 33: please replace "B 10" with --B10--.

Signed and Sealed this
Second Day of April, 2024

Katherine Kelly Vidal
*Director of the United States Patent and Trademark Office*